US007329490B2

(12) United States Patent
Ranade et al.

(10) Patent No.: US 7,329,490 B2
(45) Date of Patent: Feb. 12, 2008

(54) METHODS FOR DIAGNOSING SCHIZOPHRENIA BY DETECTING A POLYMORPHISM IN THE KALPHAM1 GENE

(75) Inventors: Koustubh Ranade, Princeton, NJ (US); Priya Sudarshan Vishnupad, Ewing, NJ (US); Terrye Aigeldinger Delmonte, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 359 days.

(21) Appl. No.: 10/941,340

(22) Filed: Sep. 15, 2004

(65) Prior Publication Data

US 2005/0059070 A1 Mar. 17, 2005

Related U.S. Application Data

(60) Provisional application No. 60/503,403, filed on Sep. 15, 2003.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ........................ 435/6; 435/91.2; 536/23.5; 536/24.31; 536/24.33

(58) Field of Classification Search ..................... None
See application file for complete search history.

(56) References Cited

U.S. PATENT DOCUMENTS 5,075,217 A 12/1991 Weber

FOREIGN PATENT DOCUMENTS

| | | |
|---|---|---|
| EP | 0 370 719 | 5/1990 |
| WO | WO 90/11369 | 10/1990 |
| WO | WO 90/13668 | 11/1990 |
| WO | WO 91/14003 | 9/1991 |
| WO | WO 95/11995 | 5/1995 |

OTHER PUBLICATIONS

Lucentini. The Scientist. Dec. 2004, p. 20).*
Ottschytsch et al. Proceedings of the National Academies of Sciences. 2002. 99(12): 7986-7991.*
Armour, J.A.L. et al., "Recent advances in minisatellite biology", FEBS Letters, vol. 307, No. 1, pp. 113-115 (1992).
Botstein, D. et al., "Construction of a Genetic Linkage Map in Man Using Restriction Fragment Length Polymorphisms", Am. J. Hum. Genet., vol. 32, pp. 314-331 (1980).
Donis-Keller, H. et al., "A Genetic Linkage Map of the Human Genome", Cell, vol. 51, pp. 319-337.
Gusella, J.F., "DNA Polymorphism and Human Disease", Ann. Rev. Biochem., vol. 55, pp. 831-854 (1986).
Lander, E.S. et al., "Mapping Mendelian Factors Underlying Quantitative Traits Using RFLP Linkage Maps", Genetics, vol. 121, pp. 185-199 (1989).

* cited by examiner

*Primary Examiner*—Carla Myers
(74) *Attorney, Agent, or Firm*—Melissa Handler; John A. Lamerdin

(57) ABSTRACT

The invention provides polynucleotide fragments corresponding to the genomic and/or coding regions of these genes which comprise at least one polymorphic site per fragment. Allele-specific primers and probes that hybridize to these regions, and/or that comprise at least one polymorphic site are also provided. The polynucleotides, primers, and probes of the present invention are useful in phenotype correlations, paternity testing, medicine, and genetic analysis. Also provided are vectors, host cells, antibodies, and recombinant and synthetic methods for producing said polypeptides. The invention further relates to diagnostic and therapeutic methods for applying these novel polypeptides to the diagnosis, treatment, and/or prevention of various diseases and/or disorders, particularly cardiovascular diseases related to these polypeptides. The invention further relates to screening methods for identifying agonists and antagonists of the polynucleotides and polypeptides of the present invention.

6 Claims, 7 Drawing Sheets

FIG. 1

BGS-5 cDNA Sequence 1 ctcagatgtg ctccttggag ctggtgtgca gtgtcctgac tgtaagatca agtccaaacc
61 tgttttggaa ttgaggaaac ttctcttttg atctcagccc ttggtggtcc aggtcttcat
121 gctgctgtgg gtgatattac tggtcctggc tcctgtcagt ggacagtttg caaggacacc
181 caggcccatt attttcctcc agcctccatg gaccacagtc ttccaaggag agagagtgac
241 cctcacttgc aagggatttc gcttctactc accacagaaa acaaaatggt accatcggta
301 ccttgggaaa gaaatactaa gagaaacccc agacaatatc cttgaggttc aggaatctgg
361 agagtacaga tgccaggccc agggctcccc tctcagtagc cctgtgcact tggatttttc
421 ttcagagatg ggatttcctc atgctgccca ggctaatgtt gaactcctgg gctcaagtga
481 tctgctcacc tgggcctctc aaagcgctgg gattacagct tcgctgatcc tgcaagctcc
541 actttctgtg tttgaaggag actctgtggt tctgaggtgc cgggcaaagg cggaagtaac
601 actgaataat actatttaca agaatgataa tgtcctggca ttccttaata aaagaactga
661 cttccatatt cctcatgcat gtctcaagga caatggtgca tatcgctgta ctggatataa
721 ggaaagttgt tgccctgttt cttccaatac agtcaaaatc caagtccaag agccatttac
781 acgtccagtg ctgagagcca gctccttcca gcccatcagc gggaacccag tgaccctgac
841 ctgtgagacc cagctctctc tagagaggtc agatgtcccg ctccggttcc gcttcttcag
901 agatgaccag accctgggat taggctggag tctctccccg aatttccaga ttactgccat
961 gtggagtaaa gattcagggt tctactggtg taaggcagca acaatgcctA acagcCtcat
1021 atctgacagc ccgagatcct ggatacaggt gcagatccct gcatctcatc ctgtcctcac
1081 tctcagccct gaaaaggctc tgaattttga gggaaccaag gtgacacttc actgtgaaac
1141 ccaggaagat tctctgcgca ctttgtacag gttttatcat gagggtgtcc ccctgaggca
1201 caagtcagtc cgctgtgaaa ggggagcatc catcagcttc tcactgacta cagagaattc
1261 agggaactac tactgcacag ctgacaatgg ccttggcgcc aagcccagta aggctgtgag
1321 cctctcagtc actgttcccg tgtctcatcc tgtcctcaac ctcagctctc ctgaggacct
1381 gatttttgag ggagccaagg tcacacttca ctgtgaagcc cagagaggtt cactccccat
1441 cctgtaccag tttcatcatg aggatgctgc cctggagcgt aggtcggcca actctgcagg
1501 aggagtggcc atcagcttct ctctgactgc agagcattca gggaactact actgcacagc
1561 tgacaatggc tttggccccc agcgcagtaa ggcggtgagc ctctccatca ctgtccctgt
1621 gtctcatcct gtcctcaccc tcagctctgc tgaggccctg actttgaag gagccactgt
1681 gacacttcac tgtgaagtcc agagaggttc cccacaaatc ctataccagt tttatcatga
1741 ggacatgccc ctgtggagca gctcaacacc ctctgtggga agagtgtcct tcagcttctc
1801 tctgactgaa ggacattcag ggaattacta ctgcacagct gacaatggct ttggtcccca
1861 gcgcagtgaa gtggtgagcc tttttgtcac tgttccagtg tctcgcccca tcctcaccct
1921 cagggttccc agggcccagg ctgtggtggg ggacctgctg gagcttcact gtgaggcccc
1981 gagaggctct cccccaatcc tgtactggtt ttatcatgag gatgtcaccc tggggagcag
2041 ctcagccccc tctggaggag aagcttcttt caacctctct ctgactgcag aacattctgg
2101 aaactactca tgtgaggcca acaatggcct agtggcccag cacagtgaca caatatcact
2161 cagtgttata gttccagtat ctcgtcccat cctcaccttc agggctccca gggcccaggc
2221 tgtggtgggg gacctgctgg agcttcactg tgaggccctg agaggctcct ccccaatcct
2281 gtactggttt tatcatgaag atgtcaccct gggtaagatc tcagccccct ctggaggagg
2341 ggcctccttc aacctctctc tgactacaga acattctgga atctactcct gtgaggcaga
2401 caatggtctg gaggcccagc gcagtgagat ggtgacactg aaagttgcag gtgagtgggc
2461 cctgcccacc agcagcacat ctgagaactg actgtgcctg ttctccctgc agctgaaaat
2521 ggagccacag agctcctcag ggctgtttgc ttgtgtggca tcccagcaca cttcctgcct
2581 gcagaacctc cctgtgaaag tctcggatcc tttgtggtat ggttccagga atctgatgtt
2641 tcccagcagt cttcttgaag atgatcaaag cacctcacta aaaatgcaaa taagactttt
2701 ttagaacata aactatattc tgaactgaaa ttattacatg aaaatgaaac caaagaattc
2761 tgagcatatg tttctctgcc gtagaaagga ttaagctgtt tcttgtccgg attcttctct
2821 cattgacttc taagaagcct ctactcttga gtctctttca ttactgggga tgtaaatgtt
2881 ccttacattt ccacattaaa aatcctatgt taacataaaa aaaaaaaaaa aaag

FIG. 2

FL-2 cDNA Sequence

```
   1 cacgcgtccg cctgtctcaa aagaaaaaaa aaaaaaggtg aagctgaacc cagatctaca
  61 catacagcta atcttaccaa aatgtgtgga agtaaagcaa tctgaaggaa attcagtacc
 121 atacaattta ctgactgaaa tacatcatat tgctcatact aagaataaga gtggagaaga
 181 atcatttttt tcctgctaaa atgatagagg cagaagagca acagccttgc aagacagact
 241 tctattctga attgccaaaa gtggaacttc atgcccactt gaatggatcc attagttctc
 301 ataccatgaa gaaattaata gcccagaagc cagatcttaa aatccacgat cagatgactg
 361 tgattgacaa gggaaagaaa agaactttgg aagaatgttt ccagatgttt caaactattc
 421 atcagcttac tagtagccct gaagatattc taatggtcac aaaagatgtc ataaaagaat
 481 ttgcagatga cggcgtcaag tacctggaac taaggagcac acccagaaga gaaaatgcta
 541 cCggaatgac taaaaagact tatgtggaat ctatacttga aggtataaaa cagtccaaac
 601 aagaaaactt ggacattgat gttaggtatt tgatagcagt tgacagaaga ggtggcccctt
 661 tagtagccaa ggagactgta aaacttgccg aggagttctt cctttctact gagggtacag
 721 ttcttggcct tgacctcagt ggagacccta ctgtaggaca agcaaaagac ttcttggaac
 781 ctcttttaga agctaagaaa gcaggtctga agttagcatt gcatctttca gagattccaa
 841 accaaaaaaa agaaacacaa atactcctgg atctgcttcc tgacagaatc gggcatggaa
 901 catttctcaa ctccggtgag ggaggatccc tggatctggt ggactttgtg aggcaacatc
 961 ggataccact gggtaaggct tggagtttca ggtcttccag atgactctct gtctctcccc
1021 caatccccag gttgcctggg gattacagag aagtactgtt ctaaaagtac gaatgtcatc
1081 tagctattaa aagatggagt gtgtgctttc tgagccttat ttaaaacaga aagctttagc
1141 ttccattaga atataagctc tatgagagca gggcccctgc ttgtcttatt cgttgttaca
1201 ttctccaatg cttggaactc aataagaatt ttttaaagga ataaagggtc atctagaatt
1261 ttaaaatgac tttaacaaaa ttgacatgtg ttatgaaaat atgtaacatt atttaaaaat
1321 taaacatgga aaatcccaag taaaaaaaaa aaaaaaa
```

FIG. 3

GPAT-3 cDNA Sequence

```
   1 ggctccccag cgtcgcccta ggctgggact ctagtaggtc ttcggctcag ttttggctgc
  61 agcgcccgcg tagatcgctt cggccgggtt ctacgcccgg ctcaactatg agccggtgcg
 121 cccaggcggc ggaagtggcg gccacagtgc caggtgccgg cgtcgggaac gtggggctgc
 181 ggccgcccat ggtgccccgt caggcgtcct tcttcccgcc gccggtgccg aacccccttcg
 241 tgcagcagac gcagatcggc tccgcgaggc gggtccagat tgtccttctt gggattatct
 301 tgcttccaat tcgtgtctta ttggttgcgt taattttatt acttgcatgg ccatttgctg
 361 caatttcaac agtatgctgt cctgaaaagc tgacccaccc aataactggt tggaggagga
 421 aaattactca aacagctttg aaatttctgg gtcgtgctat gttcttttca atgggattta
 481 tagttgctgt aaaaggaaag attgcaagtc ctttggaagc accagttttt gttgctgccc
 541 ctcattcaac attctttgat ggaattgcct gtgttgtagc tgggttacct tctatggtat
 601 ctcgaaatga gaatgcacaa gtccctctga ttggcagact gttacgggct gtgcaaccag
 661 ttttggtgtc ccgtgtagat ccggattccc gaaaaaacac aataaatgaa ataataaagc
 721 gaacaacatc aggaggagaa tggccccaga tactagtttt cccagaaggt acttgtacta
 781 atcgttcctg tttgattact tttaaaccag gagccttcat tccaggagtt ccagtgcagc
 841 cagtcctcct cagataccca aacaagctgg atactgtgac ctggacatgg caaggatata
 901 cattcattca gctttgtatg cttactttct gccagctctt cacaaaggta gaagttgagt
 961 ttatgccagt tcaagtacca aatgatgaag aaaaaaatga tcctgtcctt tttgccaata
1021 aagtccggaa tttaatggca gaagctctgg gaataccagt aacagatcat acctatgaag
1081 actgcagatt gatgatttca gcaggacagc taacattgcc tatggaagct gggctggtgg
1141 aatttactaa aattagccga aaattgaaat tagattggga tggtgttcgt aagcatttgg
1201 atgaatatgc atctattgcg agttcctcaa aaggaggaag aattggaatt gaagaattcg
1261 ccaagtattt aaagttgcct gtttcagatg tcttgagaca actttttgca ctctttgaca
1321 ggaaccatga tggcagcatt gacttccgag agtatgtgat tggcctAgct gtcttgtgca
1381 acccttccaa cacagaggag atcatccagg tggcatttaa gctgtttgac gttgatgagg
1441 atggctacat aacggaggaa gagttctcca ccattctaca ggcttccctt ggagtgcctg
1501 accttgatgt ttctggtctc ttcaaggaaa tagcccaagg ggactcaatt tcctatgagg
1561 aatttaaaag ttttgcctta aagcatccag aatatgctaa gatatttaca acatacctag
1621 acctccagac gtgccatgtg ttttcattac caaaagaagt ccagacaacc ccctccaccg
1681 ccagtaataa agtcagccct gaaaagcatg aagagagtac ctcagacaaa aaagatgact
1741 gaaagcagta tttccaataa ggaaaacaca gtagcttttg cttgaaattg taaaggcact
1801 tattgataat acttttaatg tgttggtaat gatgtttaaa attgaaagat ttttaaaata
1861 aaaatgatag attttcttac taaaaaaaaa aaaaaaaaaa aaaaaaaaaa aa
```

FIG. 4

BMY30 cDNA Sequence

```
   1 atgctgggcc ctGcAgtcct gggcctcagc ctctgggctc tcctgcaccc tgggacgggg
  61 gccccattgt gcctgtcaca gcaacttagg atgaaggggg actacgtgct gggggggctg
 121 ttccccctgg gcgaggccga ggaggctggc ctccgcagcc ggacacggcc cccatctgcg
 181 gttctgtgtg gccccaggtt ctcctcaaac ggcctgctct gggcactggc catgaaaatg
 241 gccgtggagg agatcaacaa caagtcggat ctgctgcccg ggctgcgcct gggctacgac
 301 ctctttgata cgtgctcgga gcctgtggtg gccatgaagc ccagcctcat gttcctggcc
 361 aaggcaggca gccgcgacat cgccgcctac tgcaactaca cgcagtacca gccccgtgtg
 421 ctggctgtca tcgggcccca ctcgtcagag ctcgccatgg tcaccggcaa gttcttcagc
 481 ttcttcctca tgccccaggt cagctacggt gctagcatgg agctgctgag cgcccgggag
 541 accttcccct ccttcttccg caccgtgccc agcgaccgtg tgcagctgac ggccgccgcg
 601 gagctgctgc aggagttcgg ctggaactgg gtggccgccc tgggcagcga cgacgagtac
 661 ggccggcagg gcctgagcat cttctcggcc ctggccgcgg cacgcggcat ctgcatcgcg
 721 cacgagggcc tggtgccgct gccccgtgcc gatgactcgc ggctggggaa ggtgcaggac
 781 gtcctgcacc aggtgaacca gagcagcgtg caggtggtgc tgctgttcgc ctccgtgcac
 841 gccgcccacg ccctcttcaa ctacagcatc agcagcaggc tctcgcccaa ggtgtgggtg
 901 gccagcgagg cctggctgac ctctgacctg gtcatggggc tgcccggcat ggcccagatg
 961 ggcacggtgc ttggcttcct ccagaggggt gcccagctgc acgagttccc ccagtacgtg
1021 aagacgcacc tggccctggc caccgacccg gccttctgct ctgccctggg cgagagggag
1081 cagggtctgg aggaggacgt ggtgggccag cgctgcccgc agtgtgactg catcacgctg
1141 cagaacgtga gcgcagggct aaatcaccac cagacgttct ctgtctacgc agctgtgtat
1201 agcgtggccc aggccctgca caacactctt cagtgcaacg cctcaggctg ccccgcgcag
1261 gaccccgtga agccctggca gctcctggag aacatgtaca acctgacctt ccacgtgggc
1321 gggctgccgc tgcggttcga cagcagcgga aacgtggaca tggagtacga cctgaagctg
1381 tgggtgtggc agggctcagt gcccaggctc cacgacgtgg gcaggttcaa cggcagcctc
1441 aggacagagc gcctgaagat ccgctggcac acgtctgaca accaggtgcc cgtgtcccgg
1501 tgctcgcggc agtgccagga gggccaggtg cgccgggtca aggggttcca ctcctgctgc
1561 tacgactgtg tggactgcga ggcgggcagc taccggcaaa acccagacga catcgcctgc
1621 acctttgtg gccaggatga gtggtccccg gagcgaagca cacgctgctt ccgccgcagg
1681 tctcggttcc tggcatgggg cgagccggct gtgctgctgc tgctcctgct gctgagcctg
1741 gcgctgggcc ttgtgctggc tgctttgggg ctgttcgttc accatcggga cagcccactg
1801 gttcaggcct cgggggggcc cctggcctgc tttggcctgg tgtgcctggg cctggtctgc
1861 ctcagcgtcc tcctgttccc tggccagccc agccctgccc gatgcctggc ccagcagccc
1921 ttgtcccacc tcccgctcac gggctgcctg agcacactct tcctgcaggc ggccgagatc
1981 ttcgtggagt cagaactgcc tctgagctgg gcagaccggc tgagtggctg cctgcggggg
2041 ccctgggcct ggctggtggt gctgctggcc atgctggtgg aggtcgcact gtgcacctgg
2101 tacctggtgg ccttcccgcc ggaggtggtg acggactggc acatgctgcc cacggaggcg
2161 ctggtgcact gccgcacacg ctcctgggtc agcttcggcc tagcgcacgc caccaatgcc
2221 acgctggcct ttctctgctt cctgggcact ttcctggtgc ggagccagcc gggccgctac
2281 aaccgtgccc gtggcctcac ctttgccatg ctggcctact tcatcacctg ggtctccttt
2341 gtgcccctcc tggccaatgt gcaggtggtc ctcaggcccg ccgtgcagat gggcgccctc
2401 ctgctctgtg tcctgggcat cctggctgcc ttccacctgc ccaggtgtta cctgctcatg
2461 cggcagccag ggctcaacac ccccgagttc ttcctgggag gggccctgg ggatgcccaa
2521 ggccagaatg acgggaacac aggaaatcag gggaaacatg agtga
```

FIG. 5

BMY33 cDNA Sequence

1 atgtgttata tatatttaat atttaaagag tggacattga tattttactt cagtcttctc
61 cttttcctgc agattactcc tgcaataatg gcaaatctca caatcgtgac tgaatttatc
121 cttatggggt tttctaccaa taaaaatatg tgcattttgc attcgattct cttcttgttg
181 atttatttgt gtgccctgat ggggaatgtc ctcattatca tgatcacaac tttggaccat
241 catctccaca cccccgtgta tttcttcttg aagaatctat ctttcttgga tctctgcctt
301 atttcagtca cggctcccaa atctatcgcc aattctttga tacacaacaa ctccatttca
361 ttccttggct gtgtttccca ggtctttttg ttgctttctt cagcatctgc agagctgctc
421 ctcctcacgg tgatgtcctt tgaccgctat actgctatat gtcaccctct gcactatgat
481 gtcatcatgg acaggagcac ctgtgtccaa agagccactg tgtcttggct gtatgggggt
541 ctgattgctg tgatgcacac agctggcacc ttctccttat cctactgtgg gtccaacatg
601 gtccatcagt tcttctgtga cattccccag ttattagcta tttcttgctc agaaaattta
661 ataagagaaa ttgcactcat ccttattaat gtagttttgg atttctgctg ttttattgtc
721 atcatcatta cctatgtcca cgtcttctct acagtcaaga agatcccttc cacagaaggT
781 cagtcaaaag cctactctat ttgccttcca cacttgctgg ttgtgttatt tctttccact
841 ggattcattg cttatctgaa gccagcttca gagtctcctt ctattttgga tgctgtaatt
901 tctgtgttct acactatgct gcccccaacc tttaatccca ttatatacag tttgagaaac
961 aaggccataa aggtggctct ggggatgttg ataaagggaa agctcaccaa aaagtaa

FIG. 6

KalphaM1 cDNA Sequence

```
   1 aagtcaggct ccctttaaat atggcctaat attgctgagc agggttgtga ggccctaaaa
  61 acgtcttcct accattcctg gaattctacc ttgaaacatg tctctatcct ttaagagaaa
 121 gggaggagat aaaaaggaga gagagaagct gaagctgact caaagatccg actggatctg
 181 aacagtgccc cagggagaat ccatttgaaa aaaaaaaaaa aatgtgatca tgtgaatgga
 241 caagaaggag atggctttag atcttatatg ctctaaacga agagttacgc tgagagggaa
 301 actgacttgt catgaagtca gctttgttcc gttgctatgt gtcatccctg ctaatggtga
 361 gtttacctaa gggcagaggc taccatctca accatgaagc tgaagacaca ggcatccgta
 421 ttctatagct aattcagttg atttcatctc agcacacata cactgagcgc ttcctaagag
 481 cgaggttgac cgacattttt attagcaata atctctgcct tcttctgatt acctagagat
 541 ttaagaccac ataatcatcc tctacctcac agggtcaagg gagtggggga ggaaatgggc
 601 taagaggttc taaatccctc ctaacacttg cttcttccaa atcagcaaga ttagagcagt
 661 caacagctga ctgcgttcag accctgcagg ctgggctggc ctgcccagga cctgagaagg
 721 ggcagctccg gtggcaatgt ctgagcccct agctgtgctg gtccgggctg gcctctctaa
 781 gacagtgcag gccacgtgat ccatcctcct agaggcagtg agcaggtgag ggacccctac
 841 sacagccagg aggaaaaagc taggcgtcca ctttccgcag ccatgctcaa acagagtgag
 901 aggagacggt cctggagcta caggccctgg aacacgacgg agaatgaggg cagccaacac
 961 cgcaggagca tttgctccct gggtgcccgt tccggctccc aggccagcat ccacggctgg
1021 acagagggca actataacta ctacatcgag gaagacgaag acggsgagga ggaggaccag
1081 tggaaggacg acctggcaga agaggaccag caggcagggg aggtcaccac cgccaagccc
1141 gagggcccca gcgaccctcc ggccctgctg tccacgctga atgtgaacgt gggtggccac
1201 agctaccagc tggactactg cgagctggcc ggcttcccca agacgcgcct aggtcgcctg
1261 gccacctcca ccagccgcag ccgccagcta agcctgtgcg acgactacga ggagcagaca
1321 gacgaatact tcttcgaccg cgacccggcc gtcttccagc tggtctacaa tttctacctg
1381 tccgggggtgc tgctggtgct cgacgggctg tgtccgcgcc gcttcctgga ggagctgggc
1441 tactggggcg tgcggctcaa gtacacgcca cgctgctgcc gcatctgctt cgaggagcgg
1501 cgcgacgagc tgagcgaacg gctcaagatc cagcacgagc tgcgcgcgca ggcgcaggtc
1561 gaggaggcgg aggaactctt ccgcgacatg cgcttctacg gcccgcagcg gcgccgcctc
1621 tggaacctca tggagaagcc attctcctcg gtggccgcca aggccatcgg ggtggcstcc
1681 agcaccttcg tgctcgtctc cgtggtggcg ctggcgctca acaccgtgga ggagatgcag
1741 cagcactcgg ggcagggcga gggcggccca gacctgcggc ccatcctgga gcacgtggag
1801 atgctgtgca tgggcttctt cacgctcgag tacctgctgc gcctagcctc cacgcccgac
1861 ctgaggcgct tcgcgcgcag cgccctcaac ctggtggacc tggtggccat cctgccgctc
1921 taccttcagc tgctgctcga gtgcttcacg ggcgagggcc accaacgcgg ccagacggtg
1981 ggcagcgtgg gtaaggtggg tcaggtgttg cgcgtcatgc gcctcatgcg catcttccgc
2041 atcctcaagc tggcgcgcca ctccaccgga ctgcgtgcct tcggcttcac gctgcgccag
2101 tgctaccagc aggtgggctg cctgctgctc ttcatcgcca tgggcatctt cactttctct
2161 gcggctgtct actctgtgga gcacgatgtg cccagcacca acttcactac catcccccac
2221 tcctggtggt gggccgcggt gagcatctcc accgtgggct acggagaTat gtacccagag
2281 acccacctgg gcaggttttt tgccttcctc tgcattgctt ttgggatcat tctcaacggg
2341 atgcccattt ccatcctcta caacaagttt tctgattact acagcaagct gaaggcttat
2401 gagtatacca ccatacgcag ggagagggga gaggtgaact tcatgcagag agccagaaag
2461 aagatagctg agtgtttgGt tggaagcaac ccacagctca ccccaagaca agagaattag
2521 tattttatag gacatgtggc tggtagattc catgaacttc aaggcttcat tgctcttttt
2581 ttaatcatta tgattggcag caaaaggaaa tgtgaagcag acatacacaa aggccatttc
2641 gttcacaaag tactgcctct agaaatactc attttggccc aaactcagaa tgtctcatag
2701 ttgctctgtg ttgtgtgaaa catctgacct tctcaatgac gttgatattg aaaacctgag
2761 gggagcaaca gcttagattt tacttgtagc ttctcgtggc atctagctca ataaatattt
2821 ttggacttga aaaaaaaaaa aaaaaaaaaa
```

FIG.7

DP-24 cDNA Sequence

```
   1 gagcaggaac agttcatgga cgaactctga ggaccattct gaggacaaga ggcatccagt
  61 gtcatgagtg gaacatgcat tttatggcta cagagttaag gcaagggttg aattccacga
 121 gtcaaaaagc agcccttttc agagacccaa ctctctgggg tgctcagggg cttgggctgg
 181 attgagaaga aaactgacaa gagtaagctg ccctctcttc tctggccatc tcacaaacca
 241 cagtgcgggc caactggtcc tgcctcttta ccacacagaa ccaagcacta gggataagac
 301 agctgcccat ggtgtccgcg gcgggtctct ctggggatgg caagatgcga ggggtgctcc
 361 tggtgctgct cggccttctc tactcttcca ccagttgtgg cgtccagaaa gcttccgttt
 421 tctacggtcc tgaccccaag gagggcttgg tcagcagcat ggagttcccg tgggtggtgt
 481 cgctgcagga ctcccagtac acacacctgg ctttcggctg catcctgagc gagttctggg
 541 tcctcagcat cgcatccgcc attcagaaca ggaaggacat tgtcgttata gtgggtataa
 601 gtaacatgga tcctagcaag attgctcaca cagagtatcc agtcaatacc atcatcatcc
 661 atgaggactt tgataacaac tccatgagca acaacatagc cctcctgaag acagacacag
 721 cgatgcattt tggcaacctg gtccagtcca tctgcttcct cggcagaatg ctgcatacac
 781 caccagtctt gcagaactgc tgggtgtcag gatggaatcc cacatctgca acaggaaatc
 841 acatgacgat gGgtgtcctg aggaaaatct tcgtgaaaga tcttgacatg tgtcccctat
 901 acaaactcca gaagacagaa tgcggcagcc acacgaaaga ggaaaccaag actgcctgct
 961 tgggggaccc aggaagccca atgatgtgcc agctacagca gttcgatctg tgggttctga
1021 gaggagtcct gaacttcggt ggtgagacgt gccctggcct gtttctgtac accaaggtgg
1081 aagactacag caaatggatc acatccaagg ctgagagggc cggccctccc ctgtcctcac
1141 tccaccactg ggaaaagttg atttctttct cccaccatgg accaaatgcc accatgacac
1201 agaagacata ttctgattct gaactgggcc atgttggatc atacttgcag ggacaaagaa
1261 ggaccatcac gcattcacga ctaggaaaca gctctagaga tagtctagat gttagggaga
1321 aggatgtaaa ggaatcaggc aggtctcctg aggcgtctgt acaaccctta tactatgact
1381 attacggtgg ggaggtgggg gaaggtagga tttttgcagg tcagaacagg ttgtatcagc
1441 ccgaagaaat catcttggtt tccttcgtgc ttgttttctt ttgcagcagt atctagtcca
1501 ggagctaccc caccaaactg aagagtaaac tgagaatgct gagtgccagg cattcaccat
1561 gctgttttga tgtctgtttt tgatagttgc acactggggc tgccacggat aagcccatgg
1621 catacactgg gctggctctc cctcctctat ccctctccca ggtgtgggaa ggtcactttc
1681 actatgcttg tgaactaaat gctggctaac aagtgtcaaa aaaaaaaaaa aaaaaaaaaa
1741 aaaaa
```

METHODS FOR DIAGNOSING SCHIZOPHRENIA BY DETECTING A POLYMORPHISM IN THE KALPHAM1 GENE

CROSS-REFERENCE TO RELATED APPLICATIONS

The present patent application claims the benefit of U.S. Provisional Patent Application Ser. No. 60/503,403, filed Sep. 15, 2003, the disclosure of which is incorporated herein by reference in its entirety.

FIELD OF THE INVENTION

The invention provides polynucleotides and polypeptides corresponding to novel gene sequences associated with biologically active polypeptides, enzymes, GPCRs, ion channels, phosphatases and proteases. The invention also provides polynucleotide fragments corresponding to the genomic and/or coding regions of these genes which comprise at least one polymorphic site per fragment. Allele-specific primers and probes which hybridize to these regions, and/or which comprise at least one polymorphic site are also provided. The polynucleotides, primers, and probes of the present invention are useful for many applications, for example in phenotype correlations, paternity testing, medicine, and genetic analysis. Also provided are vectors, host cells, antibodies, and recombinant and synthetic methods for producing the polypeptides. The invention further relates to diagnostic and therapeutic methods for applying these novel polypeptides to the diagnosis, treatment, and/or prevention of various diseases and/or disorders, particularly cardiovascular diseases related to these polypeptides. The invention further relates to screening methods for identifying agonists and antagonists of the polynucleotides and polypeptides of the present invention.

BACKGROUND OF THE INVENTION

The genomes of all organisms undergo spontaneous mutation in the course of their continuing evolution, generating variant forms of progenitor nucleic acid sequences (Gusella, (1986) *Ann. Rev. Biochem.* 55:831-854). The variant form can confer an evolutionary advantage or disadvantage relative to a progenitor form, or can be neutral. In some instances, a variant form confers a lethal disadvantage and is not transmitted to subsequent generations of the organism. In other instances, a variant form confers an evolutionary advantage to the species and is eventually incorporated into the DNA of many or most members of the species and effectively becomes the progenitor form. In many instances, both the progenitor and variant form(s) survive and co-exist in a species population. The coexistence of multiple forms of a sequence gives rise to polymorphisms.

Several different types of polymorphisms have been reported. For example, a restriction fragment length polymorphism (RFLP) is a variation in DNA sequence that alters the length of a restriction fragment (Botstein et al., (1980) *Am. J. Hum. Genet.* 32:314-331). The restriction fragment length polymorphism can create or delete a restriction site, thus changing the length of the restriction fragment. RFLPs have been used in human and animal genetic analyses (see, e.g., PCT Publications WO 90/13668 and WO 90/11369; Donis-Keller, (1987) *Cell* 51:319-337; Lander et al., (1989) *Genetics* 121:85-99). When a heritable trait can be linked to a particular RFLP, the presence of the RFLP in an individual can be used to predict the likelihood that the animal will also exhibit the trait.

Other polymorphisms take the form of short tandem repeats (STRs) that include tandem di-, tri- and tetra-nucleotide repeated motifs. These tandem repeats are also referred to as "variable number tandem repeat" (VNTR) polymorphisms. VNTRs have been used in identity and paternity analysis (see, e.g., Annour et al., (1992) *FEBS Lett.* 307:113-115; U.S. Pat. No. 5,075,217; PCT Publication WO 91/14003; EP 370,719), and in a large number of genetic mapping studies.

Yet other polymorphisms take the form of single nucleotide variations between individuals of the same species. Such polymorphisms are far more frequent than RFLPs, STRs and VNTRs. Some single nucleotide polymorphisms (SNP) occur in protein-coding nucleic acid sequences, referred to as coding sequence SNPs (cSNPs). In these cases, one of the polymorphic forms can give rise to the expression of a defective or otherwise variant protein and, potentially, a genetic disease condition. Examples of genes in which polymorphisms within coding sequences give rise to genetic disease include hemoglobin S ($\beta^S$; sickle cell anemia), apoE4 (Alzheimer's Disease), Factor V Leiden (thrombosis), and CFTR (cystic fibrosis). cSNPs can alter the codon sequence of the gene and therefore specify an alternative amino acid. Such changes are called "missense" when another amino acid is substituted and "nonsense" when the alternative codon specifies a stop signal in protein translation. When the cSNP does not alter the amino acid specified the cSNP is referred to as "silent".

Other single nucleotide polymorphisms occur in noncoding regions. Some of these polymorphisms can also result in defective protein expression (e.g., as a result of defective splicing). Still other single nucleotide polymorphisms have no phenotypic effects. Single nucleotide polymorphisms can be employed in the same manner RFLPs and VNTRs can be employed, but offer several advantages.

Single nucleotide polymorphisms occur with greater frequency and are spaced more uniformly throughout the genome than other forms of polymorphism. The greater frequency and uniformity of single nucleotide polymorphisms means that there is a greater probability that such a polymorphism will be found in close proximity to a genetic locus of interest than would be the case for other polymorphisms. The different forms of characterized single nucleotide polymorphisms are sometimes easier to distinguish than other types of polymorphism (e.g., by the use of assays employing allele-specific hybridization probes or primers).

Only a small percentage of the total repository of polymorphisms in humans and other organisms has been identified. The limited number of polymorphisms identified to date is due, in part, to the large amount of work required to detect the polymorphisms by conventional methods. For example, one conventional approach for identifying polymorphisms is to sequence the same stretch of DNA in a population of individuals by dideoxy sequencing. In this approach, the amount of work required to identify the polymorphism increases in proportion to both the length of sequence and the number of individuals in a population; thus, such techniques become impractical for large stretches of DNA or large numbers of persons.

SUMMARY OF THE INVENTION

The present invention pertains to single nucleotide polymorphisms which can predispose a subject, or is implicated in, a disease condition (e.g., HDL, Type II diabetes, osteoarthritis, osteoporosis, various forms of cancer, such as breast cancer, prostate cancer, and lung cancer, hypertension, schizophrenia, or Alzheimer's disease).

A SNP of the present invention can be used to diagnose, ameliorate or eliminate include diseases and conditions related to enhanced or inhibited ion channel function, such as myokymia, epilepsy, and Bartter's syndrome, persistent hyperinsulinemic hypoglycemia of infancy, hyperkalemia and hypokalemia, cystic fibrosis, hypercalciuric nephrolithiasis, spherocytosis, ovalocytosis, renal tubular acidosis, retinitis pigmentosa, rod monochromacy, Andermann syndrome, Beckwith-Wiedemann syndrome, hypomagnesemia with secondary hypocalcemia, polycistic kidney disease, Vohwinkel syndrome, autosomal dominant, nonsyndromic sensorineural 3, ectodermal dysplasia 2, non-syndromic deafness, erythrokeratodermia variabilis, bilateral high-frequency hearing loss, cataract, zonular pulverulent 1, zonular pulverulent 3, myasthenia gravis, immune neuropathies including Isaac's and subacute autonomic neuropathies, hearing loss & polyneuropathy, schizophrenia, hyperekplexia, Jervell & Lange-Nielsen syndrome, Romano-Ward syndrome, and long QT syndrome, as well as various other ion channel-related conditions.

A SNP of the present invention can be used to diagnose, ameliorate or eliminate include diseases and conditions related to enhanced or inhibited GPCR function, such as Alzheimer's disease, Parkinson's disease, diabetes, dwarfism, color blindness, retinal pigmentosa asthma, depression, schizophrenia, sleeplessness, hypertension, anxiety, stress, renal failure, HIV infection, cancers; anorexia; bulimia; asthma; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, headache, migraine, schizophrenia, manic depression, delirium, dementia, severe mental retardation and dyskinesias, such as Huntington's disease or Gilles de la Tourette's syndrome, AIDS, Addison's disease, adult respiratory distress syndrome, allergies, anemia, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, and autoimmune thyroiditis; complications of cancer, hemodialysis, extracorporeal circulation; viral, bacterial, fungal, parasitic, protozoal, and helminthic infections, trauma, and neurological disorders including, but not limited to, akathesia, amnesia, amyotrophic lateral sclerosis, bipolar disorder, catatonia, cerebral neoplasms, dementia, depression, Down's syndrome, tardive dyskinesia, dystonias, epilepsy, Huntington's disease and multiple sclerosis, for example.

A SNP of the present invention can be used to diagnose, ameliorate or eliminate include diseases and conditions related to enhanced or inhibited phosphatase function, such as liver diseases, biliary obstruction, hepatitis, bone disease, Paget's disease, osteoblastic bone cancers, osteomalacia, rickets, skeletal diseases, anemia, leukemia, thyroid gland infection, hyperparathyroidism, von Gierke's disease, Hodgkin's Disease, cancers, HIV infection, and Alzheimer's disease, for example.

A SNP of the present invention can be used to diagnose, ameliorate or eliminate include diseases and conditions related to enhanced or inhibited protease function, as well as conditions related to enhanced or inhibited enzyme activity or activities associated with biologically active and/or relevant proteins.

Some of the SNPs described herein are cSNPs (coding SNPs) which specify a different amino acid sequence (described as "missense" under the "Type of Mutation" column of the Tables); some of the SNPs are silent cSNPs (shown as mutation type "silent" under the "Type of Mutation" column of the Tables), and some of these cSNPs may specify a stop signal in protein translation. Some of the identified SNPs were located in non-coding regions (described as "non-CDS" in the "Type of Mutation" column in the Tables).

The present invention relates to a nucleic acid molecule which comprises a single nucleotide polymorphism at a specific location. In a particular embodiment the invention relates to the variant allele of a gene or polynucleotide having a single nucleotide polymorphism, which variant allele differs from a reference allele by one nucleotide at the site(s) identified in Tables 1-5, or elsewhere herein. Complements of these nucleic acid segments are also provided. The segments can be DNA or RNA, and can be double- or single-stranded. Segments can be, for example, 5-10, 5-15, 10-20, 5-25,10-30, 10-50 or 10-100 bases long. In another embodiment, the invention relates to the reference or wild type allele of a gene or polynucleotide having a single nucleotide polymorphism, which reference or wild type allele differs from a variant allele by one nucleotide at the site(s) identified in Tables 1-5 or elsewhere herein. Complements of these nucleic acid segments are also provided. The segments can be DNA or RNA, and can be double- or single-stranded. Segments can be, for example, 5-10, 5-15, 10-20, 5-25,10-30, 10-50 or 10-100 bases long.

The invention further provides variant and reference allele-specific oligonucleotides that hybridize to a nucleic acid molecule comprising a single nucleotide polymorphism or to the complement of the nucleic acid molecule. These oligonucleotides can be probes or primers, some of which are presented in Tables 4 and 5.

The invention further provides oligonucleotides that may be used to amplify across a single nucleotide polymorphic site of the present invention. The invention further provides oligonucleotides that may be used to sequence said amplified sequence.

The invention further provides a method of analyzing a nucleic acid from a DNA sample using said amplification and sequencing primers to assess whether said sample contains the reference or variant base (allele) at the polymorphic site, comprising the steps of amplifying a sequence using appropriate PCR primers for amplifying across a polymorphic site, sequencing the resulting amplified product using appropriate sequencing primers to sequence said product, and determining whether the variant or reference base is present at the polymorphic site.

The invention further provides oligonucleotides that may be used to genotype DNA sample(s) to assess whether said sample(s) contain the reference or variant base (allele) at the polymorphic site(s). The invention provides a method of using oligonucleotides that may be used to genotype a DNA sample to assess whether said sample contains the reference or variant base (allele) at the polymorphic site comprising the steps of amplifying a sequence using appropriate PCR primers for amplifying across a polymorphic site, subjecting the product of said amplification to a genetic bit analysis (GBA) reaction, and analyzing the result.

The invention provides a method of using oligonucleotides that may be used to genotype DNA sample(s) to identify a population or individual that may be at risk of developing a condition (e.g., HDL, Type II diabetes, osteoarthritis, osteoporosis, breast cancer, prostate cancer, lung cancer, hypertension, schizophrenia, or Alzheimer's disease), to assess whether said sample(s) contains the reference or variant base (allele) at the polymorphic site(s) comprising the steps of amplifying a sequence using appropriate PCR primers for amplifying across a polymorphic site, subjecting the product of said amplification to a genetic bit analysis (GBA) reaction, analyzing the result, and optionally determining the statistical association between either the reference or variant allele at the polymorphic site(s) to the incidence of disease (e.g., HDL, Type II diabetes, osteoarthritis, osteoporosis, breast cancer, prostate cancer, lung cancer, hypertension, schizophrenia, and Alzheimer's disease).

The invention provides a method of using oligonucleotides that may be used to genotype DNA sample(s) to identify ethnic population(s) that may be at risk of developing a condition (e.g., HDL, Type II diabetes, osteoarthritis, osteoporosis, breast cancer, prostate cancer, lung cancer, hypertension, schizophrenia, or Alzheimer's disease) to assess whether said sample(s) contain the reference or variant base (allele) at the polymorphic site comprising the steps of amplifying a sequence using appropriate PCR primers for amplifying across a polymorphic site, subjecting the product of said amplification to a genetic bit analysis (GBA) reaction, analyzing the result, and optionally determining the statistical association between either the reference or variant allele at the polymorphic site(s) to the incidence of disease(e.g., HDL, Type II diabetes, osteoarthritis, osteoporosis, breast cancer, prostate cancer, lung cancer, hypertension, schizophrenia, or Alzheimer's disease).

The invention further provides a method of analyzing a nucleic acid from an individual. The method allows a determination of whether the reference or variant base is present at any one, or more, of the polymorphic sites shown in Tables 1-5 or elsewhere herein. Optionally, a set of bases occupying a set of the polymorphic sites shown in Tables 1-5 or elsewhere herein, is determined. This type of analysis can be performed on a number of individuals, who are also tested (previously, concurrently or subsequently) for the presence of a disease phenotype. The presence or absence of disease phenotype is then correlated with a base or set of bases present at the polymorphic site or sites in the individuals tested.

Thus, the invention further relates to a method of predicting the presence, absence, likelihood of the presence or absence, or severity of a particular phenotype or disorder associated with a particular genotype (e.g., HDL, Type II diabetes, osteoarthritis, osteoporosis, breast cancer, prostate cancer, lung cancer, hypertension, schizophrenia, or Alzheimer's disease). The method comprises obtaining a nucleic acid sample from an individual and determining the identity of one or more bases (nucleotides) at specific (e.g., polymorphic) sites of nucleic acid molecules described herein, wherein the presence of a particular base at that site is correlated with a specified phenotype or disorder, thereby predicting the presence, absence, likelihood of the presence: or absence, or severity of the phenotype or disorder in the individual.

The invention further relates to polynucleotides having one or more variant alleles. The invention also relates to said polynucleotides lacking a start codon. The invention further relates to polynucleotides of the present invention containing one or more variant alleles wherein said polynucleotides encode a polypeptide of the present invention. The invention relates to polypeptides of the present invention containing one or more variant amino acids encoded by one or more variant alleles.

The present invention also relates to antisense oligonucleotides corresponding to the polynucleotides of the present invention. Preferably, such antisense oligonucleotides are capable of discriminating against the reference or variant allele of the polynucleotide, preferably at one or more polymorphic sites of said polynucleotide.

The present invention relates to antibodies directed against the polypeptides of the present invention. Preferably, such antibodies are capable of discriminating against the reference or variant allele of the polypeptide, preferably at one or more polymorphic sites of said polynucleotide.

The present invention also relates to recombinant vectors, which include the isolated nucleic acid molecules of the present invention, and to host cells containing the recombinant vectors, as well as to methods of making such vectors and host cells, in addition to their use in the production of polypeptides or peptides provided herein using recombinant techniques. Synthetic methods for producing the polypeptides and polynucleotides of the present invention are provided. Also provided are diagnostic methods for detecting diseases, disorders, and/or conditions related to the polypeptides and polynucleotides provided herein, and therapeutic methods for treating such diseases, disorders, and/or conditions. The invention further relates to screening methods for identifying binding partners of the polypeptides.

The invention further provides an isolated polypeptide having an amino acid sequence encoded by a polynucleotide described herein.

The invention further relates to the identification of SNPs that have been determined to represent a random sampling of SNPs throughout the genome of a DNA sample, or sample(s), such as the SNPs provided in Tables 1-5 herein.

The invention further relates to the use of such randomly distributed SNPs as a means of increasing the accuracy of ethnic assignments for genomic control DNA sample(s) of the present invention. The increased ethnic accuracy of such genomic controls results in an increased statistical confidence in association data obtained for any one or more SNPs of the present invention.

The invention further relates to the use of such genomic control SNPs for clustering individuals to confirm known gene pool/racial/ethnic groups or to reveal cryptic SNPs in a DNA sample(s).

The invention further relates to a method of analyzing at least one nucleic acid sample, wherein said one or more polymorphic positions of said nucleic acid sequence is a polymorphic position specified in Tables 1-5 for said gene.

The invention further relates to a method of constructing haplotypes using the isolated nucleic acids referred to in Tables 1-5, comprising the step of grouping at least two of said nucleic acids.

The invention further relates to a method of constructing haplotypes further comprising the step of using said haplotypes to identify an individual for the presence of a disease phenotype (e.g., HDL, Type II diabetes, osteoarthritis, osteoporosis, breast cancer, prostate cancer, lung cancer, hypertension, schizophrenia, or Alzheimer's disease), and correlating the presence of the disease phenotype with said haplotype.

The invention further relates to a method for identifying an individual at risk of developing a disorder (e.g., HDL, Type II diabetes, osteoarthritis, osteoporosis, breast cancer, prostate cancer, lung cancer, hypertension, schizophrenia, or Alzheimer's disease) comprising the steps of (a) obtaining nucleic acid sample(s) from an individual; (b) amplifying one or more sequences from said sample(s) using appropriate PCR primers for amplifying across at least one polymorphic position; (c) comparing said at least one polymorphic position with a known data set; and (d) determining whether the result correlates with an increased or decreased risk for developing a disorder.

The invention further relates to a library of nucleic acids, each of which comprises one or more polymorphic positions within a gene encoding a human protein, wherein said polymorphic positions are selected from a group consisting of the polymorphic positions provided in Tables 1-5.

The invention further relates to a library of nucleic acids, wherein the sequence at said polymorphic position is selected from the group consisting of the sequences provided in Tables 1-5.

The invention further relates to a library of nucleic acids, wherein the sequence at said polymorphic position is selected from the group consisting of the sequences provided in Tables 1-5, wherein said library of isolated sequences represents the complimentary sequence of said sequences.

The invention further relates to a method for identifying an individual at risk of developing a disorder (e.g., HDL, Type II diabetes, osteoarthritis, osteoporosis, breast cancer, prostate cancer, lung cancer, hypertension, schizophrenia, or Alzheimer's disease) comprising the steps of (a) obtaining a nucleic acid sample(s) from said individual; (b) determining the nucleotide present at least one polymorphic position, (c) comparing said at least one polymorphic position with a known data set; and (d) determining whether the result correlates with an increased or decreased risk for developing a disorder.

The invention also relates to a method of diagnosing the presence of, or likelihood of, a subject to acquiring a disorder. In one embodiment, the method comprises: (a) obtaining a DNA sequence from an individual to be diagnosed; and (b) determining a nucleotide present at a polymorphic nucleotide position shown in Table 1, wherein the presence of the nucleotide in the "NT IN SNP (VARIANT) SEQ" column of Table 1 for a gene other than the nucleotide indicated in the "NT IN REF (PARENT) SEQ" column of Table 1 for the gene at the nucleotide position of the gene indicated in the "SNP POSITION (wrt REF SEQ)" column indicates that the subject is has or is more likely to acquire the disorder than an individual having a nucleotide indicated in the "NT IN SNP (VARIANT) SEQ" column of Table 1 that is identical to the residue indicated in the "NT in REF (PARENT) SEQ" column of Table 1. In the method, the disorder can be selected from the group consisting of undesirable HDL levels, Type II diabetes, a cancer, including breast cancer, prostate cancer and lung cancer, hypertension, schizophrenia, and melanoma.

The invention also relates to an isolated nucleic acid molecule comprising a polymorphic site, wherein the nucleic acid molecule comprises a gene selected from the group of genes in the column entitled "GENE NAME" of Table 1, the polymorphic site in the gene is indicated in the column entitled "SNP POSITION (wrt REF SEQ) for the gene, and the polymorphic nucleic acid is indicated in the column entitled NT IN SNP (VARIANT) SEQ for the gene. An oligonucleotide that specifically hybridizes with a polymorphic site indicated in Table 1 forms another aspect of the invention.

The invention further relates to a method of diagnosing the presence of, or likelihood of, a subject to acquiring a disorder. In one embodiment, the method comprises: (a) obtaining a protein sequence from an individual to be diagnosed; and (b) determining a nucleotide present at a polymorphic amino acid position shown in Table 2, wherein the presence of the nucleotide in the "AA IN SNP SEQ" column of Table 1 for a gene other than the amino acid indicated in the "AA IN REF SEQ" column of Table 2 for the gene at the amino acid position indicated in the "POSITION OF MUTATION IN REF AA SEQ" column indicates that the subject is has or is more likely to acquire the disorder than an individual having an amino acid indicated in the "AA IN SNP SEQ" column of Table 2 that is identical to the residue indicated in the "AA IN REF SEQ" column of Table 2. In the method, the disorder can be selected from the group consisting of undesirable HDL levels, Type II diabetes, a cancer, including breast cancer, prostate cancer and lung cancer, hypertension, schizophrenia, and melanoma.

The invention also relates to an isolated protein comprising a polymorphic site, wherein the protein comprises a protein encoded by a gene selected from the group of genes in the column entitled "GENE NAME" of Table 2, the polymorphic site in the protein is indicated in the column entitled "POSITION OF MUTATION IN REF AA" for the protein, and the polymorphic amino acid is indicated in the column entitled "AA IN SNP SEQ" for the protein.

The invention further relates to a method for genotyping an individual comprising the steps of (a) obtaining a nucleic acid sample(s) from said individual; (b) determining the nucleotide present at least one polymorphic position, and (c) comparing said at least one polymorphic position with a known data set.

The present invention further relates to a kit for identifying a subject that has an increased or decreased risk of a disease (e.g., HDL, Type II diabetes, osteoarthritis, osteoporosis, breast cancer, prostate cancer, lung cancer, hypertension, schizophrenia, or Alzheimer's disease). In one embodiment, the kit comprises: (a) one or more sequencing or genotyping primers; and (b) one or more sequencing or genotyping reagents, wherein the sequencing primers are primers that hybridize to at least one polymorphic position in a human gene, some of which are presented in Tables 1-5. In an embodiment of the kit, the at least one polymorphic position is selected from those presented in Tables 1-5, and combinations thereof. In yet another embodiment of the kit, the one or more sequencing primers comprise a nucleotide sequence selected presented in Tables 1-5, complements thereof and combinations thereof. In yet another embodiment of the kit, the one or more sequencing primers is labeled. A kit of the present invention can further comprise instructions for use in diagnosing a subject as having, or having a predisposition for developing, a disorder. In another embodiment, the kit comprises reagents adapted to detect the identity of a nucleic acid at a polymorphic position selected from a group consisting of the polymorphic positions provided in Tables 1-5.

Therefore, it is an object of the present invention to provide a method of predicting the likelihood that a subject will be diagnosed with a disorder (e.g., HDL, Type II diabetes, osteoarthritis, osteoporosis, breast cancer, prostate cancer, lung cancer, hypertension, schizophrenia, or Alzheimer's disease). This and other objects are achieved by employing a polynucleotide and/or polypeptide sequence of the present invention, as disclosed herein.

An object of the present invention having been stated, other objects, as well as other advantages, will become evident as the description proceeds in connection with the Figures and the Examples below.

DETAILED DESCRIPTION OF THE INVENTION

Brief Description of the Figures

FIG. 1 depicts cDNA encoding a BGS-5 protein of the present invention comprising two variant nucleotides (SEQ ID NO:210), which are noted in Table 1. Variant nucleotides within the cDNA sequence are highlighted in bold.

FIG. 2 depicts cDNA encoding a FL-2 protein of the present invention comprising one variant nucleotide (SEQ ID NO:212), which is noted in Table 1. Variant nucleotides within the cDNA sequence are highlighted in bold.

FIG. 3 depicts cDNA encoding a GPAT-3 protein of the present invention comprising one variant nucleotide (SEQ ID NO:214), which is noted in Table 1. Variant nucleotides within the cDNA sequence are highlighted in bold.

FIG. 4 depicts cDNA encoding a BMY30 protein of the present invention comprising two variant nucleotides (SEQ ID NO:216), which are noted in Table 1. Variant nucleotides within the cDNA sequence are highlighted in bold.

FIG. 5 depicts cDNA encoding a BMY33 protein of the present invention comprising one variant nucleotide (SEQ ID NO:218), which is noted in Table 1. Variant nucleotides within the cDNA sequence are highlighted in bold.

FIG. 6 depicts cDNA encoding a KalphaM1 protein of the present invention comprising two variant nucleotides (SEQ ID NO:220), which are noted in Table 1. Variant nucleotides within the cDNA sequence are highlighted in bold.

FIG. 7 depicts cDNA encoding a DP-24 protein of the present invention comprising one variant nucleotide (SEQ ID NO:222), which is noted in Table 1. Variant nucleotides within the cDNA sequence are highlighted in bold.

Brief Description of the Tables

Table 1 provides a summary of data related to the SNPs of the present invention. The legend for Table 1 is as follows:

GENE NAME refers to the unique name identifier associated with the gene in which the SNP resides. The gene names are referenced to entries in the Ensembl database maintained by EMBL-EBI and the Sanger Institute, which is publicly-accessible online;

GENE ALIAS refers to an alternate name for the gene;

SNP NAME refers to the unique internal name identifier associated with the SNP;

SNP ALIAS refers to an alternate name for the SNP;

SNP POSITION(wrt REF SEQ) refers to the nucleotide position of the SNP in the wild-type reference (parent) sequence;

NT IN REF SEQ refers to the identity of the nucleotide in the wild-type reference (parent) gene sequence at the position of the SNP;

NT IN SNP SEQ refers to the identity of the polymorphic nucleotide in the SNP sequence;

REF SEQ refers to the identity of the wild-type reference (parent) sequence in which the SNP is found. The REF SEQ is provided in terms of the sequence of a human chromosome and is publicly accessible online from NCBI. The version number of the chromosome sequence is also provided. For example, "Human_Chr__16.NCBI__30" refers to NCBI version 30 of the sequence of human chromosome 16;

STRANDEDNESS OF PARENT refers to the strand of the reference (parent) dsDNA on which the SNP is found. "1" refers to the "forward" DNA sequence of a dsDNA pair that is read 5' to 3' while "−1" refers to the "reverse" DNA sequence of a dsDNA pair that is read 3' to 5'.

REF NT SEQ ID NO refers to the unique identifier of the reference sequence in the Sequence Listing;

LOCATION OF SNP refers to the location of each predicted SNP on the gene in which the SNP resides; "5' and 3'utr" refers to an untranslated region; "intron" refers to a particular intron, which is denoted in the table; "coding" refers to a coding region of the gene; "exon" refers to a particular exon, which is denoted in the table; "5' genomic and "3' genomic" refer generally to a region of genomic DNA.

Table 2 provides a summary of data related to the SNPs of the present invention. The legend for Table 2 is as follows:

GENE NAME refers to the unique name identifier associated with the gene in which the SNP resides. The gene names are referenced to entries in the Ensembl database maintained by EMBL-EBI and the Sanger Institute, which is publicly-accessible online;

GENE ALIAS refers to an alternate name for the gene;

SNP NAME refers to the unique internal name identifier associated with the SNP;

SNP ALIAS refers to an alternate name for the SNP;

POSITION OF MUTATION IN REF SEQ refers to the nucleotide position of the SNP in the wild-type reference (parent) nucleic acid sequence;

TYPE OF MUTATION refers to the type of polymorphism for each SNP; in the table, "missense" refers to a SNP that resides within the coding region and results in a change in the amino acid sequence of the protein encoded by the SNP in which the SNP resides and "silent" refers to a SNP that resides within the coding region and does not result in a change in the amino acid sequence of the protein encoded by the SNP in which the SNP resides;

AA IN REF SEQ refers to the identity of the amino acid that occurs in the wild-type reference (parent) amino acid sequence at the site of a missense SNP;

REF AA SEQ refers to the wild-type reference (parent) amino acid sequence in the Sequence Listing.

AA IN SNP SEQ refers to the identity of the amino acid that occurs in a SNP amino acid sequence as a result of a missense SNP.

Table 3 provides a summary of data related to the SNPs of the present invention. The legend for Table 3 is as follows:

GENE NAME refers to the unique name identifier associated with the gene in which the SNP resides. The gene names are referenced to entries in the Ensembl database maintained by EMBL-EBI and the Sanger Institute, which is publicly-accessible online;

GENE ALIAS refers to an alternate name for the gene;

SNP NAME refers to the unique internal name identifier associated with the SNP;

SNP ALIAS refers to an alternate name for the SNP;

PARENT FLANK LEFT refers to a genomic nucleotide sequence immediately flanking the SNP of the present invention on the 5' side of the SNP;

PFL SEQ ID NO refers to the sequence number assigned to the PARENT FLANK LEFT sequence in the Sequence Listing;

PARENT FLANK RIGHT refers to a genomic nucleotide sequence immediately flanking the SNP of the present invention on the 3' side of the SNP;

PFR SEQ ID NO refers to the sequence number assigned to the PARENT FLAK RIGHT sequence in the Sequence Listing;

15 bp REFERENCE refers to a sequence found in the reference (parent) sequence that overlaps and flanks the polymorphic base 15 bp on each side of the polymorphic site. The identity of the polymorphic base in the reference sequence is capitalized;

15 REF SEQ ID NO refers to the sequence number assigned to the 15 bp REFERENCE sequence in the Sequence Listing;

15 bp VARIANT refers to a sequence found in the polymorphic sequence that overlaps and flanks the polymorphic base 15 bp on each side of the polymorphic site. The identity of the polymorphic base in the variant sequence is capitalized;

15 VAR SEQ ID NO refers to the sequence number assigned to the 15 bp VARIANT sequence in the Sequence Listing;

25 bp REFERENCE refers to a sequence found in the reference (parent) sequence that overlaps and flanks the polymorphic base 25 bp on each side of the polymorphic site. The identity of the polymorphic base in the reference sequence is capitalized. The 25 bp reference sequence encompasses the 15 bp reference sequence;

25 REF SEQ ID NO refers to the sequence number assigned to the 25 bp REFERENCE sequence in the Sequence Listing;

25 bp VARIANT refers to a sequence found in the polymorphic sequence that overlaps and flanks the polymorphic base 25 bp on each side of the polymorphic site. The identity of the polymorphic base in the variant sequence is capitalized. The 25 bp variant sequence encompasses the 15 bp variant sequence;

25 VAR SEQ ID NO refers to the sequence number assigned to the 25 bp VARIANT sequence in the Sequence Listing.

Table 4 provides a summary of data related to the SNPs of the present invention. The legend for Table 4 is as follows:

GENE NAME refers to the unique name identifier associated with the gene in which the SNP resides. The gene names are referenced to entries in the Ensembl database maintained by EMBL-EBI and the Sanger Institute, which is publicly-accessible online;

GENE ALIAS refers to an alternate name for the gene;

SNP NAME refers to the unique internal name identifier associated with the SNP;

SNP ALIAS refers to an alternate name for the SNP;

FWD SEQ PRIMER refers to a 3' (forward) primer that can be used to amplify or sequence a polymorphic sequence of the present invention;

SEQ ID NO FWD SEQ PRIMER refers to the sequence number assigned to a 3' (forward) sequencing primer of the present invention;

REV SEQ PRIMER refers to a 5' (reverse) primer that can be used to amplify or sequence a polymorphic sequence of the present invention;

SEQ ID NO REV SEQ PRIMER refers to the sequence number assigned to a 5' (reverse) sequencing primer of the present invention.

Table 5 provides a summary of data related to the SNPs of the present invention. The legend for Table 5 is as follows:

GENE NAME refers to the unique name identifier associated with the gene in which the SNP resides. The gene names are referenced to entries in the Ensembl database maintained by EMBL-EBI and the Sanger Institute, which is publicly-accessible online;

GENE ALIAS refers to an alternate name for the gene;

SNP NAME refers to the unique internal name identifier associated with the SNP;

SNP ALIAS refers to an alternate name for the SNP;

SBE PRIMER F refers to a 5' to 3' (forward) primer that can be used to amplify across a polymorphic locus of a SNP in a single base extension genotyping operation;

SBE PRIMER F PRIMER SEQ ID NO refers to the sequence number assigned to a 5' to 3' (forward) genotyping primer of the present invention;

SBE PRIMER R refers to a 3' to 5' (reverse) primer that can be used to amplify across a polymorphic locus of a SNP in a single base extension genotyping operation;

SBE PRIMER R PRIMER SEQ ID NO refers to the sequence number assigned to a 3' to 5' (reverse) genotyping primer of the present invention.

TAQMAN F PRIMER refers to a forward primer that can be employed in a TAQMAN assay;

TAQMAN R PRIMER SEQ ID NO refers to the sequence number assigned to the indicated TAQMAN forward primer;

TAQMAN F PRIMER refers to a reverse primer that can be employed in a TAQMAN assay;

TAQMAN F PRIMER SEQ ID NO refers to the sequence number assigned to the indicated TAQMAN reverse primer.

TAQMAN PROBE refers to a probe that can be employed in a TAQMAN assay;

TAQMAN PROBE SEQ ID NO refers to the sequence number assigned to the indicated TAQMAN probe;

Table 6 provides a summary of the association of the SNPs of the present invention with several phenotypes. The legend for Table 6 is as follows:

GENE refers to the unique name identifier associated with the gene in which the SNP resides;

SNP ID refers to the unique name identifier associated with the SNP;

SNP LOCATION refers to the location of each SNP on the gene in which the SNP resides; “5' and 3'UTR” refers to an untranslated region; “intron” refers to a particular intron, which is denoted in the table; “coding” refers to a coding region of the gene and an indication as to the nature of the SNP is provided;

PHENOTYPE refers to the phenotype with which the SNP is associated;

ODDS RATIO/P VALUE refers to the results of the statistical analysis performed as described in the Examples.

The present invention relates to nucleic acid molecules that comprise a single nucleotide polymorphism (SNP) at a specific location. The nucleic acid molecules, e.g., genes, that include the SNP has at least two alleles, referred to herein as the reference allele and the variant allele. The reference allele (prototypical or wild type allele) has been designated arbitrarily and typically corresponds to the nucleotide sequence of the native form of the nucleic acid molecule. The variant alleles differ from the reference allele by one nucleotide at the site(s) identified in Tables 1-5. The present invention also relates to variant alleles of the described genes and to complements of the variant alleles.

The invention further relates to portions of the variant alleles and portions of complements of the variant alleles which comprise (encompass) the site of the SNP and are at least nucleotides in length. Portions can be, for example, 5-10, 5-15, 0.10-20, 5-25, 10-30, 10-50 or 10-100 bases long. Polymorphisms that are the subject of this invention are defined in Tables 1-5 herein. Further, the nucleotide sequences of the present invention can be double- or single-stranded.

The invention further provides allele-specific oligonucleotides that hybridize to a gene comprising a single nucleotide polymorphism or to the complement of the gene. Such oligonucleotides will hybridize to one polymorphic form of the nucleic acid molecules described herein but not to the other polymorphic form(s) of the sequence. Thus, such oligonucleotides can be used to determine the presence or absence of particular alleles of the polymorphic sequences described herein. These oligonucleotides can be probes or primers.

The invention further provides a method of analyzing a nucleic acid from an individual. The method determines which base is present at any one of the polymorphic sites disclosed herein. Optionally, a set of bases occupying a set of the polymorphic sites disclosed herein is determined. This type of analysis can be performed on a number of individuals, who are also tested (previously, concurrently or subsequently) for the presence of a given phenotype. The presence or absence of phenotype is then correlated with a base or set of bases present at the polymorphic site or sites in the subjects tested.

Thus, the invention further relates to a method of predicting the presence, absence, likelihood of the presence or absence, or severity of a particular phenotype or disorder (e.g., HDL, Type II diabetes, osteoarthritis, osteoporosis, breast cancer, prostate cancer, lung cancer, hypertension, schizophrenia, or Alzheimer's disease) associated with a particular genotype (a SNP at a position shown in Tables 1-5 and combinations thereof) in a wild-type sequence. In one embodiment, the method comprises obtaining a nucleic acid sample from an individual and determining the identity of one or more bases (nucleotides) at polymorphic sites of nucleic acid molecules described herein, wherein the presence of a particular base is correlated with a specified phenotype or disorder, thereby predicting the presence, absence, likelihood of the presence or absence, or severity of the phenotype or disorder in the individual. The correlation between a particular polymorphic form of a gene and a phenotype can thus be used in methods of diagnosis of that phenotype, as well as in the development of treatments for the phenotype.

The invention further provides allele-specific oligonucleotides that hybridize to a gene comprising a single nucleotide polymorphism or to the complement of the gene. Such oligonucleotides will hybridize to one polymorphic form of the nucleic acid molecules described herein but not to the other polymorphic form(s) of the sequence. Thus, such oligonucleotides can be used to determine the presence or absence of particular alleles of the polymorphic sequences described herein. These oligonucleotides can be probes or primers.

The invention further provides a method of analyzing a nucleic acid from an individual. The method determines which base is present at any one of the polymorphic sites shown in Tables 1-5. Optionally, a set of bases occupying a set of the polymorphic sites shown in Tables 1-5 is determined. This type of analysis can be performed on a number of individuals, who are also tested (previously, concurrently or subsequently) for the presence of a disease phenotype. The presence or absence of a disease phenotype is then correlated with a base or set of bases present at the polymorphic site or sites in the individuals tested.

Thus, the invention relates to a method of predicting the presence, absence, likelihood of the presence or absence, or severity of a particular phenotype or disorder associated with a particular genotype. The method comprises obtaining a nucleic acid sample from an individual and determining the identity of one or more bases (nucleotides) at polymorphic sites of nucleic acid molecules described herein, wherein the presence of a particular base is correlated with a specified phenotype or disorder, thereby predicting the presence, absence, likelihood of the presence or absence, or severity of the phenotype or disorder in the individual. The correlation between a particular polymorphic form of a gene and a phenotype can thus be used in methods of diagnosis of that phenotype, as well as in the development of treatments for the phenotype.

Definitions

Following long-standing patent law convention, the terms "a" and "an" mean "one or more" when used in this application, including the claims.

As used herein, the term "about," when referring to a value or to an amount of mass, weight, time, volume, concentration or percentage is meant to encompass variations of ±20% or ±10%, more preferably ±5%, even more preferably ±1%, and still more preferably ±0.1% from the specified amount, as such variations are appropriate.

As used herein, the terms "amino acid" and "amino acid residue" are used interchangeably and mean any of the twenty naturally occurring amino acids. An amino acid is formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature abbreviations for amino acid residues are shown in tabular form presented herein above.

It is noted that all amino acid residue sequences represented herein by formulae have a left-to-right orientation in the conventional direction of amino terminus to carboxy terminus. In addition, the phrases "amino acid" and "amino acid residue" are broadly defined to include modified and unusual amino acids.

Furthermore, it is noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

As used herein, the terms "cells," "host cells" or "recombinant host cells" are used interchangeably and refer not only to the particular subject cell, but also to the progeny or potential progeny of such a cell. Because certain modifications can occur in succeeding generations due to either mutation or environmental influences, such progeny might not, in fact, be identical to the parent cell, but are still included within the scope of the term as used herein.

As used herein, the terms "chimeric protein" and "fusion protein" are used interchangeably and mean a fusion of a first amino acid sequence encoding a first polypeptide with a second amino acid sequence defining a polypeptide domain foreign to, and not homologous with, the first polypeptide. A chimeric protein can present a foreign domain that is found in an organism that also expresses the first protein, or it can be an "interspecies" or "intergenic" fusion of protein structures expressed by different kinds of organisms. Analogously, the term "chimeric gene" refers to a nucleic acid construct that encodes a "chimeric protein" or "fusion protein" as defined herein.

As used herein the term "complementary" means a nucleic acid sequence that is capable of base-pairing according to the standard Watson-Crick complementarity rules.

These rules generally hold that the larger purines will always base pair with the smaller pyrimidines to form only combinations of Guanine paired with Cytosine (G:C) and Adenine paired with either Thymine (A:T) in the case of DNA, or Adenine paired with Uracil (A:U) in the case of RNA.

As used herein, the term "DNA segment" means a DNA molecule that has been isolated free of total genomic DNA of a particular species. In one embodiment, a DNA segment refers to a DNA segment that comprises a sequence selected from the group consisting of sequences presented herein and in the Sequence Listing, but can optionally comprise fewer or additional nucleic acids, yet is isolated away from, or purified free from, total genomic DNA of a source species. Included within the scope of the term "DNA segment" are DNA segments and smaller fragments of such segments, as well as recombinant vectors, including, for example, plasmids, cosmids, phages, viruses, and the like, and primers and probes.

As used herein, the terms "expression" and "gene expression" are used interchangeably and generally refer to the cellular processes by which a polypeptide is produced from RNA.

As used herein, the term "gene" refers broadly to any segment of DNA associated with a biological function. A gene encompasses sequences including but not limited to a coding sequence, a promoter region, a cis-regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

As used herein, the term "hybridization" means the binding of a molecule (e.g., a probe molecule, such as a molecule to which a detectable moiety has been bound), to a target sample (e.g., a target nucleic acid).

As used herein, the term "hybridization techniques" refers to molecular biological techniques that involve the binding or hybridization of a probe to complementary sequences in a polynucleotide. Included among these techniques are northern blot analysis, Southern blot analysis, nuclease protection assay, etc.

As used herein, the terms "hybridization" and "binding" are used interchangeably in the context of probes and denatured DNA. Probes that are hybridized or bound to denatured DNA are aggregated to complementary sequences in the polynucleotide. Whether or not a particular probe remains aggregated with the polynucleotide depends on the degree of complementarity, the length of the probe, and the stringency of the binding conditions. The higher the stringency, the higher the degree of complementarity should be and/or the longer the probe.

As used herein, the term "intron" means a DNA sequence present in a given gene that is not translated into protein.

As used herein, the term "isolated" means a oligonucleotide sequence of interest that is substantially free of unwanted nucleic acids, proteins, lipids, carbohydrates or other materials with which the sequence of interest can be associated in vivo or in vitro, such association being either in cellular material or in a synthesis medium. The term can also be applied to polypeptides, in which case the polypeptide will be substantially free of nucleic acids, carbohydrates, lipids and other undesired polypeptides. Thus, "isolated" material means that the material in question exists in a physical milieu distinct from that in which it occurs in nature, and thus is altered "by the hand of man" from its natural state. For example, an isolated nucleic acid of the present invention can be substantially isolated with respect to the complex cellular milieu in which it naturally occurs. In some instances, the isolated material can form a part of a composition (for example, a crude extract containing other substances), buffer system or reagent mix. In other circumstances, the material can be purified to essential homogeneity, for example as determined by PAGE or column chromatography such as HPLC.

As used herein, the term "linkage" means the tendency of genes, alleles, loci or genetic markers to be inherited together as a result of their location on the same chromosome. A degree of linkage can be measured by percent recombination between the two genes, alleles, loci or genetic markers.

As used herein, the term "modified" means an alteration from an entity's normally occurring state. An entity can be modified by removing discrete chemical units or by adding discrete chemical units. The term "modified" encompasses detectable labels as well as those entities added as aids in purification.

As used herein, the terms "nucleic acid," "nucleic acid molecule," are used interchangeably and mean any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally-occurring nucleotides (e.g., deoxyribonucleotides and ribonucleotides, also referred to herein as "nucleotides" or "bases"), or analogs of naturally-occurring nucleotides (e.g., x-enantiomeric forms of naturally-occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocylcic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids," which comprise naturally-occurring or modified nucleic acid bases attached to a polyamide backbone. Nucleic acids can be single stranded or double stranded. Additionally, the terms "nucleotide sequence", "nucleic acid sequence", "nucleic acid molecule" and "nucleic acid segment" are used interchangeably and are equivalent.

By employing the disclosure presented herein, a nucleic acid molecule of the present invention encoding a polypeptide of the present invention can be obtained using standard cloning and screening procedures, such as those for cloning cDNAs using mRNA as starting material.

As used herein, the terms "oligonucleotide" and "polynucleotide" are used interchangeably and mean a single- or double-stranded DNA or RNA sequence. An oligonucleotide or a polynucleotide can be naturally occurring or synthetic, but are typically prepared by synthetic means. In the context of the present invention, an "oligonucleotide" and a "polynucleotide" includes segments of DNA, and/or their complements, including any one of the polymorphic sites disclosed and described herein. The segments can be, for example, between and 250 bases, and, in some embodiments, between 5-10, 5-20, 10-20, 10-50, 20-50 or 10-100 bases in length. The polymorphic site can occur within any position of the segment. The segments can be derived from any of the allelic forms of DNA disclosed and described herein.

Thus, the terms "oligonucleotide" and "polynucleotide" refer to a molecule comprising two or more nucleotides. For example, an "oligonucleotide" or a "polynucleotide" can comprise a nucleotide sequence of a full length cDNA sequence, including the 5' and 3' untranslated sequences, the coding region, with or without a signal sequence, the secreted protein coding region, as well as fragments, epitopes, domains, and variants of the nucleic acid sequence. An "oligonucleotide" or a "polynucleotide" of the present invention also includes those polynucleotides capable of hybridizing, under stringent hybridization conditions (described herein), to sequences described herein, or the complement thereof.

Thus, an "oligonucleotide" or a "polynucleotide" of the present invention can comprise any polyribonucleotide or polydeoxribonucleotide, and can comprise unmodified RNA or DNA or modified RNA or DNA. Additionally, an "oligonucleotide" or a "polynucleotide" can comprise single- and double-stranded DNA, DNA that is a mixture of single- and double-stranded regions, single- and double-stranded RNA, RNA that is mixture of single- and double-stranded regions, hybrid molecules comprising DNA and RNA that can be single-stranded or, more typically, double-stranded or a mixture of single- and double-stranded regions. In addition, an "oligonucleotide" or a "polynucleotide" can comprise triple-stranded regions comprising RNA or DNA or both RNA and DNA. An "oligonucleotide" or a "polynucleotide" can also contain one or more modified bases or DNA or RNA backbones modified for stability or for other reasons. "Modified" bases include, for example, tritylated bases and unusual bases such as inosine. A variety of modifications can be made to DNA and RNA; thus, the terms "oligonucleotide" and "polynucleotide" embraces chemically, enzymatically, or metabolically modified forms.

As used herein, the terms "organism", "subject" and "patient" are used interchangeably and mean any organism referenced herein, including prokaryotes, though the terms preferably refer to eukaryotic organisms, more preferably to mammals, and most preferably to humans.

As used herein, a "polymorphic marker" or "polymorphic site" is a locus at which divergence occurs. In one embodiment of the present invention, the markers have at least two alleles, each occurring at frequency of greater than 1%, and more preferably greater than 10% or 20% of a selected population. A polymorphic locus can be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as "alternative" or "variant" alleles. The allelic form occurring most frequently in a selected population is sometimes referred to as the wild type form. Diploid organisms can be homozygous or heterozygous for allelic forms. As noted, a diallelic or biallelic polymorphism has two forms; a triallelic polymorphism has three forms.

As used herein, the terms "polymorphic position", "polymorphic site", "polymorphic locus", and "polymorphic allele" are interchangeable and equivalent; these terms mean the location of a sequence identified as having more than one nucleotide represented at that location in a population comprising at least one or more individuals, and/or chromosomes.

As used herein, the term "polymorphism" means the occurrence of two or more genetically determined alternative sequences or alleles in a population. The variant sequence and the "original" sequence co-exist in the species' population. In some instances, such co-existence is in stable or quasi-stable equilibrium. A polymorphism is thus said to be "allelic," in that, due to the existence of the polymorphism, some members of a species may have the original sequence (i.e., the original "allele") whereas other members may have the variant sequence (i.e., the variant "allele"). In the simplest case, only one variant sequence can exist and the polymorphism is thus said to be di-allelic. In other cases, the species' population can contain multiple alleles and the polymorphism is termed tri-allelic, etc. A single gene can have multiple different unrelated polymorphisms. For example, it may have a di-allelic polymorphism at one site and a multi-allelic polymorphism at another site.

As used herein, the term "polypeptide" means any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide" and "peptide" are used interchangeably herein when referring to a gene product or an amino acid sequence.

A polypeptide of the present invention can comprise amino acids joined to each other by peptide bonds or modified peptide bonds, i.e., peptide isosteres, and can contain amino acids other than the 20 gene-encoded amino acids. A polypeptide can be modified by either natural processes, such as by posttranslational processing, or by chemical modification techniques which are well known in the art. Such modifications are described in basic texts and in more detailed monographs, as well as in research literature known to those of ordinary skill in the art. Modifications can occur anywhere in a polypeptide, including the peptide backbone, the amino acid side-chains and the amino or carboxyl termini. The same type of modification can be present in the same or varying degrees at several sites in a given polypeptide. Also, a given polypeptide can contain many types of modifications. A polypeptide can be branched, for example, as a result of ubiquitination, or a polypeptide can be cyclic, with or without branching. Cyclic, branched, and branched cyclic polypeptides can result from posttranslation natural processes or can be made by synthetic methods. Representative modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination (see, e.g., Creighton, *Proteins: Structures and Molecular Principles,* ($2^{nd}$ ed.) W.H. Freeman & Co., New York, (1993); *Posttranslational Covalent Modification Of Proteins,* (Johnson, ed.), Academic Press, New York, pp. 1-12 (1983); Seifter et al., (1990) *Method Enzymol.* 182: 626-646; Rattan et al., (1992) *Ann. N.Y Acad. Sci.* 663:48-62, incorporated herein by reference).

As used herein, the term "primer" means a single-stranded oligonucleotide sequence that acts as a point of initiation for template-directed DNA synthesis under appropriate conditions (e.g., in the presence of four different nucleoside triphosphates and an agent for polymerization, such as DNA or RNA polymerase or reverse transcriptase) in a suitable buffer and at a suitable temperature. The appropriate length of a primer can depend on the intended use of the primer, but typically ranges from to nucleotides. Short primer molecules generally require cooler temperatures to form sufficiently stable hybrid complexes with the template. A primer need not reflect the exact sequence of the template, but is preferably sufficiently complementary to hybridize with a template. The term "primer site" refers to the area of the target DNA to-which a primer hybridizes. The term "primer pair" refers to a set of primers comprising a 5' (upstream) primer that hybridizes with the 5' end of the DNA sequence to be amplified and a 3' (downstream) primer that hybridizes with the complement of the 3' end of the sequence to be amplified. A primer can comprise, for example, two or more deoxyribonucleotides or ribonucleotides, more than three deoxyribonucleotides or ribonucleotides, more than eight deoxyribonucleotides or ribonucleotides or at least about 20 deoxyribonucleotides or ribonucleotides of an exonic or intronic region. Such oligonucleotides can be, for example, between ten and thirty bases in length. In the context of the present invention, representative primers include, for example, the sequences which are presented herein and in the Tables and Sequence Listing, for example in Tables 4 and 5.

As used herein, the term "probe" refers to an oligonucleotide or short fragment of DNA designed, known or suspected to be sufficiently complementary to a sequence in a denatured nucleic acid to be probed and to be bound under selected stringency conditions.

Continuing, in one embodiment a probe is a hybridization probe; such a probe can be an oligonucleotide that binds, in a base-specific manner, to a complementary strand of nucleic acid. Such probes include peptide nucleic acids, such as described for example in Nielsen et al., (1991) *Science* 254:1497-1500. A probe can be of any length suitable for specific hybridization to the target nucleic acid sequence. The most appropriate length of the probe can vary, depending upon the hybridization method in which it is being used; for example, particular lengths might be more appropriate for use in microfabricated arrays, while other lengths might be more suitable for use in classical hybridization methods. Such optimizations will be known to the skilled artisan upon consideration of the present disclosure. Representative probes and primers can range from about 5 nucleotides to about 40 nucleotides in length. For example, probes and primers can be 5, 6, 8, 10, 12, 14, 16, 18, 20, 22, 24, 25, 26, or 40 nucleotides in length. In some embodiments, the probe or primer overlaps at least one polymorphic site occupied by any of the possible variant nucleotides. The nucleotide sequence can correspond to the coding sequence of the allele or to the complement of the coding sequence of the allele.

As used herein, the term "sequencing" means determining the ordered linear sequence of nucleic acids or amino acids of a DNA, RNA or protein target sample, using manual or automated laboratory techniques. Unless otherwise indicated, the nucleotide sequence of all DNA sequences disclosed herein can be determined by employing an automated DNA sequencer (such as the Model 373 available from Applied Biosystems, Inc., Foster City, Calif., USA); all amino acid sequences of polypeptides encoded by DNA molecules disclosed herein can be predicted by translating a DNA sequence or by performing a chemical operation on the amino acid sequence (e.g., Edman degradation), which can be performed on an automated system.

As used herein, the term "stringent hybridization conditions", in the context of nucleic acid hybridization experiments such as Southern and northern blot analysis, means a set of conditions under which single stranded nucleic acid sequences are unlikely to hybridize to one another unless there is substantial complementarity between the sequences. Stringent hybridization conditions can be both sequence- and environment-dependent. Longer sequences hybridize specifically at higher temperatures. An extensive guide to the hybridization of nucleic acids is found in Tijssen, *Laboratory Techniques in Biochemistry and Molecular Biology-Hybridization with Nucleic Acid Probes,* Elsevier, New York, N.Y., USA, (1993), part I, chapter 2. Generally, highly stringent hybridization and wash conditions are selected to be about 5° C. lower than the thermal melting point ($T_m$) for the specific sequence at a defined ionic strength and pH. $T_m$ is the temperature (under defined ionic strength and pH) at which 50% of the target sequence hybridizes to a perfectly matched probe. Very stringent conditions are selected to be equal to the $T_m$ for a particular probe. Typically, under "stringent conditions" a probe will hybridize specifically to its target subsequence, but to no other sequences.

Examples of stringency conditions are shown in the table below: highly stringent conditions are those that are least as stringent as, for example, conditions A-F; stringent conditions are at least as stringent as, for example, conditions G-L; and reduced stringency conditions are at least as stringent as, for example, conditions M-R.

Table of Representative Stringency Conditions

| Stringency Condition | Polynucleotide Hybrid ± | Hybrid Length (bp) ‡ | Hyridization Temperature and Buffer † | Wash Temperature and Buffer † |
|---|---|---|---|---|
| A | DNA:DNA | > or equal to 50 | 65° C.; 1xSSC -or- 42° C.; 1xSSC, 50% formamide | 65° C.; 0.3xSSC |

-continued

Table of Representative Stringency Conditions

| Stringency Condition | Polynucleotide Hybrid ± | Hybrid Length (bp) ‡ | Hyridization Temperature and Buffer † | Wash Temperature and Buffer † |
|---|---|---|---|---|
| B | DNA:DNA | <50 | Tb*; 1xSSC | Tb*; 1xSSC |
| C | DNA:RNA | > or equal to 50 | 67° C.; 1xSSC -or- 45° C.; 1xSSC, 50% formamide | 67° C.; 0.3xSSC |
| D | DNA:RNA | <50 | Td*; 1xSSC | Td*; 1xSSC |
| E | RNA:RNA | > or equal to 50 | 70° C.; 1xSSC -or- 50° C.; 1xSSC, 50% formamide | 70° C.; 0.3xSSC |
| F | RNA:RNA | <50 | Tf*; 1xSSC | Tf*; 1xSSC |
| G | DNA:DNA | > or equal to 50 | 65° C.; 4xSSC -or- 45° C.; 4xSSC, 50% formamide | 65° C.; 1xSSC |
| H | DNA:DNA | <50 | Th*; 4xSSC | Th*; 4xSSC |
| I | DNA:RNA | > or equal to 50 | 67° C.; 4xSSC -or- 45° C.; 4xSSC, 50% formamide | 67° C.; 1xSSC |
| J | DNA:RNA | <50 | Tj*; 4xSSC | Tj*; 4xSSC |
| K | RNA:RNA | > or equal to 50 | 70° C.; 4xSSC -or- 40° C.; 6xSSC, 50% formamide | 67° C.; 1xSSC |
| L | RNA:RNA | <50 | Tl*; 2xSSC | Tl*; 2xSSC |
| M | DNA:DNA | > or equal to 50 | 50° C.; 4xSSC -or- 40° C. 6xSSC, 50% formamide | 50° C.; 2xSSC |
| N | DNA:DNA | <50 | Tn*; 6xSSC | Tn*; 6xSSC |
| O | DNA:RNA | > or equal to 50 | 55° C.; 4xSSC -or- 42° C.; 6xSSC, 50% formamide | 55° C.; 2xSSC |
| P | DNA:RNA | <50 | Tp*; 6xSSC | Tp*; 6xSSC |
| Q | RNA:RNA | > or equal to 50 | 60° C.; 4xSSC -or- 45° C.; 6xSSC, 50% formamide | 60° C.; 2xSSC |
| R | RNA:RNA | <50 | Tr*; 4xSSC | Tr*; 4xSSC |

‡: The "hybrid length" is the anticipated length for the hybridized region(s) of the hybridizing polynucleotides. When hybridizing a polynucleotide of unknown sequence, the hybrid is assumed to be that of the hybridizing polynucleotide of the present invention. When polynucleotides of known sequence are hybridized, the hybrid length can be determined by aligning the sequences of the polynucleotides and identifying the region or regions of optimal sequence complementarity. Methods of aligning two or more polynucleotide sequences and/or determining the percent identity between two polynucleotide sequences are well known in the art (e.g., MEGALIGN program of the DNA*Star suite of programs (DNAStar Inc., Madison, Wisconsin), etc).

†: SSPE (1xSSPE is 0.15M NaCl, 10 mM $NaH_2PO_4$, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete. The hydridizations and washes may additionally include 5× Denhardt's reagent, .5-1.0% SDS, 100 μg/ml denatured, fragmented salmon sperm DNA, 0.5% sodium pyrophosphate, and up to 50% formamide.

*Tb—Tr: The hybridization temperature for hybrids anticipated to be less than 50 base pairs in length should be 5-10° C. less than the melting temperature Tm of the hybrids there Tm is determined according to the following equations. For hybrids less than 18 base pairs in length, Tm(° C.) = 2(# of A + T bases) + 4(# of G + C bases). For hybrids between 18 and 49 base pairs in length, Tm(° C.) = 81.5 + 16.6($log_{10}[Na^+]$) + 0.41(% G + C) − (600/N), where N is the number of bases in the hybrid, and $[Na^+]$ is the concentration of sodium ions in the hybridization buffer ($[Na^+]$ for 1×SSC = 0.165M).

±: The present invention encompasses the substitution of any one, or more DNA or RNA hybrid partners with either a PNA, or a modified polynucleotide. Such modified polynucleotides are known in the art and are more particularly described elsewhere herein.

Additional examples of stringency conditions for polynucleotide hybridization are provided, for example, in Sambrook et al., *Molecular Cloning: A Laboratory Manual,* (3rd ed.) Cold Spring Harbor Laboratory Press, Cold Spring Harbor, N.Y., USA (2001), chapters 9 and 11, and *Current Protocols in Molecular Biology,* (Ausubel et al., eds.), Greene Publishing Associates and Wiley-Interscience, New York (2002) sections 2.10 and 6.3-6.4, which references are hereby incorporated by reference herein in their entireties.

Preferably, hybridizing polynucleotides have at least 70% sequence identity (more preferably, at least 80% identity; and most preferably at least 90% or 95% identity) with the polynucleotide of the present invention to which they hybridize, where sequence identity is determined by comparing the sequences of the hybridizing polynucleotides when aligned so as to maximize overlap and identity while minimizing sequence gaps. The determination of identity is well known in the art, and discussed more specifically elsewhere herein.

As used herein, the term "variant" means a polynucleotide or polypeptide differing from a polynucleotide or polypeptide of the present invention by one or more amino acids or nucleotides, but retaining essential properties thereof. Generally, variants are overall closely similar, and, in many regions, identical to a polynucleotide or polypeptide of the present invention. For example, a variant can comprise a "conservative" change, wherein a substituted amino acid has similar structural or chemical properties, e.g., replacement of leucine with isoleucine. More rarely, a variant can have a "nonconservative" change, e.g., replacement of a glycine with a tryptophan. Similar minor variations can also include amino acid deletions or insertions, or both. Guidance in determining which amino acid residues can be substituted, inserted, or deleted without abolishing biological or immunological activity may be found using computer programs well known in the art, for example, DNASTAR software (DNAStar Inc., Madison, Wis.).

As used herein, the term "vector" means a DNA molecule having sequences that enable its replication in a compatible host cell. A vector also includes nucleotide sequences to permit ligation of nucleotide sequences within the vector, wherein such nucleotide sequences are also replicated in a compatible host cell. A vector can also mediate recombinant production of a polypeptide of the present invention, as described further herein. Some representative vectors include, but are not limited to, pCMV (Invitrogen, Carlsbad, Calif., USA) pBluescript (Stratagene, La Jolla, Calif., USA), pUC18, pBLCAT3 (Luckow and Schutz, (1987) *Nucleic Acids Res* 15: 5490), pLNTK (Gorman et al., (1996) *Immunity* 5: 241-252), and pBAD/gIII (Stratagene, La Jolla, Calif.). A representative host cell is a human embryonic kidney cell, such as HEK293.

Polynucleotides and Polypeptides of the Invention

The polypeptides encoded by the polynucleotides of the present invention comprise several unique features. Some of these features are described in the following sections.

Features of Reference and Variant Polypeptides Encoded by the Alleles of the Present Invention The present invention relates to isolated nucleic acid molecules comprising, or alternatively, consisting of all or a portion of one or more variant alleles of a variety of human genes The SNPs in these variant forms are identified in Tables 1-5. Preferred portions are at least 10, preferably at least 20, preferably at least 40, preferably at least 100, contiguous polynucleotides and comprise one or more alternate (or variant) allele(s) at the nucleotide position(s) provided in Tables 1-5. The invention further relates to isolated gene products, e.g., polypeptides and/or proteins, which are encoded by a nucleic acid molecule comprising all or a portion of at least one or more variant allele(s) of the gene.

The present invention further relates to isolated proteins or polypeptides comprising, or alternatively, consisting of all or a portion of the variant amino acid sequence encoded by an allele of the present invention. Preferred portions are at least 10, preferably at least 20, preferably at least 40, preferably at least 100, contiguous polypeptides and comprises the reference amino acid allele at the amino acid position provided in Tables 1-5 of the polypeptide encoded by the alleles described herein. The invention further relates to isolated nucleic acid molecules encoding such polypeptides or proteins, as well as to antibodies that bind to such proteins or polypeptides.

In one embodiment, the invention relates to a method for predicting the likelihood that an individual will have a disorder, or be susceptible to acquiring a disorder (e.g., HDL, Type II diabetes, osteoarthritis, osteoporosis, breast cancer, prostate cancer, lung cancer, hypertension, schizophrenia, or Alzheimer's disease), associated with one or more reference allele(s) at the nucleotide position(s) provided in Tables 1-5 for the alleles described herein (or diagnosing or aiding in the diagnosis of such a disorder) comprising the steps of obtaining a DNA sample from an individual to be assessed and determining the nucleotide present at said nucleotide position. The presence of the reference allele at said position indicates that the individual has a greater or lesser likelihood of having a disorder associated therewith than an individual having the alternate (variant) allele(s) at said position(s), or a greater likelihood of having more severe symptoms.

In one embodiment, the invention relates to a method for predicting the likelihood that an individual will have a disorder, or be susceptible to acquiring a disorder (e.g., HDL, Type II diabetes, osteoarthritis, osteoporosis, breast cancer, prostate cancer, lung cancer, hypertension, schizophrenia, or Alzheimer's disease), associated with one or more reference allele(s) at the nucleotide position(s) provided in Tables 1-5 (or diagnosing or aiding in the diagnosis of such a disorder) comprising the steps of obtaining a DNA sample from an individual to be assessed and determining the nucleotide present at said nucleotide position. The presence of the reference allele at said position indicates that the individual has a greater or lesser likelihood of having a disorder associated therewith than an individual having the alternate (variant) allele(s) at said position(s), or a greater likelihood of having more severe symptoms.

Production of the Polynucleotides and Polypeptides of the Present Invention

The following paragraphs describe some of methods and techniques that can be employed in the production of the various polynucleotides and polypeptides of the present invention.

Production of a Polypeptide of the Present Invention

The native and mutated polypeptides, and fragments thereof, of the present invention can be chemically synthesized in whole or part using techniques that are known in the art (see, e.g., Creighton, *Proteins: Structures and Molecular Principles,* ($2^{nd}$ ed.) W.H. Freeman & Co., New York, (1993), incorporated herein by reference). Alternatively, methods that are known to those of ordinary skill in the art can be used to construct expression vectors comprising a partial or the entire native or mutated polypeptide coding sequence and appropriate transcriptional/translational control signals. These methods include in vitro recombinant DNA techniques, as described herein, synthetic techniques and in vivo recombination/genetic recombination (see, e.g., the techniques described in Sambrook et al., *Molecular Cloning: A Laboratory Manual,* ($3^{rd}$ ed.) Cold Spring Harbor Laboratory Press, Cold Spring Harbor, N.Y., USA (2001) and *Current Protocols in Molecular Biology,* (Ausubel et al., eds.), Greene Publishing Associates and Wiley-Interscience, New York (2002), both of which are incorporated herein by reference.

A variety of host-expression vector systems can be utilized to express a coding sequence of the present invention. These include, but are not limited to, microorganisms such as bacteria transformed with recombinant bacteriophage DNA, plasmid DNA or cosmid DNA expression vectors containing a coding sequence; yeast transformed with recombinant yeast expression vectors containing a coding sequence; insect cell systems infected with recombinant virus expression vectors (e.g., baculovirus) containing a coding sequence of the present invention; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a coding sequence of the present invention; or animal cell systems. The expression elements of these systems vary in their strength and specificities.

Depending on the host/vector system utilized, any of a number of suitable transcription and translation elements, including constitutive and inducible promoters, can be used in the expression vector. For example, when cloning in bacterial systems, inducible promoters such as pL of bacteriophage λ, plac, ptrp, ptac (ptrp-lac hybrid promoter) and the like can be used. When cloning in insect cell systems, promoters such as the baculovirus polyhedrin promoter can be used. When cloning in mammalian cell systems, promoters derived from the genome of mammalian cells (e.g., metallothionein promoter) or from mammalian viruses (e.g., the adenovirus late promoter or the vaccinia virus 7.5K promoter) can be used. When generating cell lines that contain multiple copies of the tyrosine kinase domain DNA, SV40-, BPV- and EBV-based vectors can be used with an appropriate selectable marker. Representative methods of producing polypeptides of the present invention are also disclosed herein.

In addition, polypeptides of the invention can be chemically synthesized using techniques known in the art (e.g., see Creighton, *Proteins: Structures and Molecular Principles,* ($2^{nd}$ ed.) W.H. Freeman & Co., New York, (1993), and Hunkapiller et al., (1984) *Nature* 310:105-111, both of which are incorporated herein by reference). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, omithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

The present invention encompasses polypeptides that are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications can be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides can also be modified with a detectable label, such as an enzymatic, fluorescent, isotopic or affinity label to allow for detection and isolation of the protein, the addition of epitope tagged peptide fragments (e.g., FLAG®, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methionine residue, etc.

Also provided by the present invention are chemically modified derivatives of the polypeptides of the present invention that can provide additional advantages such as increased solubility, stability and circulating time of the polypeptide, or decreased immunogenicity (see U.S. Pat. No. 4,179,337, incorporated herein by reference). The chemical moieties for derivitization can be selected from water soluble polymers such as polyethylene glycol, ethylene glycol/propylene glycol copolymers, carboxymethylcellulose, dextran, polyvinyl alcohol and the like. The polypeptides can be modified at random positions within the molecule, or at predetermined positions within the molecule and can include one, two, three or more attached chemical moieties.

The invention further encompasses chemical derivitization of the polypeptides of the present invention, for example where the chemical is a hydrophilic polymer residue. Exemplary hydrophilic polymers, including derivatives, can be those that include polymers in which the repeating units contain one or more hydroxy groups (polyhydroxy polymers), including, for example, poly (vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The present invention encompasses derivitization of the polypeptides of the present invention, for example, with compounds that can serve a stabilizing function (e.g., to increase the polypeptides half-life in solution, to make the polypeptides more water soluble, to increase the polypeptides hydrophilic or hydrophobic character, etc.). Polymers useful as stabilizing materials can be of natural, semisynthetic (modified natural) or synthetic origin.

Moreover, the present invention encompasses additional modifications of the polypeptides of the present invention. Such additional modifications are known in the art, and are specifically provided, in addition to methods of derivitization, etc., in U.S. Pat. No. 6,028,066, incorporated herein by reference.

The polypeptides of the present invention can be in monomers or multimers (i.e., dimers, trimers, tetramers and higher multimers). Accordingly, the present invention relates to monomers and multimers of the polypeptides of the present invention, their preparation, and compositions (e.g., therapeutics) containing them. In specific embodiments, the polypeptides of the invention are monomers, dimers, trimers or tetramers. In additional embodiments, the multimers of the invention are at least dimers, at least trimers, or at least tetramers.

A polypeptide of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Particularly, high performance liquid chromatography ("HPLC") can be employed for purification.

Polypeptides of the present invention, including their secreted forms, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention can be glycosylated or can be non-glycosylated. In addition, polypeptides of the invention can also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

Production of Nucleic Acids of the Present Invention

Nucleic acids of the present invention can be cloned, synthesized, recombinantly altered, mutagenized, or combinations thereof. Standard recombinant DNA and molecular cloning techniques used to isolate nucleic acids are well known in the art. Exemplary, non-limiting methods are described, for example, by Sambrook et al., *Molecular Cloning: A Laboratory Manual,* (3rd ed.) Cold Spring Harbor Laboratory Press, Cold Spring Harbor, N.Y., (2001); by Silhavy et al., (1984) *Experiments with Gene Fusions,* Cold Spring Harbor Laboratory Press, Cold Spring Harbor, N.Y.; by *Current Protocols in Molecular Biology,* (Ausubel et al., eds.), Greene Publishing Associates and Wiley-Interscience, New York (2002); and by Glover, (ed.) (1985) *DNA Cloning: A Practical Approach,* MRL Press, Ltd., Oxford, U.K, all of which are incorporated herein by reference. Site-specific mutagenesis to create base pair changes, deletions, or small insertions are also known in the art (see, e.g., Adelman et al., (1983) *DNA* 2:183; Sambrook et al., *Molecular Cloning: A Laboratory Manual,* (3rd ed.) Cold Spring Harbor Laboratory Press, Cold Spring Harbor, N.Y., (2001), incorporated herein by reference).

Sequences disclosed or detected by methods of the invention can be detected, subcloned, sequenced, and further evaluated by any measure well known in the art using any method usually applied to the detection of a specific DNA sequence including but not limited to dideoxy sequencing, PCR, oligomer restriction (Saiki et al., (1985) *Bio/Technology* 3:1008-1012, incorporated herein by reference), allele-specific oligonucleotide (ASO) probe analysis (Conner et al., (1983) *Proc. Natl. Acad. Sci. U.S.A.* 80:278, incorporated herein by reference), and oligonucleotide ligation assays (OLAs) (Landgren et. al., (1988) *Science* 241:1007, incorporated herein by reference). Molecular techniques for DNA analysis have been reviewed (Landgren et. al., (1988) *Science* 242:229-237, incorporated herein by reference) and can be employed in the present invention.

In other aspects, the present invention also relates to vectors comprising the polynucleotides of the present invention, host cells, and the production of polypeptides by recombinant techniques. The vector can be, for example, a phage, plasmid, viral, or retroviral vector. Retroviral vectors can be replication competent or replication defective. In the latter case, viral propagation generally will occur only in complementing host cells.

Polynucleotides can be joined with a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The polynucleotide insert should be operatively linked to an appropriate promoter, such as the phage λ PL promoter, the *E. coli* lac, trp, phoA and tac promoters, the SV40 early and late promoters and promoters of retroviral LTRs, to name a few. Other suitable promoters will be known to those of ordinary skill in the art. The expression constructs can further comprise sites for transcription initiation, termination, and, in the transcribed region, a ribosome binding site for translation. The coding portion of the transcripts expressed by the constructs can include a translation initiating codon at the beginning and a termination codon (UAA, UGA or UAG) appropriately positioned at the end of the polypeptide to be translated.

The expression vectors can include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, 293, and Bowes melanoma cells; and plant cells. Appropriate culture mediums and conditions for the above-described host cells are known in the art.

Vectors preferred for use in bacteria include pQE70, pQE60 and pQE-9, (available from QIAGEN, Inc., Chatsworth, Calif., USA); pBluescript vectors, Phagescript vectors, pNH8A, pNH 16a, pNH18A, pNH46A (available from Stratagene Cloning Systems, Inc., La Jolla, Calif., USA); and ptrc99a, pKK223-3, pKK233-3, pDR540, pRIT5 (available from Pharmacia, Piscataway, N.J., USA). Representative eukaryotic vectors include pWLNEO, pSV2CAT, pOG44, pXT1 and pSG available from Stratagene; and pSVK3, pBPV, pMSG and pSVL available from Pharmacia (Piscataway, N.J., USA). Representative expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlsbad, Calif., USA). Other suitable vectors will be readily apparent to one of ordinary skill in the art upon consideration of the present disclosure.

Various yeast vectors can also be used in the present invention, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one of ordinary skill in the art will appreciate, as long as the proposed expression construct provides appropriately located signals for transcription, translation, secretion (if desired), and the like, including an in-frame AUG, as required.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the present invention, and which activates, alters, and/or amplifies endogenous polynucleotides. For example, techniques known in the art can be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670; U.S. Pat. No. 5,733,761; PCT Publication No. WO 96/29411; PCT Publication No. WO 94/12650; Koller et al., (1989) *Proc. Natl. Acad. Sci. USA* 86:8932-8935; and Zijlstra et al., (1989) *Nature* 342:435-438, all of which are incorporated herein by reference).

Polynucleotide and Polypeptide Variants

The present invention encompasses variants (e.g., allelic variants, orthologs, etc.) of the polynucleotide sequences disclosed herein, and the complementary strand thereto. The present invention also encompasses variants of the polypeptide sequences, and/or fragments thereof, disclosed herein, a polypeptide encoded by the polynucleotide sequences in disclosed herein.

Thus, one aspect of the invention provides an isolated nucleic acid molecule comprising, or alternatively consisting of, a polynucleotide having a nucleotide sequence selected from the group consisting of: (a) a nucleotide sequence encoding a related polypeptide of the present invention having an amino acid sequence as shown in the Figures and/or Tables and/or in the Sequence Listing; (b) a nucleotide sequence encoding a mature related polypeptide of the present invention having the amino acid sequence as shown in the Figures and/or Tables and/or in the Sequence Listing; (c) a nucleotide sequence encoding a biologically active fragment of a related polypeptide of the present invention having an amino acid sequence shown in the Figures and/or Tables and/or in the Sequence Listing; (d) a nucleotide sequence encoding an antigenic fragment of a related polypeptide of the present invention having an amino acid sequence shown in the Figures and/or Tables and/or in the Sequence Listing; (e) a nucleotide sequence complimentary to any of the nucleotide sequences in (a), (b), (c), (d) and (e), above.

The present invention is also directed to polynucleotide sequences which comprise, or alternatively consist of, a polynucleotide sequence which is at least 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d) and (e), above. Polypeptides encoded by these nucleic acid molecules are also encompassed by the invention. In another embodiment, the present invention encompasses -nucleic acid molecules which comprise, or alternatively, consist of a polynucleotide which hybridizes under stringent conditions, or alternatively, under lower stringency conditions, to a polynucleotide in (a), (b), (c), (d), and (e) above. Polynucleotides which hybridize to the complement of these nucleic acid molecules under stringent hybridization conditions or alternatively, under lower stringency conditions, are also encompassed by the present invention, as are polypeptides encoded by these polypeptides.

Another aspect of the present invention provides an isolated nucleic acid molecule comprising, or alternatively, consisting of, a polynucleotide having a nucleotide sequence selected from the group consisting of: (a) a nucleotide sequence encoding a related polypeptide of the present invention having an amino acid sequence as shown in the Figures and/or in the Sequence Listing and described herein; (b) a nucleotide sequence encoding a mature related polypeptide of the present invention having the amino acid sequence as shown in the Sequence Listing and described herein; (c) a nucleotide sequence encoding a biologically active fragment of a related polypeptide of the present invention having an amino acid sequence as shown in the Sequence Listing and described herein; (d) a nucleotide sequence encoding an antigenic fragment of a related polypeptide of the present invention having an amino acid sequence as shown in the Figures and/or in the Sequence Listing and descried herein; (e) a nucleotide sequence complimentary to any of the nucleotide sequences in (a), (b), (c), (d), or (e) above.

The present invention is also directed to nucleic acid molecules that comprise, or alternatively, consist of, a nucleotide sequence which is at least 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), or (e) above.

As a practical matter, whether any particular nucleic acid molecule or polypeptide is at least 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a nucleotide sequence of the present invention can be determined conventionally using known computer programs. A representative method for determining the best overall match between a query sequence (a sequence of the present invention) and a subject sequence, also referred to as a global sequence alignment, can be determined using the CLUSTALW computer program (Thompson et al., (1994) *Nucleic Acids Research* 2 (22):4673-4680), which is based on the algorithm of Higgins et al., (1992) *Computer Applications in the Biosciences* (*CABIOS*) 8(2):189-191. In a sequence alignment the query and subject sequences are both DNA sequences. An RNA sequence can be compared by converting U's to T's. The result of said global sequence alignment is in percent identity. Representative parameters used in a CLUSTALW alignment of DNA sequences to calculate percent identify are: Matrix=BLOSUM, k-tuple=1, Number of Top Diagonals=5, Gap Penalty=3, Gap Open Penalty 10, Gap Extension Penalty=0, Scoring Method=Percent, Window Size=5 or the length of the subject nucleotide sequence, whichever is shorter.

If a subject sequence is shorter than a query sequence because of 5' or 3' deletions, not because of internal deletions, a manual correction can be made to the results. This is because the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score can be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

By a polypeptide having an amino acid sequence that is at least, for example, 95% "identical" to a query amino acid sequence of the present invention, it is intended that the amino acid sequence of the subject polypeptide is identical to the query sequence except that the subject polypeptide sequence can include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence can be inserted, deleted, or substituted with another amino acid. These alterations of the reference sequence can occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for instance, an amino acid sequence referenced herein (e.g., as shown in the Figures and/or Tables and/or in the Sequence Listing) can be determined conventionally using known computer programs. A preferred method for determining the best overall match between a query sequence (a sequence of the present invention) and a subject sequence, also referred to as a global sequence alignment, can be determined using the CLUSTALW computer program (Thompson et al., (1994) *Nucleic Acids Research* 2 (22):4673-4680), which is based on the algorithm of Higgins et al., (1992) *Computer Applications in the Biosciences* (*CABIOS*) 8(2):189-191. The result of said global sequence alignment is in percent identity.

If the subject sequence is shorter than the query sequence due to N- or C-terminal deletions, not because of internal deletions, a manual correction can be made to the results. This is because the CLUSTALW program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the CLUSTALW sequence alignment. This percentage is then subtracted from the percent identity, calculated by the above CLUSTALW program using the specified parameters, to arrive at a final percent identity score. This final percent identity score is what can be used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the CLUSTALW alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the CLUSTALW program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence, which are not matched/aligned with the query. In this case the percent identity calculated by CLUSTALW is not manually corrected. Once again, only residue positions outside the N- and C-terminal ends of the subject sequence, as displayed in the CLUSTALW alignment, which are not matched/aligned with the query sequence are manually corrected for. No other manual corrections are required for the purposes of the present invention.

The variants disclosed in, or identified or generated by the methods of, the present invention can contain alterations in the coding regions, non-coding regions, or both. In some embodiments of the present invention it can be desirable that polynucleotide variants containing alterations produce silent substitutions, additions, or deletions, but do not alter the properties or activities of the encoded polypeptide. Nucleotide variants produced by silent substitutions due to the degeneracy of the genetic code can also be desirable. Moreover, variants in which 5-10, 1-5, or 1-2 amino acids are substituted, deleted, or added in any combination are also desirable in some situations. Polynucleotide variants can be produced for a variety of reasons, e.g., to optimize codon expression for a particular host (change codons in the mRNA to those preferred by a bacterial host such as *E. coli*).

Thus, the invention further includes polypeptide variants that show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., (1990) *Science* 247:1306-1310 (incorporated herein by reference), wherein it is indicated that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids can be important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used (Cunningham & Wells, (1989) *Science* 244:1081-1085). The resulting mutant molecules can then be tested for biological activity. Introduced amino acid changes can comprise a conservative substitution.

Besides conservative amino acid substitution, variants of the present invention include, but are not limited to, the following: (i) substitutions with one or more of the non-conserved amino acid residues, where the substituted amino acid residues might or might not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides will be within the scope of those of ordinary skill in the art, upon consideration of the present disclosure.

Moreover, the invention further comprises polypeptide variants created through the application of molecular evolution ("DNA shuffling") methodology to the polynucleotides disclosed herein, and/or the cDNA encoding the polypeptides disclosed herein. Such DNA shuffling technology is known in the art (see, e.g., Stemmer, (1994) *Proc. Natl. Acad Sci.* 91:10747, incorporated herein by reference).

A further embodiment of the present invention relates to a polypeptide which comprises the amino acid sequence of the present invention having an amino acid sequence which contains, for example, at least one amino acid substitution, but not more than 50 amino acid substitutions, for example, or, in another embodiment, not more than 40 amino acid substitutions, or, in a further embodiment, not more than 30 amino acid substitutions, or, in yet another embodiment, not more than 20 amino acid substitutions. In some situations, it can be desirable for a peptide or polypeptide to comprise an amino acid sequence of the present invention, which comprises at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), can be, for example, 1-5, 5-10, 5-25, 5-50, 10-50 or 50-150, conservative amino acid substitutions.

The present invention further provides modified forms of nucleic acid sequences and corresponding proteins. Starting nucleic acid sequences can comprise one of the sequences described in Figures and/or the Sequence Listing, and the polynucleotides encoding the polypeptides described in the Figures and/or Sequence Listing. Some nucleic acids encode full-length modified forms of proteins. Modified genes can be expressed in an expression vector in which a variant gene is operably linked to a native or other promoter. Commonly, the promoter is a eukaryotic promoter for expression in a mammalian cell. The transcription regulation sequences typically include a heterologous promoter and optionally an enhancer that is recognized by the host. The selection of an appropriate promoter, for example trp, lac, phage promoters, glycolytic enzyme promoters and tRNA promoters, depends in part on the host selected. Commercially available expression vectors can be used. Vectors can include host-recognized replication systems, amplifiable genes, selectable markers, host sequences useful for insertion into the host genome, and the like.

The technique employed in introducing the expression construct into a host cell can vary with the particular construction and the target host. Suitable techniques include fusion, conjugation, transfection, transduction, electroporation or injection; such techniques are known in the art. A wide variety of host cells can be employed for expression of a modified gene, both prokaryotic and eukaryotic. Representative host cells include bacteria such as *E. coli,* yeast, filamentous fungi, insect cells, mammalian cells, typically immortalized, e.g., mouse, CHO, human and monkey cell lines and derivatives thereof. Preferably, but not necessarily, host cells are able to process the variant gene product to produce an appropriate mature polypeptide. Processing includes glycosylation, ubiquitination, disulfide bond formation, general post-translational modification, and the like. As used herein, "gene product" includes mRNA, peptide and protein products.

A protein so produced can be isolated by conventional means of protein biochemistry and purification to obtain a substantially pure product via a number of techniques and/or protocols for example those described in Jacoby, *Method Enzymol.* volume 104, Academic Press, New York, N.Y., USA (1984); Scopes, *Protein Purification Principles and Practice,* (2nd ed.), Springer-Verlag, New York, N.Y., USA (1987); and *Guide to Protein Purification,* (Deutscher, ed.), *Method Enzymol.* vol. 182 (1990), all of which are incorporated herein by reference. If the protein is secreted, it can be isolated from the supernatant in which the host cell is grown. If not secreted, the protein can be isolated from a lysate of the host cells.

The present invention further provides transgenic nonhuman animals capable of expressing an exogenous variant gene and/or having one or both alleles of an endogenous variant gene inactivated. Expression of an exogenous variant gene is often achieved by operably linking the gene to a promoter and optionally an enhancer, and microinjecting the construct into a zygote (see Hogan et al., *Manipulating the Mouse Embryo, A Laboratory Manual,* ($2^{nd}$ ed.) Cold Spring Harbor Laboratory Press, Plainview, N.Y., USA (1994), incorporated herein by reference). Inactivation of endogenous variant genes can be achieved by forming a trans gene in which a cloned variant gene is inactivated by insertion of a positive selection marker (see Capecchi, (1989) *Science* 244: 1288-1292). The transgene is then introduced into an embryonic stem cell, where it undergoes homologous recombination with an endogenous variant gene. Mice and other rodents are representative animals. Such animals provide useful drug screening systems.

Polynucleotide and Polypeptide Fragments

The present invention is also directed to polynucleotide fragments of the polynucleotides of the invention, in addition to polypeptides encoded therein by said polynucleotides and/or fragments.

In the present disclosure, a "polynucleotide fragment" means a short polynucleotide having a nucleic acid sequence which: is a portion of those sequences described herein or the complementary strand thereto, or is a portion of a polynucleotide sequence encoding a polypeptide described herein. The nucleotide fragments of the invention can comprise, for example, at least about 15 nt, at least about 20 nt, at least about 30 nt, at least about 40 nt, at least about 50 nt, at least about 75 nt, or at least about 150 nt in length. A fragment "at least 20 nt in length," for example, comprises 20 or more contiguous bases from a nucleotide sequence described herein. Consistent with the definition provided herein, in this context the term "about" includes the particularly recited value, a value larger or smaller by several (5, 4, 3, 2, or 1) nucleotides, at either terminus, or at both termini. These nucleotide fragments have uses that include, but are not limited to, as diagnostic probes and primers as discussed herein. In some cases, larger fragments (e.g., 50, 150, 500, 600, 2000 nucleotides) can be desirable.

Moreover, representative examples of polynucleotide fragments of the present invention, include, for example, fragments comprising, or alternatively consisting of, a sequence from about nucleotide number 1-50, 51-100, 101-150, 151-200, 201-250, or 250 to the end of any of the sequences described herein, or the complementary strand thereto. Again, consistent with the definition provided herein, in this context the term "about" includes the particularly recited ranges, and ranges larger or smaller by several (5, 4, 3, 2, or 1) nucleotides, at either terminus or at both termini. In one embodiment, these fragments encode a polypeptide that has biological activity. In another embodiment, these polynucleotides can be used as probes or primers as disclosed herein. Also encompassed by the present invention are polynucleotides that hybridize to these nucleic acid molecules under stringent hybridization conditions or lower stringency conditions, as are the polypeptides encoded by these polynucleotides.

In the present invention, a "polypeptide fragment" refers to an amino acid sequence which is a portion of the amino acid sequences described herein. Protein (polypeptide) fragments can be "free-standing," or a component of a larger polypeptide of which the fragment forms a part or region, most preferably as a single continuous region. Representative examples of polypeptide fragments of the present invention, include, for example, fragments comprising, or alternatively consisting of, from about amino acid number 1-20, 21-40, 41-60, 61-80, 81-100, 102-120, 121-140, 141-160, or 161 to the end of the coding region. Moreover, polypeptide fragments can be about 20, 30, 40, 50, 60, 70, 80, 90, 100, 110, 120, 130, 140, or 150 amino acids in length. Polynucleotides encoding these polypeptides are also encompassed by the invention.

A polypeptide fragment can comprise the full-length protein. Other representative polypeptide fragments include the full-length protein having a continuous series of deleted residues from the amino or the carboxy terminus, or both. For example, any number of amino acids, for example ranging from 1 to about 60, can be deleted from the amino terminus of the full-length polypeptide. Similarly, any number of amino acids, for example ranging from 1 to about 30, can be deleted from the carboxy terminus of the full-length protein. Furthermore, any combination of the above amino and carboxy terminus deletions can be made. Similarly, polynucleotides encoding these polypeptide fragments are also within the scope of the present invention.

Other exemplary polypeptide fragments comprise biologically active fragments. Biologically active fragments are those exhibiting activity similar, but not necessarily identical, to an activity of the polypeptide of the present invention. The biological activity of the fragments can include an improved desired activity, or a decreased abnormal activity. Polynucleotides encoding these polypeptide fragments are also encompassed by the invention.

In one embodiment, the biological activity displayed by a polypeptide encoded by a polynucleotide fragment of the invention can be one or more biological activities typically associated with the full-length polypeptide of the invention. Some representative biological activities are: the fragment's ability to bind to at least one of the same antibodies which bind to the full-length protein, the fragment's ability to interact with at lease one of the same proteins which associate with the full-length protein, the fragment's ability to elicit at least one of the same immune responses as the full-length protein (i.e., to cause the immune system to create antibodies specific to the same epitope, etc.), the fragment's ability to associate with at least one of the same polynucleotides as the full-length protein, the fragment's ability to associate with a receptor of the full-length protein, the fragment's ability to associate with a ligand of the full-length protein, and the fragment's ability to multimerize with the full-length protein. One of ordinary skill in the art will appreciate, however, that some fragments can have biological activities that are desirable and inapposite to the biological activity of the full-length protein. The functional activity of polypeptides of the invention, including fragments, variants, derivatives, and analogs thereof can be determined by numerous methods available to those of ordinary skill in the art, some of which are described herein.

The present invention further encompasses polypeptides comprising, or alternatively consisting of, an epitope of the polypeptide having an amino acid sequence described herein, or encoded by a polynucleotide that hybridizes to the complement of a sequence described herein, for example the sequences presented in the figures and/or Sequence Listing and/or the Tables, under stringent hybridization conditions or lower stringency hybridization conditions as defined herein. The present invention further encompasses polynucleotide sequences encoding an epitope of a polypeptide sequence of the present invention, polynucleotide sequences of the complementary strand of a polynucleotide sequence encoding an epitope of the invention, and polynucleotide sequences that hybridize to the complementary strand under stringent hybridization conditions or lower stringency hybridization conditions defined herein.

Fragments that function as epitopes are also as aspect of the present invention and can be produced by any conventional means (see, e.g., Houghten, (1985) *Proc. Natl. Acad. Sci. USA* 82:5131-5135, further described in U.S. Pat. No. 4,631,211, incorporated herein by reference).

Antibodies

In one embodiment the present invention comprises an isolated antibody that binds specifically to a polypeptide comprising an amino acid sequence comprising one or more polymorphic positions and is derived from, or corresponds to, a sequence selected from the group of amino acid sequences described herein. Methods of preparing antibodies to a given polypeptide are well known to those of ordinary skill in the art and can be employed in the present invention (see, e.g., Harlow & Lane, *Antibodies: A Laboratory Manual,* Cold Spring Harbor Press, Cold Spring Harbor, N.Y., USA (1988)).

In the context of antibodies, as used herein the phrase "specifically (or selectively) binds to an antibody", or "specifically (or selectively) immunoreactive with", when referring to a protein or peptide, refers to a binding reaction which is determinative of the presence of the protein in a heterogeneous population of proteins and other biological materials. Thus, under designated immunoassay conditions, the specified antibodies bind to a particular protein and do not show significant binding to other proteins present in the sample. Specific binding to an antibody under such conditions can require an antibody that is selected for its specificity for a particular protein. For example, antibodies raised to a protein with an amino acid sequence encoded by any of the nucleic acid sequences of the invention can be selected to obtain antibodies specifically immunoreactive with that protein and not with unrelated proteins.

Antibodies of the present invention can be used, for example, to purify, detect, and/or target a polypeptide of the present invention, in either or both in vitro and in vivo diagnostic and therapeutic methods. For example, the antibodies can be employed in immunoassays for qualitatively and quantitatively measuring levels of a polypeptide of the present invention in a biological sample (see, e.g., Harlow & Lane, *Antibodies: A Laboratory Manual, Cold* Spring Harbor Press, Cold Spring Harbor, N.Y., USA (1988)).

Representative Uses for Antibodies Directed Against a Polypeptide of the Present Invention An antibody of the present invention has various utilities. For example, such antibodies can be used in a diagnostic assay to detect the presence of, or to quantify the amount of, a variant or reference form of a polypeptide of the present invention in a sample. A representative diagnostic assay can comprise at least two steps. In the first step, a sample is contacted with an antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (see, e.g., Arenkov et al., (2000) *Anal. Biochem.* 278(2):123-131), or a chromatography column, etc. In a second step, the amount of antibody bound to the substrate is quantitated. In another embodiment, the method can additionally comprise a first step of attaching an antibody, for example covalently, electrostatically, or reversibly, to a solid support, and a second step of subjecting the bound antibody to the sample, as described herein.

Various diagnostic assay techniques are known in the art, such as competitive binding assays, direct or indirect sandwich assays and immunoprecipitation assays conducted in either heterogeneous or homogenous phases (see, e.g., Zola, *Monoclonal Antibodies: A Manual of Techniques,* CRC Press, Inc., Boca Raton, Fla., USA (1987), pp. 147-158, incorporated herein by reference in its entirety). The antibodies used in the diagnostic assays can also be labeled with a detectable moiety. The detectable moiety is preferably adapted to produce, either directly or indirectly, a detectable signal. For example, a detectable moiety can be a radioisotope, such as $^{2}H$, $^{14}C$, $^{32}P$, or $^{125}I$, a fluorescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety can be employed, including those methods described by Hunter et al., (1962) *Nature* 144:945; Dafvid et al., (1974) *Biochem.* 13:1014; Pain et al., (1981) *J. Immunol. Method* 40:219; and Nygren, (1982) *J. Histochem. Cytochem.* 30:407.

Therapeutic/Prophylactic Administration and Compositions

The present invention provides methods of treatment, inhibition and prophylaxis by administration to a subject of an effective amount of a compound or pharmaceutical composition of the invention, for example an antibody of the present invention. In one embodiment, the compound is substantially purified (e.g., substantially free from substances that limit its effect or produce undesired side-effects). The subject is can be an animal, such as a mammal, including but not limited to animals such as cows, pigs, horses, chickens, cats, dogs, rabbits, mice, rats, etc. In one embodiment, a subject is a human.

Formulations and methods of administration that can be employed when the compound comprises a nucleic acid or an immunoglobulin are described above; additional appropriate formulations and routes of administration can be selected from among those described herein below. Further formulations and routes of administration will be known to those of ordinary skill in the art upon consideration of the present disclosure.

Various delivery systems are known and can be used to administer a compound of the present invention, regardless of whether the compound comprises an antibody or other moiety, e.g., encapsulation in liposomes, microparticles, microcapsules, recombinant cells capable of expressing the compound, receptor-mediated endocytosis (see, e.g., Wu & Wu, (1987) *J. Biol. Chem.* 262:4429-4432), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions can be administered by any convenient route, for example by infusion or bolus injection, by absorption through epithelial or mucocutaneous linings (e.g., oral mucosa, rectal and intestinal mucosa, etc.) and can be administered together with other biologically active agents. Administration can be systemic or local. In addition, it can sometimes be desirable to introduce the pharmaceutical compounds or compositions of the invention into the central nervous system by any suitable route, including intraventricular and intrathecal injection; intraventricular injection can be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it might be desirable to administer the pharmaceutical compounds or compositions of the invention locally to the area in need of treatment; this can be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. When administering a protein, including an antibody, of the invention; care should be taken to use materials to which the protein does not absorb.

In another embodiment, a compound or composition can be delivered in a vesicle, in particular a liposome (see, e.g., Langer, (1990) *Science* 249:1527-1533; Treat et al., in *Liposomes in the Therapy of Infectious Disease and Cancer,* (Lopez-Berestein and Fidler, eds.), Alfred R. Liss, New York, N.Y., USA, (1989) pp. 353-365).

In yet another embodiment, the compound or composition can be delivered in a controlled release system. In one embodiment, a pump can be used (see Langer, (1990) *Science* 249:1527-1533; Sefton, (1987) *CRC Crit. Ref. Biomed. Eng.* 14:201; Buchwald et al., (1980) *Surgery* 88:507; Saudek et al., (1989) *N. Engl. J. Med.* 321:574). In another embodiment, polymeric materials can be used (see *Medical Applications of Controlled Release,* (Langer & Wise, eds.), CRC Pres., Boca Raton, Fla., USA (1984); *Controlled Drug Bioavailabilitvy Drug Product Design and Performance,* (Smolen and Ball, eds.), Wiley, New York, N.Y., USA (1984); Ranger & Peppas, (1983) *J. Macromol. Sci. Rev. Macromol. Chem.* 23:61; see also Levy et al., (1985) *Science* 228:190; During et al., (1989) *Ann. Neurol.* 25:351; Howard et al., (1989) *J. Neurosurg.* 71:105). In yet another embodiment, a controlled release system can be placed in proximity of the therapeutic target, i.e., the brain, thus requiring only a fraction of the systemic dose (see, e.g., Goodson, in *Medical Applications of Controlled Release,* vol. 2, (Langer & Wise, eds.), CRC Pres., Boca Raton, Fla., USA (1984), pp. 115-138).

Other controlled release systems are discussed in the review by Langer (Langer, (1990) *Science* 249:1527-1533).

In a specific embodiment in which a compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; BIOLISTIC®, Dupont, Wilmington, Del., USA), or coating with lipids or cell-surface receptors or transfecting agents, or by administering it in linkage to a homeobox-like peptide which is known to enter the nucleus (see, e.g., Joliot et al., (1991) *Proc. Natl. Acad. Sci. USA* 88:1864-1868, etc.). Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be a desirable carrier or carrier component when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences,* ($20^{th}$ ed.), Lippincott, Williams & Wilkins, Baltimore, Md., USA (2001), incorporated herein by reference.

Such compositions can contain a therapeutically effective amount of the compound, preferably in purified form, together with a suitable amount of carrier so as to provide the form for proper administration to the patient. The formulation should suit the mode of administration.

In one embodiment, the composition is formulated in accordance with routine procedures as a pharmaceutical composition adapted for intravenous administration to human beings. Typically, compositions for intravenous administration comprise solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of a compound of the invention that will be effective in the treatment, inhibition and prevention of a disease or disorder associated with aberrant expression and/or activity of a polypeptide of the invention can be determined by standard clinical techniques. In addition, in vitro assays can optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses can be extrapolated from dose-response curves derived from in vitro or animal model test systems.

For antibodies, the dosage administered to a patient is typically 0.1 mg/kg to 100 mg/kg of the patient's body weight. In some cases, the dosage administered to a patient can be between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention can be reduced by enhancing uptake and tissue penetration (e.g., in the liver, kidney, etc.) of the antibodies by modifications such as, for example, lipidation.

The present invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Representative Applications of the Nucleic Acids of the Present Invention

Embodiments of the present invention include an isolated nucleic acid molecule comprising a nucleotide sequence containing one or more polymorphic positions and is at least about 20, 25, 30, 35, 40, 45, or 50 contiguous nucleotides and is derived from a nucleotide sequence described herein, for example in the Tables and/or Figures and/or Sequence Listing.

Another embodiment comprises an isolated nucleic acid molecule comprising a nucleotide sequence containing at least one or more polymorphic positions and is at least about 150 contiguous nucleotides and is derived from a nucleotide sequence described herein, for example in the Tables and/or Figures and/or Sequence Listing.

Another embodiment comprises an isolated nucleic acid molecule comprising a nucleotide sequence comprising at least one or more polymorphic positions and is at least about 500 contiguous nucleotides and is derived from a nucleotide sequence described herein, for example in the Tables and/or Figures and/or Sequence Listing.

Another embodiment comprises an isolated nucleic acid molecule comprising a nucleotide sequence containing one or more polymorphic positions and corresponds to, or is derived from, the complete nucleotide sequence described herein, for example in the Tables and/or Figures and/or Sequence Listing.

Another embodiment comprises an isolated nucleic acid molecule that hybridizes under stringent hybridization conditions to a nucleic acid molecule.

Another embodiment comprises an isolated nucleic acid molecule, wherein the nucleic acid is included in the nucleotide sequence of the complete open reading frame sequence encoded by a cDNA clone of the present invention.

The present invention also encompasses an isolated nucleic acid molecule, wherein the nucleotide sequence encodes a polypeptide of the present invention and has been optimized for expression of said polypeptide in a prokaryotic host.

The present invention also encompasses the identification of proteins, nucleic acids, or other molecules, that bind to polypeptides and polynucleotides of the present invention (for example, in a receptor-ligand interaction). The polynucleotides of the present invention can also be used in interaction trap assays (such as, for example, that described by Ozenberger and Young (Ozenberger & Young, (1995) *Mol Endocrinol.* 9(10):1321-29; and Ozenberger & Young, (1995) *Ann. N.Y. Acad. Sci.* 766:279-81, incorporated herein by reference).

The polynucleotide and polypeptides of the present invention are also useful as probes for the identification and isolation of full-length cDNAs and/or genomic DNA that correspond to the polynucleotides of the present invention, as probes to hybridize and discover novel, related DNA sequences, as probes for positional cloning of this or a related sequence, as probe to "subtract-out" known sequences in the process of discovering other novel polynucleotides, as probes to quantify gene expression, and as probes for microarrays.

Also, in other embodiments the present invention provides methods for further refining the biological function of the polynucleotides and/or polypeptides of the present invention.

Specifically, the invention provides methods of using the polynucleotides and polypeptides of the invention to identify orthologs, homologs, paralogs, variants, and/or allelic variants of the invention. Also provided are methods of using the polynucleotides and polypeptides of the present invention to identify the entire coding region of the invention, non-coding regions of the invention, regulatory sequences of the invention, and secreted, mature, pro-, and prepro-forms of the present invention (as applicable).

The present invention also comprises a method of detecting, in a biological sample comprising a nucleic acid, a nucleic acid molecule comprising a nucleotide sequence comprising at least one or more polymorphic positions and corresponds to, or is derived from, a nucleotide sequence described herein, for example in the Tables and/or Figures and/or Sequence Listing, the method comprising comparing a nucleotide of the sample with a reference sequence selected from the group and determining whether the sequence of the nucleic acid molecule in the sample comprises one or more polymorphic positions relative to the reference sequence.

In another embodiment, the above method can optionally be modified, wherein the step of comparing sequences comprises determining the extent of nucleic acid hybridization between the nucleic acid molecule(s) in the sample and the reference nucleic acid molecule. The nucleic acid molecules can comprise DNA molecules or RNA molecules.

The polynucleotides of the present invention can comprise an element of a recombinant construct. For example, in one embodiment the present invention comprises a method of making a recombinant vector comprising inserting any of the isolated nucleic acid molecule(s) of the present invention into a vector. Another representative embodiment comprises a recombinant vector produced by this method. Another representative embodiment comprises a method of making a recombinant host cell comprising introducing a vector of the present invention into a host cell, as well as the recombinant host cell produced by this method.

Determining the Presence or Absence of Allelic and Variant Polynucleotides and Polypeptides of the Present Invention The determination of the polymorphic form(s) present in an individual at one or more polymorphic sites defined herein can be used in a number of methods.

In some embodiments, the polynucleotides and polypeptides of the present invention, including allelic and variant forms thereof, have uses which include, but are not limited to diagnosing individuals to identify whether a given individual has decreased susceptibility or risk for a disease using the genotype assays of the present invention.

In another embodiment, the polynucleotides and polypeptides of the present invention, including allelic and variant forms thereof, either alone, or in combination with other polymorphic polynucleotides (haplotypes) are useful as genetic markers.

The polynucleotides and polypeptides of the present invention, including allelic and/or variant forms thereof, are useful for creating recombinant vectors and hosts cells for the expression of variant and mutant forms of the polypeptides of the present invention.

The polynucleotides and polypeptides of the present invention, including allelic and/or variant forms thereof, are useful for creating antagonists directed against these polynucleotides and polypeptides, particularly antibody antagonists, for diagnostic, and/or therapeutic applications.

Additionally, the polynucleotides and polypeptides of the present invention, including allelic and/or variant forms thereof, are useful for creating additional antagonists directed against these polynucleotides and polypeptides, which include, but are not limited to the design of antisense RNA, ribozymes, PNAs, recombinant zinc finger proteins (Wolfe et al., (2000) *Structure, Fold, Des.* 8(7):739-50; Kang et al., (2000) *J. Biol, Chem.* 275 (12):8742-8; Wang & Pabo, (1999) *Proc. Natl. Acad Sci. USA* 96(17):9568-73; McColl et al., (1999) *Proc. Natl. Acad. Sci. USA* 96(17): 9521-6; Segal et al., (1999) *Proc. Natl. Acad. Sci. USA* 96(6):2758-63; Wolfe et al., (1999) *J. Mol. Biol.* 285(5): 1917-34; Pomerantz et al., (1998) *Biochem.* 37(4):965-70; Leon & Roth, (2000) *Mol. Biol. Res.* 33(1):21-30; Berg & Godwin, (1997) *Ann. Rev. Biophys. Biomol. Struct.* 26:357-71), in addition to other types of antagonists which are either described elsewhere herein, or known in the art.

The polynucleotides and polypeptides of the present invention, including allelic and/or variant forms thereof, are useful for creating small molecule antagonists directed against the variant forms of these polynucleotides and polypeptides, preferably wherein such small molecules are useful as therapeutic and/or pharmaceutical compounds for the treatment, detection, prognosis, and/or prevention of a variety of diseases and/or disorders, including, but not limited to, HDL, Type II diabetes, osteoarthritis, osteoporosis, breast cancer, prostate cancer, lung cancer, hypertension, schizophrenia and Alzheimer's disease.

Another representative embodiment comprises a composition of matter comprising isolated an nucleic acid molecule, wherein the nucleotide sequence of the nucleic acid molecule comprises a panel of at least two nucleotide sequences, wherein at least one sequence in the panel comprises one or more polymorphic positions and is derived from, or corresponds to, a sequence described herein, for example in the Tables and/or Figures and/or Sequence Listing and fragments thereof.

The polynucleotides and polypeptides of the present invention, including allelic and/or variant forms thereof, are useful for the treatment of cardiovascular disease, in addition to other diseases and/or conditions referenced elsewhere herein, through the application of gene therapy based regimens.

Additional uses of the polynucleotides and polypeptides of the present invention are provided herein.

Forensics

A determination of which polymorphic forms occupy a set of polymorphic sites in an individual identifies a set of polymorphic forms that distinguishes the individual from other individuals. See generally, National Research Council, *The Evaluation of Forensic DNA Evidence* (Pollard et al., eds.) National Academy Press, Washington D.C., USA (1996). The more sites that are analyzed, the lower the probability that the set of polymorphic forms in one individual is the same as that in an unrelated individual. If multiple sites are analyzed, the sites can be unlinked. Thus, polymorphisms of the invention are often used in conjunction with polymorphisms in distal genes. Preferred polymorphisms for use in forensics are biallelic because the population frequencies of two polymorphic forms can usually be determined with greater accuracy than those of multiple polymorphic forms at multi-allelic loci.

The capacity to identify a distinguishing or unique set of forensic markers in an individual is useful in forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers does match, one can conclude that the DNA from the suspect is consistent with that found at the crime scene. If frequencies of the polymorphic forms at the loci tested have been determined (e.g., by analysis of a suitable population of individuals), one can perform a statistical analysis to determine the probability that a match of suspect and crime scene sample would occur by chance.

The probability that two random individuals have the same polymorphic or allelic form at a given polymorphic site is denoted "p(ID)". In biallelic loci, four genotypes are possible: AA, AB, BA, and BB. If alleles A and B occur in a haploid genome of the organism with frequencies x and y, the probability of each genotype in a diploid organism is (see PCT Publication WO 95/12607):

Homozygote: $p(AA)=x^2$

Homozygote: $p(BB)=y^2=(1-x)^2$

Single Heterozygote: $p(AB)=p(BA)=xy=x(1-x)$

Both Heterozygotes: $p(AB+BA)=2xy=2x\ (1-x)$

The probability of identity at one locus (i.e., the probability that two individuals, picked at random from a population will have identical polymorphic forms at a given locus) is given by the equation:

$$p(ID)=(x^2)^2+(2xy)^2+(y^2)^2.$$

These calculations can be extended for any number of polymorphic forms at a given locus. For example, the probability of identity p (m) for a 3-allele system where the alleles have the frequencies in the population of x, y and z, respectively, is equal to the sum of the squares of the genotype frequencies:

$$p(ID)=x^4+(2xy)^2+(2yz)^2+(2xz)^2+z^4+y^4$$

In a locus of n alleles, the appropriate binomial expansion is used to calculate p(ID) and p(exc).

The cumulative probability of identity (cum p (ID)) for each of multiple unlinked loci is determined by multiplying the probabilities provided by each locus.

$$cum\ p(ID)=p(ID1)p(ID2)p(ID3)\ldots p(IDn)$$

The cumulative probability of non-identity for n loci (i.e. the probability that two random individuals will be different at 1 or more loci) is given by the equation:

cum p(nonID)=1−cum p(ID).

If several polymorphic loci are tested, the cumulative probability of non-identity for random individuals becomes very high (e.g., one billion to one). Such probabilities can be taken into account together with other evidence in determining the guilt or innocence of the suspect.

Paternity Testing

An object of paternity testing is to determine whether a male is the father of a child. In most cases, the mother of the child is known and thus, the mother's contribution to the child's genotype can be traced. Paternity testing investigates whether the part of the child's genotype not attributable to the mother is consistent with that of the putative father. Paternity testing can be performed by analyzing sets of polymorphisms in the putative father and the child.

If the set of polymorphisms in the child attributable to the father does not match the set of polymorphisms of the putative father, it can be concluded, barring experimental error, that the putative father is not the true father.

If the set of polymorphisms in the child attributable to the father does match the set of polymorphisms of the putative father, a statistical calculation can be performed to determine the probability of coincidental match.

The probability of parentage exclusion (representing the probability that a random male will have a given polymorphic form at a given polymorphic site that makes him incompatible as the father) is given by the equation (see PCT Publication WO 95/12607):

p(exc)=xy(1−xy)

where x and y are the population frequencies of alleles A and B of a biallelic polymorphic site. (At a triallelic site p(exc) =xy (1−xy)+yz(1−yz)+xz(1−xz)+3xyz(1−xyz), where x, y and z and the respective population frequencies of alleles A, B and C).

The probability of non-exclusion is p(non-exc)=1−p(exc)

The cumulative probability of non-exclusion (representing the value obtained when n loci are used) is thus:

cum p(non-exc)=p(non-exc1)p(non-exc2)p (non-exc3) . . . p(non-excn)

The cumulative probability of exclusion for n loci (representing the probability that a random male will be excluded)

cum p(exc)=1−cum p(non-exc).

If several polymorphic loci are included in the analysis, the cumulative probability of exclusion of a random male is very high. This probability can be taken into account in assessing the liability of a putative father whose polymorphic marker set matches the child's polymorphic marker set attributable to his/her father.

Correlation of Polymorphisms with Phenotypic Traits

The polymorphisms of the present invention can contribute to the phenotype of an organism in different ways. Some polymorphisms occur within a protein coding sequence and contribute to phenotype by affecting protein structure. The effect can be neutral, beneficial or detrimental, or both beneficial and detrimental, depending on the circumstances. For example, a heterozygous sickle cell mutation confers resistance to malaria, but a homozygous sickle cell mutation is usually lethal. Other polymorphisms occur in noncoding regions but can exert phenotypic effects indirectly via influence on replication, transcription, and translation. A single polymorphism can affect more than one phenotypic trait. Likewise, a single phenotypic trait can be affected by polymorphisms in different genes. Further, some polymorphisms predispose an individual to a distinct mutation that is causally related to a certain phenotype.

Phenotypic traits include diseases that have known but hitherto unmapped genetic components (e.g., agammaglobulimenia, diabetes insipidus, Lesch-Nyhan syndrome, muscular dystrophy, Wiskott-Aldrich syndrome, Fabry's disease, familial hypercholesterolemia, polycystic kidney disease, hereditary spherocytosis, von Willebrand's disease, tuberous sclerosis, hereditary hemorrhagic telangiectasia, familial colonic polyposis, Ehlers-Danlos syndrome, osteogenesis imperfecta, and acute intermittent porphyria). Phenotypic traits also include symptoms of, or susceptibility to, multifactorial diseases of which a component is or might be genetic, such as autoimmune diseases, inflammation, cancer, diseases of the nervous system, cardiovascular disease and infection by pathogenic microorganisms. Some examples of autoimmune diseases include rheumatoid arthritis, multiple sclerosis, diabetes (insulin-dependent and non-independent), systemic lupus erythematosus and Graves disease. Some examples of cancers include cancers of the bladder, brain, breast, colon, esophagus, kidney, leukemia, liver, lung, oral cavity, ovary, pancreas, prostate, skin, stomach and uterus. Phenotypic traits also include characteristics such as longevity, appearance (e.g., baldness, obesity), strength, speed, endurance, fertility, decreased risk for a condition, and susceptibility or receptivity to particular drugs or therapeutic treatments.

The correlation of one or more polymorphisms with phenotypic traits can be facilitated by knowledge of the gene product of the wildtype (reference) gene. The genes in which SNPs of the present invention have been identified are genes that have been previously sequenced and characterized in one of their allelic forms. Thus, the SNPs of the invention can be used to identify correlations between one or another allelic form of the gene with a disorder with which the gene is associated, thereby identifying causative or predictive allelic forms of the gene.

Correlation can be performed for a population of individuals who have been tested for the presence or absence of a phenotypic trait of interest and for polymorphic markers sets. To perform such analysis, the presence or absence of a set of polymorphisms (i.e. a polymorphic set) is determined for a set of the individuals, some of whom exhibit a particular trait, and some of whom exhibit lack of the trait. The alleles of each polymorphism of the set are then reviewed to determine whether the presence or absence of a particular allele is associated with the trait of interest. Correlation can be performed by standard statistical methods such as a Chi-squared test and statistically significant correlations between polymorphic form(s) and phenotypic characteristics are noted. For example, it might be found that the presence of allele A1 at polymorphism A correlates with heart disease. As a further example, it might be found that the combined presence of allele A1 at polymorphism A and allele B1 at polymorphism B correlates with increased milk production of a farm animal.

Such correlations can be exploited in several ways. In the case of a strong correlation between a set of one or more polymorphic forms and a disease for which treatment is available, detection of the polymorphic form set in a human or animal patient might justify immediate administration of treatment, or at least the institution of regular monitoring of the patient. Detection of a polymorphic form correlated with serious disease in a couple contemplating a family might also be valuable to the couple in their reproductive decisions. For example, the female partner might elect to undergo in vitro fertilization to avoid the possibility of transmitting such a polymorphism from her husband to her offspring. In the case of a weaker, but still statistically significant correlation between a polymorphic set and human disease, immediate therapeutic intervention or monitoring might not be justified. Nevertheless, the patient can be motivated to begin simple life-style changes (e.g., diet, exercise) that can be accomplished at little cost to the patient but confer potential benefits in reducing the risk of conditions to which the patient might have increased susceptibility by virtue of variant alleles. Identification of a polymorphic set in a patient correlated with enhanced receptiveness to one of several treatment regimes for a disease indicates that this treatment regime should be followed.

Genetic Mapping of Phenotypic Traits

Another application of the present invention comprises identification of a physical linkage between a genetic locus associated with a trait of interest and polymorphic markers that are not associated with the trait, but are in physical proximity with the genetic locus responsible for the trait and cosegregate with it. Such analysis is useful for mapping a genetic locus associated with a phenotypic trait to a chromosomal position, and thereby cloning gene(s) responsible for the trait (see, e.g., Lander et al., (1986) *Proc. Natl. Acad. Sci. USA* 83:7353-7357; Lander et al., (1987) *Proc. Natl. Acad. Sci. USA* 84:2363-2367; Donis-Keller et al., (1987) *Cell* 51:319-337; and Lander et al., (1989) *Genetics* 121: 185-1999, incorporated herein by reference). Genes localized by linkage can be cloned by a process known as directional cloning (Winwright, (1993) *Med. J. Australia* 159:170-174; Collins, (1992) *Nature Genetics* 1:3-6, incorporated herein by reference).

Linkage studies are typically performed on members of a family. Available members of the family are characterized for the presence or absence of a phenotypic trait and for a set of polymorphic markers. The distribution of polymorphic markers in an informative meiosis is then analyzed to determine which polymorphic markers cosegregate with a phenotypic trait (see, e.g., Kerem et al., (1989) *Science* 245:1073-1080; Monaco et al., (1985) *Nature* 316:842; Yamoka et al., (1990) *Neurology* 40:222-226 (1990); Rossiter et al., (1991) *FASEB J.* 5:21-27).

Linkage is analyzed by calculation of LOD (log of the odds) values. A LOD value is the relative likelihood of obtaining observed segregation data for a marker and a genetic locus when the two are located at a recombination fraction θ, versus the situation in which the two are not linked, and thus segregating independently (Thompson & Thompson, *Genetics in Medicine* ($5^{th}$ ed.) W.B. Saunders Company, Philadelphia, Pa., USA (1991); Strachan, in *The Human Genome,* BIOS Scientific Publishers Ltd, Oxford, UK, Chapter 4). A series of likelihood ratios are calculated at various recombination fractions (θ), ranging from θ=0.0 (coincident loci) to θ=0.50 (unlinked). Thus, the likelihood that a given value of θ is the ratio of the probability of data if loci linked at θ to the probability of data if loci are unlinked. The computed likelihoods are usually expressed as the log10 of this ratio (i.e., a LOD score). For example, a LOD score of 3 indicates 1000:1 odds against an apparent observed linkage being a coincidence. The use of logarithms allows data collected from different families to be combined by simple algorithm. Computer programs are available for the calculation of LOD scores for differing values of θ (e.g., LIPED, MLINK (Lathro, (1984) *Proc. Nat. Acad. Sci. USA* 81:3443-3446). For any particular LOD score, a recombination fraction can be determined from mathematical tables (see Smith et al., *Mathematical Tables For Research Workers In Human Genetics,* Churchill, London, UK, (1961); Smith, (1968) *Ann. Hum. Genet.* 32:127-150). The value of θ at which the LOD score is the highest is considered to be the best estimate of the recombination fraction. Positive LOD score values suggest that the two loci are linked, whereas negative values suggest that linkage is less likely (at that value of θ) than the possibility that the two loci are unlinked. By convention, a combined LOD score of +3 or greater (equivalent to greater than 1000:1 odds in favor of linkage) is considered definitive evidence that two loci are linked. Similarly, by convention, a negative LOD score of −2 or less is taken as definitive evidence against linkage of the two loci being compared. Negative linkage data are useful in excluding a chromosome or a segment thereof from consideration. The search focuses on the remaining non-excluded chromosomal locations.

Haplotype-Based Genetic Analysis

The invention further provides methods of applying the polynucleotides and polypeptides of the present invention to the elucidation of haplotypes. Such haplotypes can be associated with any one or more of the conditions described herein (e.g., susceptibility to cardiovascular disease, etc.). A "haplotype" is defined as the pattern of a set of alleles of single nucleotide polymorphisms along a chromosome. For example, consider the case of three single nucleotide polymorphisms (SNP1, SNP2, and SNP3) in one chromosome region, of which SNP1 is an A/G polymorphism, SNP2 is a G/C polymorphism, and SNP3 is an A/C polymorphism. A and G are the alleles for the first, G and C for the second and A and C for the third SNP. Given two alleles for each SNP, there are three possible genotypes for individuals at each SNP. For example, for the first SNP, A/A, A/G and G/G are the possible genotypes for individuals. When an individual has a genotype for a SNP in which the alleles are not the same, for example A/G for the first SNP, then the individual is a heterozygote. When an individual has an A/G genotype at SNP1, G/C genotype at SNP2, and A/C genotype at SNP3, there are four possible combinations of haplotypes (A, B, C, and D) for this individual. The set of SNP genotypes of this individual alone would not provide sufficient information to resolve which combination of haplotypes this individual possesses. However, when this individual's parents' genotypes are available, haplotypes could then be assigned unambiguously. For example, if one parent had an A/A genotype at SNP1, a G/C genotype at SNP2, and an A/A genotype at SNP3, and the other parent had an A/G genotype at SNP1, C/C genotype at SNP2, and C/C genotype at SNP3, while the child was a heterozygote at all three SNPs, there is only one possible haplotype combination, assuming there was no crossing over in this region during meiosis.

When the genotype information of relatives is not available, haplotype assignment can be done using the long range-PCR method (Clark, (1990) *Mol. Biol. Evol.* 7(2):

111-22; Clark et al., (1998) *Am. J. Hum. Genet.* 63(2): 595-612; Fullerton et al., (2000) *Am. J. Hum. Genet.* 67(4): 881-900; Templeton et al., (2000) *Am. J. Hum. Genet.* 66(1):69-83, incorporated herein by reference). When the genotyping result of the SNPs of interest are available from general population samples, the most likely haplotypes can also be assigned using statistical methods (Excoffier & Slatkin, (1995) *Mol. Biol. Evol.* 12(5):921-7; Fallin & Schork, (2000) *Am. J. Hum. Genet.* 67(4):947-59; Long et al., (1995) *Am. J. Hum. Genet.* 56(3):799-810).

Once an individual's haplotype in a certain chromosome region (i.e., locus) has been determined, it can be used as a tool for genetic association studies using different methods, which include, for example, haplotype relative risk analysis (Knapi, et al., (1993) *Am. J. Hum. Genet.* 52(6):1085-93; Li et al., (1998) *Schizophr. Res.* 32(2):87-92; Matise, (1995) *Genet. Epidemiol.*12(6):641-5; Ott, (1989) *Genet. Epidemiol.* 6(1):127-30; Terwilliger & Ott, (1992) *Hum. Hered.* 42(6):337-46). Haplotype based genetic analysis, using a combination of SNPs, provides increased detection sensitivity, and hence statistical significance, for genetic associations of diseases, as compared to analyses using individual SNPs as markers. Multiple SNPs present in a single gene or a continuous chromosomal region are useful for such haplotype-based analyses.

Kits

The present invention further provides kits comprising at least one agent for identifying which alleleic form of the SNPs identified herein is present in a sample. For example, suitable kits can comprise at least one antibody specific for a particular protein or peptide encoded by one alleleic form of the gene, or allele-specific oligonucleotide as described herein. In one embodiment, a kit of the present invention comprises one or more pairs of allele-specific oligonucleotides hybridizing to different forms of a polymorphism. In another embodiment of a kit, the allele-specific oligonucleotides are provided immobilized on a substrate or support. For example, the same substrate or support can comprise allele-specific oligonucleotide probes for detecting one or more of the polymorphisms described in the Sequence Listing and/or the Figures and/or in the present disclosure. Optional additional components of the kit can include, for example, restriction enzymes, reverse-transcriptase or polymerase, substrate nucleoside triphosphates, for labeling a molecule (for example, an avidin-enzyme conjugate and enzyme substrate and chromogen if the label is biotin), and buffers for reverse transcription, PCR, or hybridization reactions. A kit can also comprise instructions for using the kit and interpreting the results of an experiment performed using the kit.

Chromosome Identification and Mapping

In one application, the polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can thus be used as a chromosome marker.

In this application, sequences can be mapped to chromosomes by preparing PCR primers (e.g., about 15 to about 25 bp) from the sequences described herein, for example in the Tables and/or Figures and/or Sequence Listing. Primers can be selected using computer analysis so that primers do not span more than one predicted exon in the genomic DNA. These primers are then used for PCR screening of somatic cell hybrids containing individual human chromosomes.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as about 500 or about 600 bases; however, polynucleotides between about 2,000 and about 4,000 bp are typically employed. For a review of this technique, see Verma et al., *Human Chromosomes: a Manual of Basic Techniques,* Pergamon Press, New York, N.Y., USA (1988).

For chromosome mapping, the polynucleotides can be used individually (to mark a single chromosome or a single site on that chromosome) or in panels (for marking multiple sites and/or multiple chromosomes). Representative polynucleotides correspond to the noncoding regions of the cDNAs because the coding sequences are more likely conserved within gene families, thus increasing the chance of cross hybridization during chromosomal mapping.

Linkage Analyses

Once a polynucleotide has been mapped to a precise chromosomal location, the physical position of the polynucleotide can be used in a linkage analysis. Linkage analysis establishes coinheritance between a chromosomal location and presentation of a particular disease. Disease mapping data are known in the art. Assuming a one megabase mapping resolution and one gene per 20 kb, a cDNA precisely localized to a chromosomal region associated with the disease could be one of about 50 to abut 500 potential causative genes.

Thus, once coinheritance is established, differences in the polynucleotide and the corresponding gene between affected and unaffected organisms can be examined. First, visible structural alterations in the chromosomes, such as deletions or translocations, are examined in chromosome spreads or by PCR. If no structural alterations exist, the presence of point mutations are ascertained. A mutation observed in some or all affected organisms, but not in normal organisms, indicates that the mutation might cause the disease. However, complete sequencing of the polypeptide and the corresponding gene from several normal organisms is required to distinguish the mutation from a polymorphism. If a new polymorphism is identified, this polymorphic polypeptide can be used for further linkage analysis.

Assessment of Gene Expression

Furthermore, increased or decreased expression of the gene in affected organisms as compared to unaffected organisms can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an organism and comparing the measured gene expression level with a standard level of polynucleotide expression level, whereby an increase or decrease in the gene expression level compared to the standard is indicative of a disorder.

The term "measuring the expression level of a polynucleotide of the present invention" means qualitatively or quantitatively measuring or estimating the level of the polypeptide of the present invention or the level of the MRNA encoding the polypeptide in a first biological sample either directly (e.g., by determining or estimating absolute protein level or MRNA level) or relatively (e.g., by comparing to the polypeptide level or MRNA level in a second biological sample). For example, the polypeptide level or mRNA level in a first biological sample is measured or estimated and compared to a standard polypeptide level or mRNA level, the standard being taken from a second biological sample obtained from an individual not having the disorder or being determined by averaging levels from a population of organisms not having a disorder. As will be appreciated by those of ordinary skill in the art, once a standard polypeptide level or mRNA level is known, it can be used repeatedly as a standard for comparison.

As used herein the term "biological sample" encompasses any biological sample obtained from an organism, body fluids, cell line, tissue culture, or other source that contains the polypeptide of the present invention or mRNA. As indicated, biological samples include body fluids (such as the following non-limiting examples, sputum, amniotic fluid, urine, saliva, breast milk, secretions, interstitial fluid, blood, serum, spinal fluid, etc.) which contain a polypeptide of the present invention, and other tissue sources found to express a polypeptide of the present invention. Methods for obtaining tissue biopsies and body fluids from organisms are known in the art. Where the biological sample is to include mRNA, a tissue biopsy is a preferred source.

The techniques described herein can be applied in a diagnostic method and/or a kit in which polynucleotides and/or polypeptides are attached to a solid support (e.g., a multi-welled plate or plastic pins). In one exemplary method, the support can be a "gene chip" or a "biological chip" as described in U.S. Pat. Nos. 5,837,832, 5,874,219, and 5,856,174. Further, such a gene chip with polynucleotides of the present invention attached can be used to identify polymorphisms between the polynucleotide sequences, with polynucleotides isolated from a test subject. The knowledge of such polymorphisms (e.g., their location, as well as, their existence) can be beneficial in identifying disease loci for many disorders, including proliferative diseases and conditions. Such a method is described in U.S. Pat. Nos. 5,858,659 and 5,856,104.

In addition to the foregoing, a polynucleotide can be used to control gene expression through triple helix formation or antisense DNA or RNA. Antisense techniques are known (see, e.g., Okano, (1991) *J. Neurochem.* 56:560; *Oligodeoxynucleotides as Antisense Inhibitors of Gene Expression,* CRC Press, Boca Raton, Fla., USA (1988). Triple helix formation is also known, (see, e.g., Lee et al., (1979) *Nucl. Acid Res.* 6:3073; Cooney et al., (1988) *Science* 241:456; and Dervan et al., (1991) *Science* 251:1360). Both methods rely on binding of the polynucleotide to a complementary DNA or RNA. For these techniques, polynucleotides are usually oligonucleotides about 20 to about 40 bases in length and complementary to either the region of the gene involved in transcription (triple helix—Lee et al., (1979) *Nucl. Acid Res.* 6:3073; Cooney et al., (1988) *Science* 241:456; and Dervan et al., (1991) *Science* 251:1360) or to the mRNA itself (antisense—Okano, (1991) *J. Neurochem.* 56:560; *Oligodeoxynucleotides as Antisense Inhibitors of Gene Expression,* CRC Press, Boca Raton, Fla., USA (1988)). Triple helix formation optimally results in a shut-off of RNA transcription from DNA, while antisense RNA hybridization blocks translation of a mRNA molecule into polypeptide. Both techniques are effective in model systems, and the information disclosed herein can be used to design antisense or triple helix polynucleotides in an effort to treat or prevent disease.

Gene Therapy

The polynucleotides of the present invention can also be employed in gene therapy. One goal of gene therapy is to insert a normal gene into an organism having a defective gene, in an effort to correct the genetic defect. The polynucleotides disclosed in the present invention offer an approach to targeting such genetic defects in a highly accurate manner. Another goal is to insert, a new gene that was not present in the host genome, thereby producing a new trait in the host cell. In one example, a polynucleotide sequence of the present invention can be used to construct chimeric RNA/DNA oligonucleotides corresponding to the sequences, specifically designed to induce host cell mismatch repair mechanisms in an organism upon systemic injection, for example (Bartlett et al., (2000) *Nat. Biotech.* 18:615-622). Such RNA/DNA oligonucleotides can be designed to correct genetic defects in certain host strains, and/or to introduce desired phenotypes in the host (e.g., introduction of a specific polymorphism within an endogenous gene corresponding to a polynucleotide of the present invention that can ameliorate and/or prevent a disease symptom and/or disorder, etc.). Alternatively, a polynucleotide sequence of the present invention can be used to construct duplex oligonucleotides corresponding to the sequence, specifically designed to correct genetic defects in certain host strains, and/or to introduce desired phenotypes into the host (e.g., introduction of a specific polymorphism within an endogenous gene corresponding to a polynucleotide of the present invention that can ameliorate and/or prevent a disease symptom and/or disorder, etc). Such methods of using duplex oligonucleotides are known in the art and are encompassed by the present invention (see, e.g., EP 1007712).

One aspect of the present invention is directed to gene therapy methods for treating or preventing disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide that codes for a polypeptide of the invention is operatively linked to a promoter and any other genetic elements necessary for the expression of the polypeptide by the target tissue. Such gene therapy and delivery techniques are known in the art, see, for example, PCT Publication WO 90/11092.

Thus, for example, cells from a patient can be engineered with a polynucleotide (DNA or RNA) comprising a promoter operably linked to a polynucleotide of the invention ex vivo, with the engineered cells then being provided to a patient to be treated with the polypeptide. Such methods are known in the art. For example, see Belldegrun et al., (1993) *J. Natl. Cancer Inst.* 85:207-216; Ferrantini et al., (1993) *Cancer Res.* 53:107-1112; Ferrantini et al., (1994) *J. Immunol.* 153: 604-4615; Kaido et al., (1995) *Int. J. Cancer* 60:221-229; Ogura et al., (1990) *Cancer Res.* 50: 5102-

5106; Santodonato et al., (1996) *Human Gene Therapy* 7:1-10; Santodonato et al., (1997) *Gene Therapy* 4:1246-1255; and Zhang et al., (1996) *Cancer Gene Therapy* 3:31-38). In one embodiment, the cells that are engineered are arterial cells. The arterial cells can be reintroduced into the patient through direct injection to the artery, the tissues surrounding the artery, or through catheter injection.

As described herein, a polynucleotide construct can be delivered by any method that delivers injectable materials to the cells of an animal, such as, injection into the interstitial space of tissues (heart, muscle, skin, lung, liver, and the like). A polynucleotide construct can be delivered in a pharmaceutically acceptable liquid or aqueous carrier.

In one embodiment, a polynucleotide of the present invention is delivered as a naked polynucleotide. The term "naked polynucleotide" refers to a DNA or RNA sequence that is free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art. Such methods are described, for example, in U.S. Pat. Nos. 5,593,972, 5,589,466, and 5,580,859.

A polynucleotide vector construct of the present invention used in the gene therapy method can comprise a construct that will not integrate into the host genome nor will it comprise a sequence that allows for replication. Representative vectors include pWLNEO, pSV2CAT, pOG44, pXT1 and pSG available from Stratagene, La Jolla, Calif., USA; pSVK3, pBPV, pMSG and pSVL available from Pharmacia, Piscataway, N.J., USA; and pEF1/V5, pcDNA3.1, and pRc/CMV2 available from Invitrogen, Carlsbad, Calif., USA. Other suitable vectors will be readily apparent to those of ordinary skill in the art upon consideration of the present disclosure.

Any strong promoter known to those skilled in the art can be used for driving the expression of a polynucleotide sequence of the present invention as a component of a gene therapy method. Representative promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter can also be the native promoter for the polynucleotides of the present invention.

Unlike other gene therapy techniques, one major advantage of introducing a naked nucleic acid sequence into a target cell is the transitory nature of the polynucleotide synthesis in the cells. Studies have shown that non-replicating DNA sequences can be introduced into cells to provide production of a desired polypeptide for periods of up to six months.

A polynucleotide construct of the present invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. The interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. Similarly, the term interstitial also refers to the space occupied by the plasma of the circulation and the lymph fluid of the lymphatic channels.

For the naked nucleic acid sequence injection, an effective dosage amount of DNA or RNA can be, for example, in the range of from about 0.05 mg/kg body weight to about 50 mg/kg body weight. In another example, the dosage can be from about 0.005 mg/kg to about 20 mg/kg and in yet another example, from about 0.05 mg/kg to about 5 mg/kg. Of course, as one of ordinary skill in the art will appreciate, this dosage will vary according to the tissue site of injection. The appropriate and effective dosage of nucleic acid sequence can readily be determined by one of ordinary skill in the art and can depend on the condition being treated and the route of administration.

One representative route of administration is via the parenteral route of injection into the interstitial space of tissues. Other parenteral routes can also be used, however, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns." These delivery methods are known in the art.

The constructs can also be delivered via delivery vehicles such as viral sequences, viral particles, liposome formulations, lipofectin, precipitating agents, etc. Such methods of delivery are known in the art and the applicability of these methods will be known to those of ordinary skill in the art, upon consideration of the present disclosure.

In some embodiments, a polynucleotide construct of the present invention can be complexed in a liposome preparation. Liposomal preparations for use in the instant invention include cationic (positively charged), anionic (negatively charged) and neutral preparations. Sometimes, however, cationic liposomes are preferred because a tight charge complex can be formed between the cationic liposome and the polyanionic nucleic acid. Cationic liposomes have been shown to mediate intracellular delivery of plasmid DNA (Felgner et al., (1987) *Proc. Natl. Acad. Sci. USA* 84:7413-7416); mRNA (Malone et al., (1989) *Proc. Natl. Acad. Sci. USA* 86:6077-6081); and purified transcription factors (Debs et al., (1990) *J. Biol. Chem.* 265:10189-10192), in functional form. Methods of forming liposomes are well known in the art and can be employed in the present invention.

Generally, when forming liposome/nucleic acid complexes, the ratio of DNA to liposomes will be from about 10:1 to about 1:10. Preferably, the ration will be from about 5:1 to about 1:5. More preferably, the ratio will be about 3:1 to about 1:3. Still more preferably, the ratio will be about 1:1.

In certain embodiments, cells are engineered, ex vivo or in vivo, using a retroviral particle containing RNA that comprises a sequence encoding polypeptides of the invention. Retroviruses from which the retroviral plasmid vectors can be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

A retroviral plasmid vector is typically employed to transduce packaging cell lines to form producer cell lines. Examples of packaging cells that can be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, (1990) *Human Gene Therapy* 1:5-14. The vector can transduce the packaging cells through any means known in the art. Such means include, but are not limited to, electroporation, the use of liposomes, and $CaPO_4$ precipitation. In one alternative, the retroviral plasmid vector can be encapsulated into a liposome, or coupled to a lipid, and then administered to a host.

The producer cell line generates infectious retroviral vector particles that include polynucleotide encoding polypeptides of the invention. Such retroviral vector particles can then be employed, to transduce eukaryotic cells, either in vitro or in vivo. The transduced eukaryotic cells will then express polypeptides of the present invention.

In certain other embodiments, cells are engineered, ex vivo or in vivo, with polynucleotides of the invention contained in an adenovirus vector. Adenovirus can be manipulated such that it encodes and expresses polypeptides of the invention, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz et al., (1974) *Am. Rev. Respir. Dis.* 109:233-238). Additionally, adenovirus mediated gene transfer has been demonstrated in a number of instances including transfer of alpha-1-antitrypsin and CFTR to the lungs of cotton rats (Rosenfeld et al., (1991) *Science* 252:431-434; Rosenfeld et al., (1992) *Cell* 68:143-155). Furthermore, extensive studies to attempt to establish adenovirus as a causative agent in human cancer were uniformly negative (Green et al., (1979) *Proc. Natl. Acad. Sci. USA* 76:6606).

Suitable adenoviral vectors useful in the present invention are described, for example, in Kozarsky & Wilson, (1993) *Curr. Opin. Genet. Devel.* 3:499-503; Rosenfeld et al., (1992) *Cell* 68:143-155; Engelhardt et al., (1993) *Human Genet. Ther.* 4:759-769; Yang et al., (1994) *Nature Genet.* 7:362-369; Wilson et al., (1993) *Nature* 365:691-692; and U.S. Pat. No. 5,652,224. For example, the adenovirus vector Ad2 is useful and can be grown in human embryonic kidney cells (HEK293 cells). These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

In certain other embodiments, the cells are engineered, ex vivo or in vivo, using an adeno-associated virus (AAV). AAVs are naturally occurring defective viruses that require helper viruses to produce infectious particles (Muzyczka, (1992) *Curr. Topics Microbiol. Immunol.* 158:97). It is also one of the few viruses that can integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct containing polynucleotides of the invention is inserted into the AAV vector using standard cloning methods, such as those found in Sambrook et al., *Molecular Cloning: A Laboratory Manual, (3rd ed.)* Cold Spring Harbor Laboratory Press, Cold Spring Harbor, N.Y., USA (2001). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles that contain the polynucleotide construct of the invention. These viral particles are then used to transduce eukaryotic cells, either ex vivo or in vivo. The transduced cells will contain the polynucleotide construct integrated into its genome, and will express the desired gene product.

Another method of gene therapy involves operably associating heterologous control regions and endogenous polynucleotide sequences (e.g. encoding the polypeptide sequence of interest) via homologous recombination (see, e.g., U.S. Pat. No. 5,641,670; PCT Publications WO 96/29411 and WO 94/12650; Koller et al., (1989) *Proc. Natl. Acad. Sci. USA* 86:8932-8935; and Zijistra et al., (1989) *Nature* 342:435-438. This method involves the activation of a gene which is present in the target cells, but which is not normally expressed in the cells, or is expressed at a lower level than desired.

Polynucleotide constructs are made, using standard techniques known in the art, that contain the promoter with targeting sequences flanking the promoter. Suitable promoters are described herein and are known in the art. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. In one arrangement, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. Such methods are described in more detail herein.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotides encoding polypeptides of the present invention can be administered along with another polynucleotide encoding a protein(s) of interest.

In one embodiment, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence can be homologous or heterologous to the polynucleotide of interest and can be homologous or heterologous to the cells to be transfected. Additionally, the signal sequence can be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, BIOLISTIC injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al., (1989) *Science* 243:375).

A desirable method of local administration is by direct injection. For example, a recombinant molecule of the present invention complexed with a delivery vehicle is administered by direct injection into or locally within the area of arteries. Administration of a conmposition locally within the area of arteries refers to injecting the composition within centimeters and preferably, millimeters of an artery.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration include recombinant molecules of the present invention complexed to a targeted delivery vehicle of the present invention. Suitable delivery vehicles for use with systemic administration comprise liposomes comprising ligands for targeting the vehicle to a particular site.

Representative methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., (1992) *Proc. Natl. Acad. Sci. USA* 189:11277-11281). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, for example to mammals and birds. Representative mammals include humans, dogs, cats, mice, rats, rabbits sheep, cattle, horses, pigs, and particularly humans.

Thus, the present invention provides a method of treating or preventing diseases, disorders, and/or conditions, including but not limited to the diseases, disorders and/or conditions listed herein, associated with overexpression of a polynucleotide of the present invention by administering to a patient (a) an antisense molecule directed to a polynucleotide of the present invention, and/or (b) a ribozyme directed to a polynucleotide of the present invention.

Identification of an Organism and/or Tissue Type

The polynucleotides of the present invention are also useful for identifying organisms in minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an organism's genome. These sequences can be used to prepare PCR primers for amplifying and isolating such selected DNA, which can then be sequenced. Using this technique, organisms can be identified because each organism will have a unique set of DNA sequences. Once a unique ID database is established for an organism, positive identification of that organism, living or dead, can be made from extremely small samples. Similarly, polynucleotides of the present invention can be used as polymorphic markers, in addition to, the identification of transformed or non-transformed cells and/or tissues.

There is also a need for reagents capable of identifying the source of a particular tissue. Such need arises, for example, when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination. Moreover, as mentioned above, such reagents can be used to screen and/or identify transformed and non-transformed cells and/or tissues.

Thus, the present invention comprises a method of identifying the species, tissue or cell type of a biological sample, the method comprising detecting a nucleic acid molecule in the sample, if any, comprising a nucleotide sequence containing one or more polymorphic positions and corresponding to, or derived from, a sequence described herein, for example in the Tables and/or Figures and/or Sequence Listing, and fragments thereof.

Another representative embodiment comprises a method of identifying the species, tissue or cell type of a biological sample comprising detecting polypeptide molecules in the sample, if any, comprising an amino acid sequence comprising one or more polymorphic positions and is derived from, or corresponds to, a sequence selected from the group consisting of an amino acid sequence described herein, for example in the Tables and/or Figures and/or Sequence Listing.

In any of the methods of the present invention, the step of detecting a polypeptide molecule can comprise using an antibody.

The method for identifying the species, tissue or cell type of a biological sample can comprise a step of detecting nucleic acid molecules comprising a nucleotide sequence in a panel of at least two nucleotide sequences, wherein at least one sequence in the panel contains one or more polymorphic positions to a sequence selected from the group.

In yet another application, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Representative Applications of the Polypeptides of the Present Invention

A polypeptide of the present invention can be employed in a range of applications. The following descriptions are exemplary and non-limiting; techniques for carrying out the following applications are known in the art and will be apparent to those of ordinary skill in the art upon consideration of the present disclosure and the novel nucleotide and polypeptide sequences described herein. Additional applications for the polypeptides of the present invention will become apparent to those of ordinary skill in the art upon consideration of the present disclosure.

As described herein, a polypeptide of the present invention can be produced recombinantly. Thus, in one embodiment the present invention comprises a method of making an isolated polypeptide comprising culturing a recombinant host cell of the present invention under conditions such that the polypeptide is expressed and recovering the polypeptide. Another representative embodiment comprises this method of making an isolated polypeptide, wherein the recombinant host cell is a eukaryotic cell and the polypeptide is a protein comprising an amino acid sequence selected from the group consisting of: an amino acid sequence described herein, for example in the Tables and/or Figures and/or Sequence Listing, and fragments thereof. The isolated polypeptide produced by this method is also an aspect of the present invention.

In one embodiment the present invention comprises a method for detecting, in a biological sample comprising a polypeptide, a polypeptide comprising an amino acid sequence comprising one or more polymorphic positions and is derived from, or corresponds to, a sequence described herein, for example in the Tables and/or Figures and/or Sequence Listing, and fragments thereof, the method comprising comparing an amino acid sequence of at least one polypeptide molecule in the sample with a sequence selected from the group and determining whether the sequence of said polypeptide molecule in said sample containing one or more polymorphic positions and is derived from, or corresponds to a sequence of the group.

In another embodiment the present invention comprises the above method wherein the comparing comprises determining the extent of specific binding of a polypeptide in the sample to an antibody that binds specifically to a polypeptide comprising an amino acid sequence containing one or more polymorphic positions and is derived from, or corresponds to, a sequence selected from the group consisting of: an amino acid sequence described herein, for example in the Tables and/or Figures and/or Sequence Listing, and fragments thereof.

Polypeptides of the present invention can also be used to treat, prevent, and/or diagnose disease. For example, patients can be administered a polypeptide of the present invention in an effort to replace absent or decreased levels of the polypeptide, to supplement absent or decreased levels of a different polypeptide (e.g., hemoglobin S for hemoglobin B, SOD, catalase, DNA repair proteins), to inhibit the activity of a polypeptide (e.g., an oncogene or tumor suppressor), to activate the activity of a polypeptide (e.g., by binding to a receptor), to reduce the activity of a membrane bound receptor by competing with it for free ligand, or to bring about a desired response.

Antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (or a membrane-bound receptor).

Further, a polypeptide of the present invention can be used as molecular weight markers on SDS-PAGE gels or on molecular sieve gel filtration columns using methods known to those of skill in the art. Polypeptides can also be used to raise antibodies, which in turn are used to measure protein expression from a recombinant cell, as a way of assessing transformation of the host cell.

A polypeptide of the present invention can also be used to screen for molecules that bind to the polypeptide, or for molecules to which the polypeptide binds. The binding of the polypeptide and the molecule can activate (agonist), increase, inhibit (antagonist), or decrease activity of the polypeptide or the molecule bound. Examples of such molecules include antibodies, oligonucleotides, proteins (e.g., receptors), or small molecules.

In some cases, it is desirable that, the molecule is closely related to a natural ligand of the polypeptide, e.g., a fragment of the ligand, or a natural substrate, a ligand, a structural or functional mimetic (see, Coligan et al., (1991) *Current Protocols in Immunology* 1(2):Chapter 5). Similarly, the molecule can be closely related to the natural receptor to which the polypeptide binds, or at least, a fragment of the receptor capable of being bound by the polypeptide (e.g., active site). In either case, the molecule can be rationally designed using known techniques.

Screening for these molecules can involve producing cells that express the polypeptide, either as a secreted protein or on the cell membrane. Representative cells include cells from mammals, yeast, *Drosophila,* or *E. coli.* Cells expressing the polypeptide (or cell membrane containing the expressed polypeptide) are then contacted with a test compound potentially containing the molecule to observe binding, stimulation, or inhibition of activity of either the polypeptide or the molecule.

The assay can simply test binding of a candidate compound to the polypeptide, wherein binding is detected by a label, or in an assay involving competition with a labeled competitor. Further, the assay can test whether the candidate compound results in a signal generated by binding to the polypeptide.

Alternatively, the assay can be carried out using cell-free preparations, polypeptide/molecule affixed to a solid support, chemical libraries, or natural product mixtures. The assay can also simply comprise the steps of mixing a candidate compound with a solution containing a polypeptide, measuring polypeptide/molecule activity or binding, and comparing the polypeptide/molecule activity or binding to a standard.

In one example, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan et al., (1991) *Current Protocols in Immunology* 1 (2):Chapter 5). For example, expression cloning is employed wherein polyadenylated RNA is prepared from a cell responsive to the polypeptides, for example, NIH3T3 cells which are known to contain multiple receptors for the FGF family proteins, and S.C-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clone that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") can be employed to modulate the activities of polypeptides of the invention thereby effectively generating agonists and antagonists of polypeptides of the invention. See generally, U.S. Pat. Nos. 5,605,793, 5,811,238, 5,830,721, 5,834,252, and 5,837,458, and Patten et al., (1997) *Curr. Opinion Biotechnol.* 8:724-33; Harayama, (1998) *Trends Biotechnol.* 16 (2):76-82; Hansson et al., (1999) *J. Mol. Biol.* 287:265-76; and Lorenzo & Blasco, (1998) *Biotechniques* 24(2):308-13. In one embodiment, alteration of polynucleotides and corresponding polypeptides of the invention can be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention can be altered by being subjected to random mutagenesis by error-prone. PCR, random nucleotide insertion or other methods prior to recombination. In another embodiment, one or more components, motifs, sections, parts, domains, fragments, etc., of the polypeptides of the invention can be recombined with one or more components, motifs, sections, parts, domains, fragments, etc. of one or more heterologous molecules. In some representative embodiments, the heterologous molecules are family members. In further representative embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic (dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments can include an improved desired activity, or a decreased abnormal activity.

Additionally, the present invention provides a method of screening compounds to identify those that modulate the action of the polypeptide of the present invention. An example of such an assay comprises combining a mammalian fibroblast cell, a polypeptide of the present invention, a compound to be screened and $^{3}$[H] thymidine under cell culture conditions where the fibroblast cell would normally proliferate. A control assay can be performed in the absence of the compound to be screened and compared to the amount of fibroblast proliferation in the presence of the compound to determine if the compound stimulates proliferation by determining the uptake of $^{3}$[H] thymidine in each case. The amount of fibroblast cell proliferation is measured by liquid scintillation chromatography, which measures the incorporation of $^{3}$[H] thymidine. Both agonist and antagonist compounds can be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/ molecule. Moreover, the assays can discover agents that might inhibit or enhance the production of the polypeptides of the invention from suitably manipulated cells or tissues. Therefore, the invention includes a method of identifying compounds that bind to a polypeptide of the present invention comprising the steps of: (a) incubating a candidate binding compound with a polypeptide of the present invention; and (b) determining if binding has occurred. Moreover, the invention includes a method of identifying agonists/antagonists comprising the steps of: (a) incubating a candidate compound with the polypeptide, (b) assaying a biological activity, and (c) determining if a biological activity of the polypeptide has been altered.

Another embodiment of the present invention comprises an isolated polypeptide comprising an amino acid sequence containing one or more polymorphic positions and is derived from, or corresponds to an amino acid sequence described herein, for example in the Tables and/or Figures and/or Sequence Listing, and fragments thereof

Diagnosis and Treatment of Diseases and Conditions

In one aspect, the polynucleotides, polypeptides, agonists and/or antagonists of the invention may be useful to treat, prevent, and/or diagnose diseases, disorders, and/or conditions, such as HDL, Type II diabetes, osteoarthritis, osteoporosis, breast cancer, prostate cancer, lung cancers, hypertension, schizophrenia and Alzheimer's disease, for example.

Polypeptides can be administered using any method known in the art, including, but not limited to, direct needle injection at the delivery site, intravenous injection, topical administration, catheter infusion, BIOLISTIC injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides of the invention can be administered as part of a Therapeutic, described in more detail herein. Additional methods of delivering polynucleotides of the invention follow.

In another embodiment, the present invention provides a method of delivering compositions to targeted cells expressing a receptor for a polypeptide of the present invention, or cells expressing a cell bound form of a polypeptide of the invention.

As discussed herein, polypeptides or antibodies of the invention can be associated with heterologous polypeptides, heterologous nucleic acids, toxins, or prodrugs via hydrophobic, hydrophilic, ionic and/or covalent interactions.

In one embodiment, the present invention provides a method for the specific delivery of compositions of the invention to cells by administering polypeptides of the present invention (including antibodies) that are associated with heterologous polypeptides or nucleic acids. In one example, the present invention provides a method for delivering a therapeutic protein into the targeted cell. In another example, the present invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In yet another embodiment, the present invention provides a method for the specific destruction of cells (e.g., the destruction of tumor cells) by administering polypeptides of the invention (e.g., polypeptides of the invention or antibodies of the invention) in association with toxins or cytotoxic prodrugs.

The present invention also comprises a method of diagnosing in a subject a condition associated with a polypeptide or polynucloetide of the present invention, the method comprising detecting in a biological sample obtained from a subject a nucleic acid molecule, if any, comprising a nucleotide sequence comprising one or more polymorphic positions and corresponds to, or is derived from, a sequence described herein, for example in the Tables and/or Figures and/or Sequence Listing, and fragments thereof.

The method for diagnosing a condition can comprise detecting nucleic acid molecules comprising a nucleotide sequence in a panel of at least two nucleotide sequences, wherein at least one sequence in said panel comprises one or more polymorphic positions and is derived from, or corresponds to a sequence selected from the group.

Another representative embodiment of the present invention comprises a method of treating of an individual in need of an increased level of a protein activity comprising administering to the individual a pharmaceutical composition comprising an amount of an isolated polypeptide, polynucleotide, or antibody of the present invention effective to increase the level of said protein activity in said individual.

Yet another representative embodiment comprises a method of treating of an individual in need of a decreased level of a protein activity comprising administering to the individual a pharmaceutical composition comprising an amount of an isolated polypeptide, polynucleotide, or antibody of the present invention effective to increase the level of said protein activity in said individual.

EXAMPLES

The following Examples have been included to illustrate various exemplary modes of the invention. Certain aspects of the following Examples are described in terms of techniques and procedures found or contemplated by the inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the invention.

Example 1

Method of Discovering the Single Nucleotide Polymorphisms (SNPs) of the Present Invention Discovered cDNA's were aligned with their genomic "parent" clones using a computer program employing a BLAST-type algorithm. After the genomic clones were identified (usually AC# clones), the exon/intron boundaries of the gene of interest were then determined. The coding regions of these genes were then sequenced, in addition to any 5' or 3' UTR sequences. Sequencing primers (forward and reverse) were then designed to flank each exon/coding region of the gene using the Primer 3.0 software. Sequencing primers employed are shown in Table 4.

PCR was performed on ABI 9700 machines using the sequencing primers for each exon. PCR conditions were as follows:

1) 94 degrees C. for 2 minutes
2) 94 degrees C. for 30 seconds
3) 59 degrees C. for 1 minute
4) 72 degrees C. for 30 seconds
5) 72 degrees C. for 5 minutes
6) 4 degrees C. hold Steps 2-4 were repeated for 35 cycles.

Twenty-four DNA samples purchased from the Coriell Institute (panel #M24PDR) were employed used to carry out PCR/sequencing. The panel of DNAs comprised varying ethnicity's. Once PCR was complete, the samples were sequenced on ABI 3700 machines.

When sequencing was complete, traces (i.e., the A-G-C-T sequence) were used to visually identify SNPs using a sequencing software program (i.e., Consed or Sequencher). These programs also translated the nucleotide sequence to the amino acid sequence. The nature of the SNP was then identified (i.e., whether the SNP would lead to coding changes in the protein (missense) or if the change was a silent mutation).

Alternative methods for identifying SNPs of the present invention are known in the art. One such method involves resequencing of target sequences from individuals of diverse ethnic and geographic backgrounds by hybridization to probes immobilized to microfabricated arrays. The strategy and principles for the design and use of such arrays are generally described in PCT Publication WO 95/11995.

A typical probe array used in such as analysis would have two groups of four sets of probes that respectively tile both strands of a reference sequence. A first probe set comprises a plurality of probes exhibiting perfect complementarily with one of the reference sequences. Each probe in the first probe set has an interrogation position that corresponds to a nucleotide in the reference sequence. That is, the interrogation position is aligned with the corresponding nucleotide in the reference sequence, when the probe and reference sequence are aligned to maximize complementarily between the two. For each probe in the first set, there are three corresponding probes from three additional probe sets. Thus, there are four probes corresponding to each nucleotide in the reference sequence. The probes from the three additional probe sets would be identical to the corresponding probe from the first probe set except at the interrogation position, which occurs in the same position in each of the four corresponding probes from the four probe sets, and is occupied by a different nucleotide in the four probe sets. In the present analysis, probes were nucleotides long. Arrays tiled for multiple different reference sequences can be included on the same substrate.

Publicly available sequences for a given gene can be assembled into the GAP 4.3 software package. PCR primers covering each exon, could be designed, for example, using the Primer 3 software package. Primers would not be designed in regions where there are sequence discrepancies between reads. Genomic DNA could be amplified from at least two individuals using 2.5 pmol each primer, 1.5 mM $MgCl_2$, 100~M dNTPs, 0.75~M AMPLITAQ GOLD polymerase, and about 19 ng DNA in a 15 μl reaction. Reactions could be assembled using a PACKARD MULTIPROBE robotic pipetting station and then put in MJ 96-well tetrad thermocyclers (96° C. for minutes, followed by cycles of 96° C. for seconds, 59° C. for 2 minutes, and 72° C. for 2 minutes). A subset of the PCR assays for each individual could then be run on 3% NuSieve gels in 0.5×TBE to confirm that the reaction worked.

For a given DNA, 5 μl (about 50 ng) of each PCR or RT-PCR product could be pooled (Final volume=150-200 μl). The products can be purified using QIAQUICK PCR purification from Qiagen. The samples would then be eluted once in 35 μl sterile water and 4 μl 10× One-Phor-All buffer (Pharmacia). The pooled samples are then digested with 0.2μ DNaseI (Promega) for 10 minutes at 37° C. and then labeled with 0.5 nmols biotin-N6-ddATP and 15 μl Terminal Transferase (GibcoBRL Life Technology) for 60 minutes at 37° C. Both fragmentation and labeling reactions could be terminated by incubating the pooled sample for 15 minutes at 100° C.

Low-density DNA chips (Affymetrix) may be hybridized following the manufacturer's instructions. Briefly, the hybridization cocktail consisted of 3M TMACI, mM Tris pH 7.8, 0.01% Triton X-100, 100 mg/ml herring sperm DNA (Gibco BRL), 200 pM control biotin-labeled oligo. The processed PCR products are then denatured for 7 minutes at 100° C. and then added to prewarmed (37° C.) hybridization solution. The chips are hybridized overnight at 44° C. Chips are washed in 1× SSPET and 6× SSPET followed by staining with 2 μg/ml SARPE and 0.5 mg/ml acetylated BSA in 200 μl of 6× SSPET for 8 minutes at room temperature. Chips are scanned using a Molecular Dynamics scanner.

Chip image files may be analyzed using Ulysses (Affymetrix) which uses four algorithms to identify potential polymorphisms. Candidate polymorphisms may be visually inspected and assigned a confidence value: where high confidence candidates display all three genotypes, while likely candidates show only two genotypes (homozygous for reference sequence and heterozygous for reference and variant). Some of the candidate polymorphisms may be confirmed by ABI sequencing. Identified polymorphisms could then be compared to several databases to determine if they are novel.

Example 2

Engineering the Allelic Forms of a Candidate Gene of the Present Invention

Aside from isolating the allelic genes of the present invention from DNA samples obtained from a human population, as described herein, the present invention also encompasses methods of engineering the allelic genes of the present invention through the application of site-directed mutagenesis to the isolated native forms of the genes. Such methodology can applied to synthesize allelic forms of the genes comprising at least one, or more, of the encoding SNPs of the present invention (e.g., silent, missense)—for example at least 1, 2, 3, or 4 encoding SNPs for each gene.

As described herein, the process of isolating a novel allele of the present invention is within the ordinary skill of an artisan trained in the molecular biology arts. Nonetheless, a detailed exemplary method of engineering at least one of the alleles to comprise an encoding and/or non-coding polymorphic nucleic acid sequence, in this case a variant form of a polypeptide of the present invention, is provided. In one example, cDNA clones encoding a protein of the present invention can be identified by homology searches with the BLASTN program (Altschul et al., (1990) *J. Mol. Biol.* 215: 403-10) against a GENBANK non-redundant nucleotide sequence database using published cDNA. After obtaining these clones, they can be sequenced to confirm the validity of the DNA sequences.

Once these clones are confirmed to contain the intact wild type cDNA sequence encoding a polypeptide of the present invention, a polymorphism (mutation) can be introduced into the native sequence using PCR directed in vitro mutagenesis (see, e.g., Cormack & Castano, (2002) *Method. Enzymol.* 350:199-218). In this method, synthetic oligonucleotides are designed to incorporate a point mutation at one end of an amplified fragment. Following PCR, the amplified fragments are made blunt-ended by treatment with Klenow Fragment. These fragments are then ligated and subcloned into a vector to facilitate sequence analysis. This method generally comprises the following steps.

1. Subcloning the cDNA insert into a high copy plasmid vector containing multiple cloning sites and M13 flanking sequences, such as pUC19 (Sambrook et al., *Molecular Cloning: A Laboratory Manual*, ($3^{rd}$ ed.) Cold Spring Harbor Laboratory Press, Cold Spring Harbor, N.Y., USA (2001)), in the forward orientation. Other plasmids can also be employed, and can be desirable in certain circumstances.

2. Introducing a mutation by PCR amplification of the cDNA region downstream of the mutation site using a primer comprising the mutation. (see, e.g., FIG. 8.5.2 in Cormack & Castano, (2002) *Method. Enzymol.* 350:199-218). When introducing a mutation into a polypeptide of the present invention, primers described herein, for example in shown in the Tables and/or Sequence Listing can be employed.

The mutation primer can comprises a codon designed to introduce a mutation. An M13 reverse sequencing primer can be employed and will hybridize to the pUC19 vector. Subcloned cDNA comprising the human wildtype protein is used as a template (described in Step 1 of the present Laboratory Example).

A 100 μl PCR reaction mixture is prepared using 10 ng of the template DNA, 200 μM 4dNTPs, 1 μM primers, 0.25U Taq DNA polymerase (PE), and a standard Taq DNA polymerase buffer. Typical PCR cycling condition are as follows:

20-25 cycles: 45 sec, 93 degrees
  2 min, 50 degrees
  2 min, 72 degrees
1 cycle: 10 min, 72 degrees After the final extension step of PCR, 5U Klenow Fragment is added and incubated for 15 min at 30° C. The PCR product is then digested with the restriction enzyme, EcoRI.

3. Performing PCR amplification of the upstream region, using subcloned cDNA as a template (the product of Step 1). This PCR is done using an M13 forward sequencing primer and a flanking primer, such as those described herein.

The flanking primer is complementary to the upstream flanking sequence of the introduced mutation. The M13 forward sequencing primer hybridizes to the pUC19 vector. PCR conditions and Klenow treatments can be those provided in Step 2, above. The PCR product is then digested with the restriction enzyme, HindIII.

4. Preparing the pUC19 vector for cloning the cDNA comprising the polymorphic site. The pUC19 plasmid DNA is digested with EcoRI and HindII. The resulting digested vector fragment can then be purified using techniques well known in the art, such as gel purification, for example.

5. Combining and ligating the products from Step 2 (PCR product containing mutation), Step 3 (PCR product containing the upstream region), and Step 4 (digested vector), using standard blunt-end ligation conditions (Sambrook et al., *Molecular Cloning: A Laboratory Manual*, ($3^{rd}$ ed.) Cold Spring Harbor Laboratory Press, Cold Spring Harbor, N.Y., USA (2001)).

6. Transforming *E. coli* cells with the resulting recombinant plasmid from Step 5 using methods known in the art, such as, for example, the transformation methods described in Sambrook et al., *Molecular Cloning: A Laboratory Manual*, ($3^{rd}$ ed.) Cold Spring Harbor Laboratory Press, Cold Spring Harbor, N.Y., USA (2001).

7. Analyzing the amplified fragment portion of the plasmid DNA by DNA sequencing to confirm the presence of the point mutation, and the absence of any other mutations introduced during PCR. Techniques and methods of sequencing the insert DNA, including the primers utilized, are described herein or are otherwise known in the art.

Those of ordinary skill in the art will appreciate that the methods of the present Example can be applied to engineering any polymorphic gene of the present invention through the substitution of applicable mutation, flanking, PCR, and sequencing primers for each specific gene and/or polymorphism. Some of these primers can be selected from any one of the applicable primers provided herein, can be designed using the Primer3 program (Rozen & Skaletzky, in *Bioinformatics Methods and Protocols: Methods in Molecular Biology* (Krawetz & Misener, eds.), Humana Press, Totowa, N.J., USA, (2000) pp 365-386), or designed manually, as described. Such primers can comprise at least a portion of any one of the polynucleotide sequences of the present invention.

Moreover, those of ordinary skill in the art will appreciate that the above method can be applied to engineering more than one polymorphic nucleic acid sequence of the present invention. Such an engineered gene can be created through successive rounds of site-directed mutagenesis, as described in Steps 1 through 7 above, or consolidated into a single round of mutagenesis. For example, Step 2 above can be performed for each mutation, then the products of both mutation amplifications can be combined with the product of Step 3 and 4, and the procedure followed as described.

Example 3

Method of Genotyping a SNP of the Present Invention (a) Genomic DNA Preparation Genomic DNA samples for genotyping can be prepared using the PURIGENE™ DNA extraction kit from Gentra Systems (Minneapolis, Minn., USA). After preparation, DNA samples can be diluted to a 2 ng/μl working concentration with TE buffer (10 mM Tris-Cl, pH 8.0, 0.1 mM EDTA, pH 8.0) and stored in 1 ml 96 deep well plates (VWR Scientific Products, West Chester, Pa., USA) at −20° C. until use.

Samples for genomic DNA preparations can be obtained from patients participating in a clinical study, or from other sources known in the art or otherwise described herein.

(b) Genotyping

The SNP genotyping reactions may be performed using the SNPSTREAM™ system (Orchid Bioscience, Princeton, N.J., USA) based on genetic bit analysis (Nikiforov et al., (1994) *Nucl. Acid Res.* 22:4167-75).

The regions including polymorphic sites can be amplified by the polymerase chain reaction (PCR) using a pair of primers (OPERON Technologies, Alameda, Calif.), one of which is phosphorothioated. 6 ml PCR cocktail containing 1.0 ng/μl genomic DNA, 200 μM dNTPs, 0.5 mM forward PCR primer, 0.5 μM reverse PCR primer (phosphorothioated), 0.05 u/μl Platinum Taq DNA polymerase (LifeTechnologies, Rockville, Md.), and 1.5 mM $MgCl_2$ PCR primer pairs that can be used for genotyping analysis are provided herein. The PCR reaction can be set up in 384-well plates (MJ Research, Waltham, Mass.) using a MINITRAK liquid handling station (Packard Bioscience, Meriden, Conn.). The PCR primer sequences can be selected from those provided herein, or any other primer as may otherwise be required. PCR thermocycling may be performed under the following conditions in a MJ Research (Waltham, Mass.) TETRAD machine: step 1, 95 degrees for 2 min; step 2, 94 degrees for 30 min; step 3, 55 degrees for 2 min; step 4, 72 degrees for 30 sec; step 5, go back to step 2 for an additional 39 cycles; step 6, 72 degrees for 1 min; and step 7, 12 degrees indefinitely After thermocycling, the amplified samples can be placed in the SNPSTREAM™ (Orchid Bioscience, Princeton, N.J., USA) machine, and automated genetic bit analysis (GBA) (Nikiforov et al., (1994) *Nucl. Acid Res.* 22:4167-75) reaction can then be performed. The first step of this reaction is degradation of one of the strands of the PCR products by T7 gene 6 exonuclease to make them single-stranded. The strand containing the phosphorothioated primer are resistant to T7 gene 6 nuclease, and were not degraded by this enzyme. After digestion, the single-stranded PCR products are subjected to an annealing step whereby the single stranded PCR products are annealed to the GBA primer on a solid phase, and then subjected to the GBA reaction (single base extension) using dideoxy-NTPs labeled with biotin or fluorescein. GBA primers useful for single base extension are provided in herein. C3 linkers (C3 spacer phosphoramidite) can be incorporated during synthesis of the primer. Such linkers can be commercially obtained, for example from Research Genetics, and Sigma-Genosys, for example. Incorporation of these dideoxynucleotides into a GBA primer are detected by a two color ELISA assay using anti-fluorescein alkaline phosphatase conjugate and anti-biotin horseradish peroxidase. Automated genotype calls are made by GENOPAK™ software (Orchid Bioscience, Princeton, N.J., USA), before manual correction of automated calls are done upon inspection of the resulting allelogram of each SNP.

Example 4

Alternative Method of Genotyping a SNP of the Present Invention

In addition to the methods of genotyping described herein, the skilled artisan could determine the genotype of the polymorphisms of the present invention using the herein described alternative method. This method is referred to as the “GBS method” herein and can be performed as described in conjunction with the teachings described elsewhere herein.

Briefly, the direct analysis of the sequence of the polymorphisms of the present invention can be accomplished by DNA sequencing of PCR products corresponding to the same. PCR amplicons are designed to be in close proximity to the polymorphisms of the present invention using the Primer3 program (Rozen & Skaletzky, in *Bioinformatics Methods and Protocols: Methods in Molecular Biology* (Krawetz & Misener, eds.), Humana Press, Totowa, N.J., USA, (2000) pp 365-386). An M13 Sequence is prepended to each forward PCR primer and an M13 is prepended to each reverse PCR primer. The specific forward and reverse PCR primers for each SNP of the present invention are provided herein.

PCR amplification can be performed on genomic DNA samples amplified from (20 ng) in reactions (50 μl) containing 10 mM Tris-Cl pH 8.3, 50 mM KCl, 2.5 mM $MgCl_2$, 150 μM dNTPs, 3 μM PCR primers, and 3.75 U TAQGOLD DNA polymerase (PE Biosystems, Foster City, Calif.). PCR can then be performed in MJ Research (Waltham, Mass.) TETRAD machines under a cycling condition of 94 degrees 10 min, 30 cycles of 94 degrees 30 sec, 60 degrees 30 sec, and 72 degrees 30 sec, followed by 72 degrees 7 min. PCR products can then be purified using QIAQUICK PCR purification kit (Qiagen), and sequenced by the dye-terminator method using PRISM 3700 automated DNA sequencer (Applied Biosystems, Foster City, Calif.) following the manufacturer’s instruction outlined in the Owner’s Manual (which is hereby incorporated herein by reference in its entirety) or as described in herein.

PCR products are sequenced by the dye-terminator method using the M13 primers above. The genotype can be determined by analysis of the sequencing results at the polymorphic position.

Example 5

Method of Isolating Polymorphic Forms of Candidate Genes of the Present Invention Since the allelic genes of the present invention represent genes present within at least a subset of the human population, these genes can be isolated using the methods provided herein. For example, the source DNA used to isolate the allelic gene can be obtained through a random sampling of the human population and repeated until the allelic form of the gene is obtained. Preferably, random samples of source DNA from the human population are screened using the SNPs and methods of the present invention to identify those sources that comprise the allelic form of the gene. Once identified, such a source can be used to isolate the allelic form of the gene(s). The invention encompasses the isolation of such allelic genes from both genomic and/or cDNA libraries created from such source(s).

Next, lymphoblastoid cell lines from these individuals may be obtained from the Coriell Institute. These cells can be grown in RPMI-1640 medium with L-glutamine plus 10% FCS at 37°. PolyA+ RNA are then isolated from these cells using Oligotex Direct Kit (Life Technologies, Rockville, Md.).

First strand cDNA (complementary DNA) is produced using Superscript Preamplification System for First Strand cDNA Synthesis (Life Technologies, Cat No 18089-011) using these polyA+ RNA as templates, as specified in the users manual which is hereby incorporated herein by reference in its entirety. Specific cDNA encoding the protein of interest is amplified by polymerase chain reaction (PCR) using a forward primer which hybridizes to the 5'-UTR region, a reverse primer which hybridizes to the 3'-UTR region, and these first strand cDNA as templates (Sambrook et al., *Molecular Cloning: A Laboratory Manual*, ($3^{rd}$ ed.) Cold Spring Harbor Laboratory Press, Cold Spring Harbor, N.Y., USA (2001)). For example, the primers specified herein can be used. Alternatively, these primers may be designed using Primer3 program (Rozen & Skaletzky, in *Bioinformatics Methods and Protocols: Methods in Molecular Biology* (Krawetz & Misener, eds.), Humana Press, Totowa, N.J., USA, (2000) pp 365-386). Restriction enzyme sites (example: SalI for the forward primer, and NotI for reverse primer) are added to the 5'-end of these primer sequences to facilitate cloning into expression vectors after PCR amplification. PCR amplification may be performed essentially as described in the owner’s manual of the Expand Long Template PCR System (Roche Molecular Biochemicals) following manufacturer’s standard protocol, which is hereby incorporated herein by reference in its entirety.

PCR amplification products are digested with restriction enzymes (such as SalI and NotI, for example) and ligated with expression vector DNA cut with the same set of restriction enzymes. pSPORT (Invitrogen) is one example of such an expression vector. After ligated DNA is introduced into *E. coli* cells (Sambrook et al., *Molecular Cloning: A Laboratory Manual*, ($3^{rd}$ ed.) Cold Spring Harbor Laboratory Press, Cold Spring Harbor, N.Y., USA (2001)), plasmid DNA is isolated from these bacterial cells. This plasmid DNA is sequenced to confirm the presence an intact (full-length) coding region of the human protein of interest with desired variation using methods known in the art and described elsewhere herein.

The skilled artisan will appreciate that the above method can be applied to the isolation of other novel polymorphic genes of the present invention through the simple substitution of applicable PCR and sequencing primers. Such primers can be selected from any one of the applicable primers provided herein, or may be designed using the Primer3 program (program (Rozen & Skaletzky, in *Bioinformatics Methods and Protocols: Methods in Molecular Biology* (Krawetz & Misener, eds.), Humana Press, Totowa, N.J., USA, (2000)) as described. Such primers can comprise at least a portion of any one of the polynucleotide sequences of the present invention.

Example 6

Alternative Methods of Detecting Polymorphisms Encompassed by the Present Invention (a) Preparation of Samples Polymorphisms are detected in a target nucleic acid from an individual being analyzed. For assay of genomic DNA, virtually any biological sample (other than pure red blood cells) is suitable. For example, convenient tissue samples include whole blood, semen, saliva, tears, urine, fecal material, sweat, buccal, skin and hair. For assay of cDNA or mRNA, the tissue sample must be obtained from an organ in which the target nucleic acid is expressed. For example, if the target nucleic acid is a cytochrome P450, the liver is a suitable source.

Many of the methods described below employ amplification of DNA from target samples. This can be accomplished by employing any or a range of methods, for example PCR. See generally *PCR Technology: Principles and Applications for DNA Amplification*, (Erlich, ed.) Freeman Press, New York, N.Y., (1992); *PCR Protocols: A Guide to Methods and Applications*, (Innis et al., eds.), Academic Press, San Diego, Calif., (1990); Mattila et al., (1991) *Nucl. Acid Res.* 19:4967; Eckert et al., in *PCR Methods and Applications*, Cold Spring Harbor Laboratory Press, Cold Spring Harbor, N.Y. (1991); PCR (McPherson et al., eds) IRL Press, Oxford, UK; and U.S. Pat. No. 4,683,202.

Other suitable amplification methods include the ligase chain reaction (LCR) (see Wu & Wallace, (1989) *Genomics* 4:560, Landegren et al., (1988) *Science* 241:1077, transcription amplification (Kwoh et al., (1989) *Proc. Natl. Acad. Sci. USA* 86:1173, and self-sustained sequence replication (Guatelli et al., (1990) *Proc. Nat. Acad. Sci. USA* 87:1874) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Additional methods of amplification are known in the art or are described elsewhere herein.

(b) Detection of Polymorphisms in Target DNA

There are two distinct types of analysis of target DNA for detecting polymorphisms. The first type of analysis, sometimes referred to as de novo characterization, is carried out to identify polymorphic sites not previously characterized (i.e., to identify new polymorphisms). This analysis compares target sequences in different individuals to identify points of variation, i.e., polymorphic sites. By analyzing groups of individuals representing the greatest ethnic diversity among humans and greatest breed and species variety in plants and animals, patterns characteristic of the most common alleles/haplotypes of the locus can be identified, and the frequencies of such alleles/haplotypes in the population can be determined. Additional allelic frequencies can be determined for subpopulations characterized by criteria such as geography, race, or gender. The de novo identification of polymorphisms of the invention is described in the Examples section.

The second type of analysis determines which form(s) of a characterized (known) polymorphism are present in individuals under test. Additional methods of analysis are known in the art and/or are described elsewhere herein.

1. Allele-Specific Probes

The design and use of allele-specific probes for analyzing polymorphisms is described by, e.g., Saiki et al., (1986) *Nature* 324,163-166; EP 235,726; PCT Publication WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15-mer at the 7 position; in a 16-mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

2. Tiling Arrays

Polymorphisms can also be identified by hybridization to nucleic acid arrays, some examples of which are described in PCT Publication WO 95/11995. The same arrays or different arrays can be used for analysis of characterized polymorphisms. PCT Publication WO 95/11995 also describes sub-arrays that are optimized for detection of a variant form of a precharacterized polymorphism. Such a sub-array contains probes designed to be complementary to a second reference sequence, which is an allelic variant of the first reference sequence. The second group of probes is designed by the same principles as described, except that the probes exhibit complementarity to the second reference sequence. The inclusion of a second group (or further groups) can be particularly useful for analyzing short subsequences of the primary reference sequence in which multiple mutations are expected to occur within a short distance commensurate with the length of the probes (e.g., two or more mutations within 9 to bases).

3. Allele-Specific Primers

An allele-specific primer hybridizes to a site on target DNA overlapping a polymorphism and only primes amplification of an allelic form to which the primer exhibits perfect complementarity. See Gibbs, (1989) *Nucleic Acid Res.* 17:2427-2448. This primer is used in conjunction with a second primer that hybridizes at a distal site. Amplification proceeds from the two primers, resulting in a detectable product which indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing elongation from the primer (see, e.g., PCT Publication WO 93/22456).

4. Direct-Sequencing

The direct analysis of the sequence of polymorphisms of the present invention can be accomplished using either the dideoxy chain termination method or the Maxim-Gilbert method (see Sambrook et al., *Molecular Cloning: A Laboratory Manual*, ($3^{rd}$ ed.) Cold Spring Harbor Laboratory Press, Cold Spring Harbor, N.Y., USA (2001); Zyskind et al., *Recombinant DNA Laboratory Manual*, Academic Press, New York (1988)).

5. Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution (see, e.g., *PCR Technology. Principles and Applications for DNA Amplification*, (Erlich, ed.) W. H. Freeman, New York, N.Y. (1992), Chapter 7).

6. Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., (1989) *Proc. Nat. Acad. Sci. USA* 86:2766-2770. Amplified PCR products can be generated as described above, and heated or otherwise denatured, to form single stranded amplification products. Single-stranded nucleic acids may refold or form secondary structures that are partially dependent on the base sequence. The different electrophoretic mobilities of single-stranded amplification products can be related to base-sequence differences between alleles of target sequences.

7. Single Base Extension

An alternative method for identifying and analyzing polymorphisms is based on single-base extension (SBE) of a fluorescently-labeled primer coupled with fluorescence resonance energy transfer (FRET) between the label of the added base and the label of the primer. Typically, the method employed, such as that described by Chen et al., (Chen et al., (1997) *Proc. Natl. Acad. Sci. USA* 94:10756-61), uses a locus-specific oligonucleotide primer labeled on the 5' terminus with 5-carboxyfluorescein. This labeled primer is designed so that the 3' end is immediately adjacent to the polymorphic site of interest. The labeled primer is hybridized to the locus, and single base extension of the labeled primer is performed with fluorescently-labeled dideoxyribonucleotides (ddNTPs) in dye-terminator sequencing fashion. An increase in fluorescence of the added ddNTP in response to excitation at the wavelength of the labeled primer is used to infer the identity of the added nucleotide.

Example 7

Bacterial Expression of a Polypeptide of the Present Invention

A polynucleotide encoding a polypeptide of the present invention can be amplified using PCR oligonucleotide primers corresponding to the 5' and 3' ends of the DNA sequence, as outlined in the Examples herein or otherwise known in the art, to synthesize insertion fragments. The primers used to amplify the cDNA insert preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen Inc., Chatsworth, Calif., USA). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, that expresses the lacI repressor and also confers kanamycin resistance (Kanr). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 μg/ml) and Kan (25 μg/ml). The O/N culture is used to inoculate a large culture at a ratio of 1:100 to 1:250. The cells are grown to an optical density 600 ($OD_{600}$) of between 0.4 and 0.6. IPTG (isopropyl-B-D-thiogalacto pyranoside) is then added to a final concentration of 1 mM. IPTG induces by inactivating the lacd repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6M guanidine HCl by stirring for 3-4 hours at 4 degree C. The cell debris is removed by centrifugation, and the supernatant containing the polypeptide is loaded onto a nickel-nitrilo-tri-acetic acid (Ni-NTA) affinity resin column (available from QIAGEN, Inc., Chatsworth, Calif., USA). Proteins with a 6× His tag bind to the Ni-NTA resin with high affinity and can be purified in a simple one-step procedure (for details see: "The QIAexpressionist" (1995) QIAGEN, Inc., Chatsworth, Calif., USA).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. T he renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified protein is stored at 4 degree C or frozen at −80 degree C.

Example 8

Purification of a Polypeptide of the Present Invention from an Inclusion Body

The following alternative method can be used to purify a polypeptide expressed in *E coli* when it is present in the form of inclusion bodies. Unless otherwise specified, all of the following steps are conducted at 4-10 degree C.

Upon completion of the production phase of the *E. coli* fermentation, the cell culture is cooled to 4-10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (e.g., such as those available from Microfluidics, Corp. or APV Gaulin, Inc.) twice at 4000-6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5M guanidine hydrochloride (GuHCl) for 2-4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 μm membrane filter with appropriate surface area (e.g., filters available from Filtron, Northboro, Mass.), equilibrated with 40 mM sodium acetate, pH 6.0 is employed. The filtered sample is loaded onto a cation exchange resin (e.g., Poros HS-50, Perseptive Biosystems, Foster City, Calif.). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perceptive Biosystems, Foster City, Calif.) and weak anion (Poros CM-20, Perseptive Biosystems, Foster City, Calif.) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Coomassie blue stained 16% SDS-PAGE gel when 5 μg of purified protein is loaded. The purified protein can also be tested for endotoxin/LPS contamination, and typically the LPS content is less than 0.1 ng/ml according to LAL assays.

Example 9

Cloning and Expression of a Polypeptide of the Present Invention in a Baculovirus Expression System In this example, the plasmid shuttle vector pAc373 is used to insert a polynucleotide into a baculovirus to express a polypeptide. A typical baculovirus expression vector contains the strong polyhedrin promoter of the *Autographa californica* nuclear polyhedrosis virus (AcMNPV) followed by convenient restriction sites, which can include, for example BamHI, Xba I and Asp718. The polyadenylation site of the simian virus 40 (SV40) is often used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pVL941 and pAcIM1, as one of ordinary skill in the art will readily appreciate, as long as the construct provides appropriately located signals for transcription, translation, secretion and the like, including a signal peptide and an in-frame-AUG as required. Such vectors are described, for instance, in Luckow et al., (1989) *Virology* 170:31-39.

A polynucleotide encoding a polypeptide of the present invention is amplified using PCR oligonucleotide primers corresponding to the 5' and 3' ends of the DNA sequence, as outlined in the Examples above or otherwise known in the art, to synthesize insertion fragments. The primers used to amplify the cDNA insert preferably contain restriction sites at the 5' end of the primers in order to clone the amplified product into the expression vector. Specifically, the cDNA sequence contained in the deposited clone, including the AUG initiation codon and the naturally associated leader sequence identified elsewhere herein (if applicable), is amplified using the PCR protocol described herein. If the naturally occurring signal sequence is used to produce the protein, the vector used does not need a second signal peptide. Alternatively, the vector can be modified to include a baculovirus leader sequence, using the standard methods described in Summers et al., "A Manual of Methods for Baculovirus Vectors and Insect Cell Culture Procedures" Texas Agricultural Experimental Station Bulletin No. 1555 (1987).

The amplified fragment is isolated from a 1% agarose gel using a commercially available product (e.g., GENECLEAN™ available from BIO 101 Inc., La Jolla, Calif., USA). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit (e.g., GENECLEAN™ available from BIO 101 Inc., La Jolla, Calif., USA).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif., USA) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five μg of a plasmid containing the polynucleotide is co-transformed with 1.0 μg of a commercially available linearized baculovirus DNA (BACULOGOLD™ baculovirus DNA, Pharmingen, San Diego, Calif., USA), using the lipofection method described by Felgner et al., (1987) *Proc. Natl. Acad. Sci. USA* 84:7413-7417. One μg of BACULOGOLD™ virus DNA and 5 μg of the plasmid are mixed in a sterile well of a microtiter plate containing 50 μl of serum-free Grace's medium (Life Technologies Inc., Gaithersburg, Md., USA). Afterwards, 10 μl lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers et al. (Summers et al., "A Manual of Methods for Baculovirus Vectors and Insect Cell Culture Procedures" Texas Agricultural Experimental Station Bulletin No. 1555 (1987)). An agarose gel with BLUE GAL (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, Md., USA, page 9-10.) After appropriate incubation, blue stained plaques are picked with the tip of a micropipettor (e.g., an EPPENDORF micropipettor). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md., USA). After 42 hours, 5 μCi of $^{35}$S-methionine and 5 μCi $^{35}$S-cysteine (available from Amersham Biosciences, Piscataway, N.J., USA) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein can be used to determine the amino terminal sequence of the produced protein.

Example 10

Expression of a Polypeptide of the Present Invention in Mammalian Cells

A polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Piscataway, N.J., USA), pRSVcat (ATCC 37152), pSV2dhfr (ATCC 37146), pBC12MI (ATCC 67109), pCMVSport 2.0, and pCMVSport 3.0. Mammalian host cells that could be used include, human HeLa, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transformation with a selectable marker such as dhfr, gpt, neomycin, hygromycin allows the identification and isolation of the transformed cells.

The transformed gene can also be amplified to express large amounts of the encoded protein. The DHFR (dihydrofolate reductase) marker is useful in developing cell lines that carry several hundred or even several thousand copies of the gene of interest (See, e.g., Alt et al., (1978) *J. Biol. Chem.* 253:1357-1370; Hamlin & Ma, (1990) *Biochem. Biophys. Acta* 1097:107-143; Page & Sydenham, (1991) *Biotechnology* 9:64-68). Another useful selection marker is the enzyme glutamine synthase (GS) (Murphy et al., (1991) *Biochem. J.* 227:277; Bebbington et al., (1992) *Bio/Technology* 10:169-175). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

A polynucleotide of the present invention is amplified according to the protocol outlined in herein. If the naturally occurring signal sequence is used to produce the protein, the vector does not need a second signal peptide. Alternatively, if the naturally occurring signal sequence is not used, the vector can be modified to include a heterologous signal sequence (see, e.g., PCT Publication WO 96/34891). The amplified fragment is isolated from a 1% agarose gel using a commercially available kit (GENECLEAN® BIO 101

Inc., La Jolla, Calif., USA). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC6 using, for instance, restriction enzyme analysis.

In one example, Chinese hamster ovary cells lacking an active DHFR gene are used for transformation. Five μg of an expression plasmid is cotransformed with 0.5 μg of the plasmid pSVneo using lipofectin (Felgner et al., (1987) *Proc. Natl. Acad. Sci. USA* 84:7413-7417). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100-200 μM. Expression of the desired gene product is analyzed, for instance, by SDS-PAGE and Western blot or by reversed phase HPLC analysis.

Example 11

Production of an Antibody from a Polypeptide of the Present Invention

The antibodies of the present invention can be prepared by a variety of methods (see, e.g., *Current Protocols in Molecular Biology*, (Ausubel et al., eds.), Greene Publishing Associates and Wiley-Interscience, New York (2002), Chapter 2, incorporated herein by reference in its entirety). As one example of such methods, cells expressing a polypeptide of the present invention are administered to an animal to induce the production of sera containing polyclonal antibodies. In a representative method, a preparation of the protein is prepared and purified to render it substantially free of natural contaminants. Such a preparation is then introduced into an animal in order to produce polyclonal antisera of greater specific activity.

In a preferred method, the antibodies of the present invention are monoclonal antibodies (or protein binding fragments thereof). Such monoclonal antibodies can be prepared using hybridoma technology. (Köhler et al., (1975) *Nature* 256:495; Köhler et al., (1976) *Eur. J. Immunol.* 6:511; Köhler et al., (1976) *Eur. J. Immunol.* 6:292; Hammerlins et al., in: *Monoclonal Antibodies and T-Cell Hybridomas*, Elsevier, N.Y., pp. 563-681 (1981), incorporated herein by reference). In general, such procedures involve immunizing an animal (preferably a mouse) with polypeptide or, more preferably, with a polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Wands et al., (1981) *Gastroenterology* 80:225-232). The hybridoma cells obtained through such a selection are then assayed to identify clones that secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention can be used according to the methods disclosed herein. Such fragments are typically produced by proteolytic cleavage, using enzymes such as papain (to produce Fab fragments) or pepsin (to produce F(ab')2 fragments). Alternatively, protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art (see, e.g., Morrison, (1985) *Science* 229:1202; Oi et al., (1986) *BioTechniques* 4:214; U.S. Pat. No. 4,816,567; EP 171496; EP 173494; PCT Publications WO 86/01533 and WO 8702671; Boulianne et al., (1984) *Nature* 312:643; Neuberzer et al., (1985) *Nature* 314:268, incorporated herein by reference).

Moreover, in another representative method, the antibodies directed against the polypeptides of the present invention can be produced in plants. Specific methods are disclosed in U.S. Pat. Nos. 5,959,177, and 6,080,560. These references not only describe methods of expressing antibodies, but also the means of assembling foreign multimeric proteins in plants (i.e., antibodies, etc,), and the subsequent secretion of such antibodies from the plant.

Example 12

Method of Detecting Abnormal Levels of a Polypeptide of the Present Invention in a Biological Sample A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

In one example, antibody-sandwich ELISAs are used to detect polypeptides in a sample, preferably a biological sample. Wells of a microtiter plate are coated with specific antibodies, at a final concentration of 0.2 to 10 μg/ml. The antibodies are either monoclonal or polyclonal and are produced by the method described elsewhere herein. The wells are blocked so that non-specific binding of the polypeptide to the well is reduced.

The coated wells are then incubated for at least two hours at RT with a sample containing the polypeptide. Preferably, serial dilutions of the sample should be used to validate results. The plates are then washed three times with deionized or distilled water to remove unbounded polypeptide.

Next, 50 μl of specific antibody-alkaline phosphatase conjugate, at a concentration of 25-400 ng, is added and incubated for 2 hours at room temperature. The plates are again washed three times with deionized or distilled water to remove unbounded conjugate.

Add 75 μl of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 13

Method of Treatment Using Gene Therapy—Ex Vivo

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask; approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerges. The monolayer is trypsinized and scaled into larger flasks.

pMV-7 (Kirschmeier et al., (1988) *DNA* 7:219-25), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in the Examples herein or otherwise known in the art, using primers and having appropriate restriction sites and initiation/stop codons, if necessary. Preferably, the 5' primer contains an EcoRi site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagle's Medium (DMEM) with 10% calf serum (CS), penicillin and streptomycin. The vector containing the gene and any other desired sequence (e.g., a sequence from a murine sarcoma virus (MSV)) is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a filter (e.g., a Millipore filter) to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on CYTODEX 3 microcarrier beads (Amersham Biosciences, Piscataway, N.J.).

Example 14

Method of Treatment Using Gene Therapy—In Vivo

Another aspect of the present invention comprises using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. A polynucleotide of the present invention may be operatively linked to a promoter or any other genetic elements necessary for the expression of the polypeptide by the target tissue. Such gene therapy and delivery techniques and methods are known in the art, (see, for example, PCT Publications WO 90/11092 and WO 98/11779; U.S. Pat. Nos. 5,693,622, 5,705,151, 5,580,859; Tabata et al., (1997) *Cardiovasc. Res.* 35(3):470-479; Chao et al., (1997) *Pharmacol. Res.* 35(6):517-522; Wolff, (1997) *Neuromuscul. Disord.* 7(5):314-318; Schwartz et al., (1996) *Gene Ther.* 3(5):405-411; Tsurumi et al., (1996) *Circulation* 94 (12):3281-3290, incorporated herein by reference).

The polynucleotide constructs can be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner et al., (1995) *Ann. NY Acad. Sci.* 772:126-139 and Abdallah et al., (1995) *Biol. Cell* 85 (1):1-7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. A preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., about 7 days) muscle extracts are prepared by excising the entire quadriceps. Every fifth 15 μm cross-section of the individual quadriceps muscles is histochemically stained for protein expression. A time course for protein expression can be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 15

Additional Methods of Genotyping the SNPs of the Present Invention

There are a number of methods that may be employed for genotyping a SNP of the present invention. The present invention encompasses the following non-limiting types of genotype assays: PCR-free genotyping methods, single-step homogeneous methods, homogeneous detection with fluorescence polarization, pyrosequencing, "tag" based DNA chip system, bead-based methods, fluorescent dye chemistry, mass spectrometry based genotyping assays, TAQMAN genotype assays, invader genotype assays, and microfluidic genotype assays, among others.

Specifically encompassed by the present invention are the following, non-limiting genotyping methods: Landegren et al., (1998) *Genome Res.* 8:769-776; Kwok, (2000) *Pharmacogenomics* 1:95-100; Gut, (2001) *Hum. Mutat.* 17:475-492; Whitcombe et al., (1998) *Curr. Opin. Biotechnol.* 9:602-608; Tillib & Mirzabekov, (2001) *Curr. Opin. Biotechnol.* 12:53-58; Winzeler et al., (1998) *Science* 281:1194-1197; Lyamichev et al., (1999) *Nat. Biotechnol.* 17:292-296; Hall et al., (2000) *Proc. Natl. Acad. Sci. USA* 97:8272-8277; Mein et al., (2000) *Genome Res.* 10:333-343; Ohnishi et al., (2001) *J. Hum. Genet.* 46:471-477; Nilsson et al., (1994) *Science* 265:2085-2088; Baner et al., (1998) *Nucl. Acid Res.* 26:5073-5078; Baner et al., (2001) *Curr. Opin. Biotechnol.* 12:11-15; Hatch et al., (1999) *Genet. Anal.* 15:35-40; Lizardi et al., (1998) *Nat. Genet.* 19:225-232; Zhong et al., (2001) *Proc. Natl. Acad. Sci. USA* 98:3940-3945; Faruqui et al., (2001) *BMC Genomics* 2:4; Livak, (1999) *Genet. Anal.* 14:143-149; Marras et al., (1999) *Genet. Anal.* 14:151-156; Ranade et al., (2001) *Genome Res.* 11:1262-1268; Myakishev et al., (2001) *Genome Res.* 11:163-169; Beaudet et al., (2001) *Genome Res.* 11:600-608; Chen et al., (1999) *Genome Res.* 9:492-498; Gibson et al., (1997) *Clin. Chem.* 43:1336-1341; Latif et al., (2001) *Genome Res.* 11:436-440; Hsu et al., (2001) *Clin. Chem.* 47:1373-1377; Alderborn et al., (2000) *Genome Res.* 10:1249-1258; Ronaghi et al., (1998) *Science* 281:363-365; Ronaghi, (2001) *Genome Res.* 11:3-11; Pease et al., (1994) *Proc. Natl. Acad Sci. USA* 91:5022-5026; Southern et al., (1993) *Genomics* 13:1008-1017; Wang et al., (1998) *Science* 280:1077-1082; Brown & Botstein, (1999) *Nat. Genet.* 21:33-37; Cargill et al., (1999) *Nat. Genet.* 22:231-238; Dong et al., (2001) *Genome Res.* 11:1418-1424; Halushka et al., (1999) *Nat. Genet.* 22:239-247; Hacia, (1999) *Nat. Genet.* 21:42-47; Lipshutz et al., (1999) *Nat. Genet.* 21:20-24; Sapolsky et al., (1999) Genet. Anal. 14:187-192; Tsuchihashi & Brown, (1994) *J. Virol.* 68: 5863; Herschlag, (1995) *J. Biol. Chem.* 270:20871-20874; Head et al., (1997) *Nucl. Acid Res.* 25:5065-5071; Nikiforov et al., (1994) *Nucl. Acid Res.* 22:4167-4175; Syvanen et al., (1992) *Genomics* 12:590-595; Shumaker et al., (1996) *Hum. Mutat.* 7:346-354; Lindroos et al., (2001) *Nucl. Acids Res.* 29:E69-9; Lindblad-Toh et al., (2000) *Nat. Genet.* 24:381-386; Pastinen et al., (2000) *Genome Res.* 10:1031-1042; Fan et al., (2000) *Genome Res.* 10:853-860 (2000); Hirschhorn et al., (2000) *Proc. Natl. Acad. Sci. USA* 97:12164-12169; Bouchie, (2001) *Nat. Biotechnol.* 19:704; Hensel et al., (1995) *Science* 269:400-403; Shoemaker et al., (1996) *Nat. Genet.* 14:450-456; Gerry et al., (1999) *J. Mol. Biol.* 292:251-262; Ladner et al., (2001) *Lab. Invest.* 81:1079-1086; Iannone et al., (2000) *Cytometry* 39:131-140; Fulton et al., (1997) *Clin. Chem.* 43:1749-1756; Armstrong et al., (2000) *Cytometry* 40:102-108; Cai et al., (2000) *Genomics* 69:395; Chen et al., (2000) *Genome Res.* 10:549-557; Ye et al., (2001) *Hum. Mutat.* 17:305-316; Michael et al., (1998) *Anal. Chem.* 70:1242-1248; Steemers et al., (2000) *Nat. Biotechnol.* 18:91-94; Chan & Nie, (1998) *Science* 281:2016-2018; Han et al., (2001) *Nat. Biotechnol.* 19:631-635; Griffin & Smith, (2000) *Trends Biotechnol.* 18:77-84; Jackson et al., (2000) *Mol. Med. Today* 6:271-276; Haff & Smirnov, (1997) *Genome Res.* 7:378-388; Ross et al., (1998) *Nat. Biotechnol.* 16:1347-1351; Bray et al., (2001) *Hum. Mutat.* 17:296-304; Sauer et al., (2000) *Nucleic Acids Res.* 28:E13; Sauer et al., (2000) *Nucleic Acid Res.* 28:E100; Sun et al., (2000) *Nucleic Acids Res.* 28:E68; Tang et al., (1999) *Proc. Natl. Acad Sci. USA* 91:10016-10020; Li et al., (1999) *Electrophoresis* 20:1258-1265; Little et al., (1997) *Nat. Med.* 3:1413-1416; Little et al., (1997) *Anal. Chem.* 69:4540-4546; Griffin et al., (1997) *Nat. Biotechnol.* 15:1368-1372; Ross et al., (1997) *Anal. Chem.* 69:4197-4202; Jiang-Baucom et al., (1997) *Anal. Chem.* 69:4894-4898; Griffin et al., (1999) *Proc. Natl. Acad Sci. USA* 96:6301-6306; Kokoris et al., (2000) *Mol. Diagn.* 5:329-340; Jurinke, (2001); and/or Taranenko et al., (1996) *Genet. Anal.* 13:87-94, incorporated herein by reference.

Example 16

Method of Genotyping the SNPs of the Present Invention

Genomic DNA samples from subjects with and without a particular condition were evaluated. In one study, 989 subjects were analyzed; 496 were diabetic and 493 were non-diabetics matched for race, age and sex. In another study, 514 subjects were analyzed; 247 had breast cancer and 267 did not; the subjects were matched for race and age. In another study, 595 subjects were analyzed; 322 had lung cancer and 273 did not; the subjects were matched for race, age and sex. In another study, 952 subjects were analyzed; 502 had a melanoma and 450 did not; the subjects were matched for race, age and sex. In one study, 736 subjects were analyzed; 368 had postate cancer and 368 did not; the subjects were matched for race and age. In another study, 575 subjects were analyzed; 294 had undesirable HDL levels and 281 did not; the subjects were matched for race and age. In one study, 614 subjects were analyzed; 322 exhibited hypertension and 292 did not; the subjects were matched for race and age. In another study, 646 subjects were analyzed; 320 were schizophrenic and 326 were not; the subjects were matched for race, age and sex. All subjects gave written informed consent.

Genotyping was performed by Sequenom Inc. using a mass spectrometric method described in Nelson et al., (2004) *Genome Research* 14:1664-1668, which is incorporated by reference herein in its entirety.

Example 17

Statistical Analysis of the Association between Diabetes and the SNPs of the Present Invention The association between diabetes and the single nucleotide polymorphisms of the present invention were investigated by applying statistical analysis to the results of the genotyping assays described elsewhere herein. The central hypothesis of this analysis is that a predisposition to develop diabetes may be conferred by specific genomic factors.

SNPs of the present invention were examined for association with diabetes using 3 (genotypes)×2 (diabetes and no diabetes) contingency tables.

Methods

Measures. Single nucleotide polymorphisms (SNPS) in various human genes were genotyped on all subjects essentially as described in Example 16 herein. The SNPs that were genotyped likely represent a sample of the polymorphic variation in each gene and are not exhaustive with regard to coverage of the total genetic variation that may be present in each gene. Specifically, the SNPs referenced herein were genotyped and statistically analyzed, as described. The SNPs for which a statistical association to diabetes susceptibility was confirmed are provided (see Table 6).

Statistical Analyses. Conditional logistic regression (Hosmer and Lemeshow 2000) was used to examine the associations between genotypes of gene SNPs and the development of diabetes. All SNPs are bi-allelic with three possible genotypes. For each SNP, in the overall sample and each subgroup, allele frequencies are estimated. For consistency in SNP genotype parameter coding in the logistic regression models, the less frequent allele of each SNP was designated as the rare allele and the number of copies of that allele that each subject carried, either 0, 1, or 2, was then determined. Three possible genotypes for each SNP leaves two degrees of freedom for parameters in the conditional logistic regression model representing the information contained in these three genotype categories. Two dummy variables are therefore created based on the copies of the rare allele for each subject for use in the conditional logistic regression model, $x1=1$ if copies of rare allele$=1$, 0 otherwise and $x2=1$ if copies of rare allele$=2$, 0 otherwise.

The full conditional logistic regression model used was $$\pi_k(x) = \frac{e^{\alpha_k + \beta_1' x_1 + \beta_2' x_2}}{1 + e^{\alpha_k + \beta_1' x_1 + \beta_2' x_2}},$$

where x in πk (x) is the vector of dummy variables representing the SNP genotypes described herein, k is the matching stratum index specific to each matched case-control set of subjects, πk (x) is the matching stratum-specific expected probability that a subject is a case given x, αk is the matching stratum-specific contribution to πk (x) of all the matching variables constant within the kth stratum and each β' represents the contribution of the respective dummy variable to πk (x).

For each SNP, the null hypothesis was that the vector of β' are all equal to 0 and was tested using the scores test (Hosmer and Lemeshow 2000). The degrees of freedom for the scores test statistic was equal to one less than the number of genotypes. Exponentiation of each slope coefficient, β', provided an estimate of the ratio of the odds of an adverse event (e.g., diabetes) in subjects carrying the specified copies of the rare allele represented in the definition of the coefficient, relative to controls matched for age, sex, and race, over the odds of such an adverse event for similarly matched subjects not carrying any copies of the rare allele. 95% confidence interval limits are estimated for each odds ratio based on the standard error estimate of the respective slope coefficient.

Since the SNP coverage within the human genes was not exhaustive of the genetic variation that may be present and possibly related to event susceptibility in this gene, inferences about these SNP associations with diabetes events are therefore related to the hypothesis that genetic variation in the studied genes may be involved in susceptibility to such events.

Example 18

Statistical Analysis of the Association between Breast Cancer and the SNPs of the Present Invention The association between breast cancer and the single nucleotide polymorphisms of the present invention were investigated by applying statistical analysis to the results of the genotyping assays described elsewhere herein. The central hypothesis of this analysis is that a predisposition to develop breast cancer may be conferred by specific genomic factors.

SNPs of the present invention were examined for association with breast cancer using 3 (genotypes)×2 (breast cancer and no breast cancer) contingency tables.

Methods

Measures. Single nucleotide polymorphisms (SNPs) in various human genes were genotyped on all subjects essentially as described in Example 16 herein. The SNPs that were genotyped likely represent a sample of the polymorphic variation in each gene and are not exhaustive with regard to coverage of the total genetic variation that may be present in each gene. Specifically, the SNPs referenced herein were genotyped and statistically analyzed, as described. The SNPs for which a statistical association to breast cancer susceptibility was confirmed are provided (see Table 6).

Statistical Analyses. Conditional logistic regression (Hosmer and Lemeshow 2000) was used to examine the associations between genotypes of gene SNPs and the development of breast cancer. All SNPs are bi-allelic with three possible genotypes. For each SNP, in the overall sample and each subgroup, allele frequencies are estimated. For consistency in SNP genotype parameter coding in the logistic regression models, the less frequent allele of each SNP was designated as the rare allele and the number of copies of that allele that each subject carried, either 0, 1, or 2, was then determined. Three possible genotypes for each SNP leaves two degrees of freedom for parameters in the conditional logistic regression model representing the information contained in these three genotype categories. Two dummy variables are therefore created based on the copies of the rare allele for each subject for use in the conditional logistic regression model, x1=1 if copies of rare allele=1, 0 otherwise and x2=1 if copies of rare allele=2, 0 otherwise.

The full conditional logistic regression model used was $$\pi_k(x) = \frac{e^{\alpha_k + \beta_1' x_1 + \beta_2' x_2}}{1 + e^{\alpha_k + \beta_1' x_1 + \beta_2' x_2}},$$

where x in πk (x) is the vector of dummy variables representing the SNP genotypes described herein, k is the matching stratum index specific to each matched case-control set of subjects, πk (x) is the matching stratum-specific expected probability that a subject is a case given x, αk is the matching stratum-specific contribution to πk (x) of all the matching variables constant within the kth stratum and each β' represents the contribution of the respective dummy variable to πk (x).

For each SNP, the null hypothesis was that the vector of β' are all equal to 0 and was tested using the scores test (Hosmer and Lemeshow 2000). The degrees of freedom for the scores test statistic was equal to one less than the number of genotypes. Exponentiation of each slope coefficient, β', provided an estimate of the ratio of the odds of an adverse event (e.g., breast cancer) in subjects carrying the specified copies of the rare allele represented in the definition of the coefficient, relative to controls matched for age and race, over the odds of such an adverse event for similarly matched subjects not carrying any copies of the rare allele. 95% confidence interval limits are estimated for each odds ratio based on the standard error estimate of the respective slope coefficient.

Since the SNP coverage within the human genes was not exhaustive of the genetic variation that may be present and possibly related to event susceptibility in this gene, inferences about these SNP associations with breast cancer events are therefore related to the hypothesis that genetic variation in the studied genes may be involved in susceptibility to such events.

Example 19

Statistical Analysis of the Association between Lung Cancer and the SNPs of the Present Invention The association between lung cancer and the single nucleotide polymorphisms of the present invention were investigated by applying statistical analysis to the results of the genotyping assays described elsewhere herein. The central hypothesis of this analysis is that a predisposition to develop lung cancer may be conferred by specific genomic factors.

SNPs of the present invention were examined for association with lung cancer using 3 (genotypes)×2 (lung cancer and no lung cancer) contingency tables.

Methods

Measures. Single nucleotide polymorphisms (SNPs) in various human genes were genotyped on all subjects essentially as described in Example 16 herein. The SNPs that were genotyped likely represent a sample of the polymorphic variation in each gene and are not exhaustive with regard to coverage of the total genetic variation that may be present in each gene. Specifically, the SNPs referenced herein were genotyped and statistically analyzed, as described. The SNPs for which a statistical association to lung cancer susceptibility was confirmed are provided (see Table 6).

Statistical Analyses. Conditional logistic regression (Hosmer and Lemeshow 2000) was used to examine the associations between genotypes of gene SNPs and the development of lung cancer. All SNPs are bi-allelic with three possible genotypes. For each SNP, in the overall sample and each subgroup, allele frequencies are estimated. For consistency in SNP genotype parameter coding in the logistic regression models, the less frequent allele of each SNP was designated as the rare allele and the number of copies of that allele that each subject carried, either 0, 1, or 2, was then determined. Three possible genotypes for each SNP leaves two degrees of freedom for parameters in the conditional logistic regression model representing the information contained in these three genotype categories. Two dummy variables are therefore created based on the copies of the rare allele for each subject for use in the conditional logistic regression model, x1=1 if copies of rare allele=1, 0 otherwise and x2=1 if copies of rare allele=2, 0 otherwise.

The full conditional logistic regression model used was $$\pi_k(x) = \frac{e^{\alpha_k + \beta_1' x_1 + \beta_2' x_2}}{1 + e^{\alpha_k + \beta_1' x_1 + \beta_2' x_2}},$$

where x in πk (x) is the vector of dummy variables representing the SNP genotypes described herein, k is the matching stratum index specific to each matched case-control set of subjects, πk (x) is the matching stratum-specific expected probability that a subject is a case given x, αk is the matching stratum-specific contribution to πk (x) of all the matching variables constant within the kth stratum and each β' represents the contribution of the respective dummy variable to πk (x).

For each SNP, the null hypothesis was that the vector of β' are all equal to 0 and was tested using the scores test (Hosmer and Lemeshow 2000). The degrees of freedom for the scores test statistic was equal to one less than the number of genotypes. Exponentiation of each slope coefficient, β', provided an estimate of the ratio of the odds of an adverse event (e.g., lung cancer) in subjects carrying the specified copies of the rare allele represented in the definition of the coefficient, relative to controls matched for age, sex and race, over the odds of such an adverse event for similarly matched subjects not carrying any copies of the rare allele. 95% confidence interval limits are estimated for each odds ratio based on the standard error estimate of the respective slope coefficient.

Since the SNP coverage within the human genes was not exhaustive of the genetic variation that may be present and possibly related to event susceptibility in this gene, inferences about these SNP associations with lung cancer events are therefore related to the hypothesis that genetic variation in the studied genes may be involved in susceptibility to such events.

Example 20

Statistical Analysis of the Association between Melanoma and the SNPs of the Present Invention The association between melanoma and the single nucleotide polymorphisms of the present invention were investigated by applying statistical analysis to the results of the genotyping assays described elsewhere herein. The central hypothesis of this analysis is that a predisposition to develop melanoma may be conferred by specific genomic factors.

SNPs of the present invention were examined for association with melanoma using 3 (genotypes)×2 (melanoma and no melanoma) contingency tables.

Methods

Measures. Single nucleotide polymorphisms (SNPs) in various human genes were genotyped on all subjects essentially as described in Example 16 herein. The SNPs that were genotyped likely represent a sample of the polymorphic variation in each gene and are not exhaustive with regard to coverage of the total genetic variation that may be present in each gene. Specifically, the SNPs referenced herein were genotyped and statistically analyzed, as described. The SNPs for which a statistical association to melanoma susceptibility was confirmed are provided (see Table 6).

Statistical Analyses. Conditional logistic regression (Hosmer and Lemeshow 2000) was used to examine the associations between genotypes of gene SNPs and the development of melanoma. All SNPs are bi-allelic with three possible genotypes. For each SNP, in the overall sample and each subgroup, allele frequencies are estimated. For consistency in SNP genotype parameter coding in the logistic regression models, the less frequent allele of each SNP was designated as the rare allele and the number of copies of that allele that each subject carried, either 0, 1, or 2, was then determined. Three possible genotypes for each SNP leaves two degrees of freedom for parameters in the conditional logistic regression model representing the information contained in these three genotype categories. Two dummy variables are therefore created based on the copies of the rare allele for each subject for use in the conditional logistic regression model, x1=1 if copies of rare allele=1, 0 otherwise and x2=1 if copies of rare allele=2, 0 otherwise.

The full conditional logistic regression model used was $$\pi_k(x) = \frac{e^{\alpha_k + \beta_1' x_1 + \beta_2' x_2}}{1 + e^{\alpha_k + \beta_1' x_1 + \beta_2' x_2}},$$

where x in πk (x) is the vector of dummy variables representing the SNP genotypes described herein, k is the matching stratum index specific to each matched case-control set of subjects, πk (x) is the matching stratum-specific expected probability that a subject is a case given x, αk is the matching stratum-specific contribution to πk (x) of all the matching variables constant within the kth stratum and each β' represents the contribution of the respective dummy variable to πk (x).

For each SNP, the null hypothesis was that the vector of β' are all equal to 0 and was tested using the scores test (Hosmer and Lemeshow 2000). The degrees of freedom for the scores test statistic was equal to one less than the number of genotypes. Exponentiation of each slope coefficient, β', provided an estimate of the ratio of the odds of an adverse event (e.g., melanoma) in subjects carrying the specified copies of the rare allele represented in the definition of the coefficient, relative to controls matched for age, sex and race, over the odds of such an adverse event for similarly matched subjects not carrying any copies of the rare allele. 95% confidence interval limits are estimated for each odds ratio based on the standard error estimate of the respective slope coefficient.

Since the SNP coverage within the human genes was not exhaustive of the genetic variation that may be present and possibly related to event susceptibility in this gene, inferences about these SNP associations with melanoma events are therefore related to the hypothesis that genetic variation in the studied genes may be involved in susceptibility to such events.

Example 21

Statistical Analysis of the Association between Prostate Cancer and the SNPs of the Present Invention The association between prostate cancer and the single nucleotide polymorphisms of the present invention were investigated by applying statistical analysis to the results of the genotyping assays described elsewhere herein. The central hypothesis of this analysis is that a predisposition to develop prostate cancer may be conferred by specific genomic factors.

SNPs of the present invention were examined for association with prostate cancer using 3 (genotypes)×2 (prostate cancer and no prostate cancer) contingency tables.

Methods

Measures. Single nucleotide polymorphisms (SNPs) in various human genes were genotyped on all subjects essentially as described in Example 16 herein. The SNPs that were genotyped likely represent a sample of the polymorphic variation in each gene and are not exhaustive with regard to coverage of the total genetic variation that may be present in each gene. Specifically, the SNPs referenced herein were genotyped and statistically analyzed, as described. The SNPs for which a statistical association to prostate cancer susceptibility was confirmed are provided (see Table 6).

Statistical Analyses. Conditional logistic regression (Hosmer and Lemeshow 2000) was used to examine the associations between genotypes of gene SNPs and the development of prostate cancer. All SNPs are bi-allelic with three possible genotypes. For each SNP, in the overall sample and each subgroup, allele frequencies are estimated. For consistency in SNP genotype parameter coding in the logistic regression models, the less frequent allele of each SNP was designated as the rare allele and the number of copies of that allele that each subject carried, either 0, 1, or 2, was then determined. Three possible genotypes for each SNP leaves two degrees of freedom for parameters in the conditional logistic regression model representing the information contained in these three genotype categories. Two dummy variables are therefore created based on the copies of the rare allele for each subject for use in the conditional logistic regression model, x1=1 if copies of rare allele=1, 0 otherwise and x2=1 if copies of rare allele=2, 0 otherwise.

The full conditional logistic regression model used was $$\pi_k(x) = \frac{e^{\alpha_k + \beta_1' x_1 + \beta_2' x_2}}{1 + e^{\alpha_k + \beta_1' x_1 + \beta_2' x_2}},$$

where x in πk (x) is the vector of dummy variables representing the SNP genotypes described herein, k is the matching stratum index specific to each matched case-control set of subjects, πk (x) is the matching stratum-specific expected probability that a subject is a case given x, αk is the matching stratum-specific contribution to πk (x) of all the matching variables constant within the kth stratum and each β' represents the contribution of the respective dummy variable to πk (x).

For each SNP, the null hypothesis was that the vector of β' are all equal to 0 and was tested using the scores test (Hosmer and Lemeshow 2000). The degrees of freedom for the scores test statistic was equal to one less than the number of genotypes. Exponentiation of each slope coefficient, β', provided an estimate of the ratio of the odds of an adverse event (e.g., prostate cancer) in subjects carrying the specified copies of the rare allele represented in the definition of the coefficient, relative to controls matched for age and race, over the odds of such an adverse event for similarly matched subjects not carrying any copies of the rare allele. 95% confidence interval limits are estimated for each odds ratio based on the standard error estimate of the respective slope coefficient.

Since the SNP coverage within the human genes was not exhaustive of the genetic variation that may be present and possibly related to event susceptibility in this gene, inferences about these SNP associations with prostate cancer events are therefore related to the hypothesis that genetic variation in the studied genes may be involved in susceptibility to such events.

Example 22

Statistical Analysis of the Association between Undesirable HDL Levels and the SNPs of the Present Invention The association between undesirable HDL levels and the single nucleotide polymorphisms of the present invention were investigated by applying statistical analysis to the results of the genotyping assays described elsewhere herein. The central hypothesis of this analysis is that a predisposition to develop undesirable HDL levels may be conferred by specific genomic factors.

SNPs of the present invention were examined for association with undesirable HDL levels using 3 (genotypes)×2 (undesirable HDL levels and no undesirable HDL levels) contingency tables.

Methods

Measures. Single nucleotide polymorphisms (SNPs) in various human genes were genotyped on all subjects essentially as described in Example 16 herein. The SNPs that were genotyped likely represent a sample of the polymorphic variation in each gene and are not exhaustive with regard to coverage of the total genetic variation that may be present in each gene. Specifically, the SNPs referenced herein were genotyped and statistically analyzed, as described. The SNPs for which a statistical association to undesirable HDL levels susceptibility was confirmed are provided (see Table 6).

Statistical Analyses. Conditional logistic regression (Hosmer and Lemeshow 2000) was used to examine the associations between genotypes of gene SNPs and the development of undesirable HDL levels. All SNPs are bi-allelic with three possible genotypes. For each SNP, in the overall sample and each subgroup, allele frequencies are estimated. For consistency in SNP genotype parameter coding in the logistic regression models, the less frequent allele of each SNP was designated as the rare allele and the number of copies of that allele that each subject carried, either 0, 1, or 2, was then determined. Three possible genotypes for each SNP leaves two degrees of freedom for parameters in the conditional logistic regression model representing the information contained in these three genotype categories. Two dummy variables are therefore created based on the copies of the rare allele for each subject for use in the conditional logistic regression model, x1=1 if copies of rare allele=1, 0 otherwise and x2=1 if copies of rare allele=2, 0 otherwise.

The full conditional logistic regression model used was $$\pi_k(x) = \frac{e^{\alpha_k + \beta_1' x_1 + \beta_2' x_2}}{1 + e^{\alpha_k + \beta_1' x_1 + \beta_2' x_2}},$$

where x in πk (x) is the vector of dummy variables representing the SNP genotypes described herein, k is the matching stratum index specific to each matched case-control set of subjects, πk (x) is the matching stratum-specific expected probability that a subject is a case given x, αk is the matching stratum-specific contribution to πk (x) of all the matching variables constant within the kth stratum and each β' represents the contribution of the respective dummy variable to πk (x).

For each SNP, the null hypothesis was that the vector of β' are all equal to 0 and was tested using the scores test (Hosmer and Lemeshow 2000). The degrees of freedom for the scores test statistic was equal to one less than the number of genotypes. Exponentiation of each slope coefficient, β', provided an estimate of the ratio of the odds of an adverse event (e.g., undesirable HDL levels) in subjects carrying the specified copies of the rare allele represented in the definition of the coefficient, relative to controls matched for age and race, over the odds of such an adverse event for similarly matched subjects not carrying any copies of the rare allele. 95% confidence interval limits are estimated for each odds ratio based on the standard error estimate of the respective slope coefficient.

Since the SNP coverage within the human genes was not exhaustive of the genetic variation that may be present and possibly related to event susceptibility in this gene, inferences about these SNP associations with undesirable HDL levels events are therefore related to the hypothesis that genetic variation in the studied genes may be involved in susceptibility to such events.

Example 23

Statistical Analysis of the Association between Hypertension and the SNPs of the Present Invention The association between hypertension and the single nucleotide polymorphisms of the present invention were investigated by applying statistical analysis to the results of the genotyping assays described elsewhere herein. The central hypothesis of this analysis is that a predisposition to develop hypertension may be conferred by specific genomic factors.

SNPs of the present invention were examined for association with hypertension using 3 (genotypes)×2 (hypertension and no hypertension) contingency tables.

Methods

Measures. Single nucleotide polymorphisms (SNPs) in various human genes were genotyped on all subjects essentially as described in Example 16 herein. The SNPs that were genotyped likely represent a sample of the polymorphic variation in each gene and are not exhaustive with regard to coverage of the total genetic variation that may be present in each gene. Specifically, the SNPs referenced herein were genotyped and statistically analyzed, as described. The SNPs for which a statistical association to hypertension susceptibility was confirmed are provided (see Table 6).

Statistical Analyses. Conditional logistic regression (Hosmer and Lemeshow 2000) was used to examine the associations between genotypes of gene SNPs and the development of hypertension. All SNPs are bi-allelic with three possible genotypes. For each SNP, in the overall sample and each subgroup, allele frequencies are estimated. For consistency in SNP genotype parameter coding in the logistic regression models, the less frequent allele of each SNP was designated as the rare allele and the number of copies of that allele that each subject carried, either 0, 1, or 2, was then determined. Three possible genotypes for each SNP leaves two degrees of freedom for parameters in the conditional logistic regression model representing the information contained in these three genotype categories. Two dummy variables are therefore created based on the copies of the rare allele for each subject for use in the conditional logistic regression model, x1=1 if copies of rare allele=1, 0 otherwise and x2=1 if copies of rare allele=2, 0 otherwise.

The full conditional logistic regression model used was $$\pi_k(x) = \frac{e^{\alpha_k + \beta_1' x_1 + \beta_2' x_2}}{1 + e^{\alpha_k + \beta_1' x_1 + \beta_2' x_2}},$$

where x in πk (x) is the vector of dummy variables representing the SNP genotypes described herein, k is the matching stratum index specific to each matched case-control set of subjects, πk (x) is the matching stratum-specific expected probability that a subject is a case given x, αk is the matching stratum-specific contribution to πk (x) of all the matching variables constant within the kth stratum and each β' represents the contribution of the respective dummy variable to πk (x).

For each SNP, the null hypothesis was that the vector of β' are all equal to 0 and was tested using the scores test (Hosmer and Lemeshow 2000). The degrees of freedom for the scores test statistic was equal to one less than the number of genotypes. Exponentiation of each slope coefficient, β', provided an estimate of the ratio of the odds of an adverse event (e.g., hypertension) in subjects carrying the specified copies of the rare allele represented in the definition of the coefficient, relative to controls matched for age and race, over the odds of such an adverse event for similarly matched subjects not carrying any copies of the rare allele. 95% confidence interval limits are estimated for each odds ratio based on the standard error estimate of the respective slope coefficient.

Since the SNP coverage within the human genes was not exhaustive of the genetic variation that may be present and possibly related to event susceptibility in this gene, inferences about these SNP associations with hypertension events are therefore related to the hypothesis that genetic variation in the studied genes may be involved in susceptibility to such events.

Example 24

Statistical Analysis of the Association between Schizophrenia and the SNPs of the Present Invention The association between schizophrenia and the single nucleotide polymorphisms of the present invention were investigated by applying statistical analysis to the results of the genotyping assays described elsewhere herein. The central hypothesis of this analysis is that a predisposition to develop schizophrenia may be conferred by specific genomic factors.

SNPs of the present invention were examined for association with schizophrenia using 3 (genotypes)×2 (schizophrenia and no schizophrenia) contingency tables.

Methods

Measures. Single nucleotide polymorphisms (SNPs) in various human genes were genotyped on all subjects essentially as described in Example 16 herein. The SNPs that were genotyped likely represent a sample of the polymorphic variation in each gene and are not exhaustive with regard to coverage of the total genetic variation that may be present in each gene. Specifically, the SNPs referenced herein were genotyped and statistically analyzed, as described. The SNPs for which a statistical association to schizophrenia susceptibility was confirmed are provided (see Table 6).

Statistical Analyses. Conditional logistic regression (Hosmer and Lemeshow 2000) was used to examine the associations between genotypes of gene SNPs and the development of schizophrenia. All SNPs are bi-allelic with three possible genotypes. For each SNP, in the overall sample and each subgroup, allele frequencies are estimated. For consistency in SNP genotype parameter coding in the logistic regression models, the less frequent allele of each SNP was designated as the rare allele and the number of copies of that allele that each subject carried, either 0, 1, or 2, was then determined. Three possible genotypes for each SNP leaves two degrees of freedom for parameters in the conditional logistic regression model representing the information contained in these three genotype categories. Two dummy variables are therefore created based on the copies of the rare allele for each subject for use in the conditional logistic regression model, x1=1 if copies of rare allele=1, 0 otherwise and x2=1 if copies of rare allele=2, 0 otherwise.

The full conditional logistic regression model used was $$\pi_k(x) = \frac{e^{\alpha_k^+ \beta_1' x_1 + \beta_2' x_2}}{1 + e^{\alpha_k^+ \beta_1' x_1 + \beta_2' x_2}},$$

where x in πk (x) is the vector of dummy variables representing the SNP genotypes described herein, k is the matching stratum index specific to each matched case-control set of subjects, πk (x) is the matching stratum-specific expected probability that a subject is a case given x, αk is the matching stratum-specific contribution to πk (x) of all the matching variables constant within the kth stratum and each β' represents the contribution of the respective dummy variable to πk (x).

For each SNP, the null hypothesis was that the vector of β' are all equal to 0 and was tested using the scores test (Hosmer and Lemeshow 2000). The degrees of freedom for the scores test statistic was equal to one less than the number of genotypes. Exponentiation of each slope coefficient, β', provided an estimate of the ratio of the odds of an adverse event (e.g., schizophrenia) in subjects carrying the specified copies of the rare allele represented in the definition of the coefficient, relative to controls matched for age, sex and race, over the odds of such an adverse event for similarly matched subjects not carrying any copies of the rare allele. 95% confidence interval limits are estimated for each odds ratio based on the standard error estimate of the respective slope coefficient.

Since the SNP coverage within the human genes was not exhaustive of the genetic variation that may be present and possibly related to event susceptibility in this gene, inferences about these SNP associations with schizophrenia events are therefore related to the hypothesis that genetic variation in the studied genes may be involved in susceptibility to such events.

References

The entire disclosure of each document cited (including patents, patent applications, journal articles, abstracts, laboratory manuals, books, or other disclosures) referenced herein is hereby incorporated herein by reference. Further, the hard copy of the Sequence Listing submitted herewith and the corresponding computer readable form are both incorporated herein by reference in their entireties.

It will be clear that the invention may be practiced otherwise than as particularly described in the foregoing description and examples. Numerous modifications and variations of the present invention are possible in light of the above teachings and, therefore, are within the scope of the appended claims. Thus, various details of the present invention can be changed without departing from the scope of the invention. Furthermore, the foregoing description is for the purpose of illustration only and not for purposes of limitation.

TABLE 1

| GENE NAME | GENE ALIAS | SNP NAME | SNP ALIAS | SNP POSITION (wrt REF SEQ) | NT IN REF (PARENT) SEQ | NT IN SNP (VARIANT) SEQ |
|---|---|---|---|---|---|---|
| ENSG00000143297 | BGS-5 | BIOLOGICSNP28 | KR28 | 155383270 | G | A |
| ENSG00000153294 | BMY28 | GPCRSNP104 | KR228 | 47688294 | C | A |
| ENSG00000169962 | BMY30 | GPCRSNP129 | KR252 | 792685 | T | A |
| | BMY33 | GPCRSNP145 | KR268 | 245827762 | C | T |
| ENSG00000165370 | BMY22 | GPCRSNP220 | KR343 | 130682936 | C | T |
| ENSG00000168263 | KalphaM1 | ION_CHANNELSNP153 | KR542 | 2883464 | C | T |
| ENSG00000168263 | KalphaM1 | ION_CHANNELSNP169 | KR558 | 2883675 | C | G |
| ENSG00000151364 | KbetaM1 | ION_CHANNELSNP183 | KR572 | 80053997 | G | A |
| ENSG00000162687 | BMYCH48 | ION_CHANNELSNP7 | KR397 | 194101365 | G | A |
| ENSG00000103023 | DP-24 | PROTEASESNP10 | KR643 | 48713232 | A | G |
| ENSG00000170054 | LSI-1 | PROTEASESNP22 | KR655 | 92443444 | G | T |
| ENSG00000168803 | FL-2 | ENZYMESNP34 | KR66 | 39000206 | T | C |
| ENSG00000168803 | FL-2 | ENZYMESNP36 | KR68 | 39005642 | T | C |
| ENSG00000087253 | GPAT-3 | ENZYMESNP52 | KR84 | 46023533 | G | A |
| ENSG00000169962 | BMY30 | GPCRSNP121 | KR244 | 792683 | A | G |
| ENSG00000143297 | BGS-5 | BIOLOGICSNP23 | KR23 | 155383276 | T | C |

| GENE NAME | REF SEQ | STRANDEDNESS OF PARENT | LOCATION OF SNP |
|---|---|---|---|
| ENSG00000143297 | Human_Chr_1.NCBI_30 | −1 | coding (Val/Ile) |
| ENSG00000153294 | Human_Chr_6.NCBI_30 | 1 | 3'UTR |
| ENSG00000169962 | Human_Chr_1.NCBI_30 | 1 | coding (silent) |
| | Human_Chr_1.NCBI_30 | 1 | coding (silent) |
| ENSG00000165370 | Human_Chr_X.NCBI_30 | 1 | 3'UTR |
| ENSG00000168263 | Human_Chr_9.NCBI_30 | 1 | coding (silent) |
| ENSG00000168263 | Human_Chr_9.NCBI_30 | 1 | coding (Leu/Val) |
| ENSG00000151364 | Human_Chr_11.NCBI_30 | −1 | 3'UTR |
| ENSG00000162687 | Human_Chr_1.NCBI_30 | −1 | Intron |
| ENSG00000103023 | Human_Chr_16.NCBI_30 | 1 | coding (Ser/Gly) |
| ENSG00000170054 | Human_Chr_14.NCBI_30 | 1 | 5'UTR |
| ENSG00000168803 | Human_Chr_15.NCBI_30 | 1 | coding (silent) |
| ENSG00000168803 | Human_Chr_15.NCBI_30 | 1 | coding (silent) |
| ENSG00000087253 | Human_Chr_16.NCBI_30 | 1 | coding (silent) |
| ENSG00000169962 | Human_Chr_1.NCBI_30 | 1 | coding (Ala/Thr) |
| ENSG00000143297 | Human_Chr_1.NCBI_30 | −1 | coding (His/Tyr) |

TABLE 2

| GENE NAME | GENE ALIAS | SNP NAME | SNP ALIAS | POSITION OF MUTATION IN REF AA SEQ | TYPE OF MUTATION | AA IN REF SEQ | REF AA SEQ | AA IN SNP SEQ |
|---|---|---|---|---|---|---|---|---|
| ENSG00000143297 | BGS-5 | BIOLOGICSNP28 | KR28 | 269 | Missense | V | ENSP00000271529 | I |
| ENSG00000153294 | BMY28 | GPCRSNP104 | KR228 | | | | | |
| ENSG00000169962 | BMY30 | GPCRSNP129 | KR252 | 1 | Silent | A | ENSP00000307671 | A |
| | BMY33 | GPCRSNP145 | KR268 | 260 | Silent | G | | G |
| ENSG00000165370 | BMY22 | GPCRSNP220 | KR343 | | | | | |
| ENSG00000168263 | KalphaM1 | ION_CHANNELSNP153 | KR542 | 462 | Silent | D | ENSP00000305105 | D |
| ENSG00000168263 | KalphaM1 | ION_CHANNELSNP169 | KR558 | 533 | Missense | L | ENSP00000305105 | V |
| ENSG00000151364 | KbetaM1 | ION_CHANNELSNP183 | KR572 | | | | | |
| ENSG00000162687 | BMYCH48 | ION_CHANNELSNP7 | KR397 | | | | | |
| ENSG00000103023 | DP-24 | PROTEASESNP10 | KR643 | 182 | Missense | S | ENSP00000219301 | G |
| ENSG00000170054 | LSI-1 | PROTEASESNP22 | KR655 | | | | | |
| ENSG00000168803 | FL-2 | ENZYMESNP34 | KR66 | 30 | silent | T | ENSP00000343499 | T |
| ENSG00000168803 | FL-2 | ENZYMESNP36 | KR68 | | | | | |
| ENSG00000087253 | GPAT-3 | ENZYMESNP52 | KR84 | 303 | silent | L | ENSP00000339518 | L |
| ENSG00000169962 | BMY30 | GPCRSNP121 | KR244 | 1 | missense | A | ENSP00000307671 | T |
| ENSG00000143297 | BGS-5 | BIOLOGICSNP23 | KR23 | 267 | missense | H | ENSP00000271529 | Y |

TABLE 3

| GENE NAME | GENE NAME | GENE ALIAS | SNP NAME | SNP ALIAS | PARENT FLANK LEFT | PFL SEQ ID NO | PARENT FLANK RIGHT | PFR SEQ ID NO |
|---|---|---|---|---|---|---|---|---|
| ENSG | ENSG0 | BGS-5 | BIOLO | KR28 | TCTAGAGCCATTTAC | 1 | TCATATCTGACAGCC | 2 |
| 000001 | 000014 | | GICSN | | ACGTCCAGTGCTGAG | | CGAGATCCTGGATAC | |
| 43297 | 3297 | | P28 | | AGCCAGCTCCTTCCA | | AGGTGCAGAGTAAGT | |
| | | | | | GCCCATCAGCGGGAA | | GTTGGTGGAACCTGA | |
| | | | | | CCCAGTGACCCTGAC | | GATTTGCTGCAGAGA | |
| | | | | | CTGTGAGACCCAGCT | | GGGCTGGAAAAGTGG | |
| | | | | | CTCTCTAGAGAGGTC | | GACAGGGCTGCATAT | |
| | | | | | AGATGTCCCGCTCCG | | CAGCGTGGGTCACCA | |
| | | | | | GTTCCGCTTCTTCAG | | GTCTCTGTAGAAAAA | |
| | | | | | AGATGACCAGACCCT | | ACTCGTACCTGTGAG | |
| | | | | | GGGATTAGGCTGGAG | | AATGGGAGTTGTGCA | |
| | | | | | TCTCTCCCCGAATTTC | | AGCAAAGAGACCTCT | |
| | | | | | CAGATTACTGCCATG | | ACTCTTGTGAACATCT | |
| | | | | | TGGAGTAAAGATTCA | | TAGAAGAGCTTAGAC | |
| | | | | | GGGTTCTACTGGTGT | | CCAGGAAAATCCAAG | |
| | | | | | AAGGCAGCAACAATG | | AAAAGAAAGGTCTAA | |
| | | | | | CCTTACAGC | | TTTTTTTTC | |
| ENSG | ENSG0 | BMY2 | GPCRS | KR228 | ATAATTTACTTCTGTG | 7 | AATGCCCCTTGTGA | 8 |
| 000001 | 000015 | 8 | NP104 | | TAGCTATATCAGTGT | | CCACACTATTGCCT | |
| 53294 | 3294 | | | | GGGTACTCCTTTTCAT | | GCTACGTGCTGCCA | |
| | | | | | GTATTCATTTTCACAT | | GAATGAGGTGGGAG | |
| | | | | | ATTTATCTCTAGAGA | | GGGAAGAGGGGGA | |
| | | | | | GGGATATACATTTTG | | CATCTTTTTCAAAGA | |
| | | | | | TCAATATAATTACTC | | ATGGAAACATCTTT | |
| | | | | | ATTACCACTACTGTT | | ATTGTCTAGCACAT | |
| | | | | | ATTTTTCCCCCACTTA | | AAATGAAAATATGT | |
| | | | | | GAATGCATCACTAGG | | ACATTTTCTGTAAA | |
| | | | | | CCCAACCAATGGATC | | ACCTATGTCATCTCA | |
| | | | | | TAAATTAATGAATCG | | GCTTACATGACCAA | |
| | | | | | TCAAGGATGAAATGT | | ACCCATCACACCTG | |
| | | | | | GAGTATTAAAAATAT | | CTGTCTACAGTGCTC | |
| | | | | | AAAGAGAAATTTCAC | | ACATACCTTAATTCC | |
| | | | | | TTGCAATTTGTGTCA | | ATCTTGTCAGTGAG | |
| | | | | | ATCCAC | | TAATAACACTCATA | |
| | | | | | | | ATAGCCCCA | |
| ENSG | ENSG0 | BMY3 | GPCRS | KR252 | TGCCTGCCGGTCAAC | 13 | GTCCTGGGCCTCAG | 14 |
| 000001 | 000016 | 0 | NP129 | | GCTGGCCATAGAGCC | | CCTCTGGGCTCTCCT | |

TABLE 3-continued

| | | | | | | | | |
|---|---|---|---|---|---|---|---|---|
| 69962 | 9962 | | | | TGGCAGTGGCCTCAG | | GCACCCTGGGACGG | |
| | | | | | GCAGAGTCTGACGCG | | GGGCCCCATTGTGC | |
| | | | | | CACAAACTTTCAGGC | | CTGTCACAGCAACT | |
| | | | | | CCAGGAAGCGAGGA | | TAGGATGAAGGGGG | |
| | | | | | CACCACTGGGGCCCC | | ACTACGTGCTGGGG | |
| | | | | | AGGGTGTGGCAAGTG | | GGGCTGTTCCCCCT | |
| | | | | | AGGATGGCAAGGGTT | | GGGCGAGGCCGAGG | |
| | | | | | TTGCTAAACAAATCC | | AGGCTGGCCTCCGC | |
| | | | | | TCTGCCCGCTCCCCG | | AGCCGGACACGGCC | |
| | | | | | CCCCGGGCTCACTCC | | CAGCAGCCCTGTGT | |
| | | | | | ATGTGAGGCCCCAGT | | GCACCAGGTACAGA | |
| | | | | | CGGGGCAGCCACCTG | | GGTGGGACGGCCTG | |
| | | | | | CCGTGCCTGTTGGAA | | GGTCGGGGTCAGGG | |
| | | | | | GTTGCCTCTGCCATG | | TGACCAGGTCTGGG | |
| | | | | | CTGGGCCCTGC | | GTGCTCCTGAGCTG | |
| | | | | | | | GGGCCGAGGTG | |
| | | BMY3 | GPCRS | KR268 | TGTATGGGGGTCTGA | 19 | CAGTCAAAAGCCTA | 20 |
| | | 3 | NP145 | | TTGCTGTGATGCACA | | CTCTATTTGCCTTCC | |
| | | | | | CAGCTGGCACCTTCT | | ACACTTGCTGGTTGT | |
| | | | | | CCTTATCCTACTGTG | | GTTATTTCTTTCCAC | |
| | | | | | GGTCCAACATGGTCC | | TGGATTCATTGCTTA | |
| | | | | | ATCAGTTCTTCTGTG | | TCTGAAGCCAGCTT | |
| | | | | | ACATTCCCCAGTTAT | | CAGAGTCTCCTTCTA | |
| | | | | | TAGCTATTTCTTGCTC | | TTTTGGATGCTGTAA | |
| | | | | | AGAAAATTTAATAAG | | TTTCTGTGTTCTACA | |
| | | | | | AGAAATTGCACTCAT | | CTATGCTGCCCCCA | |
| | | | | | CCTTATTAATGTAGTT | | ACCTTTAATCCCATT | |
| | | | | | TTGGATTTCTGCTGTT | | ATATACAGTTTGAG | |
| | | | | | TTATTGTCATCATCAT | | AAACAAGGCCATAA | |
| | | | | | TACCTATGTCCACGT | | AGGTGGCTCTGGGG | |
| | | | | | CTTCTCTACAGTCAA | | ATGTTGATAAAGGG | |
| | | | | | GAAGATCCCTTCCAC | | AAAGCTCACCAAAA | |
| | | | | | AGAAGG | | AGTAAAAGCTGTTG | |
| | | | | | | | CTTT | |
| ENSG | ENS0 | BMY2 | GPCRS | KR343 | AACTTGAGTTCTAAT | 25 | CCATGCCCTCAGAA | 26 |
| 000001 | 000016 | 2 | NP220 | | AAAGGCATGACAATC | | ATGTATATGTATATC | |
| 65370 | 5370 | | | | ACACAAGAATGAGGC | | CCTGCCCAAAGTTA | |
| | | | | | TAAACTCTGAAGATG | | TTTTGCGGTTTGGGA | |
| | | | | | GTCATCTTACATCAT | | TTTGAGGAATGTTC | |
| | | | | | ACAACTACCTGATTA | | CTGTGAATTGACCC | |

TABLE 3-continued

| | | | | | | | | |
|---|---|---|---|---|---|---|---|---|
| | | | | | ACCATTTTCAACCAA | | TAGGGATAATTTAG | |
| | | | | | ACACTCCCTCCACCC | | ATATTGTTAAAGTTT | |
| | | | | | ATATTGACAGTGGAT | | TCCCAACGTGATTT | |
| | | | | | TTCTGCATGAACAGT | | ATTTCAACAGCATT | |
| | | | | | TGGTTGACTCTGGAG | | AATTAGGATATGTC | |
| | | | | | TTGCTTTAACTTGTTC | | TGATCTGAATGCTCT | |
| | | | | | TGTAGGAGGATCAAA | | GATTTTAGGACTGTT | |
| | | | | | AACACTGGCTTGACT | | TGGAATAGGTTACA | |
| | | | | | GTTTTTTTGGTTCCAT | | TGTTTTCTAGGTATT | |
| | | | | | GTTACTTGGTCACAT | | GTGAAATCATCCTC | |
| | | | | | ACATACGG | | TTTGTCATTTCTGAC | |
| | | | | | | | TCTCT | |
| ENSG | ENSG0 | Kalpha | ION_C | KR542 | TTCAGCCAAAGTCTT | 31 | ATGTACCCAGAGAC | 32 |
| 000001 | 000016 | M1 | HANN | | TCAGCTCCATCCATA | | CCACCTGGGCAGGT | |
| 68263 | 8263 | | ELSNP | | GCTTCTGTTCTTTTCA | | TTTTTGCCTTCCTCT | |
| | | | 153 | | TGACACAGGTCCTAG | | GCATTGCTTTTGGG | |
| | | | | | AGGGAGTCTTCCTGG | | ATCATTCTCAACGG | |
| | | | | | TACCTCCTAAAGCAG | | GATGCCCATTTCCAT | |
| | | | | | GCTCCGTGGGAAGCC | | CCTCTACAACAAGT | |
| | | | | | ATTACACTTCCCATG | | TTTCTGATTACTACA | |
| | | | | | TGTACCCACAGGGAG | | GCAAGCTGAAGGCT | |
| | | | | | GACGCTTCCCTGCTT | | TATGAGTATACCAC | |
| | | | | | GCTCCTCTCCCTTTCT | | CATACGCAGGGAGA | |
| | | | | | TCTCCTCCCCGATCTT | | GGGGAGAGGTGAAC | |
| | | | | | AGTGCTAACAATTCC | | TTCATGCAGAGAGC | |
| | | | | | ATCCTGCTTTCCTTCC | | CAGAAAGAAGATAG | |
| | | | | | TCTACAGGTGAGCAT | | CTGAGTGTTTGCTTG | |
| | | | | | CTCCACCGTGGGCTA | | GAAGCAACCCACAG | |
| | | | | | CGGAGA | | CTCACCCCAAGACA | |
| | | | | | | | AGAGAATT | |
| ENSG | ENSG0 | Kalpha | ION_C | KR558 | TCCTCTACAGGTGAG | 37 | TTGGAAGCAACCCA | 38 |
| 000001 | 000016 | M1 | HANN | | CATCTCCACCGTGGG | | CAGCTCACCCCAAG | |
| 68263 | 8263 | | ELSNP | | CTACGGAGACATGTA | | ACAAGAGAATTAGT | |
| | | | 169 | | CCCAGAGACCCACCT | | ATTTTATAGGACAT | |
| | | | | | GGGCAGGTTTTTTGC | | GTGGCTGGTAGATT | |
| | | | | | CTTCCTCTGCATTGCT | | CCATGAACTTCAAG | |
| | | | | | TTTGGGATCATTCTC | | GCTTCATTGCTCTTT | |
| | | | | | AACGGGATGCCCATT | | TTTTAATCATTATGA | |
| | | | | | TCCATCCTCTACAAC | | TTGGCAGCAAAAGG | |

TABLE 3-continued

| | | | | | | | | |
|---|---|---|---|---|---|---|---|---|
| | | | | | AAGTTTTCTGATTACT ACAGCAAGCTGAAGG CTTATGAGTATACCA CCATACGCAGGGAGA GGGGAGAGGTGAACT TCATGCAGAGAGCCA GAAAGAAGATAGCTG AGTGTTTG | | AAATGTGAAGCAGA CATACACAAAGGCC ATTTCGTTCACAAA GTACTGCCTCTAGA AATACTCATTTTGGC CCAAACTCAGAATG TCTCATAGTTGCTCT GTGTTGTGTGAAAC ATCTGACC | |
| ENSG 000001 51364 | ENSG0 000015 1364 | Kbeta M1 | ION_C HANN ELSNP 183 | KR572 | TGACCTAAAGATGTA GTCTACATAGCCCCA GCTTGGGGTCCAATC CATCTGTCCCTGGCA TGTGCCTTCATGTAG TAGGTGCTTTCCTGA TCCCCTTTGCGAGAT GCTGTGGGTGCTAAC ACCTCAGAGCTGTCC TCTTCTCTAGAGTGG AGGTTTTCAAAGTGC ATCATCAGCATTACC TGTGAACTTGCTGGA AATACAAATCCTCAG GCCCCACCTCAGACC TACTGAATCAGAATC TCTGGGGTT | 43 | GCACAGCATTCTGA TTTACCAAACCCTCC AAGTGATTTTGATG TATTCTAATTTTGAG ACCATCTCTAGAAA AGAATTGCTACCTC TTGTATGGAGGTAC AAAAGACTGACCTC TTACATCAAGGAAC TTCCTTTCCCAGAGC TCCTCATGGAATCA AGCTGAAGTCAGTC TTCTTCTGAGAGCA CATTCTTACTCAGTT TTTTTCCTCTGTCCT ACGCTGCTTCCCTCA CTCCCCTTCTCCTAA GAGCA | 44 |
| ENSG 000001 62687 | ENSG0 000016 2687 | BMYC H48 | ION_C HANN ELSNP 7 | KR397 | GCAATCGCCAGAACA ATGGCAGAAGATGTA CGGTAGATGCTCCGG GAATGAAGTCTACCA CATTGTTTTGGAAGA AAGTACATTTTTTGCT GAATATGAAGGAAA GAGTTTTACATATGC CTCTTTCCATGCACA CAAAAAGTATGTTTC TGCCTCAGAGAAAAA TTAAAATATCAATCA GTCAAGCATATCATG | 49 | GAATTTTTGTCACA ATATTCCCCAATGTT GAAACATTTGAACC CTGGTGTCTGTATG GTCTCTATAAGACA CTCAGGAGTAAATT ATAATTTAGTAGGA ATATTTCATTTAGCC ACTTTTAAAGTCTTT TTAAAATATTTTAAT CCATTAAGAATTTA CATACATATGAAAA TCTTCTTCACAGATC | 50 |

TABLE 3-continued

| | | | | | | | | |
|---|---|---|---|---|---|---|---|---|
| | | | | | TGAAAATAGTTTTCA | | TGAATTTTAAGATG | |
| | | | | | AAAATAGAATGCATA | | TTGATTAGGAACTA | |
| | | | | | TTGTGTTCATGTGTTT | | AAACAAAGTAACAC | |
| | | | | | AGGCATTCC | | TAATATTTCTAAAA | |
| | | | | | | | ACTGTAC | |
| ENSG | ENSG0 | DP-24 | PROTE | KR643 | TATTCACTCCAGAGA | | CATCGTCATGTGATT | |
| 000001 | 000010 | | ASESN | | CAGCCACTCATCCCA | | TCCTGTCTGGACCAT | |
| 03023 | 3023 | | P10 | | AGCCCTGCCCTCACA | | GCAACAGAGAGCCC | |
| | | | | | GAGCTCCCCATCTAG | | AGGGATTATTAACG | |
| | | | | | GGAAGGGGAGTCCTG | | AGAAGGCAGTCCCC | |
| | | | | | AGGCTCCCCTGGATG | | TATGTCAACACAAC | |
| | | | | | TGACCAAGGCTTACT | | TCCCACTCATATAG | |
| | | | | | CTCAACACTTAGCTT | | CCAAACGAGAGTGA | |
| | | | | | CTACTCCATGATGTT | | GAATTTTTTTTTTT | |
| | | | | | CTTACCAAGCAGGCA | | TTTGAGTTGGAGTCT | |
| | | | | | GTCTTGGTTTCCTCTT | | TGTTCTGTCACGCA | |
| | | | | | TCGTGTGGCTGCCGC | | GGCTGGAGTACAGT | |
| | | | | | ATTCTGTCTTCTGGA | | GGTGTGATCTTGGC | |
| | | | | | GTTTGTATAGGGGAC | | TCACTGCAACTTCTG | |
| | | | | | ACATGTCAAGATCTT | | CCTTTCGGGTTCAA | |
| | | | | | TCACGAAGATTTTCC | | GCAATTCTCCTGCCT | |
| | | | | | TCAGGACAC | | CAGCTTCCGGAGTA | |
| | | | | | | | GCTGGG | |
| ENSG | ENSG0 | LSI-1 | PROTE | KR655 | AAGATGTTCTGACTC | 61 | GGTAAACTGAGGGT | 62 |
| 000001 | 000017 | | ASESN | | GGGGTCTCCAAAACC | | CCAGGCCCTGAATC | |
| 70054 | 0054 | | P22 | | AGCCTGCGGTATAGG | | AGAGACCCTTTAAC | |
| | | | | | CGGAAGGCAAAGTCG | | ACCCCCACGCCATC | |
| | | | | | GTGTTGAGGGAATAC | | AGCAGCAGAATGAG | |
| | | | | | ACCTGTGAGGCAGGG | | GACAGATAGGCCAG | |
| | | | | | GTGCTCTTTGTGGAG | | TTAGCAGAGCTCTC | |
| | | | | | GAAGGGCGGGGGTAT | | TCACATAATCTCTG | |
| | | | | | GCACTGGGGGCATTG | | AGCCTCACAATATT | |
| | | | | | GCCGGGGACACACAG | | CCCATGATGTAGAT | |
| | | | | | TAGATTGGAGCACAG | | CTTATTATTGCTGTT | |
| | | | | | AGGCCAACAGCAAA | | TTACTTGCAAATGA | |
| | | | | | GAGTACTCCATAAAG | | GTAAACAGGCCACA | |
| | | | | | GTAAGATGCCATTTT | | GAGAGTCTGTGCAA | |
| | | | | | GGAACAAAATATGTC | | CTTACCCCAAATAG | |
| | | | | | TGCAAGAGAAGTAAG | | CATGGTTGACTTGTC | |

TABLE 3-continued

| | | | | | | | | |
|---|---|---|---|---|---|---|---|---|
| | | | | | AACCATTGAGG | | TGTGTTCTGTGTGGG CTTCAAAGT | |
| ENSG 000001 68803 | ENSG0 000016 8803 | FL-2 | ENZY MESN P34 | KR66 | CCATCAGGGATGTGA CAAAGTGGATAATCT CTACCACGTGAGAAA CTTCCAACATTACTT GCAAATCAGATTTAA TGAATAAAATAAAGC TGTAGCACTTGGCAC ATTCATTGGGACCCT TACCCAAACATTATC AATATTGTGTACGTT ATCTTTATTATCAGGT CACAAAAGATGTCAT AAAAGAATTTGCAGA TGACGGCGTCAAGTA CCTGGAACTAAGGAG CACACCCAGAAGAGA AAATGCTAC | 67 | GGTAGAATTTATAC TTCTCAGCAAATGT ACTGTCCTTTTCCTA TGTGCTTTGATCACT CACATGTTTGTGAG TGGGAATATGAAGC ACTAACTTTTATACT ATTGTGTTGTTCTGT ATTTCATTGAACCTT TAGTCAACAGTCCA AGTCCTCTCTCTGAT GTACATTAATGATG TTCATTTTGTTTGTT TTAGAGACAGGGTC TTGCTGTCTTGCCCA GGCTGGAGTGCAGT GGTGCAAACATAGC TCAC | 68 |
| ENSG 000001 68803 | ENSG0 000016 8803 | FL-2 | ENZY MESN P36 | KR68 | GATACATTGACTTAC ACAAAGTGTGGACCT TGTTTGGATCCTGAA TCAAACAAACTGAAG AAACAAATACAGGA ACAAAAAAACCTCGA AAGACAACTGTAAAT CTGAACAGTGACTGG ATGCTTGATGCTATTT AGGAATTCATGTCTC AGTCCGTATGACAAA GTAAAATGTCATGTT GTCTAGATTCAGTCA GGCTATACTTTTCCTA GTGAGATGTATTACA CGTAGTCTGCCATCT CTGTCTGGC | 73 | GTACTCAGAATTGT CTTTTTCATCTGTGT CATATTAGTTTTCAA CTCTGTCTTTCTTAC ATTAAAGGTATTTG ATAGCAGTTGACAG AAGAGGTGGCCCTT TAGTAGCCAAGGAG ACTGTAAAACTTGC CGAGGAGTTCTTCC TTTCTACTGAGGGT ACAGTTCTTGGCCTT GACCTCAGTGGAGA CCCTACTGTAAGTT ATTTTTCCTACGTAC ATTTTAATTCTAAAA GGTAGAATCAGTGG GATAAG | 74 |
| ENSG 000000 | ENSG0 000008 | GPAT-3 | ENZY MESN | KR84 | TATTTATTGCTGAAC AGAAAATATATTTTT | 79 | GCTGTCTTGTGCAA CCCTTCCAACACAG | 80 |

TABLE 3-continued

| | | | | | | | | |
|---|---|---|---|---|---|---|---|---|
| 87253 | 7253 | | P52 | | CTTCCTTCTTGGGAAT | | AGGAGATCATCCAG | |
| | | | | | AGTTGGGCTACTTGC | | GTGGCATTTAAGGT | |
| | | | | | TTGCTGTTCCTTCTTA | | ACTGTCAGCCCCAT | |
| | | | | | GTGAGACTTTTCTCC | | TGAAAGCATCTTGG | |
| | | | | | AAATAGTGAATGATG | | TCTGCCTTGTAAAC | |
| | | | | | AGGTTGAGCTATAAG | | AAGTGTTGACTCTA | |
| | | | | | ACATACCTGAATTTT | | AGTGTATTATTTGA | |
| | | | | | ACCTTGTAGTAGGAT | | AAATCAGTGAATCT | |
| | | | | | TAATAGTAATTCCAC | | ATTATGTGATTTTAT | |
| | | | | | TAGTGGCCCTCCTAA | | AGATCTGCTGTGAC | |
| | | | | | TTGATTTATCCCATCC | | ATGTACAGGACAAT | |
| | | | | | TTTCACAGAACCATG | | AATGTGATTAAGTC | |
| | | | | | ATGGCAGCATTGACT | | AGTTGCTACTAAGA | |
| | | | | | TCCGAGAGTATGTGA | | ATAAAGAAAACACA | |
| | | | | | TTGGCCT | | AGCATTTATTTAAG | |
| | | | | | | | CAAAAAGTTTC | |
| ENSG | ENSG0 | BMY3 | GPCRS | KR244 | CCTGCCTGCCGGTCA | 85 | CTGTCCTGGGCCTC | 86 |
| 000001 | 000016 | 0 | NP121 | | ACGCTGGCCATAGAG | | AGCCTCTGGGCTCT | |
| 69962 | 9962 | | | | CCTGGCAGTGGCCTC | | CCTGCACCCTGGGA | |
| | | | | | AGGCAGAGTCTGACG | | CGGGGGCCCCATTG | |
| | | | | | CGCACAAACTTTCAG | | TGCCTGTCACAGCA | |
| | | | | | GCCCAGGAAGCGAG | | ACTTAGGATGAAGG | |
| | | | | | GACACCACTGGGGCC | | GGGACTACGTGCTG | |
| | | | | | CCAGGGTGTGGCAAG | | GGGGGGCTGTTCCC | |
| | | | | | TGAGGATGGCAAGGG | | CCTGGGCGAGGCCG | |
| | | | | | TTTTGCTAAACAAAT | | AGGAGGCTGGCCTC | |
| | | | | | CCTCTGCCCGCTCCC | | CGCAGCCGGACACG | |
| | | | | | CGCCCCGGGCTCACT | | GCCCAGCAGCCCTG | |
| | | | | | CCATGTGAGGCCCCA | | TGTGCACCAGGTAC | |
| | | | | | GTCGGGGCAGCCACC | | AGAGGTGGGACGGC | |
| | | | | | TGCCGTGCCTGTTGG | | CTGGGTCGGGGTCA | |
| | | | | | AAGTTGCCTCTGCCA | | GGGTGACCAGGTCT | |
| | | | | | TGCTGGGCCCT | | GGGGTGCTCCTGAG | |
| | | | | | | | CTGGGGCCGAGG | |
| ENSG | ENSG0 | BGS-5 | BIOLO | KR23 | CTTCTCTCTAGAGCC | 91 | ACAGCGTCATATCT | 92 |
| 000001 | 000014 | | GICSN | | ATTTACACGTCCAGT | | GACAGCCCGAGATC | |
| 43297 | 3297 | | P23 | | GCTGAGAGCCAGCTC | | CTGGATACAGGTGC | |
| | | | | | CTTCCAGCCCATCAG | | AGAGTAAGTGTTGG | |
| | | | | | CGGGAACCCAGTGAC | | TGGAACCTGAGATT | |

TABLE 3-continued

| | |
|---|---|
| CCTGACCTGTGAGAC | TGCTGCAGAGAGGG |
| CCAGCTCTCTCTAGA | CTGGAAAAGTGGGA |
| GAGGTCAGATGTCCC | CAGGGCTGCATATC |
| GCTCCGGTTCCGCTT | AGCGTGGGTCACCA |
| CTTCAGAGATGACCA | GTCTCTGTAGAAAA |
| GACCCTGGGATTAGG | AACTCGTACCTGTG |
| CTGGAGTCTCTCCCC | AGAATGGGAGTTGT |
| GAATTTCCAGATTAC | GCAAGCAAAGAGAC |
| TGCCATGTGGAGTAA | CTCTACTCTTGTGAA |
| AGATTCAGGGTTCTA | CATCTTAGAAGAGC |
| CTGGTGTAAGGCAGC | TTAGACCCAGGAAA |
| AACAATGCCT | ATCCAAGAAAAGAA |
| | AGGTCTAATTT |

| GENE NAME | GENE NAME | 15 bp REFERENCE | 15 REF SEQ ID NO | 15 bp VARIANT | 15 VAR SEQ ID NO | 25 bp REFERENCE | 25 REF SEQ ID NO | 25 bp VARIANT | 25 VAR SEQ ID NO |
|---|---|---|---|---|---|---|---|---|---|
| ENSG00000143297 | ENSG00000143297 | acaatgccttacagcGtcatatctgacagcc | 3 | acaatgccttacagcAtcatatctgacagcc | 4 | taaggcagcaacaatgccttacagcGtcatatctgacagcccgagatcctg | 5 | taaggcagcaacaatgccttacagcAtcatatctgacagcccgagatcctg | 6 |
| ENSG00000153294 | ENSG00000153294 | tttgtgtcaatccacCaatgccccttgtgac | 9 | tttgtgtcaatccacAaatgccccttgtgac | 10 | tcacttgcaatttgtgtcaatccacCaatgccccttgtgaccacactattg | 11 | tcacttgcaatttgtgtcaatccacAaatgccccttgtgaccacactattg | 12 |
| ENSG00000169962 | ENSG00000169962 | catgctgggccctgcTgtcctgggcctcagc | 15 | catgctgggccctgcAgtcctgggcctcagc | 16 | ttgcctctgccatgctgggccctgcTgtcctgggcctcagcctctgggctc | 17 | ttgcctctgccatgctgggccctgcAgtcctgggcctcagcctctgggctc | 18 |
| | | cccttccacagaaggCcagtcaaaagcctac | 21 | cccttccacagaaggTcagtcaaaagcctac | 22 | tcaagaagatcccttccacagaaggCcagtcaaaagcctactctatttgcc | 23 | tcaagaagatcccttccacagaaggTcagtcaaaagcctactctatttgcc | 24 |
| ENSG00000165370 | ENS00000165370 | gtcacatacatacggCccatgccctcagaaa | 27 | gtcacatacatacggTccatgccctcagaaa | 28 | atgttacttggtcacatacatacggCccatgccctcagaaat | 29 | atgttacttggtcacatacatacggTccatgccct | 30 |

TABLE 3-continued

| | | | | | | | | | |
|---|---|---|---|---|---|---|---|---|---|
| | | | | | | gtatatgta | | cagaaatgtata<br>tgta | |
| ENSG<br>000001<br>68263 | ENSG0<br>000016<br>8263 | cgtgggctacgga<br>gaCatgtacccag<br>agacc | 33 | cgtgggctacg<br>gagaTatgtac<br>ccagagacc | 34 | gcatctccaccgtg<br>ggctacggagaC<br>atgtacccagagac<br>ccacctgggca | 35 | gcatctccacc<br>gtgggctacgg<br>agaTatgtacc<br>cagagaccca<br>cctgggca | 36 |
| ENSG<br>000001<br>68263 | ENSG0<br>000016<br>8263 | atagctgagtgtttg<br>Cttggaagcaacc<br>cac | 39 | atagctgagtgt<br>ttgGttggaag<br>caacccac | 40 | cagaaagaagata<br>gctgagtgtttgCtt<br>ggaagcaacccac<br>agctcacccc | 41 | cagaaagaag<br>atagctgagtgt<br>ttgGttggaag<br>caacccacagc<br>tcacccc | 42 |
| ENSG<br>000001<br>51364 | ENSG0<br>000015<br>1364 | gaatctctgggggt<br>tGgcacagcattct<br>gat | 45 | gaatctctggg<br>ggttAgcaca<br>gcattctgat | 46 | tactgaatcagaat<br>ctctgggggttGg<br>cacagcattctgatt<br>taccaaacc | 47 | tactgaatcaga<br>atctctgggggt<br>tAgcacagcat<br>tctgatttacca<br>aacc | 48 |
| ENSG<br>000001<br>62687 | ENSG0<br>000016<br>2687 | gtgtttaggcattcc<br>Ggaatttttgtcaca<br>a | 51 | gtgtttaggcat<br>tccAgaatttt<br>gtcacaa | 52 | ttgtgttcatgtgttt<br>aggcattccGgaa<br>tttttgtcacaatatt<br>ccccaa | 53 | ttgtgttcatgtg<br>tttaggcattcc<br>Agaatttttgtc<br>acaatattcccc<br>aa | 54 |
| ENSG<br>000001<br>03023 | ENSG0<br>000010<br>3023 | ttttcctcaggacac<br>Tcatcgtcatgtga<br>tt | | ttttcctcagga<br>cacCcatcgtc<br>atgtgatt | | ttcacgaagattttc<br>ctcaggacacTca<br>tcgtcatgtgatttc<br>ctgtctgg | | ttcacgaagatt<br>ttcctcaggaca<br>cCcatcgtcat<br>gtgatttcctgtc<br>tgg | |
| ENSG<br>000001<br>70054 | ENSG0<br>000017<br>0054 | taagaaccattgag<br>gGggtaaactgag<br>ggtc | 63 | taagaaccattg<br>aggTggtaaa<br>ctgagggtc | 64 | gcaagagaagtaa<br>gaaccattgaggG<br>ggtaaactgagggt<br>ccaggccctga | 65 | gcaagagaagt<br>aagaaccattg<br>aggTggtaaa<br>ctgagggtcca<br>ggccctga | 66 |
| ENSG<br>000001<br>68803 | ENSG0<br>000016<br>8803 | aagagaaaatgcta<br>cAggtagaatttat<br>act | 69 | aagagaaaatg<br>ctaGggtag<br>aatttatact | 70 | gcacacccagaag<br>agaaaatgctacA<br>ggtagaatttatact<br>tctcagcaaa | 71 | gcacacccag<br>aagagaaaatg<br>ctacGggtag<br>aatttatacttct<br>cagcaaa | 72 |
| ENSG<br>000001<br>68803 | ENSG0<br>000016<br>8803 | ccatctctgtctggc<br>Tgtactcagaattg<br>tc | 75 | ccatctctgtct<br>ggcCgtactca<br>gaattgtc | 76 | acgtagtctgccat<br>ctctgtctggcTgt<br>actcagaattgtcttt | 77 | acgtagtctgc<br>catctctgtctg<br>gcCgtactcag | 78 |

TABLE 3-continued

| | | | | | | | | | |
|---|---|---|---|---|---|---|---|---|---|
| | | | | | | ttcatct | | aattgtctttttca tct | |
| ENSG 000000 87253 | ENSG0 000008 7253 | gtatgtgattggcct Ggctgtcttgtgca ac | 81 | gtatgtgattgg cctAgctgtctt gtgcaac | 82 | acttccgagagtat gtgattggcctGg ctgtcttgtgcaacc cttccaaca | 83 | acttccgagag tatgtgattggc ctAgctgtcttg tgcaacccttcc aaca | 84 |
| ENSG 000001 69962 | ENSG0 000016 9962 | gccatgctgggcc ctGctgtcctgggc ctca | 87 | gccatgctggg ccctActgtcc tgggcctca | 88 | agttgcctctgccat gctgggccctGct gtcctgggcctcag cctctgggc | 89 | agttgcctctgc catgctgggcc ctActgtcctg ggcctcagcct ctgggc | 90 |
| ENSG 000001 43297 | ENSG0 000014 3297 | gcagcaacaatgc ctTacagcgtcata tctg | 93 | gcagcaacaat gcctCacagc gtcatatctg | 94 | ctggtgtaaggcag caacaatgcctTa cagcgtcatatctg acagcccgag | 95 | ctggtgtaagg cagcaacaatg cctCacagcgt catatctgacag cccgag | 96 |

TABLE 4

| GENE NAME | GENE ALIAS | SNP NAME | SNP ALIAS | FWD SEQ PRIMER | SEQ ID NO FWD SEQ PRIMER | REV SEQ PRIMER | SEQ ID NO REV SEQ PRI-MER |
|---|---|---|---|---|---|---|---|
| ENSG00000143297 | BGS-5 | BIOLOGICSNP28 | KR28 | CTCAGATGTGCTCCTTGGAG | 97 | ATGTTAACATAGGATTTTTAATGT GGAAA | 98 |
| ENSG00000153294 | BMY28 | GPCRSNP104 | KR228 | ATGAAAATGAAGTCCCAGGC | 99 | TCATCCTTGACGATTCATTAATTTA G | 100 |
| ENSG00000169962 | BMY30 | GPCRSNP129 | KR252 | ATGCTGGGCCCTACAGTC | 101 | TCACTCATG1TTCCCCTGATT | 102 |
| | BMY33 | GPCRSNP145 | KR268 | ATGTGTTATATATATTTAATA TTTAAAGAGTGGAC | 103 | TTACTTTTTGGTGAGCTTTCCC | 104 |
| ENSG00000165370 | BMY22 | GPCRSNP220 | KR343 | ATGACGTCCACCTGCACC | 105 | TCAAGGAAAAGTAGCAGAATCGT AG | 106 |
| ENSG00000168263 | KalphaM1 | ION_CHANNELSN P153 | KR542 | AAGTCAGGCTCCCTTTAAATA TGG | 107 | CAAGTCCAAAAATATTTATTGAGC TAGAT | 108 |
| ENSG00000168263 | KalphaM1 | ION_CHANNELSN P169 | KR558 | AAGTCAGGCTCCCTTTAAATA TGG | 109 | CAAGTCCAAAAATATTTATTGAGC TAGAT | 110 |
| ENSG00000151364 | KbetaM1 | ION_CHANNELSN P183 | KR572 | CCACGCGTCCGGTGA | 111 | CTCGTGCAAGTGGTTTATTGAT | 112 |

TABLE 4-continued

| GENE NAME | GENE ALIAS | SNP NAME | SNP ALIAS | FWD SEQ PRIMER | SEQ ID NO FWD SEQ PRIMER | REV SEQ PRIMER | SEQ ID NO REV SEQ PRI-MER |
|---|---|---|---|---|---|---|---|
| ENSG00000162687 | BMYCH48 | ION_CHANNELSNP7 | KR397 | CCAGAGATCAAGTCTAAGGATACG | 113 | CATTAGAAATAATTTTATTATTTATTTTAAAGCAG | 114 |
| ENSG00000103023 | DP-24 | PROTEASESNP10 | KR643 | | | | |
| ENSG00000170054 | LSI-1 | PROTEASESNP22 | KR655 | CCCACGCGTCCGATT | 117 | CATATTTTAGTTTTATTGAATGTGTTATTGTAATT | 118 |
| ENSG00000168803 | FL-2 | ENZYMESNP34 | KR66 | CACGCGTCCGCCTGT | 119 | ACTTGGGATTTTCCATGTTTAATTT | 120 |
| ENSG00000168803 | FL-2 | ENZYMESNP36 | KR68 | CACGCGTCCGCCTGT | 121 | ACTTGGGATTTTCCATGTTTAATTT | 122 |
| ENSG00000087253 | GPAT-3 | ENZYMESNP52 | KR84 | GGCTCCCCAGCGTCG | 123 | AGTAAGAAAATCTATCATTTTTATTTTAAAAATCT | 124 |
| ENSG00000169962 | BMY30 | GPCRSNP121 | KR244 | ATGCTGGGCCCTACAGTC | 125 | TCACTCATGTTTCCCCTGATT | 126 |
| ENSG00000143297 | BGS-5 | BIOLOGICSNP23 | KR23 | CTCAGATGTGCTCCTTGGAG | 127 | ATGTTAACATAGGATTTTTAATGTGGAAA | 128 |

TABLE 5

| GENE NAME | GENE ALIAS | SNP NAME | SNP ALIAS | SBE PRIMER F | SBE F PRIMER SEQ ID NO | SBE PRIMER R | SBE R PRIMER SEQ ID NO |
|---|---|---|---|---|---|---|---|
| ENSG00000143297 | BGS-5 | BIOLOGICSNP28 | KR28 | acaatgccttacagc | 129 | ggctgtcagatatga | 130 |
| ENSG00000153294 | BMY28 | GPCRSNP104 | KR228 | tttgtgtcaatccac | 134 | gtcacaaggggcatt | 135 |
| ENSG00000169962 | BMY30 | GPCRSNP129 | KR252 | catgctgggccctgc | 139 | gctgaggcccaggac | 140 |
| | BMY33 | GPCRSNP145 | KR268 | cccttccacagaagg | 144 | gtaggcttttgactg | 145 |
| ENSG00000165370 | BMY22 | GPCRSNP220 | KR343 | tttctgagggcatgg | 149 | gtcacatacatacgg | 150 |
| ENSG00000168263 | KalphaM1 | ION_CHANNELSNP153 | KR542 | cgtgggctacggaga | 154 | ggtctctgggtacat | 155 |

TABLE 5-continued

| | | | | | | | |
|---|---|---|---|---|---|---|---|
| ENSG00000168263 | KalphaM1 | ION_CHANNELSNP169 | KR558 | atagctgagtgtttg | 159 | gtgggttgcttccaa | 160 |
| ENSG00000151364 | KbetaM1 | ION_CHANNELSNP183 | KR572 | gaatctctgggggtt | 164 | atcagaatgctgtgc | 165 |
| ENSG00000162687 | BMYCH48 | ION_CHANNELSNP7 | KR397 | gtgtttaggcattcc | 169 | ttgtgacaaaaattc | 170 |
| ENSG00000103023 | DP-24 | PROTEASESNP10 | KR643 | | | | |
| ENSG00000170054 | LSI-1 | PROTEASESNP22 | KR655 | taagaaccattgagg | 179 | gaccctcagtttacc | 180 |
| ENSG00000168803 | FL-2 | ENZYMESNP34 | KR66 | aagagaaaatgctac | 184 | agtataaattctacc | 185 |
| ENSG00000168803 | FL-2 | ENZYMESNP36 | KR68 | ccatctctgtctggc | 189 | gacaattctgagtac | 190 |
| ENSG00000087253 | GPAT-3 | ENZYMESNP52 | KR84 | gtatgtgattggcct | 194 | gttgcacaagacagc | 195 |
| ENSG00000169962 | BMY30 | GPCRSNP121 | KR244 | gccatgctgggccct | 199 | tgaggcccaggacag | 200 |
| ENSG00000143297 | BGS-5 | BIOLOGICSNP23 | KR23 | gcagcaacaatgcct | 204 | cagatatgacgctgt | 205 |

| GENE NAME | TAQMAN F PRIMER | TAQMAN F PRIMER SEQ ID NO | TAQMAN R PRIMER | TAQMAN R PRIMER SEQ ID NO | TAQMAN PROBE | TAQMAN PROBE SEQ ID NO |
|---|---|---|---|---|---|---|
| ENSG00000143297 | accagaccctggattaggc | 131 | cttttccagccctctctgca | 132 | fam-ccttacagcatcatatctgac | 133 |

TABLE 5-continued

| | | | | | | |
|---|---|---|---|---|---|---|
| | | | | | agcccg | |
| ENSG0 000015 3294 | ggcccaaccaat ggatctaa | 136 | aaagatgtcccc ctcttccc | 137 | fam- caatccacaa atgccccttgt gac | 138 |
| ENSG0 000016 9962 | ggatggcaaggg ttttgcta | 141 | ttgctgtgacag gcacaatg | 142 | fam- cccaggact gcagggccc | 143 |
| | tcatcatcattacct atgtccacg | 146 | caaccagcaagt gtggaagg | 147 | fam- cttccacaga aggtcagtca aaagcc | 148 |
| ENSG0 000016 5370 | accgcaaaataac tttgggc | 151 | tccctccacccat attgaca | 152 | fam- cacatacata cggtccatgc cctca | 153 |
| ENSG0 000016 8263 | cttccctgcttgct cctctc | 156 | aaagcaatgca gaggaaggc | 157 | fam- ctgggtacat gtctccgtag ccca | 158 |
| ENSG0 000016 8263 | gggagaggggga gaggtgaac | 161 | cacatttc- cttttg ctgcca | 162 | fam- tgggttgcttc caagcaaac actc | 163 |
| ENSG0 000015 1364 | tacaaatcctcag gccccac | 166 | ggagctctggg aaaggaagtt | 167 | fam- cagaatgctg tgctaacccc cagag | 168 |
| ENSG0 000016 2687 | gcctctttccatgc acacaa | 171 | ccatacagacac cagggttcaa | 172 | fam- tgtttaggcat tcca- gaattttt gtcacaa | 173 |
| ENSG0 000017 0054 | gccggggacaca cagtagat | 181 | gggggtgttaaa gggtctctg | 182 | fam- ccctcagttta ccccctcaat ggttc | 183 |
| ENSG0 000016 | tgggacccttacc caaacat | 186 | tcaaagcacata ggaaaaggaca | 187 | fam- attctaccggt | 188 |

TABLE 5-continued

| | | | | | | |
|---|---|---|---|---|---|---|
| 8803 | | | | | agcattttctct tctggg | |
| ENSG0 000016 8803 | tcatgttgtctagat tcagtcaggct | 191 | aagggccacct cttctgtcaa | 192 | fam- tgccatctctg tctggccgta ctca | 193 |
| ENSG0 000008 7253 | accatgatggcag cattgac | 196 | gccacctggatg atctcctc | 197 | fam- tgcacaagac agctaggcc aatcac | 198 |
| ENSG0 000016 9962 | ggatggcaaggg ttttgcta | 201 | ttgctgtgacag gcacaatg | 202 | fam- cccaggaca gtagggccc agc | 203 |
| ENSG0 000014 3297 | gagatgaccaga ccctggga | 206 | agccctctctgc agcaaatc | 207 | fam- cagcaacaat gcctcacagc gtc | 208 |

TABLE 6

| SNP ID | SNP location | Phenotype | Odds ratio/P value |
|---|---|---|---|
| KR000572 | 3' UTR | Breast cancer | 1.7/0.009 |
| KR000228 | 3' UTR | Breast cancer | 1.4/0.02 |
| KR000343 | 3' UTR | Lung cancer | 0.6/0.01 |
| KR000084 | coding (silent) | Lung cancer | 2.2/0.009 |
| KR000643 | Coding (Ser/Gly) | Melanoma | 1.3/0.02 |
| KR000023 | Coding (His/Tyr) | Prostate cancer | 0.8/0.03 |
| KR000028 | Coding (Val/Ile) | Prostate cancer | 0.7/0.003 |
| KR000655 | 5' UTR | Diabetes | 1.7/0.00005 |
| KR000397 | Intron | Diabetes | 0.7/0.02 |
| KR000066 | Coding (silent) | Diabetes | 0.8/0.02 |

TABLE 6-continued

| SNP ID | SNP location | Phenotype | Odds ratio/P value |
|---|---|---|---|
| KR000068 | Coding (silent) | Diabetes | 0.8/0.03 |
| KR000244 | Coding (Ala/Thr) | HDL | 0.6/0.02 |
| KR000252 | Coding (silent) | HDL | 0.6/0.04 |
| KR000268 | Coding (silent) | Hypertension | 0.4/0.0009 |
| KR000542 | Coding (silent) | Schizophrenia | 0.6/0.008 |
| KR000558 | Coding (Leu/Val) | Schizophrenia | 1.8/0.006 |

What is claimed is:

1. A method of diagnosing the presence of, or likelihood of, a human subject acquiring schizophrenia, the method comprising:

(a) obtaining a KalphaM1 DNA sequence from the subject to be diagnosed; and (b) analyzing the KalphaM1 DNA sequence from said subject to determine a nucleotide present at a polymorphic nucleotide position, wherein said polymorphic nucleotide position is located at nucleotide 2479 of SEQ ID NO: 220, and wherein the presence of a G at nucleotide 2479 of SEQ ID NO: 220 indicates that the subject has or is more likely to acquire schizophrenia than subjects having a C at nucleotide 2479 of SEQ ID NO: 220, thereby diagnosing the presence of, or likelihood of, the subject acquiring schizophrenia.

2. The method of claim 1, wherein the determining comprises sequencing the KalphaM1 DNA sequence.

3. The method of claim 1, wherein the determining comprises the step of amplifying the KalphaM1 DNA sequence.

4. The method according to claim 3, further comprising the step of subjecting a product(s) of the amplifying to a genetic bit analysis (GBA) reaction.

5. The method of claim 3, wherein the amplifying comprises the step of amplifying the KalphaM1 DNA sequence by polymerase chain reaction (PCR).

6. A method for determining whether a human subject has an increased likelihood of having or developing schizophrenia wherein the method comprises:

(a) obtaining a nucleic acid sample from the subject;

(b) analyzing KalphaM1 nucleic acids present in the nucleic acid sample to determine the nucleotide present at nucleotide position 2479 of SEQ ID NO:220; and (c) determining that the subject has an increased likelihood of having or developing schizophrenia if the subject is homozygous or heterozygous for a G at nucleotide position 2479 of SEQ ID NO:220 as compared to subjects having a C at nucleotide position 2479 of SEQ ID NO:220.

* * * * *

SEQUENCE LISTING

<160> NUMBER OF SEQ ID NOS: 222

<210> SEQ ID NO 1
<211> LENGTH: 250
<212> TYPE: DNA
<213> ORGANISM: Homo sapiens

<400> SEQUENCE: 1
tctagagcca tttacacgtc cagtgctgag agccagctcc ttccagccca tcagcgggaa 60

-continued cccagtgacc ctgacctgtg agacccagct ctctctagag aggtcagatg tcccgctccg 120
gttccgcttc ttcagagatg accagaccct gggattaggc tggagtctct ccccgaattt 180
ccagattact gccatgtgga gtaaagattc agggttctac tggtgtaagg cagcaacaat 240
gccttacagc 250

<210> SEQ ID NO 2
<211> LENGTH: 250
<212> TYPE: DNA
<213> ORGANISM: Homo sapiens

<400> SEQUENCE: 2
tcatatctga cagcccgaga tcctggatac aggtgcagag taagtgttgg tggaacctga 60
gatttgctgc agagagggct ggaaaagtgg gacagggctg catatcagcg tgggtcacca 120
gtctctgtag aaaaaactcg tacctgtgag aatgggagtt gtgcaagcaa agagacctct 180
actcttgtga acatcttaga agagcttaga cccaggaaaa tccaagaaaa gaaaggtcta 240
atttttttc 250

<210> SEQ ID NO 3
<211> LENGTH: 31
<212> TYPE: DNA
<213> ORGANISM: Homo sapiens

<400> SEQUENCE: 3
acaatgcctt acagcgtcat atctgacagc c 31

<210> SEQ ID NO 4
<211> LENGTH: 31
<212> TYPE: DNA
<213> ORGANISM: Homo sapiens

<400> SEQUENCE: 4
acaatgcctt acagcatcat atctgacagc c 31

<210> SEQ ID NO 5
<211> LENGTH: 51
<212> TYPE: DNA
<213> ORGANISM: Homo sapiens

<400> SEQUENCE: 5
taaggcagca acaatgcctt acagcgtcat atctgacagc ccgagatcct g 51

<210> SEQ ID NO 6
<211> LENGTH: 51
<212> TYPE: DNA
<213> ORGANISM: Homo sapiens

<400> SEQUENCE: 6
taaggcagca acaatgcctt acagcatcat atctgacagc ccgagatcct g 51

<210> SEQ ID NO 7
<211> LENGTH: 250
<212> TYPE: DNA
<213> ORGANISM: Homo sapiens

<400> SEQUENCE: 7
ataatttact tctgtgtagc tatatcagtg tgggtactcc ttttcatgta ttcattttca 60
catatttatc tctagagagg gatatacatt ttgtcaatat aattactcat taccactact 120
gttatttttc ccccacttag aatgcatcac taggcccaac caatggatct aaattaatga 180

-continued atcgtcaagg atgaaatgtg agtattaaaa atataaagag aaatttcact tgcaatttgt 240
gtcaatccac 250

<210> SEQ ID NO 8
<211> LENGTH: 250
<212> TYPE: DNA
<213> ORGANISM: Homo sapiens

<400> SEQUENCE: 8
aatgcccctt gtgaccacac tattgcctgc tacgtgctgc cagaatgagg tgggagggga 60
agagggggac atctttttca aagaatggaa acatctttat tgtctagcac ataaatgaaa 120
atatgtacat tttctgtaaa acctatgtca tctcagctta catgaccaaa cccatcacac 180
ctgctgtcta cagtgctcac ataccttaat tccatcttgt cagtgagtaa taacactcat 240
aatagcccca 250

<210> SEQ ID NO 9
<211> LENGTH: 31
<212> TYPE: DNA
<213> ORGANISM: Homo sapiens

<400> SEQUENCE: 9
tttgtgtcaa tccaccaatg ccccttgtga c 31

<210> SEQ ID NO 10
<211> LENGTH: 31
<212> TYPE: DNA
<213> ORGANISM: Homo sapiens

<400> SEQUENCE: 10
tttgtgtcaa tccacaaatg ccccttgtga c 31

<210> SEQ ID NO 11
<211> LENGTH: 51
<212> TYPE: DNA
<213> ORGANISM: Homo sapiens

<400> SEQUENCE: 11
tcacttgcaa tttgtgtcaa tccaccaatg ccccttgtga ccacactatt g 51

<210> SEQ ID NO 12
<211> LENGTH: 51
<212> TYPE: DNA
<213> ORGANISM: Homo sapiens

<400> SEQUENCE: 12
tcacttgcaa tttgtgtcaa tccacaaatg ccccttgtga ccacactatt g 51

<210> SEQ ID NO 13
<211> LENGTH: 250
<212> TYPE: DNA
<213> ORGANISM: Homo sapiens

<400> SEQUENCE: 13
tgcctgccgg tcaacgctgg ccatagagcc tggcagtggc ctcaggcaga gtctgacgcg 60
cacaaacttt caggcccagg aagcgaggac accactgggg ccccagggtg tggcaagtga 120
ggatggcaag ggttttgcta aacaaatcct ctgcccgctc cccgccccgg gctcactcca 180
tgtgaggccc cagtcggggc agccacctgc cgtgcctgtt ggaagttgcc tctgccatgc 240

-continued

```
tgggccctgc                                                          250


<210> SEQ ID NO 14
<211> LENGTH: 250
<212> TYPE: DNA
<213> ORGANISM: Homo sapiens

<400> SEQUENCE: 14

gtcctgggcc tcagcctctg ggctctcctg caccctggga cgggggcccc attgtgcctg     60

tcacagcaac ttaggatgaa gggggactac gtgctggggg ggctgttccc cctgggcgag    120

gccgaggagg ctggcctccg cagccggaca cggcccagca gccctgtgtg caccaggtac    180

agaggtggga cggcctgggt cggggtcagg gtgaccaggt ctggggtgct cctgagctgg    240

ggccgaggtg                                                          250


<210> SEQ ID NO 15
<211> LENGTH: 31
<212> TYPE: DNA
<213> ORGANISM: Homo sapiens

<400> SEQUENCE: 15

catgctgggc cctgctgtcc tgggcctcag c                                   31


<210> SEQ ID NO 16
<211> LENGTH: 31
<212> TYPE: DNA
<213> ORGANISM: Homo sapiens

<400> SEQUENCE: 16

catgctgggc cctgcagtcc tgggcctcag c                                   31


<210> SEQ ID NO 17
<211> LENGTH: 51
<212> TYPE: DNA
<213> ORGANISM: Homo sapiens

<400> SEQUENCE: 17

ttgcctctgc catgctgggc cctgctgtcc tgggcctcag cctctgggct c             51


<210> SEQ ID NO 18
<211> LENGTH: 51
<212> TYPE: DNA
<213> ORGANISM: Homo sapiens

<400> SEQUENCE: 18

ttgcctctgc catgctgggc cctgcagtcc tgggcctcag cctctgggct c             51


<210> SEQ ID NO 19
<211> LENGTH: 250
<212> TYPE: DNA
<213> ORGANISM: Homo sapiens

<400> SEQUENCE: 19

tgtatggggg tctgattgct gtgatgcaca cagctggcac cttctcctta tcctactgtg     60

ggtccaacat ggtccatcag ttcttctgtg acattcccca gttattagct atttcttgct    120

cagaaaattt aataagagaa attgcactca tccttattaa tgtagttttg gatttctgct    180

gttttattgt catcatcatt acctatgtcc acgtcttctc tacagtcaag aagatccctt    240

ccacagaagg                                                          250
```

-continued

<210> SEQ ID NO 20
<211> LENGTH: 250
<212> TYPE: DNA
<213> ORGANISM: Homo sapiens

<400> SEQUENCE: 20
cagtcaaaag cctactctat ttgccttcca cacttgctgg ttgtgttatt tctttccact 60
ggattcattg cttatctgaa gccagcttca gagtctcctt ctattttgga tgctgtaatt 120
tctgtgttct acactatgct gcccccaacc tttaatccca ttatatacag tttgagaaac 180
aaggccataa aggtggctct ggggatgttg ataaagggaa agctcaccaa aaagtaaaag 240
ctgttgcttt 250

<210> SEQ ID NO 21
<211> LENGTH: 31
<212> TYPE: DNA
<213> ORGANISM: Homo sapiens

<400> SEQUENCE: 21
cccttccaca gaaggccagt caaaagccta c 31

<210> SEQ ID NO 22
<211> LENGTH: 31
<212> TYPE: DNA
<213> ORGANISM: Homo sapiens

<400> SEQUENCE: 22
cccttccaca gaaggtcagt caaaagccta c 31

<210> SEQ ID NO 23
<211> LENGTH: 51
<212> TYPE: DNA
<213> ORGANISM: Homo sapiens

<400> SEQUENCE: 23
tcaagaagat cccttccaca gaaggccagt caaaagccta ctctatttgc c 51

<210> SEQ ID NO 24
<211> LENGTH: 51
<212> TYPE: DNA
<213> ORGANISM: Homo sapiens

<400> SEQUENCE: 24
tcaagaagat cccttccaca gaaggtcagt caaaagccta ctctatttgc c 51

<210> SEQ ID NO 25
<211> LENGTH: 250
<212> TYPE: DNA
<213> ORGANISM: Homo sapiens

<400> SEQUENCE: 25
aacttgagtt ctaataaagg catgacaatc acacaagaat gaggctaaac tctgaagatg 60
gtcatcttac atcatacaac tacctgatta accattttca accaaacact ccctccaccc 120
atattgacag tggatttctg catgaacagt tggttgactc tggagttgct ttaacttgtt 180
ctgtaggagg atcaaaaaca ctggcttgac tgtttttttg gttccatgtt acttggtcac 240
atacatacgg 250

<210> SEQ ID NO 26
<211> LENGTH: 250
<212> TYPE: DNA

-continued

<213> ORGANISM: Homo sapiens

<400> SEQUENCE: 26
ccatgccctc agaaatgtat atgtatatcc ctgcccaaag ttattttgcg gtttgggatt 60
tgaggaatgt tcctgtgaat tgaccctagg gataatttag atattgttaa agttttccca 120
acgtgattta tttcaacagc attaattagg atatgtctga tctgaatgct ctgattttag 180
gactgtttgg aataggttac atgttttcta ggtattgtga aatcatcctc tttgtcattt 240
ctgactctct 250

<210> SEQ ID NO 27
<211> LENGTH: 31
<212> TYPE: DNA
<213> ORGANISM: Homo sapiens

<400> SEQUENCE: 27
gtcacataca tacggcccat gccctcagaa a 31

<210> SEQ ID NO 28
<211> LENGTH: 31
<212> TYPE: DNA
<213> ORGANISM: Homo sapiens

<400> SEQUENCE: 28
gtcacataca tacggtccat gccctcagaa a 31

<210> SEQ ID NO 29
<211> LENGTH: 51
<212> TYPE: DNA
<213> ORGANISM: Homo sapiens

<400> SEQUENCE: 29
atgttacttg gtcacataca tacggcccat gccctcagaa atgtatatgt a 51

<210> SEQ ID NO 30
<211> LENGTH: 51
<212> TYPE: DNA
<213> ORGANISM: Homo sapiens

<400> SEQUENCE: 30
atgttacttg gtcacataca tacggtccat gccctcagaa atgtatatgt a 51

<210> SEQ ID NO 31
<211> LENGTH: 250
<212> TYPE: DNA
<213> ORGANISM: Homo sapiens

<400> SEQUENCE: 31
ttcagccaaa gtctttcagc tccatccata gcttctgttc ttttcatgac acaggtccta 60
gagggagtct tcctggtacc tcctaaagca ggctccgtgg gaagccatta cacttcccat 120
gtgtacccac agggaggacg cttccctgct tgctcctctc cctttcttct cctccccgat 180
cttagtgcta acaattccat cctgctttcc ttcctctaca ggtgagcatc tccaccgtgg 240
gctacggaga 250

<210> SEQ ID NO 32
<211> LENGTH: 250
<212> TYPE: DNA
<213> ORGANISM: Homo sapiens

<400> SEQUENCE: 32

-continued

```
atgtacccag agacccacct gggcaggttt tttgccttcc tctgcattgc ttttgggatc     60

attctcaacg ggatgcccat ttccatcctc tacaacaagt tttctgatta ctacagcaag    120

ctgaaggctt atgagtatac caccatacgc agggagaggg gagaggtgaa cttcatgcag    180

agagccagaa agaagatagc tgagtgtttg cttggaagca acccacagct caccccaaga    240

caagagaatt                                                           250
```

<210> SEQ ID NO 33
<211> LENGTH: 31
<212> TYPE: DNA
<213> ORGANISM: Homo sapiens

<400> SEQUENCE: 33

```
cgtgggctac ggagacatgt acccagagac c                                    31
```

<210> SEQ ID NO 34
<211> LENGTH: 31
<212> TYPE: DNA
<213> ORGANISM: Homo sapiens

<400> SEQUENCE: 34

```
cgtgggctac ggagatatgt acccagagac c                                    31
```

<210> SEQ ID NO 35
<211> LENGTH: 51
<212> TYPE: DNA
<213> ORGANISM: Homo sapiens

<400> SEQUENCE: 35

```
gcatctccac cgtgggctac ggagacatgt acccagagac ccacctgggc a              51
```

<210> SEQ ID NO 36
<211> LENGTH: 51
<212> TYPE: DNA
<213> ORGANISM: Homo sapiens

<400> SEQUENCE: 36

```
gcatctccac cgtgggctac ggagatatgt acccagagac ccacctgggc a              51
```

<210> SEQ ID NO 37
<211> LENGTH: 250
<212> TYPE: DNA
<213> ORGANISM: Homo sapiens

<400> SEQUENCE: 37

```
tcctctacag gtgagcatct ccaccgtggg ctacggagac atgtacccag agacccacct     60

gggcaggttt tttgccttcc tctgcattgc ttttgggatc attctcaacg ggatgcccat    120

ttccatcctc tacaacaagt tttctgatta ctacagcaag ctgaaggctt atgagtatac    180

caccatacgc agggagaggg gagaggtgaa cttcatgcag agagccagaa agaagatagc    240

tgagtgtttg                                                           250
```

<210> SEQ ID NO 38
<211> LENGTH: 250
<212> TYPE: DNA
<213> ORGANISM: Homo sapiens

<400> SEQUENCE: 38

```
ttggaagcaa cccacagctc accccaagac aagagaatta gtattttata ggacatgtgg     60
```

-continued

```
ctggtagatt ccatgaactt caaggcttca ttgctctttt tttaatcatt atgattggca    120

gcaaaaggaa atgtgaagca gacatacaca aaggccattt cgttcacaaa gtactgcctc    180

tagaaatact cattttggcc caaactcaga atgtctcata gttgctctgt gttgtgtgaa    240

acatctgacc                                                           250


<210> SEQ ID NO 39
<211> LENGTH: 31
<212> TYPE: DNA
<213> ORGANISM: Homo sapiens

<400> SEQUENCE: 39

atagctgagt gtttgcttgg aagcaaccca c                                    31


<210> SEQ ID NO 40
<211> LENGTH: 31
<212> TYPE: DNA
<213> ORGANISM: Homo sapiens

<400> SEQUENCE: 40

atagctgagt gtttggttgg aagcaaccca c                                    31


<210> SEQ ID NO 41
<211> LENGTH: 51
<212> TYPE: DNA
<213> ORGANISM: Homo sapiens

<400> SEQUENCE: 41

cagaaagaag atagctgagt gtttgcttgg aagcaaccca cagctcaccc c              51


<210> SEQ ID NO 42
<211> LENGTH: 51
<212> TYPE: DNA
<213> ORGANISM: Homo sapiens

<400> SEQUENCE: 42

cagaaagaag atagctgagt gtttggttgg aagcaaccca cagctcaccc c              51


<210> SEQ ID NO 43
<211> LENGTH: 250
<212> TYPE: DNA
<213> ORGANISM: Homo sapiens

<400> SEQUENCE: 43

tgacctaaag atgtagtcta catagcccca gcttggggtc caatccatct gtccctggca     60

tgtgccttca tgtagtaggt gctttcctga tcccctttgc gagatgctgt gggtgctaac    120

acctcagagc tgtcctcttc tctagagtgg aggttttcaa agtgcatcat cagcattacc    180

tgtgaacttg ctggaaatac aaatcctcag gccccacctc agacctactg aatcagaatc    240

tctgggggtt                                                           250


<210> SEQ ID NO 44
<211> LENGTH: 250
<212> TYPE: DNA
<213> ORGANISM: Homo sapiens

<400> SEQUENCE: 44

gcacagcatt ctgatttacc aaaccctcca agtgattttg atgtattcta attttgagac     60

catctctaga aaagaattgc tacctcttgt atggaggtac aaaagactga cctcttacat    120

caaggaactt cctttcccag agctcctcat ggaatcaagc tgaagtcagt cttcttctga    180
```

-continued

```
gagcacattc ttactcagtt tttttcctct gtcctacgct gcttccctca ctccccttct    240

cctaagagca                                                            250


<210> SEQ ID NO 45
<211> LENGTH: 31
<212> TYPE: DNA
<213> ORGANISM: Homo sapiens

<400> SEQUENCE: 45

gaatctctgg gggttggcac agcattctga t                                     31


<210> SEQ ID NO 46
<211> LENGTH: 31
<212> TYPE: DNA
<213> ORGANISM: Homo sapiens

<400> SEQUENCE: 46

gaatctctgg gggttagcac agcattctga t                                     31


<210> SEQ ID NO 47
<211> LENGTH: 51
<212> TYPE: DNA
<213> ORGANISM: Homo sapiens

<400> SEQUENCE: 47

tactgaatca gaatctctgg gggttggcac agcattctga tttaccaaac c               51


<210> SEQ ID NO 48
<211> LENGTH: 51
<212> TYPE: DNA
<213> ORGANISM: Homo sapiens

<400> SEQUENCE: 48

tactgaatca gaatctctgg gggttagcac agcattctga tttaccaaac c               51


<210> SEQ ID NO 49
<211> LENGTH: 250
<212> TYPE: DNA
<213> ORGANISM: Homo sapiens

<400> SEQUENCE: 49

gcaatcgcca gaacaatggc agaagatgta cggtagatgc tccgggaatg aagtctacca     60

cattgttttg gaagaaagta cattttttgc tgaatatgaa ggaaagagtt ttacatatgc    120

ctctttccat gcacacaaaa agtatgtttc tgcctcagag aaaaattaaa atatcaatca    180

gtcaagcata tcatgtgaaa atagttttca aaaatagaat gcatattgtg ttcatgtgtt    240

taggcattcc                                                            250


<210> SEQ ID NO 50
<211> LENGTH: 250
<212> TYPE: DNA
<213> ORGANISM: Homo sapiens

<400> SEQUENCE: 50

gaatttttgt cacaatattc cccaatgttg aaacatttga accctggtgt ctgtatggtc     60

tctataagac agtcaggagt aaattataat ttagtaggaa tatttcattt agccactttt    120

aaagtctttt taaaatattt taatccatta agaatttaca tacatatgaa aatcttcttc    180

acagatctga attttaagat gttgattagg aactaaaaca aagtaacact aatatttcta    240
```

-continued aaaactgtac 250

<210> SEQ ID NO 51
<211> LENGTH: 31
<212> TYPE: DNA
<213> ORGANISM: Homo sapiens

<400> SEQUENCE: 51
gtgtttaggc attccggaat ttttgtcaca a 31

<210> SEQ ID NO 52
<211> LENGTH: 31
<212> TYPE: DNA
<213> ORGANISM: Homo sapiens

<400> SEQUENCE: 52
gtgtttaggc attccagaat ttttgtcaca a 31

<210> SEQ ID NO 53
<211> LENGTH: 51
<212> TYPE: DNA
<213> ORGANISM: Homo sapiens

<400> SEQUENCE: 53
ttgtgttcat gtgtttaggc attccggaat ttttgtcaca atattcccca a 51

<210> SEQ ID NO 54
<211> LENGTH: 51
<212> TYPE: DNA
<213> ORGANISM: Homo sapiens

<400> SEQUENCE: 54
ttgtgttcat gtgtttaggc attccagaat ttttgtcaca atattcccca a 51

<210> SEQ ID NO 55
<211> LENGTH: 250
<212> TYPE: DNA
<213> ORGANISM: Homo sapiens

<400> SEQUENCE: 55
tattcactcc agagacagcc actcatccca agccctgccc tcacagagct ccccatctag 60
ggaaggggag tcctgaggct cccctggatg tgaccaaggc ttactctcaa cacttagctt 120
ctactccatg atgttcttac caagcaggca gtcttggttt cctctttcgt gtggctgccg 180
cattctgtct tctggagttt gtatagggga cacatgtcaa gatctttcac gaagattttc 240
ctcaggacac 250

<210> SEQ ID NO 56
<211> LENGTH: 250
<212> TYPE: DNA
<213> ORGANISM: Homo sapiens

<400> SEQUENCE: 56
catcgtcatg tgatttcctg tctggaccat gcaacagaga gcccagggat tattaacgag 60
aaggcagtcc cctatgtcaa cacaactccc actcatatag ccaaacgaga gtgagaattt 120
tttttttttt ttgagttgga gtcttgttct gtcacgcagg ctggagtaca gtggtgtgat 180
cttggctcac tgcaacttct gcctttcggg ttcaagcaat tctcctgcct cagcttccgg 240
agtagctggg 250

-continued

<210> SEQ ID NO 57
<211> LENGTH: 31
<212> TYPE: DNA
<213> ORGANISM: Homo sapiens

<400> SEQUENCE: 57
ttttcctcag gacactcatc gtcatgtgat t 31

<210> SEQ ID NO 58
<211> LENGTH: 31
<212> TYPE: DNA
<213> ORGANISM: Homo sapiens

<400> SEQUENCE: 58
ttttcctcag gacacccatc gtcatgtgat t 31

<210> SEQ ID NO 59
<211> LENGTH: 51
<212> TYPE: DNA
<213> ORGANISM: Homo sapiens

<400> SEQUENCE: 59
ttcacgaaga ttttcctcag gacactcatc gtcatgtgat ttcctgtctg g 51

<210> SEQ ID NO 60
<211> LENGTH: 51
<212> TYPE: DNA
<213> ORGANISM: Homo sapiens

<400> SEQUENCE: 60
ttcacgaaga ttttcctcag gacacccatc gtcatgtgat ttcctgtctg g 51

<210> SEQ ID NO 61
<211> LENGTH: 250
<212> TYPE: DNA
<213> ORGANISM: Homo sapiens

<400> SEQUENCE: 61
aagatgttct gactcggggt ctccaaaacc agcctgcggt ataggcggaa ggcaaagtcg 60
gtgttgaggg aatacacctg tgaggcaggg gtgctctttg tggaggaagg gcgggggtat 120
gcactggggg cattggccgg ggacacacag tagattggag cacagaggcc aacagcaaag 180
agtactccat aaaggtaaga tgccattttg gaacaaaata tgtctgcaag agaagtaaga 240
accattgagg 250

<210> SEQ ID NO 62
<211> LENGTH: 250
<212> TYPE: DNA
<213> ORGANISM: Homo sapiens

<400> SEQUENCE: 62
ggtaaactga gggtccaggc cctgaatcag agaccctta acacccccac gccatcagca 60
gcagaatgag gacagatagg ccagttagca gagctctctc acataatctc tgagcctcac 120
aatattccca tgatgtagat cttattattg ctgttttact tgcaaatgag taaacaggcc 180
acagagagtc tgtgcaactt accccaaata gcatggttga cttgtctgtg ttctgtgtgg 240
gcttcaaagt 250

<210> SEQ ID NO 63
<211> LENGTH: 31
<212> TYPE: DNA

-continued

<213> ORGANISM: Homo sapiens

<400> SEQUENCE: 63
taagaaccat tgagggggta aactgagggt c 31

<210> SEQ ID NO 64
<211> LENGTH: 31
<212> TYPE: DNA
<213> ORGANISM: Homo sapiens

<400> SEQUENCE: 64
taagaaccat tgaggtggta aactgagggt c 31

<210> SEQ ID NO 65
<211> LENGTH: 51
<212> TYPE: DNA
<213> ORGANISM: Homo sapiens

<400> SEQUENCE: 65
gcaagagaag taagaaccat tgagggggta aactgagggt ccaggccctg a 51

<210> SEQ ID NO 66
<211> LENGTH: 51
<212> TYPE: DNA
<213> ORGANISM: Homo sapiens

<400> SEQUENCE: 66
gcaagagaag taagaaccat tgaggtggta aactgagggt ccaggccctg a 51

<210> SEQ ID NO 67
<211> LENGTH: 250
<212> TYPE: DNA
<213> ORGANISM: Homo sapiens

<400> SEQUENCE: 67
ccatcaggga tgtgacaaag tggataatct ctaccacgtg agaaacttcc aacattactt 60
gcaaatcaga tttaatgaat aaaataaagc tgtagcactt ggcacattca ttgggaccct 120
tacccaaaca ttatcaatat tgtgtacgtt atctttatta tcaggtcaca aaagatgtca 180
taaaagaatt tgcagatgac ggcgtcaagt acctggaact aaggagcaca cccagaagag 240
aaaatgctac 250

<210> SEQ ID NO 68
<211> LENGTH: 250
<212> TYPE: DNA
<213> ORGANISM: Homo sapiens

<400> SEQUENCE: 68
ggtagaattt atacttctca gcaaatgtac tgtccttttc ctatgtgctt tgatcactca 60
catgtttgtg agtgggaata tgaagcacta acttttatac tattgtgttg ttctgtattt 120
cattgaacct ttagtcaaca gtccaagtcc tctctctgat gtacattaat gatgttcatt 180
ttgtttgttt tagagacagg gtcttgctgt cttgcccagg ctggagtgca gtggtgcaaa 240
catagctcac 250

<210> SEQ ID NO 69
<211> LENGTH: 31
<212> TYPE: DNA
<213> ORGANISM: Homo sapiens

<400> SEQUENCE: 69

-continued aagagaaaat gctacaggta gaatttatac t 31

<210> SEQ ID NO 70
<211> LENGTH: 31
<212> TYPE: DNA
<213> ORGANISM: Homo sapiens

<400> SEQUENCE: 70
aagagaaaat gctacgggta gaatttatac t 31

<210> SEQ ID NO 71
<211> LENGTH: 51
<212> TYPE: DNA
<213> ORGANISM: Homo sapiens

<400> SEQUENCE: 71
gcacacccag aagagaaaat gctacaggta gaatttatac ttctcagcaa a 51

<210> SEQ ID NO 72
<211> LENGTH: 51
<212> TYPE: DNA
<213> ORGANISM: Homo sapiens

<400> SEQUENCE: 72
gcacacccag aagagaaaat gctacgggta gaatttatac ttctcagcaa a 51

<210> SEQ ID NO 73
<211> LENGTH: 250
<212> TYPE: DNA
<213> ORGANISM: Homo sapiens

<400> SEQUENCE: 73
gatacattga cttacacaaa gtgtggacct tgtttggatc ctgaatcaaa caaactgaag 60
aaacaaatac aggaacaaaa aaacctcgaa agacaactgt aaatctgaac agtgactgga 120
tgcttgatgc tatttaggaa ttcatgtctc agtccgtatg acaaagtaaa atgtcatgtt 180
gtctagattc agtcaggcta tacttttcct agtgagatgt attacacgta gtctgccatc 240
tctgtctggc 250

<210> SEQ ID NO 74
<211> LENGTH: 250
<212> TYPE: DNA
<213> ORGANISM: Homo sapiens

<400> SEQUENCE: 74
gtactcagaa ttgtcttttt catctgtgtc atattagttt tcaactctgt ctttcttaca 60
ttaaaggtat ttgatagcag ttgacagaag aggtggccct ttagtagcca aggagactgt 120
aaaacttgcc gaggagttct tcctttctac tgagggtaca gttcttggcc ttgacctcag 180
tggagaccct actgtaagtt atttttccta cgtacatttt aattctaaaa ggtagaatca 240
gtgggataag 250

<210> SEQ ID NO 75
<211> LENGTH: 31
<212> TYPE: DNA
<213> ORGANISM: Homo sapiens

<400> SEQUENCE: 75
ccatctctgt ctggctgtac tcagaattgt c 31

-continued

<210> SEQ ID NO 76
<211> LENGTH: 31
<212> TYPE: DNA
<213> ORGANISM: Homo sapiens

<400> SEQUENCE: 76
ccatctctgt ctggccgtac tcagaattgt c 31

<210> SEQ ID NO 77
<211> LENGTH: 51
<212> TYPE: DNA
<213> ORGANISM: Homo sapiens

<400> SEQUENCE: 77
acgtagtctg ccatctctgt ctggctgtac tcagaattgt ctttttcatc t 51

<210> SEQ ID NO 78
<211> LENGTH: 51
<212> TYPE: DNA
<213> ORGANISM: Homo sapiens

<400> SEQUENCE: 78
acgtagtctg ccatctctgt ctggccgtac tcagaattgt ctttttcatc t 51

<210> SEQ ID NO 79
<211> LENGTH: 250
<212> TYPE: DNA
<213> ORGANISM: Homo sapiens

<400> SEQUENCE: 79
tatttattgc tgaacagaaa atatattttt cttccttctt gggaatagtt gggctacttg 60
cttgctgttc cttcttagtg agacttttct ccaaatagtg aatgatgagg ttgagctata 120
agacatacct gaattttacc ttgtagtagg attaatagta attccactag tggccctcct 180
aattgattta tcccatcctt tcacagaacc atgatggcag cattgacttc cgagagtatg 240
tgattggcct 250

<210> SEQ ID NO 80
<211> LENGTH: 250
<212> TYPE: DNA
<213> ORGANISM: Homo sapiens

<400> SEQUENCE: 80
gctgtcttgt gcaacccttc caacacagag gagatcatcc aggtggcatt taaggtactg 60
tcagccccat tgaaagcatc ttggtctgcc ttgtaaacaa gtgttgactc taagtgtatt 120
atttgaaaat cagtgaatct attatgtgat tttatagatc tgctgtgaca tgtacaggac 180
aataatgtga ttaagtcagt tgctactaag aataaagaaa acacaagcat ttatttaagc 240
aaaaagtttc 250

<210> SEQ ID NO 81
<211> LENGTH: 31
<212> TYPE: DNA
<213> ORGANISM: Homo sapiens

<400> SEQUENCE: 81
gtatgtgatt ggcctggctg tcttgtgcaa c 31

<210> SEQ ID NO 82
<211> LENGTH: 31

-continued

<212> TYPE: DNA
<213> ORGANISM: Homo sapiens

<400> SEQUENCE: 82
gtatgtgatt ggcctagctg tcttgtgcaa c 31

<210> SEQ ID NO 83
<211> LENGTH: 51
<212> TYPE: DNA
<213> ORGANISM: Homo sapiens

<400> SEQUENCE: 83
acttccgaga gtatgtgatt ggcctggctg tcttgtgcaa cccttccaac a 51

<210> SEQ ID NO 84
<211> LENGTH: 51
<212> TYPE: DNA
<213> ORGANISM: Homo sapiens

<400> SEQUENCE: 84
acttccgaga gtatgtgatt ggcctagctg tcttgtgcaa cccttccaac a 51

<210> SEQ ID NO 85
<211> LENGTH: 250
<212> TYPE: DNA
<213> ORGANISM: Homo sapiens

<400> SEQUENCE: 85
cctgcctgcc ggtcaacgct ggccatagag cctggcagtg gcctcaggca gagtctgacg 60
cgcacaaact ttcaggccca ggaagcgagg acaccactgg ggccccaggg tgtggcaagt 120
gaggatggca agggttttgc taaacaaatc ctctgcccgc tccccgcccc gggctcactc 180
catgtgaggc cccagtcggg gcagccacct gccgtgcctg ttggaagttg cctctgccat 240
gctgggccct 250

<210> SEQ ID NO 86
<211> LENGTH: 250
<212> TYPE: DNA
<213> ORGANISM: Homo sapiens

<400> SEQUENCE: 86
ctgtcctggg cctcagcctc tgggctctcc tgcaccctgg gacgggggcc ccattgtgcc 60
tgtcacagca acttaggatg aagggggact acgtgctggg ggggctgttc cccctgggcg 120
aggccgagga ggctggcctc cgcagccgga cacggcccag cagccctgtg tgcaccaggt 180
acagaggtgg gacggcctgg gtcggggtca gggtgaccag gtctggggtg ctcctgagct 240
ggggccgagg 250

<210> SEQ ID NO 87
<211> LENGTH: 31
<212> TYPE: DNA
<213> ORGANISM: Homo sapiens

<400> SEQUENCE: 87
gccatgctgg gccctgctgt cctgggcctc a 31

<210> SEQ ID NO 88
<211> LENGTH: 31
<212> TYPE: DNA
<213> ORGANISM: Homo sapiens -continued

<400> SEQUENCE: 88
gccatgctgg gccctactgt cctgggcctc a 31

<210> SEQ ID NO 89
<211> LENGTH: 51
<212> TYPE: DNA
<213> ORGANISM: Homo sapiens

<400> SEQUENCE: 89
agttgcctct gccatgctgg gccctgctgt cctgggcctc agcctctggg c 51

<210> SEQ ID NO 90
<211> LENGTH: 51
<212> TYPE: DNA
<213> ORGANISM: Homo sapiens

<400> SEQUENCE: 90
agttgcctct gccatgctgg gccctactgt cctgggcctc agcctctggg c 51

<210> SEQ ID NO 91
<211> LENGTH: 250
<212> TYPE: DNA
<213> ORGANISM: Homo sapiens

<400> SEQUENCE: 91
cttctctcta gagccattta cacgtccagt gctgagagcc agctccttcc agcccatcag 60
cgggaaccca gtgaccctga cctgtgagac ccagctctct ctagagaggt cagatgtccc 120
gctccggttc cgcttcttca gagatgacca gaccctggga ttaggctgga gtctctcccc 180
gaatttccag attactgcca tgtggagtaa agattcaggg ttctactggt gtaaggcagc 240
aacaatgcct 250

<210> SEQ ID NO 92
<211> LENGTH: 250
<212> TYPE: DNA
<213> ORGANISM: Homo sapiens

<400> SEQUENCE: 92
acagcgtcat atctgacagc ccgagatcct ggatacaggt gcagagtaag tgttggtgga 60
acctgagatt tgctgcagag agggctggaa aagtgggaca gggctgcata tcagcgtggg 120
tcaccagtct ctgtagaaaa aactcgtacc tgtgagaatg ggagttgtgc aagcaaagag 180
acctctactc ttgtgaacat cttagaagag cttagaccca ggaaaatcca agaaaagaaa 240
ggtctaattt 250

<210> SEQ ID NO 93
<211> LENGTH: 31
<212> TYPE: DNA
<213> ORGANISM: Homo sapiens

<400> SEQUENCE: 93
gcagcaacaa tgccttacag cgtcatatct g 31

<210> SEQ ID NO 94
<211> LENGTH: 31
<212> TYPE: DNA
<213> ORGANISM: Homo sapiens

<400> SEQUENCE: 94
gcagcaacaa tgcctcacag cgtcatatct g 31

-continued

<210> SEQ ID NO 95
<211> LENGTH: 51
<212> TYPE: DNA
<213> ORGANISM: Homo sapiens

<400> SEQUENCE: 95
ctggtgtaag gcagcaacaa tgccttacag cgtcatatct gacagcccga g 51

<210> SEQ ID NO 96
<211> LENGTH: 51
<212> TYPE: DNA
<213> ORGANISM: Homo sapiens

<400> SEQUENCE: 96
ctggtgtaag gcagcaacaa tgcctcacag cgtcatatct gacagcccga g 51

<210> SEQ ID NO 97
<211> LENGTH: 20
<212> TYPE: DNA
<213> ORGANISM: Homo sapiens

<400> SEQUENCE: 97
ctcagatgtg ctccttggag 20

<210> SEQ ID NO 98
<211> LENGTH: 29
<212> TYPE: DNA
<213> ORGANISM: Homo sapiens

<400> SEQUENCE: 98
atgttaacat aggattttta atgtggaaa 29

<210> SEQ ID NO 99
<211> LENGTH: 20
<212> TYPE: DNA
<213> ORGANISM: Homo sapiens

<400> SEQUENCE: 99
atgaaaatga agtcccaggc 20

<210> SEQ ID NO 100
<211> LENGTH: 26
<212> TYPE: DNA
<213> ORGANISM: Homo sapiens

<400> SEQUENCE: 100
tcatccttga cgattcatta atttag 26

<210> SEQ ID NO 101
<211> LENGTH: 18
<212> TYPE: DNA
<213> ORGANISM: Homo sapiens

<400> SEQUENCE: 101
atgctgggcc ctacagtc 18

<210> SEQ ID NO 102
<211> LENGTH: 21
<212> TYPE: DNA
<213> ORGANISM: Homo sapiens

<400> SEQUENCE: 102

-continued tcactcatgt ttcccctgat t 21

<210> SEQ ID NO 103
<211> LENGTH: 35
<212> TYPE: DNA
<213> ORGANISM: Homo sapiens

<400> SEQUENCE: 103
atgtgttata tatatttaat atttaaagag tggac 35

<210> SEQ ID NO 104
<211> LENGTH: 22
<212> TYPE: DNA
<213> ORGANISM: Homo sapiens

<400> SEQUENCE: 104
ttactttttg gtgagctttc cc 22

<210> SEQ ID NO 105
<211> LENGTH: 18
<212> TYPE: DNA
<213> ORGANISM: Homo sapiens

<400> SEQUENCE: 105
atgacgtcca cctgcacc 18

<210> SEQ ID NO 106
<211> LENGTH: 25
<212> TYPE: DNA
<213> ORGANISM: Homo sapiens

<400> SEQUENCE: 106
tcaaggaaaa gtagcagaat cgtag 25

<210> SEQ ID NO 107
<211> LENGTH: 24
<212> TYPE: DNA
<213> ORGANISM: Homo sapiens

<400> SEQUENCE: 107
aagtcaggct ccctttaaat atgg 24

<210> SEQ ID NO 108
<211> LENGTH: 29
<212> TYPE: DNA
<213> ORGANISM: Homo sapiens

<400> SEQUENCE: 108
caagtccaaa aatatttatt gagctagat 29

<210> SEQ ID NO 109
<211> LENGTH: 24
<212> TYPE: DNA
<213> ORGANISM: Homo sapiens

<400> SEQUENCE: 109
aagtcaggct ccctttaaat atgg 24

<210> SEQ ID NO 110
<211> LENGTH: 29
<212> TYPE: DNA
<213> ORGANISM: Homo sapiens

<400> SEQUENCE: 110

-continued caagtccaaa aatatttatt gagctagat 29

<210> SEQ ID NO 111
<211> LENGTH: 15
<212> TYPE: DNA
<213> ORGANISM: Homo sapiens

<400> SEQUENCE: 111
ccacgcgtcc ggtga 15

<210> SEQ ID NO 112
<211> LENGTH: 22
<212> TYPE: DNA
<213> ORGANISM: Homo sapiens

<400> SEQUENCE: 112
ctcgtgcaag tggtttattg at 22

<210> SEQ ID NO 113
<211> LENGTH: 24
<212> TYPE: DNA
<213> ORGANISM: Homo sapiens

<400> SEQUENCE: 113
ccagagatca agtctaagga tacg 24

<210> SEQ ID NO 114
<211> LENGTH: 35
<212> TYPE: DNA
<213> ORGANISM: Homo sapiens

<400> SEQUENCE: 114
cattagaaat aattttatta tttattttaa agcag 35

<210> SEQ ID NO 115
<211> LENGTH: 21
<212> TYPE: DNA
<213> ORGANISM: Homo sapiens

<400> SEQUENCE: 115
gagcaggaac agttcatgga c 21

<210> SEQ ID NO 116
<211> LENGTH: 25
<212> TYPE: DNA
<213> ORGANISM: Homo sapiens

<400> SEQUENCE: 116
gacacttgtt agccagcatt tagtt 25

<210> SEQ ID NO 117
<211> LENGTH: 15
<212> TYPE: DNA
<213> ORGANISM: Homo sapiens

<400> SEQUENCE: 117
cccacgcgtc cgatt 15

<210> SEQ ID NO 118
<211> LENGTH: 35
<212> TYPE: DNA
<213> ORGANISM: Homo sapiens -continued

<400> SEQUENCE: 118
catattttag ttttattgaa tgtgttattg taatt 35

<210> SEQ ID NO 119
<211> LENGTH: 15
<212> TYPE: DNA
<213> ORGANISM: Homo sapiens

<400> SEQUENCE: 119
cacgcgtccg cctgt 15

<210> SEQ ID NO 120
<211> LENGTH: 25
<212> TYPE: DNA
<213> ORGANISM: Homo sapiens

<400> SEQUENCE: 120
acttgggatt ttccatgttt aattt 25

<210> SEQ ID NO 121
<211> LENGTH: 15
<212> TYPE: DNA
<213> ORGANISM: Homo sapiens

<400> SEQUENCE: 121
cacgcgtccg cctgt 15

<210> SEQ ID NO 122
<211> LENGTH: 25
<212> TYPE: DNA
<213> ORGANISM: Homo sapiens

<400> SEQUENCE: 122
acttgggatt ttccatgttt aattt 25

<210> SEQ ID NO 123
<211> LENGTH: 15
<212> TYPE: DNA
<213> ORGANISM: Homo sapiens

<400> SEQUENCE: 123
ggctccccag cgtcg 15

<210> SEQ ID NO 124
<211> LENGTH: 35
<212> TYPE: DNA
<213> ORGANISM: Homo sapiens

<400> SEQUENCE: 124
agtaagaaaa tctatcattt ttattttaaa aatct 35

<210> SEQ ID NO 125
<211> LENGTH: 18
<212> TYPE: DNA
<213> ORGANISM: Homo sapiens

<400> SEQUENCE: 125
atgctgggcc ctacagtc 18

<210> SEQ ID NO 126
<211> LENGTH: 21
<212> TYPE: DNA
<213> ORGANISM: Homo sapiens -continued

<400> SEQUENCE: 126
tcactcatgt ttcccctgat t 21

<210> SEQ ID NO 127
<211> LENGTH: 20
<212> TYPE: DNA
<213> ORGANISM: Homo sapiens

<400> SEQUENCE: 127
ctcagatgtg ctccttggag 20

<210> SEQ ID NO 128
<211> LENGTH: 29
<212> TYPE: DNA
<213> ORGANISM: Homo sapiens

<400> SEQUENCE: 128
atgttaacat aggattttta atgtggaaa 29

<210> SEQ ID NO 129
<211> LENGTH: 15
<212> TYPE: DNA
<213> ORGANISM: Homo sapiens

<400> SEQUENCE: 129
acaatgcctt acagc 15

<210> SEQ ID NO 130
<211> LENGTH: 15
<212> TYPE: DNA
<213> ORGANISM: Homo sapiens

<400> SEQUENCE: 130
ggctgtcaga tatga 15

<210> SEQ ID NO 131
<211> LENGTH: 20
<212> TYPE: DNA
<213> ORGANISM: Homo sapiens

<400> SEQUENCE: 131
accagaccct gggattaggc 20

<210> SEQ ID NO 132
<211> LENGTH: 20
<212> TYPE: DNA
<213> ORGANISM: Homo sapiens

<400> SEQUENCE: 132
cttttccagc cctctctgca 20

<210> SEQ ID NO 133
<211> LENGTH: 27
<212> TYPE: DNA
<213> ORGANISM: Homo sapiens

<400> SEQUENCE: 133
ccttacagca tcatatctga cagcccg 27

<210> SEQ ID NO 134
<211> LENGTH: 15
<212> TYPE: DNA

-continued

<213> ORGANISM: Homo sapiens

<400> SEQUENCE: 134
tttgtgtcaa tccac 15

<210> SEQ ID NO 135
<211> LENGTH: 15
<212> TYPE: DNA
<213> ORGANISM: Homo sapiens

<400> SEQUENCE: 135
gtcacaaggg gcatt 15

<210> SEQ ID NO 136
<211> LENGTH: 20
<212> TYPE: DNA
<213> ORGANISM: Homo sapiens

<400> SEQUENCE: 136
ggcccaacca atggatctaa 20

<210> SEQ ID NO 137
<211> LENGTH: 20
<212> TYPE: DNA
<213> ORGANISM: Homo sapiens

<400> SEQUENCE: 137
aaagatgtcc ccctcttccc 20

<210> SEQ ID NO 138
<211> LENGTH: 24
<212> TYPE: DNA
<213> ORGANISM: Homo sapiens

<400> SEQUENCE: 138
caatccacaa atgccccttg tgac 24

<210> SEQ ID NO 139
<211> LENGTH: 15
<212> TYPE: DNA
<213> ORGANISM: Homo sapiens

<400> SEQUENCE: 139
catgctgggc cctgc 15

<210> SEQ ID NO 140
<211> LENGTH: 15
<212> TYPE: DNA
<213> ORGANISM: Homo sapiens

<400> SEQUENCE: 140
gctgaggccc aggac 15

<210> SEQ ID NO 141
<211> LENGTH: 20
<212> TYPE: DNA
<213> ORGANISM: Homo sapiens

<400> SEQUENCE: 141
ggatggcaag ggttttgcta 20

<210> SEQ ID NO 142
<211> LENGTH: 20

-continued

<212> TYPE: DNA
<213> ORGANISM: Homo sapiens

<400> SEQUENCE: 142
ttgctgtgac aggcacaatg 20

<210> SEQ ID NO 143
<211> LENGTH: 18
<212> TYPE: DNA
<213> ORGANISM: Homo sapiens

<400> SEQUENCE: 143
cccaggactg cagggccc 18

<210> SEQ ID NO 144
<211> LENGTH: 15
<212> TYPE: DNA
<213> ORGANISM: Homo sapiens

<400> SEQUENCE: 144
cccttccaca gaagg 15

<210> SEQ ID NO 145
<211> LENGTH: 15
<212> TYPE: DNA
<213> ORGANISM: Homo sapiens

<400> SEQUENCE: 145
gtaggctttt gactg 15

<210> SEQ ID NO 146
<211> LENGTH: 24
<212> TYPE: DNA
<213> ORGANISM: Homo sapiens

<400> SEQUENCE: 146
tcatcatcat tacctatgtc cacg 24

<210> SEQ ID NO 147
<211> LENGTH: 20
<212> TYPE: DNA
<213> ORGANISM: Homo sapiens

<400> SEQUENCE: 147
caaccagcaa gtgtggaagg 20

<210> SEQ ID NO 148
<211> LENGTH: 26
<212> TYPE: DNA
<213> ORGANISM: Homo sapiens

<400> SEQUENCE: 148
cttccacaga aggtcagtca aaagcc 26

<210> SEQ ID NO 149
<211> LENGTH: 15
<212> TYPE: DNA
<213> ORGANISM: Homo sapiens

<400> SEQUENCE: 149
tttctgaggg catgg 15

<210> SEQ ID NO 150

-continued

<211> LENGTH: 15
<212> TYPE: DNA
<213> ORGANISM: Homo sapiens

<400> SEQUENCE: 150
gtcacataca tacgg 15

<210> SEQ ID NO 151
<211> LENGTH: 20
<212> TYPE: DNA
<213> ORGANISM: Homo sapiens

<400> SEQUENCE: 151
accgcaaaat aactttgggc 20

<210> SEQ ID NO 152
<211> LENGTH: 20
<212> TYPE: DNA
<213> ORGANISM: Homo sapiens

<400> SEQUENCE: 152
tccctccacc catattgaca 20

<210> SEQ ID NO 153
<211> LENGTH: 25
<212> TYPE: DNA
<213> ORGANISM: Homo sapiens

<400> SEQUENCE: 153
cacatacata cggtccatgc cctca 25

<210> SEQ ID NO 154
<211> LENGTH: 15
<212> TYPE: DNA
<213> ORGANISM: Homo sapiens

<400> SEQUENCE: 154
cgtgggctac ggaga 15

<210> SEQ ID NO 155
<211> LENGTH: 15
<212> TYPE: DNA
<213> ORGANISM: Homo sapiens

<400> SEQUENCE: 155
ggtctctggg tacat 15

<210> SEQ ID NO 156
<211> LENGTH: 20
<212> TYPE: DNA
<213> ORGANISM: Homo sapiens

<400> SEQUENCE: 156
cttccctgct tgctcctctc 20

<210> SEQ ID NO 157
<211> LENGTH: 20
<212> TYPE: DNA
<213> ORGANISM: Homo sapiens

<400> SEQUENCE: 157
aaagcaatgc agaggaaggc 20

-continued

<210> SEQ ID NO 158
<211> LENGTH: 24
<212> TYPE: DNA
<213> ORGANISM: Homo sapiens

<400> SEQUENCE: 158
ctgggtacat gtctccgtag ccca 24

<210> SEQ ID NO 159
<211> LENGTH: 15
<212> TYPE: DNA
<213> ORGANISM: Homo sapiens

<400> SEQUENCE: 159
atagctgagt gtttg 15

<210> SEQ ID NO 160
<211> LENGTH: 15
<212> TYPE: DNA
<213> ORGANISM: Homo sapiens

<400> SEQUENCE: 160
gtgggttgct tccaa 15

<210> SEQ ID NO 161
<211> LENGTH: 20
<212> TYPE: DNA
<213> ORGANISM: Homo sapiens

<400> SEQUENCE: 161
gggagagggg agaggtgaac 20

<210> SEQ ID NO 162
<211> LENGTH: 20
<212> TYPE: DNA
<213> ORGANISM: Homo sapiens

<400> SEQUENCE: 162
cacatttcct tttgctgcca 20

<210> SEQ ID NO 163
<211> LENGTH: 24
<212> TYPE: DNA
<213> ORGANISM: Homo sapiens

<400> SEQUENCE: 163
tgggttgctt ccaagcaaac actc 24

<210> SEQ ID NO 164
<211> LENGTH: 15
<212> TYPE: DNA
<213> ORGANISM: Homo sapiens

<400> SEQUENCE: 164
gaatctctgg gggtt 15

<210> SEQ ID NO 165
<211> LENGTH: 15
<212> TYPE: DNA
<213> ORGANISM: Homo sapiens

<400> SEQUENCE: 165
atcagaatgc tgtgc 15

-continued

<210> SEQ ID NO 166
<211> LENGTH: 20
<212> TYPE: DNA
<213> ORGANISM: Homo sapiens

<400> SEQUENCE: 166
tacaaatcct caggccccac 20

<210> SEQ ID NO 167
<211> LENGTH: 21
<212> TYPE: DNA
<213> ORGANISM: Homo sapiens

<400> SEQUENCE: 167
ggagctctgg gaaaggaagt t 21

<210> SEQ ID NO 168
<211> LENGTH: 25
<212> TYPE: DNA
<213> ORGANISM: Homo sapiens

<400> SEQUENCE: 168
cagaatgctg tgctaacccc cagag 25

<210> SEQ ID NO 169
<211> LENGTH: 15
<212> TYPE: DNA
<213> ORGANISM: Homo sapiens

<400> SEQUENCE: 169
gtgtttaggc attcc 15

<210> SEQ ID NO 170
<211> LENGTH: 15
<212> TYPE: DNA
<213> ORGANISM: Homo sapiens

<400> SEQUENCE: 170
ttgtgacaaa aattc 15

<210> SEQ ID NO 171
<211> LENGTH: 20
<212> TYPE: DNA
<213> ORGANISM: Homo sapiens

<400> SEQUENCE: 171
gcctctttcc atgcacacaa 20

<210> SEQ ID NO 172
<211> LENGTH: 22
<212> TYPE: DNA
<213> ORGANISM: Homo sapiens

<400> SEQUENCE: 172
ccatacagac accagggttc aa 22

<210> SEQ ID NO 173
<211> LENGTH: 30
<212> TYPE: DNA
<213> ORGANISM: Homo sapiens

<400> SEQUENCE: 173
tgtttaggca ttccagaatt tttgtcacaa 30

-continued

<210> SEQ ID NO 174
<211> LENGTH: 15
<212> TYPE: DNA
<213> ORGANISM: Homo sapiens

<400> SEQUENCE: 174
aatcacatga cgatg 15

<210> SEQ ID NO 175
<211> LENGTH: 15
<212> TYPE: DNA
<213> ORGANISM: Homo sapiens

<400> SEQUENCE: 175
ttttcctcag gacac 15

<210> SEQ ID NO 176
<211> LENGTH: 20
<212> TYPE: DNA
<213> ORGANISM: Homo sapiens

<400> SEQUENCE: 176
gctctctgtt gcatggtcca 20

<210> SEQ ID NO 177
<211> LENGTH: 20
<212> TYPE: DNA
<213> ORGANISM: Homo sapiens

<400> SEQUENCE: 177
ctgccgcatt ctgtcttctg 20

<210> SEQ ID NO 178
<211> LENGTH: 26
<212> TYPE: DNA
<213> ORGANISM: Homo sapiens

<400> SEQUENCE: 178
tcctcaggac actcatcgtc atgtga 26

<210> SEQ ID NO 179
<211> LENGTH: 15
<212> TYPE: DNA
<213> ORGANISM: Homo sapiens

<400> SEQUENCE: 179
taagaaccat tgagg 15

<210> SEQ ID NO 180
<211> LENGTH: 15
<212> TYPE: DNA
<213> ORGANISM: Homo sapiens

<400> SEQUENCE: 180
gaccctcagt ttacc 15

<210> SEQ ID NO 181
<211> LENGTH: 20
<212> TYPE: DNA
<213> ORGANISM: Homo sapiens

<400> SEQUENCE: 181

-continued gccggggaca cacagtagat 20

<210> SEQ ID NO 182
<211> LENGTH: 21
<212> TYPE: DNA
<213> ORGANISM: Homo sapiens

<400> SEQUENCE: 182
gggggtgtta aagggtctct g 21

<210> SEQ ID NO 183
<211> LENGTH: 26
<212> TYPE: DNA
<213> ORGANISM: Homo sapiens

<400> SEQUENCE: 183
ccctcagttt accccctcaa tggttc 26

<210> SEQ ID NO 184
<211> LENGTH: 15
<212> TYPE: DNA
<213> ORGANISM: Homo sapiens

<400> SEQUENCE: 184
aagagaaaat gctac 15

<210> SEQ ID NO 185
<211> LENGTH: 15
<212> TYPE: DNA
<213> ORGANISM: Homo sapiens

<400> SEQUENCE: 185
agtataaatt ctacc 15

<210> SEQ ID NO 186
<211> LENGTH: 20
<212> TYPE: DNA
<213> ORGANISM: Homo sapiens

<400> SEQUENCE: 186
tgggaccctt acccaaacat 20

<210> SEQ ID NO 187
<211> LENGTH: 23
<212> TYPE: DNA
<213> ORGANISM: Homo sapiens

<400> SEQUENCE: 187
tcaaagcaca taggaaaagg aca 23

<210> SEQ ID NO 188
<211> LENGTH: 29
<212> TYPE: DNA
<213> ORGANISM: Homo sapiens

<400> SEQUENCE: 188
attctaccgg tagcattttc tcttctggg 29

<210> SEQ ID NO 189
<211> LENGTH: 15
<212> TYPE: DNA
<213> ORGANISM: Homo sapiens

<400> SEQUENCE: 189

-continued ccatctctgt ctggc 15

<210> SEQ ID NO 190
<211> LENGTH: 15
<212> TYPE: DNA
<213> ORGANISM: Homo sapiens

<400> SEQUENCE: 190
gacaattctg agtac 15

<210> SEQ ID NO 191
<211> LENGTH: 26
<212> TYPE: DNA
<213> ORGANISM: Homo sapiens

<400> SEQUENCE: 191
tcatgttgtc tagattcagt caggct 26

<210> SEQ ID NO 192
<211> LENGTH: 21
<212> TYPE: DNA
<213> ORGANISM: Homo sapiens

<400> SEQUENCE: 192
aagggccacc tcttctgtca a 21

<210> SEQ ID NO 193
<211> LENGTH: 25
<212> TYPE: DNA
<213> ORGANISM: Homo sapiens

<400> SEQUENCE: 193
tgccatctct gtctggccgt actca 25

<210> SEQ ID NO 194
<211> LENGTH: 15
<212> TYPE: DNA
<213> ORGANISM: Homo sapiens

<400> SEQUENCE: 194
gtatgtgatt ggcct 15

<210> SEQ ID NO 195
<211> LENGTH: 15
<212> TYPE: DNA
<213> ORGANISM: Homo sapiens

<400> SEQUENCE: 195
gttgcacaag acagc 15

<210> SEQ ID NO 196
<211> LENGTH: 20
<212> TYPE: DNA
<213> ORGANISM: Homo sapiens

<400> SEQUENCE: 196
accatgatgg cagcattgac 20

<210> SEQ ID NO 197
<211> LENGTH: 20
<212> TYPE: DNA
<213> ORGANISM: Homo sapiens -continued

<400> SEQUENCE: 197
gccacctgga tgatctcctc 20

<210> SEQ ID NO 198
<211> LENGTH: 25
<212> TYPE: DNA
<213> ORGANISM: Homo sapiens

<400> SEQUENCE: 198
tgcacaagac agctaggcca atcac 25

<210> SEQ ID NO 199
<211> LENGTH: 15
<212> TYPE: DNA
<213> ORGANISM: Homo sapiens

<400> SEQUENCE: 199
gccatgctgg gccct 15

<210> SEQ ID NO 200
<211> LENGTH: 15
<212> TYPE: DNA
<213> ORGANISM: Homo sapiens

<400> SEQUENCE: 200
tgaggcccag gacag 15

<210> SEQ ID NO 201
<211> LENGTH: 20
<212> TYPE: DNA
<213> ORGANISM: Homo sapiens

<400> SEQUENCE: 201
ggatggcaag ggttttgcta 20

<210> SEQ ID NO 202
<211> LENGTH: 20
<212> TYPE: DNA
<213> ORGANISM: Homo sapiens

<400> SEQUENCE: 202
ttgctgtgac aggcacaatg 20

<210> SEQ ID NO 203
<211> LENGTH: 21
<212> TYPE: DNA
<213> ORGANISM: Homo sapiens

<400> SEQUENCE: 203
cccaggacag tagggcccag c 21

<210> SEQ ID NO 204
<211> LENGTH: 15
<212> TYPE: DNA
<213> ORGANISM: Homo sapiens

<400> SEQUENCE: 204
gcagcaacaa tgcct 15

<210> SEQ ID NO 205
<211> LENGTH: 15
<212> TYPE: DNA
<213> ORGANISM: Homo sapiens -continued

<400> SEQUENCE: 205
cagatatgac gctgt 15

<210> SEQ ID NO 206
<211> LENGTH: 20
<212> TYPE: DNA
<213> ORGANISM: Homo sapiens

<400> SEQUENCE: 206
gagatgacca gaccctggga 20

<210> SEQ ID NO 207
<211> LENGTH: 20
<212> TYPE: DNA
<213> ORGANISM: Homo sapiens

<400> SEQUENCE: 207
agccctctct gcagcaaatc 20

<210> SEQ ID NO 208
<211> LENGTH: 23
<212> TYPE: DNA
<213> ORGANISM: Homo sapiens

<400> SEQUENCE: 208
cagcaacaat gcctcacagc gtc 23

<210> SEQ ID NO 209
<211> LENGTH: 2934
<212> TYPE: DNA
<213> ORGANISM: Homo sapiens

<400> SEQUENCE: 209
ctcagatgtg ctccttggag ctggtgtgca gtgtcctgac tgtaagatca agtccaaacc 60
tgttttggaa ttgaggaaac ttctcttttg atctcagccc ttggtggtcc aggtcttcat 120
gctgctgtgg gtgatattac tggtcctggc tcctgtcagt ggacagtttg caaggacacc 180
caggcccatt attttcctcc agcctccatg gaccacagtc ttccaaggag agagagtgac 240
cctcacttgc aagggatttc gcttctactc accacagaaa acaaaatggt accatcggta 300
ccttgggaaa gaaatactaa gagaaacccc agacaatatc cttgaggttc aggaatctgg 360
agagtacaga tgccaggccc agggctcccc tctcagtagc cctgtgcact tggatttttc 420
ttcagagatg ggatttcctc atgctgccca ggctaatgtt gaactcctgg gctcaagtga 480
tctgctcacc tgggcctctc aaagcgctgg gattacagct tcgctgatcc tgcaagctcc 540
actttctgtg tttgaaggag actctgtggt tctgaggtgc cgggcaaagg cggaagtaac 600
actgaataat actatttaca agaatgataa tgtcctggca ttccttaata aaagaactga 660
cttccatatt cctcatgcat gtctcaagga caatggtgca tatcgctgta ctggatataa 720
ggaaagttgt tgccctgttt cttccaatac agtcaaaatc caagtccaag agccatttac 780
acgtccagtg ctgagagcca gctccttcca gcccatcagc gggaacccag tgaccctgac 840
ctgtgagacc cagctctctc tagagaggtc agatgtcccg ctccggttcc gcttcttcag 900
agatgaccag accctgggat taggctggag tctctccccg aatttccaga ttactgccat 960
gtggagtaaa gattcagggt tctactggtg taaggcagca acaatgcctg acagcttcat 1020
atctgacagc ccgagatcct ggatacaggt gcagatccct gcatctcatc ctgtcctcac 1080

-continued

```
tctcagccct gaaaaggctc tgaattttga gggaaccaag gtgacacttc actgtgaaac   1140
ccaggaagat tctctgcgca ctttgtacag gttttatcat gagggtgtcc ccctgaggca   1200
caagtcagtc cgctgtgaaa ggggagcatc catcagcttc tcactgacta cagagaattc   1260
agggaactac tactgcacag ctgacaatgg ccttggcgcc aagcccagta aggctgtgag   1320
cctctcagtc actgttcccg tgtctcatcc tgtcctcaac ctcagctctc ctgaggacct   1380
gatttttgag ggagccaagg tgacacttca ctgtgaagcc cagagaggtt cactccccat   1440
cctgtaccag tttcatcatg aggatgctgc cctggagcgt aggtcggcca actctgcagg   1500
aggagtggcc atcagcttct ctctgactgc agagcattca gggaactact actgcacagc   1560
tgacaatggc tttggccccc agcgcagtaa ggcggtgagc ctctccatca ctgtccctgt   1620
gtctcatcct gtcctcaccc tcagctctgc tgaggccctg acttttgaag gagccactgt   1680
gacacttcac tgtgaagtcc agagaggttc cccacaaatc ctataccagt tttatcatga   1740
ggacatgccc ctgtggagca gctcaacacc ctctgtggga agagtgtcct tcagcttctc   1800
tctgactgaa ggacattcag ggaattacta ctgcacagct gacaatggct ttggtcccca   1860
gcgcagtgaa gtggtgagcc tttttgtcac tgttccagtg tctcgcccca tcctcaccct   1920
cagggttccc agggcccagg ctgtggtggg ggacctgctg gagcttcact gtgaggcccc   1980
gagaggctct cccccaatcc tgtactggtt ttatcatgag gatgtcaccc tggggagcag   2040
ctcagccccc tctggaggag aagcttcttt caacctctct ctgactgcag aacattctgg   2100
aaactactca tgtgaggcca acaatggcct agtggcccag cacagtgaca caatatcact   2160
cagtgttata gttccagtat ctcgtcccat cctcaccttc agggctccca gggcccaggc   2220
tgtggtgggg gacctgctgg agcttcactg tgaggccctg agaggctcct ccccaatcct   2280
gtactggttt tatcatgaag atgtcaccct gggtaagatc tcagcccct ctggaggagg    2340
ggcctccttc aacctctctc tgactacaga acattctgga atctactcct gtgaggcaga   2400
caatggtctg gaggcccagc gcagtgagat ggtgacactg aaagttgcag gtgagtgggc   2460
cctgcccacc agcagcacat ctgagaactg actgtgcctg ttctccctgc agctgaaaat   2520
ggagccacag agctcctcag ggctgtttgc ttgtgtggca tcccagcaca cttcctgcct   2580
gcagaacctc cctgtgaaag tctcggatcc tttgtggtat ggttccagga atctgatgtt   2640
tcccagcagt cttcttgaag atgatcaaag cacctcacta aaaatgcaaa taagactttt   2700
ttagaacata aactatattc tgaactgaaa ttattacatg aaaatgaaac caaagaattc   2760
tgagcatatg tttctctgcc gtagaaagga ttaagctgtt tcttgtccgg attcttctct   2820
cattgacttc taagaagcct ctactcttga gtctctttca ttactgggga tgtaaatgtt   2880
ccttacattt ccacattaaa aatcctatgt taacataaaa aaaaaaaaaa aaag         2934
```

<210> SEQ ID NO 210
<211> LENGTH: 2934
<212> TYPE: DNA
<213> ORGANISM: Homo sapiens

<400> SEQUENCE: 210

```
ctcagatgtg ctccttggag ctggtgtgca gtgtcctgac tgtaagatca agtccaaacc     60
tgttttggaa ttgaggaaac ttctcttttg atctcagccc ttggtggtcc aggtcttcat    120
gctgctgtgg gtgatattac tggtcctggc tcctgtcagt ggacagtttg caaggacacc    180
caggcccatt attttcctcc agcctccatg gaccacagtc ttccaaggag agagagtgac    240
cctcacttgc aagggatttc gcttctactc accacagaaa acaaaatggt accatcggta    300
```

-continued

```
ccttgggaaa gaaatactaa gagaaacccc agacaatatc cttgaggttc aggaatctgg    360
agagtacaga tgccaggccc agggctcccc tctcagtagc cctgtgcact tggatttttc    420
ttcagagatg ggatttcctc atgctgccca ggctaatgtt gaactcctgg gctcaagtga    480
tctgctcacc tgggcctctc aaagcgctgg gattacagct tcgctgatcc tgcaagctcc    540
actttctgtg tttgaaggag actctgtggt tctgaggtgc cgggcaaagg cggaagtaac    600
actgaataat actatttaca agaatgataa tgtcctggca ttccttaata aaagaactga    660
cttccatatt cctcatgcat gtctcaagga caatggtgca tatcgctgta ctggatataa    720
ggaaagttgt tgccctgttt cttccaatac agtcaaaatc caagtccaag agccatttac    780
acgtccagtg ctgagagcca gctccttcca gcccatcagc gggaacccag tgaccctgac    840
ctgtgagacc cagctctctc tagagaggtc agatgtcccg ctccggttcc gcttcttcag    900
agatgaccag accctgggat taggctggag tctctccccg aatttccaga ttactgccat    960
gtggagtaaa gattcagggt tctactggtg taaggcagca acaatgccta acagcctcat   1020
atctgacagc ccgagatcct ggatacaggt gcagatccct gcatctcatc ctgtcctcac   1080
tctcagccct gaaaaggctc tgaattttga gggaaccaag gtgacacttc actgtgaaac   1140
ccaggaagat tctctgcgca ctttgtacag gttttatcat gagggtgtcc ccctgaggca   1200
caagtcagtc cgctgtgaaa ggggagcatc catcagcttc tcactgacta cagagaattc   1260
agggaactac tactgcacag ctgacaatgg ccttggcgcc aagcccagta aggctgtgag   1320
cctctcagtc actgttcccg tgtctcatcc tgtcctcaac ctcagctctc ctgaggacct   1380
gatttttgag ggagccaagg tgacacttca ctgtgaagcc cagagaggtt cactccccat   1440
cctgtaccag tttcatcatg aggatgctgc cctggagcgt aggtcggcca actctgcagg   1500
aggagtggcc atcagcttct ctctgactgc agagcattca gggaactact actgcacagc   1560
tgacaatggc tttggccccc agcgcagtaa ggcggtgagc ctctccatca ctgtccctgt   1620
gtctcatcct gtcctcaccc tcagctctgc tgaggccctg acttttgaag gagccactgt   1680
gacacttcac tgtgaagtcc agagaggttc cccacaaatc ctataccagt tttatcatga   1740
ggacatgccc ctgtggagca gctcaacacc ctctgtggga agagtgtcct tcagcttctc   1800
tctgactgaa ggacattcag ggaattacta ctgcacagct gacaatggct ttggtcccca   1860
gcgcagtgaa gtggtgagcc tttttgtcac tgttccagtg tctcgcccca tcctcaccct   1920
cagggttccc agggcccagg ctgtggtggg ggacctgctg gagcttcact gtgaggcccc   1980
gagaggctct cccccaatcc tgtactggtt ttatcatgag gatgtcaccc tggggagcag   2040
ctcagccccc tctggaggag aagcttcttt caacctctct ctgactgcag aacattctgg   2100
aaactactca tgtgaggcca acaatggcct agtggcccag cacagtgaca caatatcact   2160
cagtgttata gttccagtat ctcgtcccat cctcaccttc agggctccca gggcccaggc   2220
tgtggtgggg gacctgctgg agcttcactg tgaggccctg agaggctcct ccccaatcct   2280
gtactggttt tatcatgaag atgtcaccct gggtaagatc tcagccccct ctggaggagg   2340
ggcctccttc aacctctctc tgactacaga acattctgga atctactcct gtgaggcaga   2400
caatggtctg gaggcccagc gcagtgagat ggtgacactg aaagttgcag gtgagtgggc   2460
cctgcccacc agcagcacat ctgagaactg actgtgcctg ttctccctgc agctgaaaat   2520
ggagccacag agctcctcag ggctgtttgc ttgtgtggca tcccagcaca cttcctgcct   2580
gcagaacctc cctgtgaaag tctcggatcc tttgtggtat ggttccagga atctgatgtt   2640
```

-continued tcccagcagt cttcttgaag atgatcaaag cacctcacta aaaatgcaaa taagactttt 2700
ttagaacata aactatattc tgaactgaaa ttattacatg aaaatgaaac caaagaattc 2760
tgagcatatg tttctctgcc gtagaaagga ttaagctgtt tcttgtccgg attcttctct 2820
cattgacttc taagaagcct ctactcttga gtctctttca ttactgggga tgtaaatgtt 2880
ccttacattt ccacattaaa aatcctatgt taacataaaa aaaaaaaaaa aaag 2934

<210> SEQ ID NO 211
<211> LENGTH: 1357
<212> TYPE: DNA
<213> ORGANISM: Homo sapiens

<400> SEQUENCE: 211
cacgcgtccg cctgtctcaa aagaaaaaaa aaaaaaggtg aagctgaacc cagatctaca 60
catacagcta atcttaccaa aatgtgtgga agtaaagcaa tctgaaggaa attcagtacc 120
atacaattta ctgactgaaa tacatcatat tgctcatact aagaataaga gtggagaaga 180
atcatttttt tcctgctaaa atgatagagg cagaagagca acagccttgc aagacagact 240
tctattctga attgccaaaa gtggaacttc atgcccactt gaatggatcc attagttctc 300
ataccatgaa gaaattaata gcccagaagc cagatcttaa aatccacgat cagatgactg 360
tgattgacaa gggaaagaaa agaactttgg aagaatgttt ccagatgttt caaactattc 420
atcagcttac tagtagccct gaagatattc taatggtcac aaaagatgtc ataaaagaat 480
ttgcagatga cggcgtcaag tacctggaac taaggagcac acccagaaga gaaaatgcta 540
ctggaatgac taaaaagact tatgtggaat ctatacttga aggtataaaa cagtccaaac 600
aagaaaactt ggacattgat gttaggtatt tgatagcagt tgacagaaga ggtggccctt 660
tagtagccaa ggagactgta aaacttgccg aggagttctt cctttctact gagggtacag 720
ttcttggcct tgacctcagt ggagacccta ctgtaggaca agcaaaagac ttcttggaac 780
ctcttttaga agctaagaaa gcaggtctga agttagcatt gcatctttca gagattccaa 840
accaaaaaaa agaaacacaa atactcctgg atctgcttcc tgacagaatc gggcatggaa 900
catttctcaa ctccggtgag ggaggatccc tggatctggt ggactttgtg aggcaacatc 960
ggataccact gggtaaggct tggagtttca ggtcttccag atgactctct gtctctcccc 1020
caatccccag gttgcctggg gattacagag aagtactgtt ctaaaagtac gaatgtcatc 1080
tagctattaa aagatggagt gtgtgctttc tgagccttat ttaaaacaga aagctttagc 1140
ttccattaga atataagctc tatgagagca gggcccctgc ttgtcttatt cgttgttaca 1200
ttctccaatg cttggaactc aataagaatt ttttaaagga ataaagggtc atctagaatt 1260
ttaaaatgac tttaacaaaa ttgacatgtg ttatgaaaat atgtaacatt atttaaaaat 1320
taaacatgga aaatcccaag taaaaaaaaa aaaaaaa 1357

<210> SEQ ID NO 212
<211> LENGTH: 1357
<212> TYPE: DNA
<213> ORGANISM: Homo sapiens

<400> SEQUENCE: 212
cacgcgtccg cctgtctcaa aagaaaaaaa aaaaaaggtg aagctgaacc cagatctaca 60
catacagcta atcttaccaa aatgtgtgga agtaaagcaa tctgaaggaa attcagtacc 120
atacaattta ctgactgaaa tacatcatat tgctcatact aagaataaga gtggagaaga 180
atcatttttt tcctgctaaa atgatagagg cagaagagca acagccttgc aagacagact 240

-continued

```
tctattctga attgccaaaa gtggaacttc atgcccactt gaatggatcc attagttctc    300
ataccatgaa gaaattaata gcccagaagc cagatcttaa aatccacgat cagatgactg    360
tgattgacaa gggaaagaaa agaactttgg aagaatgttt ccagatgttt caaactattc    420
atcagcttac tagtagccct gaagatattc taatggtcac aaaagatgtc ataaaagaat    480
ttgcagatga cggcgtcaag tacctggaac taaggagcac acccagaaga gaaaatgcta    540
ccggaatgac taaaaagact tatgtggaat ctatacttga aggtataaaa cagtccaaac    600
aagaaaactt ggacattgat gttaggtatt tgatagcagt tgacagaaga ggtggccctt    660
tagtagccaa ggagactgta aaacttgccg aggagttctt cctttctact gagggtacag    720
ttcttggcct tgacctcagt ggagacccta ctgtaggaca agcaaaagac ttcttggaac    780
ctcttttaga agctaagaaa gcaggtctga agttagcatt gcatctttca gagattccaa    840
accaaaaaaa agaaacacaa atactcctgg atctgcttcc tgacagaatc gggcatggaa    900
catttctcaa ctccggtgag ggaggatccc tggatctggt ggactttgtg aggcaacatc    960
ggataccact gggtaaggct tggagtttca ggtcttccag atgactctct gtctctcccc   1020
caatccccag gttgcctggg gattacagag aagtactgtt ctaaaagtac gaatgtcatc   1080
tagctattaa aagatggagt gtgtgctttc tgagccttat ttaaaacaga aagctttagc   1140
ttccattaga atataagctc tatgagagca gggcccctgc ttgtcttatt cgttgttaca   1200
ttctccaatg cttggaactc aataagaatt ttttaaagga ataaagggtc atctagaatt   1260
ttaaaatgac tttaacaaaa ttgacatgtg ttatgaaaat atgtaacatt atttaaaaat   1320
taaacatgga aaatcccaag taaaaaaaaa aaaaaaa                            1357
```

<210> SEQ ID NO 213
<211> LENGTH: 1912
<212> TYPE: DNA
<213> ORGANISM: Homo sapiens

<400> SEQUENCE: 213

```
ggctccccag cgtcgcccta ggctgggact ctagtaggtc ttcggctcag ttttggctgc     60
agcgcccgcg tagatcgctt cggccgggtt ctacgcccgg ctcaactatg agccggtgcg    120
cccaggcggc ggaagtggcg gccacagtgc caggtgccgg cgtcgggaac gtggggctgc    180
ggccgcccat ggtgccccgt caggcgtcct tcttcccgcc gccggtgccg aaccccttcg    240
tgcagcagac gcagatcggc tccgcgaggc gggtccagat tgtccttctt gggattatct    300
tgcttccaat tcgtgtctta ttggttgcgt taattttatt acttgcatgg ccatttgctg    360
caatttcaac agtatgctgt cctgaaaagc tgacccaccc aataactggt tggaggagga    420
aaattactca aacagctttg aaatttctgg gtcgtgctat gttcttttca atgggattta    480
tagttgctgt aaaaggaaag attgcaagtc ctttggaagc accagttttt gttgctgccc    540
ctcattcaac attctttgat ggaattgcct gtgttgtagc tgggttacct tctatggtat    600
ctcgaaatga gaatgcacaa gtccctctga ttggcagact gttacgggct gtgcaaccag    660
ttttggtgtc ccgtgtagat ccggattccc gaaaaaacac aataaatgaa ataataaagc    720
gaacaacatc aggaggagaa tggccccaga tactagtttt cccagaaggt acttgtacta    780
atcgttcctg tttgattact tttaaaccag gagccttcat tccaggagtt ccagtgcagc    840
cagtcctcct cagataccca aacaagctgg atactgtgac ctggacatgg caaggatata    900
cattcattca gctttgtatg cttactttct gccagctctt cacaaaggta gaagttgagt    960
```

-continued

```
ttatgccagt tcaagtacca aatgatgaag aaaaaaatga tcctgtcctt tttgccaata   1020
aagtccggaa tttaatggca gaagctctgg gaataccagt aacagatcat acctatgaag   1080
actgcagatt gatgatttca gcaggacagc taacattgcc tatggaagct gggctggtgg   1140
aatttactaa aattagccga aaattgaaat tagattggga tggtgttcgt aagcatttgg   1200
atgaatatgc atctattgcg agttcctcaa aaggaggaag aattggaatt gaagaattcg   1260
ccaagtattt aaagttgcct gtttcagatg tcttgagaca actttttgca ctctttgaca   1320
ggaaccatga tggcagcatt gacttccgag agtatgtgat tggcctggct gtcttgtgca   1380
acccttccaa cacagaggag atcatccagg tggcatttaa gctgtttgac gttgatgagg   1440
atggctacat aacggaggaa gagttctcca ccattctaca ggcttccctt ggagtgcctg   1500
accttgatgt ttctggtctc ttcaaggaaa tagcccaagg ggactcaatt tcctatgagg   1560
aatttaaaag ttttgcctta aagcatccag aatatgctaa gatatttaca acatacctag   1620
acctccagac gtgccatgtg ttttcattac caaaagaagt ccagacaacc ccctccaccg   1680
ccagtaataa agtcagccct gaaaagcatg aagagagtac ctcagacaaa aaagatgact   1740
gaaagcagta tttccaataa ggaaaacaca gtagcttttg cttgaaattg taaaggcact   1800
tattgataat acttttaatg tgttggtaat gatgtttaaa attgaaagat tttaaaaata   1860
aaaatgatag attttcttac taaaaaaaaa aaaaaaaaaa aaaaaaaaaa aa           1912
```

<210> SEQ ID NO 214
<211> LENGTH: 1912
<212> TYPE: DNA
<213> ORGANISM: Homo sapiens

<400> SEQUENCE: 214

```
ggctccccag cgtcgcccta ggctgggact ctagtaggtc ttcggctcag ttttggctgc     60
agcgcccgcg tagatcgctt cggccgggtt ctacgcccgg ctcaactatg agccggtgcg    120
cccaggcggc ggaagtggcg gccacagtgc caggtgccgg cgtcgggaac gtggggctgc    180
ggccgcccat ggtgccccgt caggcgtcct tcttcccgcc gccggtgccg aacccccttcg   240
tgcagcagac gcagatcggc tccgcgaggc gggtccagat tgtccttctt gggattatct    300
tgcttccaat tcgtgtctta ttggttgcgt taattttatt acttgcatgg ccatttgctg    360
caatttcaac agtatgctgt cctgaaaagc tgacccaccc aataactggt tggaggagga    420
aaattactca aacagctttg aaatttctgg gtcgtgctat gttcttttca atgggattta    480
tagttgctgt aaaaggaaag attgcaagtc ctttggaagc accagttttt gttgctgccc    540
ctcattcaac attctttgat ggaattgcct gtgttgtagc tgggttacct tctatggtat    600
ctcgaaatga gaatgcacaa gtccctctga ttggcagact gttacgggct gtgcaaccag    660
ttttggtgtc ccgtgtagat ccggattccc gaaaaaacac aataaatgaa ataataaagc    720
gaacaacatc aggaggagaa tggccccaga tactagtttt cccagaaggt acttgtacta    780
atcgttcctg tttgattact tttaaaccag gagccttcat tccaggagtt ccagtgcagc    840
cagtcctcct cagataccca aacaagctgg atactgtgac ctggacatgg caaggatata    900
cattcattca gctttgtatg cttactttct gccagctctt cacaaaggta gaagttgagt    960
ttatgccagt tcaagtacca aatgatgaag aaaaaaatga tcctgtcctt tttgccaata   1020
aagtccggaa tttaatggca gaagctctgg gaataccagt aacagatcat acctatgaag   1080
actgcagatt gatgatttca gcaggacagc taacattgcc tatggaagct gggctggtgg   1140
aatttactaa aattagccga aaattgaaat tagattggga tggtgttcgt aagcatttgg   1200
```

-continued

```
atgaatatgc atctattgcg agttcctcaa aaggaggaag aattggaatt gaagaattcg   1260
ccaagtattt aaagttgcct gtttcagatg tcttgagaca actttttgca ctctttgaca   1320
ggaaccatga tggcagcatt gacttccgag agtatgtgat tggcctagct gtcttgtgca   1380
acccttccaa cacagaggag atcatccagg tggcatttaa gctgtttgac gttgatgagg   1440
atggctacat aacggaggaa gagttctcca ccattctaca ggcttccctt ggagtgcctg   1500
accttgatgt ttctggtctc ttcaaggaaa tagcccaagg ggactcaatt tcctatgagg   1560
aatttaaaag ttttgcctta aagcatccag aatatgctaa gatatttaca acatacctag   1620
acctccagac gtgccatgtg ttttcattac caaaagaagt ccagacaacc ccctccaccg   1680
ccagtaataa agtcagccct gaaaagcatg aagagagtac ctcagacaaa aaagatgact   1740
gaaagcagta tttccaataa ggaaaacaca gtagcttttg cttgaaattg taaaggcact   1800
tattgataat acttttaatg tgttggtaat gatgtttaaa attgaaagat ttttaaaata   1860
aaaatgatag attttcttac taaaaaaaaa aaaaaaaaaa aaaaaaaaaa aa           1912
```

<210> SEQ ID NO 215
<211> LENGTH: 2565
<212> TYPE: DNA
<213> ORGANISM: Homo sapiens

<400> SEQUENCE: 215

```
atgctgggcc ctactgtcct gggcctcagc ctctgggctc tcctgcaccc tgggacgggg     60
gccccattgt gcctgtcaca gcaacttagg atgaaggggg actacgtgct ggggggggctg    120
ttcccccctgg gcgaggccga ggaggctggc ctccgcagcc ggacacggcc cccatctgcg    180
gttctgtgtg gccccaggtt ctcctcaaac ggcctgctct gggcactggc catgaaaatg    240
gccgtggagg agatcaacaa caagtcggat ctgctgcccg ggctgcgcct gggctacgac    300
ctctttgata cgtgctcgga gcctgtggtg gccatgaagc ccagcctcat gttcctggcc    360
aaggcaggca gccgcgacat cgccgcctac tgcaactaca cgcagtacca gccccgtgtg    420
ctggctgtca tcgggcccca ctcgtcagag ctcgccatgg tcaccggcaa gttcttcagc    480
ttcttcctca tgccccaggt cagctacggt gctagcatgg agctgctgag cgcccgggag    540
accttcccct ccttcttccg caccgtgccc agcgaccgtg tgcagctgac ggccgccgcg    600
gagctgctgc aggagttcgg ctggaactgg gtggccgccc tgggcagcga cgacgagtac    660
ggccggcagg gcctgagcat cttctcggcc ctggccgcgg cacgcggcat ctgcatcgcg    720
cacgagggcc tggtgccgct gccccgtgcc gatgactcgc ggctggggaa ggtgcaggac    780
gtcctgcacc aggtgaacca gagcagcgtg caggtggtgc tgctgttcgc ctccgtgcac    840
gccgcccacg ccctcttcaa ctacagcatc agcagcaggc tctcgcccaa ggtgtgggtg    900
gccagcgagg cctggctgac ctctgacctg gtcatggggc tgcccggcat ggcccagatg    960
ggcacggtgc ttggcttcct ccagaggggt gcccagctgc acgagttccc ccagtacgtg   1020
aagacgcacc tggccctggc caccgacccg gccttctgct ctgccctggg cgagagggag   1080
cagggtctgg aggaggacgt ggtgggccag cgctgcccgc agtgtgactg catcacgctg   1140
cagaacgtga gcgcagggct aaatcaccac cagacgttct ctgtctacgc agctgtgtat   1200
agcgtggccc aggccctgca caacactctt cagtgcaacg cctcaggctg ccccgcgcag   1260
gaccccgtga agccctggca gctcctggag aacatgtaca acctgacctt ccacgtgggc   1320
gggctgccgc tgcggttcga cagcagcgga aacgtggaca tggagtacga cctgaagctg   1380
```

-continued

```
tgggtgtggc agggctcagt gcccaggctc cacgacgtgg gcaggttcaa cggcagcctc   1440
aggacagagc gcctgaagat ccgctggcac acgtctgaca accaggtgcc cgtgtcccgg   1500
tgctcgcggc agtgccagga gggccaggtg cgccgggtca aggggttcca ctcctgctgc   1560
tacgactgtg tggactgcga ggcgggcagc taccggcaaa acccagacga catcgcctgc   1620
acctttgtg gccaggatga gtggtccccg gagcgaagca cacgctgctt ccgccgcagg    1680
tctcggttcc tggcatgggg cgagccggct gtgctgctgc tgctcctgct gctgagcctg   1740
gcgctgggcc ttgtgctggc tgctttgggg ctgttcgttc accatcggga cagcccactg   1800
gttcaggcct cggggggccc cctggcctgc tttggcctgg tgtgcctggg cctggtctgc   1860
ctcagcgtcc tcctgttccc tggccagccc agccctgccc gatgcctggc ccagcagccc   1920
ttgtcccacc tcccgctcac gggctgcctg agcacactct tcctgcaggc ggccgagatc   1980
ttcgtggagt cagaactgcc tctgagctgg gcagaccggc tgagtggctg cctgcggggg   2040
ccctgggcct ggctggtggt gctgctggcc atgctggtgg aggtcgcact gtgcacctgg   2100
tacctggtgg ccttcccgcc ggaggtggtg acggactggc acatgctgcc cacggaggcg   2160
ctggtgcact gccgcacacg ctcctgggtc agcttcggcc tagcgcacgc caccaatgcc   2220
acgctggcct ttctctgctt cctgggcact ttcctggtgc ggagccagcc gggccgctac   2280
aaccgtgccc gtggcctcac ctttgccatg ctggcctact tcatcacctg ggtctccttt   2340
gtgcccctcc tggccaatgt gcaggtggtc ctcaggcccg ccgtgcagat gggcgccctc   2400
ctgctctgtg tcctgggcat cctggctgcc ttccacctgc ccaggtgtta cctgctcatg   2460
cggcagccag ggctcaacac ccccgagttc ttcctgggag gggccctggg ggatgcccaa   2520
ggccagaatg acgggaacac aggaaatcag gggaaacatg agtga                   2565
```

```
<210> SEQ ID NO 216
<211> LENGTH: 2565
<212> TYPE: DNA
<213> ORGANISM: Homo sapiens

<400> SEQUENCE: 216
```

```
atgctgggcc ctgcagtcct gggcctcagc ctctgggctc tcctgcaccc tgggacgggg     60
gccccattgt gcctgtcaca gcaacttagg atgaaggggg actacgtgct ggggggggctg   120
ttcccccctgg gcgaggccga ggaggctggc ctccgcagcc ggacacggcc cccatctgcg   180
gttctgtgtg gccccaggtt ctcctcaaac ggcctgctct gggcactggc catgaaaatg   240
gccgtggagg agatcaacaa caagtcggat ctgctgcccg ggctgcgcct gggctacgac   300
ctctttgata cgtgctcgga gcctgtggtg gccatgaagc ccagcctcat gttcctggcc   360
aaggcaggca gccgcgacat cgccgcctac tgcaactaca cgcagtacca gccccgtgtg   420
ctggctgtca tcgggcccca ctcgtcagag ctcgccatgg tcaccggcaa gttcttcagc   480
ttcttcctca tgccccaggt cagctacggt gctagcatgg agctgctgag cgcccgggag   540
accttcccct ccttcttccg caccgtgccc agcgaccgtg tgcagctgac ggccgccgcg   600
gagctgctgc aggagttcgg ctggaactgg gtggccgccc tgggcagcga cgacgagtac   660
ggccggcagg gcctgagcat cttctcggcc ctggccgcgg cacgcggcat ctgcatcgcg   720
cacgagggcc tggtgccgct gccccgtgcc gatgactcgc ggctggggaa ggtgcaggac   780
gtcctgcacc aggtgaacca gagcagcgtg caggtggtgc tgctgttcgc ctccgtgcac   840
gccgcccacg ccctcttcaa ctacagcatc agcagcaggc tctcgcccaa ggtgtgggtg   900
gccagcgagg cctggctgac ctctgacctg gtcatggggc tgcccggcat ggcccagatg   960
```

-continued

```
ggcacggtgc ttggcttcct ccagaggggt gcccagctgc acgagttccc ccagtacgtg   1020

aagacgcacc tggccctggc caccgacccg gccttctgct ctgccctggg cgagagggag   1080

cagggtctgg aggaggacgt ggtgggccag cgctgcccgc agtgtgactg catcacgctg   1140

cagaacgtga gcgcagggct aaatcaccac cagacgttct ctgtctacgc agctgtgtat   1200

agcgtggccc aggccctgca caacactctt cagtgcaacg cctcaggctg ccccgcgcag   1260

gaccccgtga agccctggca gctcctggag aacatgtaca acctgacctt ccacgtgggc   1320

gggctgccgc tgcggttcga cagcagcgga aacgtggaca tggagtacga cctgaagctg   1380

tgggtgtggc agggctcagt gcccaggctc cacgacgtgg gcaggttcaa cggcagcctc   1440

aggacagagc gcctgaagat ccgctggcac acgtctgaca accaggtgcc cgtgtcccgg   1500

tgctcgcggc agtgccagga gggccaggtg cgccgggtca aggggttcca ctcctgctgc   1560

tacgactgtg tggactgcga ggcgggcagc taccggcaaa acccagacga catcgcctgc   1620

accttttgtg gccaggatga gtggtccccg gagcgaagca cacgctgctt ccgccgcagg   1680

tctcggttcc tggcatgggg cgagccggct gtgctgctgc tgctcctgct gctgagcctg   1740

gcgctgggcc ttgtgctggc tgctttgggg ctgttcgttc accatcggga cagcccactg   1800

gttcaggcct cggggggggcc cctggcctgc tttggcctgg tgtgcctggg cctggtctgc   1860

ctcagcgtcc tcctgttccc tggccagccc agccctgccc gatgcctggc ccagcagccc   1920

ttgtcccacc tcccgctcac gggctgcctg agcacactct tcctgcaggc ggccgagatc   1980

ttcgtggagt cagaactgcc tctgagctgg gcagaccggc tgagtggctg cctgcggggg   2040

ccctgggcct ggctggtggt gctgctggcc atgctggtgg aggtcgcact gtgcacctgg   2100

tacctggtgg ccttcccgcc ggaggtggtg acggactggc acatgctgcc cacggaggcg   2160

ctggtgcact gccgcacacg ctcctgggtc agcttcggcc tagcgcacgc caccaatgcc   2220

acgctggcct ttctctgctt cctgggcact ttcctggtgc ggagccagcc gggccgctac   2280

aaccgtgccc gtggcctcac ctttgccatg ctggcctact tcatcacctg ggtctccttt   2340

gtgcccctcc tggccaatgt gcaggtggtc ctcaggcccg ccgtgcagat gggcgccctc   2400

ctgctctgtg tcctgggcat cctggctgcc ttccacctgc ccaggtgtta cctgctcatg   2460

cggcagccag ggctcaacac ccccgagttc ttcctgggag ggggccctgg ggatgcccaa   2520

ggccagaatg acgggaacac aggaaatcag gggaaacatg agtga                   2565
```

<210> SEQ ID NO 217
<211> LENGTH: 1017
<212> TYPE: DNA
<213> ORGANISM: Homo sapiens

<400> SEQUENCE: 217

```
atgtgttata tatatttaat atttaaagag tggacattga tattttactt cagtcttctc     60

cttttcctgc agattactcc tgcaataatg gcaaatctca caatcgtgac tgaatttatc    120

cttatggggt tttctaccaa taaaaatatg tgcattttgc attcgattct cttcttgttg    180

atttatttgt gtgccctgat ggggaatgtc ctcattatca tgatcacaac tttggaccat    240

catctccaca cccccgtgta tttcttcttg aagaatctat ctttcttgga tctctgcctt    300

atttcagtca cggctcccaa atctatcgcc aattctttga tacacaacaa ctccatttca    360

ttccttggct gtgtttccca ggtctttttg ttgctttctt cagcatctgc agagctgctc    420

ctcctcacgg tgatgtcctt tgaccgctat actgctatat gtcaccctct gcactatgat    480
```

-continued gtcatcatgg acaggagcac ctgtgtccaa agagccactg tgtcttggct gtatgggggt 540
ctgattgctg tgatgcacac agctggcacc ttctccttat cctactgtgg gtccaacatg 600
gtccatcagt tcttctgtga cattccccag ttattagcta tttcttgctc agaaaattta 660
ataagagaaa ttgcactcat ccttattaat gtagttttgg atttctgctg ttttattgtc 720
atcatcatta cctatgtcca cgtcttctct acagtcaaga agatcccttc cacagaaggc 780
cagtcaaaag cctactctat ttgccttcca cacttgctgg ttgtgttatt tctttccact 840
ggattcattg cttatctgaa gccagcttca gagtctcctt ctattttgga tgctgtaatt 900
tctgtgttct acactatgct gcccccaacc tttaatccca ttatatacag tttgagaaac 960
aaggccataa aggtggctct ggggatgttg ataaagggaa agctcaccaa aaagtaa 1017

<210> SEQ ID NO 218
<211> LENGTH: 1017
<212> TYPE: DNA
<213> ORGANISM: Homo sapiens

<400> SEQUENCE: 218
atgtgttata tatatttaat atttaaagag tggacattga tattttactt cagtcttctc 60
cttttcctgc agattactcc tgcaataatg gcaaatctca caatcgtgac tgaatttatc 120
cttatggggt tttctaccaa taaaaatatg tgcattttgc attcgattct cttcttgttg 180
atttatttgt gtgccctgat ggggaatgtc ctcattatca tgatcacaac tttggaccat 240
catctccaca cccccgtgta tttcttcttg aagaatctat ctttcttgga tctctgcctt 300
atttcagtca cggctcccaa atctatcgcc aattctttga tacacaacaa ctccatttca 360
ttccttggct gtgtttccca ggtctttttg ttgctttctt cagcatctgc agagctgctc 420
ctcctcacgg tgatgtcctt tgaccgctat actgctatat gtcaccctct gcactatgat 480
gtcatcatgg acaggagcac ctgtgtccaa agagccactg tgtcttggct gtatgggggt 540
ctgattgctg tgatgcacac agctggcacc ttctccttat cctactgtgg gtccaacatg 600
gtccatcagt tcttctgtga cattccccag ttattagcta tttcttgctc agaaaattta 660
ataagagaaa ttgcactcat ccttattaat gtagttttgg atttctgctg ttttattgtc 720
atcatcatta cctatgtcca cgtcttctct acagtcaaga agatcccttc cacagaaggt 780
cagtcaaaag cctactctat ttgccttcca cacttgctgg ttgtgttatt tctttccact 840
ggattcattg cttatctgaa gccagcttca gagtctcctt ctattttgga tgctgtaatt 900
tctgtgttct acactatgct gcccccaacc tttaatccca ttatatacag tttgagaaac 960
aaggccataa aggtggctct ggggatgttg ataaagggaa agctcaccaa aaagtaa 1017

<210> SEQ ID NO 219
<211> LENGTH: 2850
<212> TYPE: DNA
<213> ORGANISM: Homo sapiens

<400> SEQUENCE: 219
aagtcaggct ccctttaaat atggcctaat attgctgagc agggttgtga ggccctaaaa 60
acgtcttcct accattcctg gaattctacc ttgaaacatg tctctatcct ttaagagaaa 120
gggaggagat aaaaaggaga gagagaagct gaagctgact caaagatccg actggatctg 180
aacagtgccc cagggagaat ccatttgaaa aaaaaaaaaa aatgtgatca tgtgaatgga 240
caagaaggag atggctttag atcttatatg ctctaaacga agagttacgc tgagagggaa 300
actgacttgt catgaagtca gctttgttcc gttgctatgt gtcatccctg ctaatggtga 360

-continued

```
gtttacctaa gggcagaggc taccatctca accatgaagc tgaagacaca ggcatccgta    420
ttctatagct aattcagttg atttcatctc agcacacata cactgagcgc ttcctaagag    480
cgaggttgac cgacattttt attagcaata atctctgcct tcttctgatt acctagagat    540
ttaagaccac ataatcatcc tctacctcac agggtcaagg gagtggggga ggaaatgggc    600
taagaggttc taaatccctc ctaacacttg cttcttccaa atcagcaaga ttagagcagt    660
caacagctga ctgcgttcag accctgcagg ctgggctggc ctgcccagga cctgagaagg    720
ggcagctccg gtggcaatgt ctgagcccct agctgtgctg gtccgggctg gcctctctaa    780
gacagtgcag gccacgtgat ccatcctcct agaggcagtg agcaggtgag ggacccctac    840
sacagccagg aggaaaaagc taggcgtcca ctttccgcag ccatgctcaa acagagtgag    900
aggagacggt cctggagcta caggccctgg aacacgacgg agaatgaggg cagccaacac    960
cgcaggagca tttgctccct gggtgcccgt tccggctccc aggccagcat ccacggctgg   1020
acagagggca actataacta ctacatcgag gaagacgaag acggsgagga ggaggaccag   1080
tggaaggacg acctggcaga agaggaccag caggcagggg aggtcaccac cgccaagccc   1140
gagggcccca gcgaccctcc ggccctgctg tccacgctga atgtgaacgt gggtggccac   1200
agctaccagc tggactactg cgagctggcc ggcttcccca agacgcgcct aggtcgcctg   1260
gccacctcca ccagccgcag ccgccagcta agcctgtgcg acgactacga ggagcagaca   1320
gacgaatact tcttcgaccg cgacccggcc gtcttccagc tggtctacaa tttctacctg   1380
tccggggtgc tgctggtgct cgacgggctg tgtccgcgcc gcttcctgga ggagctgggc   1440
tactggggcg tgcggctcaa gtacacgcca cgctgctgcc gcatctgctt cgaggagcgg   1500
cgcgacgagc tgagcgaacg gctcaagatc cagcacgagc tgcgcgcgca ggcgcaggtc   1560
gaggaggcgg aggaactctt ccgcgacatg cgcttctacg gcccgcagcg gcgccgcctc   1620
tggaacctca tggagaagcc attctcctcg gtggccgcca aggccatcgg ggtggcstcc   1680
agcaccttcg tgctcgtctc cgtggtggcg ctggcgctca acaccgtgga ggagatgcag   1740
cagcactcgg ggcagggcga gggcggccca gacctgcggc ccatcctgga gcacgtggag   1800
atgctgtgca tgggcttctt cacgctcgag tacctgctgc gcctagcctc cacgcccgac   1860
ctgaggcgct tcgcgcgcag cgccctcaac ctggtggacc tggtggccat cctgccgctc   1920
taccttcagc tgctgctcga gtgcttcacg ggcgagggcc accaacgcgg ccagacggtg   1980
ggcagcgtgg gtaaggtggg tcaggtgttg cgcgtcatgc gcctcatgcg catcttccgc   2040
atcctcaagc tggcgcgcca ctccaccgga ctgcgtgcct tcggcttcac gctgcgccag   2100
tgctaccagc aggtgggctg cctgctgctc ttcatcgcca tgggcatctt cactttctct   2160
gcggctgtct actctgtgga gcacgatgtg cccagcacca acttcactac catcccccac   2220
tcctggtggt gggccgcggt gagcatctcc accgtgggct acggagacat gtacccagag   2280
acccacctgg gcaggttttt tgccttcctc tgcattgctt ttgggatcat tctcaacggg   2340
atgcccattt ccatcctcta caacaagttt tctgattact acagcaagct gaaggcttat   2400
gagtatacca ccatacgcag ggagagggga gaggtgaact tcatgcagag agccagaaag   2460
aagatagctg agtgtttgct tggaagcaac ccacagctca ccccaagaca agagaattag   2520
tattttatag gacatgtggc tggtagattc catgaacttc aaggcttcat tgctcttttt   2580
ttaatcatta tgattggcag caaaaggaaa tgtgaagcag acatacacaa aggccatttc   2640
gttcacaaag tactgcctct agaaatactc attttggccc aaactcagaa tgtctcatag   2700
```

-continued ttgctctgtg ttgtgtgaaa catctgacct tctcaatgac gttgatattg aaaacctgag 2760
gggagcaaca gcttagattt tacttgtagc ttctcgtggc atctagctca ataaatattt 2820
ttggacttga aaaaaaaaaa aaaaaaaaaa 2850

<210> SEQ ID NO 220
<211> LENGTH: 2850
<212> TYPE: DNA
<213> ORGANISM: Homo sapiens

<400> SEQUENCE: 220
aagtcaggct ccctttaaat atggcctaat attgctgagc agggttgtga ggccctaaaa 60
acgtcttcct accattcctg gaattctacc ttgaaacatg tctctatcct ttaagagaaa 120
gggaggagat aaaaaggaga gagagaagct gaagctgact caaagatccg actggatctg 180
aacagtgccc cagggagaat ccatttgaaa aaaaaaaaaa aatgtgatca tgtgaatgga 240
caagaaggag atggctttag atcttatatg ctctaaacga agagttacgc tgagagggaa 300
actgacttgt catgaagtca gctttgttcc gttgctatgt gtcatccctg ctaatggtga 360
gtttacctaa gggcagaggc taccatctca accatgaagc tgaagacaca ggcatccgta 420
ttctatagct aattcagttg atttcatctc agcacacata cactgagcgc ttcctaagag 480
cgaggttgac cgacattttt attagcaata atctctgcct tcttctgatt acctagagat 540
ttaagaccac ataatcatcc tctacctcac agggtcaagg gagtggggga ggaaatgggc 600
taagaggttc taaatccctc ctaacacttg cttcttccaa atcagcaaga ttagagcagt 660
caacagctga ctgcgttcag accctgcagg ctgggctggc ctgcccagga cctgagaagg 720
ggcagctccg gtggcaatgt ctgagcccct agctgtgctg gtccgggctg gcctctctaa 780
gacagtgcag gccacgtgat ccatcctcct agaggcagtg agcaggtgag ggacccctac 840
sacagccagg aggaaaaagc taggcgtcca ctttccgcag ccatgctcaa acagagtgag 900
aggagacggt cctggagcta caggccctgg aacacgacgg agaatgaggg cagccaacac 960
cgcaggagca tttgctccct gggtgcccgt tccggctccc aggccagcat ccacggctgg 1020
acagagggca actataacta ctacatcgag gaagacgaag acggsgagga ggaggaccag 1080
tggaaggacg acctggcaga agaggaccag caggcagggg aggtcaccac cgccaagccc 1140
gagggcccca gcgaccctcc ggccctgctg tccacgctga atgtgaacgt gggtggccac 1200
agctaccagc tggactactg cgagctggcc ggcttcccca agacgcgcct aggtcgcctg 1260
gccacctcca ccagccgcag ccgccagcta agcctgtgcg acgactacga ggagcagaca 1320
gacgaatact tcttcgaccg cgacccggcc gtcttccagc tggtctacaa tttctacctg 1380
tccggggtgc tgctggtgct cgacgggctg tgtccgcgcc gcttcctgga ggagctgggc 1440
tactggggcg tgcggctcaa gtacacgcca cgctgctgcc gcatctgctt cgaggagcgg 1500
cgcgacgagc tgagcgaacg gctcaagatc cagcacgagc tgcgcgcgca ggcgcaggtc 1560
gaggaggcgg aggaactctt ccgcgacatg cgcttctacg gcccgcagcg gcgccgcctc 1620
tggaacctca tggagaagcc attctcctcg gtggccgcca aggccatcgg ggtggcstcc 1680
agcaccttcg tgctcgtctc cgtggtggcg ctggcgctca acaccgtgga ggagatgcag 1740
cagcactcgg ggcagggcga gggcggccca gacctgcggc ccatcctgga gcacgtggag 1800
atgctgtgca tgggcttctt cacgctcgag tacctgctgc gcctagcctc cacgcccgac 1860
ctgaggcgct tcgcgcgcag cgccctcaac ctggtggacc tggtggccat cctgccgctc 1920
taccttcagc tgctgctcga gtgcttcacg ggcgagggcc accaacgcgg ccagacggtg 1980

-continued

```
ggcagcgtgg gtaaggtggg tcaggtgttg cgcgtcatgc gcctcatgcg catcttccgc   2040

atcctcaagc tggcgcgcca ctccaccgga ctgcgtgcct tcggcttcac gctgcgccag   2100

tgctaccagc aggtgggctg cctgctgctc ttcatcgcca tgggcatctt cactttctct   2160

gcggctgtct actctgtgga gcacgatgtg cccagcacca acttcactac catcccccac   2220

tcctggtggt gggccgcggt gagcatctcc accgtgggct acggagatat gtacccagag   2280

acccacctgg gcaggttttt tgccttcctc tgcattgctt ttgggatcat tctcaacggg   2340

atgcccattt ccatcctcta caacaagttt tctgattact acagcaagct gaaggcttat   2400

gagtatacca ccatacgcag ggagaggga gaggtgaact tcatgcagag agccagaaag   2460

aagatagctg agtgtttggt tggaagcaac ccacagctca ccccaagaca agagaattag   2520

tattttatag gacatgtggc tggtagattc catgaacttc aaggcttcat tgctcttttt   2580

ttaatcatta tgattggcag caaaaggaaa tgtgaagcag acatacacaa aggccatttc   2640

gttcacaaag tactgcctct agaaatactc attttggccc aaactcagaa tgtctcatag   2700

ttgctctgtg ttgtgtgaaa catctgacct tctcaatgac gttgatattg aaaacctgag   2760

gggagcaaca gcttagattt tacttgtagc ttctcgtggc atctagctca ataaatattt   2820

ttggacttga aaaaaaaaaa aaaaaaaaaa                                     2850
```

```
<210> SEQ ID NO 221
<211> LENGTH: 1745
<212> TYPE: DNA
<213> ORGANISM: Homo sapiens
<220> FEATURE:
<221> NAME/KEY: misc_feature
<222> LOCATION: (852)..(852)
<223> OTHER INFORMATION: R = A or G

<400> SEQUENCE: 221

gagcaggaac agttcatgga cgaactctga ggaccattct gaggacaaga ggcatccagt     60

gtcatgagtg gaacatgcat tttatggcta cagagttaag gcaagggttg aattccacga    120

gtcaaaaagc agcccttttc agagacccaa ctctctgggg tgctcagggg cttgggctgg    180

attgagaaga aaactgacaa gagtaagctg ccctctcttc tctggccatc tcacaaacca    240

cagtgcgggc caactggtcc tgcctcttta ccacacagaa ccaagcacta gggataagac    300

agctgcccat ggtgtccgcg gcgggtctct ctggggatgg caagatgcga ggggtgctcc    360

tggtgctgct cggccttctc tactcttcca ccagttgtgg cgtccagaaa gcttccgttt    420

tctacggtcc tgaccccaag gagggcttgg tcagcagcat ggagttcccg tgggtggtgt    480

cgctgcagga ctcccagtac acacacctgg ctttcggctg catcctgagc gagttctggg    540

tcctcagcat cgcatccgcc attcagaaca ggaaggacat tgtcgttata gtgggtataa    600

gtaacatgga tcctagcaag attgctcaca cagagtatcc agtcaatacc atcatcatcc    660

atgaggactt tgataacaac tccatgagca acaacatagc cctcctgaag acagacacag    720

cgatgcattt tggcaacctg gtccagtcca tctgcttcct cggcagaatg ctgcatacac    780

caccagtctt gcagaactgc tgggtgtcag gatggaatcc cacatctgca acaggaaatc    840

acatgacgat grgtgtcctg aggaaaatct tcgtgaaaga tcttgacatg tgtcccctat    900

acaaactcca gaagacagaa tgcggcagcc acacgaaaga ggaaaccaag actgcctgct    960

tgggggaccc aggaagccca atgatgtgcc agctacagca gttcgatctg tgggttctga   1020

gaggagtcct gaacttcggt ggtgagacgt gccctggcct gtttctgtac accaaggtgg   1080
```

-continued

```
aagactacag caaatggatc acatccaagg ctgagagggc cggccctccc ctgtcctcac   1140
tccaccactg ggaaaagttg atttctttct cccaccatgg accaaatgcc accatgacac   1200
agaagacata ttctgattct gaactgggcc atgttggatc atacttgcag ggacaaagaa   1260
ggaccatcac gcattcacga ctaggaaaca gctctagaga tagtctagat gttagggaga   1320
aggatgtaaa ggaatcaggc aggtctcctg aggcgtctgt acaaccctta tactatgact   1380
attacggtgg ggaggtgggg gaaggtagga tttttgcagg tcagaacagg ttgtatcagc   1440
ccgaagaaat catcttggtt tccttcgtgc ttgttttctt ttgcagcagt atctagtcca   1500
ggagctaccc caccaaactg aagagtaaac tgagaatgct gagtgccagg cattcaccat   1560
gctgttttga tgtctgtttt tgatagttgc acactggggc tgccacggat aagcccatgg   1620
catacactgg gctggctctc cctcctctat ccctctccca ggtgtgggaa ggtcactttc   1680
actatgcttg tgaactaaat gctggctaac aagtgtcaaa aaaaaaaaaa aaaaaaaaaa   1740
aaaaa                                                               1745
```

<210> SEQ ID NO 222
<211> LENGTH: 1745
<212> TYPE: DNA
<213> ORGANISM: Homo sapiens

<400> SEQUENCE: 222

```
gagcaggaac agttcatgga cgaactctga ggaccattct gaggacaaga ggcatccagt     60
gtcatgagtg gaacatgcat tttatggcta cagagttaag gcaagggttg aattccacga    120
gtcaaaaagc agccctttc agagacccaa ctctctgggg tgctcagggg cttgggctgg    180
attgagaaga aaactgacaa gagtaagctg ccctctcttc tctggccatc tcacaaacca    240
cagtgcgggc caactggtcc tgcctcttta ccacacagaa ccaagcacta gggataagac    300
agctgcccat ggtgtccgcg gcgggtctct ctggggatgg caagatgcga ggggtgctcc    360
tggtgctgct cggccttctc tactcttcca ccagttgtgg cgtccagaaa gcttccgttt    420
tctacggtcc tgaccccaag gagggcttgg tcagcagcat ggagttcccg tgggtggtgt    480
cgctgcagga ctcccagtac acacacctgg ctttcggctg catcctgagc gagttctggg    540
tcctcagcat cgcatccgcc attcagaaca ggaaggacat tgtcgttata gtgggtataa    600
gtaacatgga tcctagcaag attgctcaca cagagtatcc agtcaatacc atcatcatcc    660
atgaggactt tgataacaac tccatgagca acaacatagc cctcctgaag acagacacag    720
cgatgcattt tggcaacctg gtccagtcca tctgcttcct cggcagaatg ctgcatacac    780
caccagtctt gcagaactgc tgggtgtcag gatggaatcc cacatctgca acaggaaatc    840
acatgacgat gggtgtcctg aggaaaatct tcgtgaaaga tcttgacatg tgtcccctat    900
acaaactcca gaagacagaa tgcggcagcc acacgaaaga ggaaaccaag actgcctgct    960
tgggggaccc aggaagccca atgatgtgcc agctacagca gttcgatctg tgggttctga   1020
gaggagtcct gaacttcggt ggtgagacgt gccctggcct gtttctgtac accaaggtgg   1080
aagactacag caaatggatc acatccaagg ctgagagggc cggccctccc ctgtcctcac   1140
tccaccactg ggaaaagttg atttctttct cccaccatgg accaaatgcc accatgacac   1200
agaagacata ttctgattct gaactgggcc atgttggatc atacttgcag ggacaaagaa   1260
ggaccatcac gcattcacga ctaggaaaca gctctagaga tagtctagat gttagggaga   1320
aggatgtaaa ggaatcaggc aggtctcctg aggcgtctgt acaaccctta tactatgact   1380
attacggtgg ggaggtgggg gaaggtagga tttttgcagg tcagaacagg ttgtatcagc   1440
```

-continued

```
ccgaagaaat catcttggtt tccttcgtgc ttgttttctt ttgcagcagt atctagtcca   1500
ggagctaccc caccaaactg aagagtaaac tgagaatgct gagtgccagg cattcaccat   1560
gctgttttga tgtctgtttt tgatagttgc acactggggc tgccacggat aagcccatgg   1620
catacactgg gctggctctc cctcctctat ccctctccca ggtgtgggaa ggtcactttc   1680
actatgcttg tgaactaaat gctggctaac aagtgtcaaa aaaaaaaaaa aaaaaaaaaa   1740
aaaaa                                                               1745
```